United States Patent
Rowbottom et al.

(10) Patent No.: US 11,072,585 B2
(45) Date of Patent: *Jul. 27, 2021

(54) FLUORINATED LYSYL OXIDASE-LIKE 2 INHIBITORS AND USES THEREOF

(71) Applicant: PharmAkea, Inc., San Diego, CA (US)

(72) Inventors: Martin W. Rowbottom, San Diego, CA (US); John Howard Hutchinson, San Diego, CA (US); Imelda Calderon, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/713,314

(22) Filed: Dec. 13, 2019

(65) Prior Publication Data

US 2020/0115341 A1     Apr. 16, 2020

Related U.S. Application Data

(60) Continuation of application No. 16/138,680, filed on Sep. 21, 2018, now Pat. No. 10,570,094, which is a division of application No. 15/695,911, filed on Sep. 5, 2017, now Pat. No. 10,150,732, which is a continuation of application No. PCT/US2016/020732, filed on Mar. 3, 2016.

(60) Provisional application No. 62/129,543, filed on Mar. 6, 2015.

(51) Int. Cl.

| | |
|---|---|
| *C07D 213/643* | (2006.01) |
| *C07D 213/74* | (2006.01) |
| *C07D 213/75* | (2006.01) |
| *C07D 213/38* | (2006.01) |
| *C07D 213/64* | (2006.01) |
| *C07D 213/70* | (2006.01) |
| *C07D 401/12* | (2006.01) |
| *C07D 401/14* | (2006.01) |
| *C07D 405/14* | (2006.01) |
| *C07D 413/12* | (2006.01) |
| *C07D 413/14* | (2006.01) |
| *C07D 401/06* | (2006.01) |
| *C07D 405/12* | (2006.01) |
| *C07D 409/12* | (2006.01) |
| *C07D 491/107* | (2006.01) |
| *C07D 498/10* | (2006.01) |
| *A61P 11/00* | (2006.01) |
| *A61P 35/00* | (2006.01) |

(52) U.S. Cl.
CPC .......... *C07D 213/643* (2013.01); *A61P 11/00* (2018.01); *A61P 35/00* (2018.01); *C07D 213/38* (2013.01); *C07D 213/64* (2013.01); *C07D 213/70* (2013.01); *C07D 213/74* (2013.01); *C07D 213/75* (2013.01); *C07D 401/06* (2013.01); *C07D 401/12* (2013.01); *C07D 401/14* (2013.01); *C07D 405/12* (2013.01); *C07D 405/14* (2013.01); *C07D 409/12* (2013.01); *C07D 413/12* (2013.01); *C07D 413/14* (2013.01); *C07D 491/107* (2013.01); *C07D 498/10* (2013.01)

(58) Field of Classification Search
CPC ............. C07D 213/643; C07D 401/06; C07D 405/12; C07D 413/14; C07D 409/12; C07D 413/12; C07D 491/107; C07D 498/10; C07D 213/70; C07D 213/64; C07D 213/38; C07D 213/74; C07D 213/75; C07D 401/12; C07D 401/14; C07D 405/14; A61P 11/00; A61P 35/00
See application file for complete search history.

(56) References Cited

U.S. PATENT DOCUMENTS

| | | |
|---|---|---|
| 4,229,447 A | 10/1980 | Porter |
| 4,596,795 A | 6/1986 | Pitha |
| 4,755,386 A | 7/1988 | Hsiao et al. |
| 5,021,456 A | 6/1991 | Palfreyman et al. |
| 5,324,837 A | 6/1994 | Renga et al. |
| 5,739,136 A | 4/1998 | Ellinwood, Jr. et al. |
| 6,878,714 B2 | 4/2005 | Askew et al. |
| 6,956,047 B1 | 10/2005 | Chen |
| 6,995,162 B2 | 2/2006 | Chen et al. |
| 7,060,697 B2 | 6/2006 | Marsilje et al. |
| 7,067,664 B1 | 6/2006 | Chen |
| 7,101,868 B2 | 9/2006 | Elbaum et al. |
| 7,102,009 B2 | 9/2006 | Patel et al. |
| 7,105,682 B2 | 9/2006 | Chen et al. |
| 7,307,088 B2 | 12/2007 | Huang et al. |

(Continued)

FOREIGN PATENT DOCUMENTS

| | | |
|---|---|---|
| EP | 0110405 A2 | 6/1984 |
| EP | 0706795 A2 | 4/1996 |

(Continued)

OTHER PUBLICATIONS

CAS Registry No. 953903-03-2 (Year: 2017).*
Ansel. Pharmaceutical Dosage Forms and Drug Delivery Systems 7th ed. (pp. 48-53) (1999).
Barr et al. American translation, modification, and validation of the St. George's Respiratory Questionnaire. Clin Ther. 22(9):1121-45 (2000).
Bates et al. A general method for the formation of aryl-sulfur bonds using copper(I) catalysts. Org. Lett. 4:2803-2806 (2002).

(Continued)

*Primary Examiner* — Erich A Leeser

(74) *Attorney, Agent, or Firm* — Wilson Sonsini Goodrich & Rosati

(57) ABSTRACT

Described herein are compounds that are LOXL2 inhibitors, methods of making such compounds, pharmaceutical compositions and medicaments comprising such compounds, and methods of using such compounds in the treatment of conditions, diseases, or disorders associated with LOXL2 activity.

17 Claims, No Drawings

(56) References Cited

U.S. PATENT DOCUMENTS

| | | | |
|---|---|---|---|
| 7,378,448 | B2 | 5/2008 | Chappell et al. |
| 7,381,750 | B2 | 6/2008 | De La Torre et al. |
| 7,482,340 | B2 | 1/2009 | Otsomaa et al. |
| 7,507,748 | B2 | 3/2009 | Yuan et al. |
| 7,514,564 | B2 | 4/2009 | Chen et al. |
| 7,687,643 | B2 | 3/2010 | Askew et al. |
| 7,723,331 | B2 | 5/2010 | Giordanetto et al. |
| 7,759,493 | B2 | 7/2010 | Ge et al. |
| 7,902,372 | B2 | 3/2011 | Chappell et al. |
| 8,058,445 | B2 | 11/2011 | Chen et al. |
| 8,247,430 | B2 | 8/2012 | Yuan et al. |
| 8,338,611 | B2 | 12/2012 | Chappell et al. |
| 8,343,944 | B2 | 1/2013 | Xia et al. |
| 8,642,624 | B2 | 2/2014 | Chen et al. |
| 1,015,073 | A1 | 12/2018 | Rowbottom et al. |
| 10,150,732 | B2 * | 12/2018 | Rowbottom ......... C07D 213/70 |
| 1,077,406 | A1 | 9/2020 | Longergan et al. |
| 2002/0147198 | A1 | 10/2002 | Chen et al. |
| 2004/0087568 | A1 | 5/2004 | Huang et al. |
| 2005/0171086 | A1 | 8/2005 | Brodney et al. |
| 2006/0040966 | A1 | 2/2006 | Yuan et al. |
| 2007/0066658 | A1 | 3/2007 | Chappell et al. |
| 2007/0105866 | A1 | 5/2007 | Hutchinson et al. |
| 2007/0123522 | A1 | 5/2007 | Hutchinson et al. |
| 2007/0149579 | A1 | 6/2007 | Blouin et al. |
| 2007/0173508 | A1 | 7/2007 | Hutchinson et al. |
| 2007/0219206 | A1 | 9/2007 | Hutchinson et al. |
| 2007/0225285 | A1 | 9/2007 | Hutchinson et al. |
| 2007/0270430 | A1 | 11/2007 | Ice et al. |
| 2008/0004269 | A1 | 1/2008 | Xu et al. |
| 2008/0027050 | A1 | 1/2008 | Terauchi et al. |
| 2008/0051405 | A1 | 2/2008 | Giordanetto et al. |
| 2008/0318926 | A1 | 12/2008 | Ice et al. |
| 2009/0143355 | A1 | 6/2009 | Yuan et al. |
| 2011/0076272 | A1 | 3/2011 | Smith et al. |
| 2011/0136763 | A1 | 6/2011 | Xia et al. |
| 2012/0149681 | A1 | 6/2012 | Rodgers et al. |
| 2014/0120102 | A1 | 5/2014 | Bornstein et al. |
| 2014/0302524 | A1 | 10/2014 | McCauley et al. |
| 2016/0222128 | A1 | 8/2016 | Neufeld et al. |
| 2018/0057458 | A1 | 3/2018 | Rowbottom et al. |
| 2019/0119211 | A1 | 4/2019 | Rowbottom et al. |
| 2019/0192495 | A1 | 6/2019 | Bain et al. |

FOREIGN PATENT DOCUMENTS

| | | |
|---|---|---|
| EP | 1775347 A2 | 4/2007 |
| WO | WO-9932117 A1 | 7/1999 |
| WO | WO-0153263 A1 | 7/2001 |
| WO | WO-03087057 A1 | 10/2003 |
| WO | WO-2005090286 A1 | 9/2005 |
| WO | WO-2006053555 A2 | 5/2006 |
| WO | WO-2007016784 A1 | 2/2007 |
| WO | WO-2008009963 A2 | 1/2008 |
| WO | WO-2009017833 A2 | 2/2009 |
| WO | WO-2011017125 A1 | 2/2011 |
| WO | WO-2011097594 A2 | 8/2011 |
| WO | WO-2011109799 A1 | 9/2011 |
| WO | WO-2011150201 A2 | 12/2011 |
| WO | WO-2012041476 A1 | 4/2012 |
| WO | WO-2012068450 A1 | 5/2012 |
| WO | WO-2013026025 A1 | 2/2013 |
| WO | WO-2013059587 A1 | 4/2013 |
| WO | WO-2013161308 A1 | 10/2013 |
| WO | WO-2014070939 A1 | 5/2014 |
| WO | WO-2014098098 A1 | 6/2014 |
| WO | WO-2016020732 A1 | 2/2016 |
| WO | WO-2016028686 A1 | 2/2016 |
| WO | WO-2016128529 A1 | 8/2016 |
| WO | WO-2016144702 A1 | 9/2016 |
| WO | WO-2016144703 A1 | 9/2016 |
| WO | WO-2018048942 A1 | 3/2018 |
| WO | WO-2018048943 A1 | 3/2018 |

OTHER PUBLICATIONS

Burgos et al. Significantly improved method for the pd-catalyzed coupling of phenols with aryl halides: understanding ligand effects. Angew. Chem. Int. Ed. 45:4321-4326 (2006).

Chan et al. New N- and O-arylations with phenylboronic acids and cupric acetate. Tetrahedron Lett. 39:2933-2936 (1998).

Chang et al. Pre-clinical evaluation of small molecule LOXL2 inhibitors in breast cancer. Oncotarget 8(16):26066-26078 (2017).

Chen et al. 1,1,1-tris(hydroxymethyl)ethane as a new, efficient, and versatile tripod ligand for copper-catalyzed cross-coupling reactions of aryl iodides with amides, thiols, and phenols. Org. Lett. 8:5609-5612 (2006).

Cosgrove et al. Ultrastructural, physiological, and molecular defects in the inner ear of a gene-knockout mouse model for autosomal Alport syndrome. Hear Res 121:84-98 (1998).

Dai et al. Efficient synthesis of 2',3'-dideoxy-2'-amino-3'-thiouridine. Org. Lett. 5:2169-2171 (2003).

Erasmus et al. Linking LOXL2 to Cardiac Interstitial Fibrosis. Int J Mol Sci. 21(16):5913 (2020).

Evans et al. Synthesis of Diaryl Ethers through the Copper-Promoted Arylation of Phenols with Arylboronic Acids. An Expedient Synthesis of Thyroxine. Tetrahendron Letters 39:2937-2940 (1998).

Friedlander. Fibrosis and diseases of the eye. J Clin Invest. 117:576-586 (2007).

Girogescu. Non-invasive Biochemical Markers of Liver Fibrosis. J. Gastrointestin. Liver Dis. 15(2):149-159 (2006).

Ikenaga et al. Selective targeting of lysyl oxidase-like 2 (LOXL2) suppresses hepatic fibrosis progression and accelerates its reversal. Gut 66(9):1697-1708 (2017).

Ishii et al. Fluid and Fibrosis in the Human Middle Ear. Am. J Otolaryngol 6(3):196-199 (1985).

Jones et al. A self-complete measure of health status for chronic airflow limitation. Am Rev Respir Dis 145:1321-1327 (1992).

Jones et al. The St. George's Respiratory Questionnaire. Resp Med 85:2531 (1991).

Jones. Interpreting thresholds for a clinically significant change in health status in asthma and COPD. Eur Respir J. 19(3):398-404 (2002).

Klepfish et al. LOXL2 Inhibition Paves the Way for Macrophage-Mediated Collagen Degradation in Liver Fibrosis. Front Immunol. 11:480 (2020).

Li et al. Liver fibrogenesis and the role of hepatic stellate cells: new insights and prospects for therapy. Gastroenterol. Hepatol. 14:618-633 (1999).

Liu et al. Facile N-arylation of amines and sulfonamides and o-arylation of phenols and arenecarboxylic acids. J Org. Chem. 71:3198-3209 (2006).

Ma et al. N,N-dimethyl glycine-promoted Ullmann coupling reaction of phenols and aryl halides. Org. Lett. 5:3799-3802 (2003).

Mahjour et al. Mechanism for oral tumor cell lysyl oxidaselike-2 in cancer development: synergy with PDGF-AB. Oncogenesis 8:34 (2019).

Matsuoka et al. Wnt signaling and Loxl2 promote aggressive osteosarcoma. Cell research 30:885-901 (2020).

Mehal et al. Scraping fibrosis: expressway to the core of fibrosis. Nat Med. 17:552-553 (2011).

Moon et al. Human lysyl oxidase-like 2. Bioorg. Chem. 57:231-241 (2014).

Nicholas et al. Lung Fibrosis: Fibroblast Biology, Thematic: Identification of Novel Small-Molecule Loxl2 Inhibitors by High Throughput Screening. Poster Session 2014 (1 pg.).

Nishimura. Handbook of Heterogeneous Catalytic Hydrogenation for Organic Synthesis (1st ed.). Wiley-Interscience. pp. 254-277 (2001).

Papadantonakis et al. Megakaryocyte pathology and bone marrow fibrosis: the lysyl oxidase connection. Blood. 120(9):1774-1781 (2012).

Puente et al. LOXL2—A New Target in Antifibrogenic Therapy? Int J Mol Sci. 20(7):1634 (2019).

(56) References Cited

OTHER PUBLICATIONS

Rajagopalan et al. Biochemical and functional characterization of lysyl oxidase like 2 (LOXL2) inhibitors. Eur Resp Journal (44):p. 1518 (2014) (Abstract only).
Sato et al. Comparative analysis of gene expression profiles in intact and damaged regions of human osteoarthritic cartilage. Arthritis & Rheumatism 54(3):808-817 (2006).
Schena et al. Pathogenic Mechanisms of Diabetic Nephropathy. J. Am. Soc. Nephrol. 16:S30-33 (2005).
Stagenberg et al. Lysyl oxidase-like 2 inhibition ameliorates glomerulosclerosis and albuminuria in diabetic nephropathy. Scientific reports 8:9423 (2018).
Tadmor et al. The expression of lysyl-oxidase gene family members in myeloproliferative neoplasms. Am J Hematol 88(5):355-358 (2013).
Tolboom et al. Invasiveness of fibroblast-like synoviocytes is an individual patient characteristic associated with the rate of joint destruction in patients with rheumatoid arthritis. Arthritis Rheum 52:1999-2002 (2005).
Van Bergen et al. The role of LOX and LOXL2 in scar formation after glaucoma surgery. Invest Ophthalmol Vis Sci. 54:5788-5796 (2013).
Whaley-Cannell et al. Chronic Kidney Disease and the Cardiometabolic Syndrome. J. Clin. Hypert. 8(8):546-48 (2006).
Wu et al. The function and mechanisms of action of LOXL2 in cancer (Review). Int J Mol Sci. 36(5):1200-1204 (2015).
Xiao et al. Lysyl oxidase, extracellular matrix remodeling and cancer metastasis. Cancer Microenviron. 5(3):261-273 (2012).
Xie et al. Inhibition of LOXL2 Enhances the Radiosensitivity of Castration-Resistant Prostate Cancer Cells Associated with the Reversal of the EMT Process. Biomed Res Int 2019:4012590 (2019).
Yang et al. Targeting LOXL2 for cardiac interstitial fibrosis and heart failure treatment. Nat Commun 7:13710 (2016).
Yeom et al. DBU-Mediated Mild and Chemoselective Deprotection of Aryl Silyl Ethers and Tandem Biaryl Ether Formation. 2007(1):Synlett 146-150 (2007).
Allais et al. Metal-free multicomponent syntheses of pyridines. Chem Rev 114:10829-10868 (2014).
Barry-Hamilton et al. Allosteric inhibition of lysyl oxidase-like-2 impedes the development of a pathologic microenvironment. Nat Med 16(9):1009-1017 (2010).
Bertini et al. Alkylamino derivatives of 4-aminomethylpyridine as inhibitors of copper-containing amine oxidases. J Med Chem 48(3):664-670 (2005).
Cano et al. LOXL2 in epithelial cell plasticity and tumor progression. Future Oncol 8(9):1095-1108 (2012).
Chemical Abstract compounds, STN express—RN 1156824-90-6 (1 pg.) (Entered STN: Jun. 14, 2009).
Chemical Abstract compounds, STN express—RN 1270589-17-7 (1 pg.) (Entered STN: Mar. 27, 2011).
Chemical Abstract compounds, STN express—RN 1270700-69-0 (1 pg.) (Entered STN: Mar. 27, 2011).
Chemical Abstract compounds, STN express—RN 1270718-02-9 (1 pg.) (Entered STN: Mar. 27, 2011).
Chemical Abstract compounds, STN express—RN 1470575-43-9 (1 pg.) (Entered STN: Nov. 10, 2013).
Chemical Abstract compounds, STN express—RN 1493615-64-7 (1 pg.) (Entered STN: Dec. 12, 2013).
Chemical Abstract compounds, STN express—RN 1507533-77-8 (1 pg.) (Entered STN: Dec. 31, 2013).
Chemical Abstract compounds, STN express—RN 1543432-15-0 (1 pg.) (Entered STN: Feb. 14, 2014).
Chemical Abstract compounds, STN express—RN 1543664-24-9 (1 pg.) (Entered STN: Feb. 14, 2014).
Chemical Abstract compounds, STN express—RN 1543836-80-1 (1 pg.) (Entered STN: Feb. 14, 2014).
Chemical Abstract compounds, STN express—RN 953903-03-2 (1 pg.) (Entered STN: Nov. 15, 2007).
Chemical Abstract compounds, STN express—RN 1544074-67-0 (1 pg.) (Entered STN: Feb. 14, 2014).
Chemical Structure Search Report, dated Nov. 10, 2014 (292 pgs.).
Chien et al. Serum lysyl oxidase-like 2 levels and idiopathic pulmonary fibrosis disease progression. Eur Respir J 43(5):1430-1438 (2014).
Cottet et al. Trifluoromethyl-Substituted Pyridines Through Displacement of Iodine by in situ Generated (Trifluoromethyl)copper. Eur J Org Chem 2002(2):327-330 (2002).
Gabrielsen et al. Identification of Novel Serotonin Transporter Compounds by Virtual Screening. J Chem Inf Model 54(3):933-943 (2014).
Hase et al. LOXL2 Status Correlates with Tumor Stage and Regulates Integrin Levels to Promote Tumor Progression in ccRCC. Mol Cancer Res 12(12):1807-1817 (2014).
Hutchinson et al. Small Molecule Lysyl Oxidase-like 2 (LOXL2) Inhibitors: The Identification of an Inhibitor Selective for LOXL2 over LOX. ACS Med. Chem. Lett. 8(4):423-427 (2017).
Ikenaga et al. A new Mdr2(−/−) mouse model of sclerosing cholangitis with rapid fibrosis progression, early-onset portal hypertension, and liver cancer. Am J Pathology 185:325-334 (2015).
Liu et al. Recent progress in the synthesis of pyridinylboronic acids and esters. ARKIVOC 2013(i):135-153 (2013).
Londregan et al. General and mild preparation of 2-aminopyridines. Org Lett 12:5254-5257 (2010).
PCT/US2015/020732 International Search Report and Written Opinion dated Aug. 18, 2016.
PCT/US2016/020731 International Search Report and Written Opinion dated Aug. 18, 2016.
PCT/US2018/022513 Third Party Observation dated Jul. 15, 2019.
Popov et al. Tissue transglutaminase does not affect fibrotic matrix stability or regression of liver fibrosis in mice. Gastroenterology 140(5):1642-1652. (2011).
Rodriguez et al. Modulation of lysyl oxidase-like 2 enzymatic activity by an allosteric antibody inhibitor. J Biol Chem 285(27):20964-20974 (2010).
Rowbottom et al. Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2). J Med Chem 50:4403-4423 (2017).
Tang et al. Beta-substituted ethylamine derivatives as suicide inhibitors of lysyl oxidase. J Biol Chem 259(2):975-979 (1984).
Van Bergen et al. The Role of LOX and LOXL2 in the Pathogenesis of an Experimental Model of Choroidal Neovascularization. Invest Ophthalmol Vis Sci 56(9):5280-5289 (2015).
West. Solid state chemistry and its applications Wiley New York pp. 358 and 365 (1988).
Williamson et al. Electronegativity of aromatic amines as a basis for the development of ground state inhibitors of lysyl oxidase. J Biol Chem 262(30):14520-14524 (1987).
Yin et al. A general and efficient 2-amination of pyridines and quinolines. J Org Chem 72:4554-4557 (2007).
Zablocki et al. Potent in vitro and in vivo inhibitors of platelet aggregation based upon the Arg-Gly-Asp sequence of fibrinogen. (Aminobenzamidino)succinyl (ABAS) series of orally active fibrinogen receptor antagonists. J Med Chem 38:2378-2394 (1995).

\* cited by examiner

FLUORINATED LYSYL OXIDASE-LIKE 2 INHIBITORS AND USES THEREOF

RELATED APPLICATIONS

This application is a Continuation of U.S. patent application Ser. No. 16/138,680, filed Sep. 21, 2018, which is a Divisional Application of U.S. application Ser. No. 15/695,911, filed on Sep. 5, 2017, which is a Continuation of International Patent Application No. PCT/US2016/020732 entitled "FLUORINATED LYSYL OXIDASE-LIKE 2 INHIBITORS AND USES THEREOF" filed on Mar. 3, 2016, which claims the benefit of U.S. Provisional Patent Application No. 62/129,543 filed on Mar. 6, 2015, each of which is herein incorporated by reference in its entirety.

FIELD OF THE INVENTION

Described herein are compounds that are fluorinated lysyl oxidase-like 2 (LOXL2) inhibitors, methods of making such compounds, pharmaceutical compositions and medicaments comprising such compounds, and methods of using such compounds in the treatment of conditions, diseases, or disorders associated with LOXL2 activity.

BACKGROUND OF THE INVENTION

Lysyl oxidase like-2 (LOXL2) is an amine oxidase enzyme that catalyzes crosslinking of extracellular matrix proteins. LOXL2 is also involved in intracellular processes such as mediating epithelial-to-mesenchymal transition of cells. LOXL2 signaling is implicated in, for example, in fibrotic diseases and cancer.

SUMMARY OF THE INVENTION

In one aspect, described herein are LOXL2 inhibitors and uses thereof. In some embodiments, the LOXL2 inhibitors described herein have the structure of Formula (I), or a pharmaceutically acceptable salt thereof.

In one aspect, described herein is a compound of Formula (I), or a pharmaceutically acceptable salt thereof:

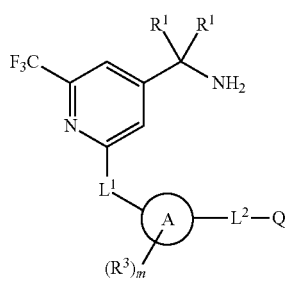

Formula (I)

wherein, each $R^1$ is independently H, D, or F;

$L^1$ is absent, $X^1$, $X^1$—$C_1$-$C_6$alkylene, or $C_1$-$C_6$alkylene; $X^1$ is —O—, —S—, —S(=O)—, —S(=O)$_2$—, —C(=O)—, —C(=O)O—, —C(=O)NR$^2$—, —NR$^2$C(=O)—, or —NR$^2$—;

$R^2$ is H, substituted or unsubstituted $C_1$-$C_6$alkyl, $C_1$-$C_6$fluoroalkyl, or $C_1$-$C_6$deuteroalkyl;

each $R^3$ is independently H, D, halogen, —CN, —OR$^5$, —SR$^5$, —S(=O)R$^4$, —S(=O)$_2$R$^4$, —S(=O)$_2$N(R$^5$)$_2$, —NR$^2$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^2$C(=O)R$^4$, —NR$^2$C(=O)OR$^4$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

m is 0, 1, or 2;

each $R^4$ is independently selected from $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl;

each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl; or two $R^5$ on the same N atom are taken together with the N atom to which they are attached to a substituted or unsubstituted N-containing heterocycle;

Ring A is monocyclic carbocycle, bicyclic carbocycle, monocyclic heterocycle, or bicyclic heterocycle;

$L^2$ is absent, —$X^2$—, or —$C_1$-$C_6$alkylene-$X^2$—; $X^2$ is —O—, —S—, —S(=O)—, —S(=O)$_2$—, —S(=O)$_2$NR$^6$—, —C(=O)—, —C(=O)O—, —C(=O)NR$^6$—, —C(=O)NR$^6$O—, —NR$^6$C(=O)—, —NR$^6$S(=O)$_2$—, or —NR$^6$—;

$R^6$ is H, $C_1$-$C_6$alkyl, $C_1$-$C_6$fluoroalkyl, or $C_1$-$C_6$deuteroalkyl;

Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, —$C_1$-$C_4$alkylene-(substituted or unsubstituted $C_3$-$C_8$cycloalkyl), substituted or unsubstituted $C_2$-$C_8$heterocycloalkyl, —$C_1$-$C_4$alkylene-(substituted or unsubstituted $C_2$-$C_8$heterocycloalkyl), substituted or unsubstituted aryl, —$C_1$-$C_4$alkylene-(substituted or unsubstituted aryl), substituted or unsubstituted heteroaryl, or —$C_1$-$C_4$alkylene-(substituted or unsubstituted heteroaryl); wherein if Q is substituted then Q is substituted with one or more $R^8$;

or Q and $R^6$ are taken together with the N atom to which they are attached to form ring B, wherein ring B is a substituted or unsubstituted N-containing heterocycle, wherein if ring B is substituted then ring B is substituted with 1-3 $R^8$;

each $R^8$ is independently D, halogen, CN, —OR$^5$, —SR$^5$, —S(=O)R$^4$, —S(=O)$_2$R$^4$, —S(=O)$_2$N(R$^5$)$_2$, NR$^5$S(=O)$_2$R$^4$, C(=O)R$^4$, OC(=O)R$^4$, CO$_2$R$^5$, OCO$_2$R$^4$, N(R$^4$)$_2$, OC(=O)N(R$^5$)$_2$, —NHC(=O)R$^4$, —NHC(=O)OR$^4$, $C_1$-$C_6$alkyl, $C_1$-$C_6$alkenyl, $C_1$-$C_6$alkynyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;

or two $R^8$ groups attached to the same carbon atom are taken together with carbon atom to which they are attached to form either a substituted or unsubstituted carbocycle or substituted or unsubstituted heterocycle.

For any and all of the embodiments, substituents are selected from among a subset of the listed alternatives. For example, in some embodiments, each $R^1$ is independently H, D, or F. In some other embodiments, each $R^1$ is independently H, or F. In other embodiments, each $R^1$ is H. In some embodiments, each $R^1$ is D. In some embodiments, each $R^1$ is F.

In some embodiments, each $R^1$ is H; $L^1$ is absent, $X^1$, or $X^1$—$C_1$-$C_6$alkylene.

In some embodiments, $X^1$ is —O—.

In some embodiments, $L^1$ is absent, —O—, or —O—$CH_2$—.

In some embodiments, the compound of Formula (I) has the structure of Formula (II), or a pharmaceutically acceptable salt thereof:

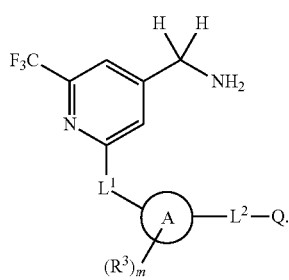

Formula (II)

In some embodiments, $L^1$ is —O—, or —O—$CH_2$—.

In some embodiments, the compound of Formula (I) has the structure of Formula (III), or a pharmaceutically acceptable salt thereof:

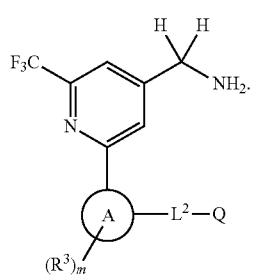

Formula (III)

In some embodiments, Ring A is monocyclic $C_3$-$C_6$carbocycle, bicyclic $C_5$-$C_{12}$carbocycle, monocyclic $C_1$-$C_5$heterocycle, bicyclic $C_5$-$C_{10}$heterocycle.

In some embodiments, Ring A is monocyclic $C_3$-$C_6$carbocycle, bicyclic $C_9$-$C_{10}$carbocycle, monocyclic $C_1$-$C_5$heterocycle, bicyclic $C_6$-$C_9$heterocycle.

In some embodiments, Ring A is monocyclic $C_3$-$C_6$carbocycle.

In some embodiments, Ring A is phenyl, cyclopropyl, cyclobutyl, cyclopentyl, or cyclohexyl.

In some embodiments, Ring A is phenyl.

In some embodiments, Ring A is

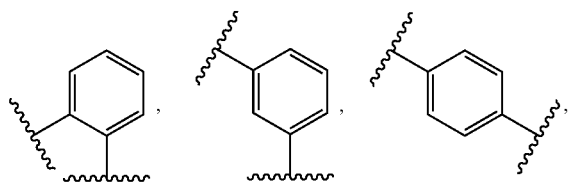

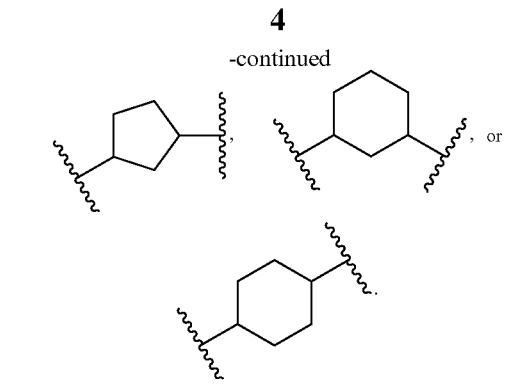

In some embodiments, Ring A is

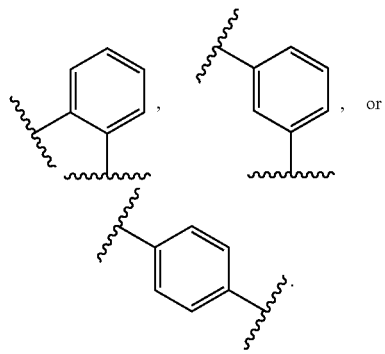

In some embodiments, Ring A is a bicyclic $C_5$-$C_{12}$carbocycle. In some embodiments, Ring A is a bicyclic $C_5$-$C_{12}$carbocycle that is a fused $C_5$-$C_{12}$carbocycle, bridged $C_5$-$C_{12}$carbocycle, or spirocyclic $C_5$-$C_{12}$carbocycle.

In some embodiments, Ring A is bicyclic $C_9$-$C_{10}$carbocycle.

In some embodiments, Ring A is naphthyl, indanyl, indenyl, or tetrahyodronaphthyl.

In some embodiments, Ring A is a monocyclic heterocycle containing 1-4 N atoms and 0 or 1 O or S atom, monocyclic heterocycle containing 0-4 N atoms and 1 O or S atoms, bicyclic heterocycle containing 1-4 N atoms and 0 or 1 O or S atoms, or bicyclic heterocycle containing 0-4 N atoms and 1 O or S atoms.

In some embodiments, Ring A is pyrrolidinyl, pyrrolidinonyl, tetrahydrofuranyl, tetrahydrofuranonyl, dihydrofuranonyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, indolinyl, indolinonyl, 1,2,3,4-tetrahydroquinolinyl, 1,2,3,4-tetrahydroisoquinolinyl, 3,4-dihydro-2(1H)-quinolinonyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is pyrrolidinyl, pyrrolidinonyl, piperidinyl, piperazinyl, indolinyl, indolinonyl, 1,2,3,4-tetrahydroquinolinyl, 1,2,3,4-tetrahydroisoquinolinyl, 3,4-dihydro-2(1H)-quinolinonyl, pyrrolyl, imidazolyl, pyrazolyl, pyridinyl, pyrimidinyl, pyrazinyl, pyridazinyl, indolyl, indazolyl, or benzimidazolyl.

In some embodiments, Ring A is

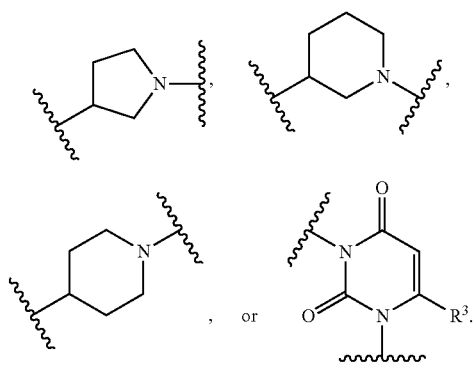

In some embodiments, Ring A is a bicyclic $C_5$-$C_{10}$heterocycle containing 1-4 N atoms and 0 or 1 O or S atoms, or bicyclic heterocycle containing 0-4 N atoms and 1 O or S atoms that is a fused bicyclic $C_5$-$C_{10}$heterocycle, bridged bicyclic $C_5$-$C_{10}$ heterocycle, or spiro bicyclic $C_5$-$C_{10}$heterocycle.

In some embodiments, Ring A is

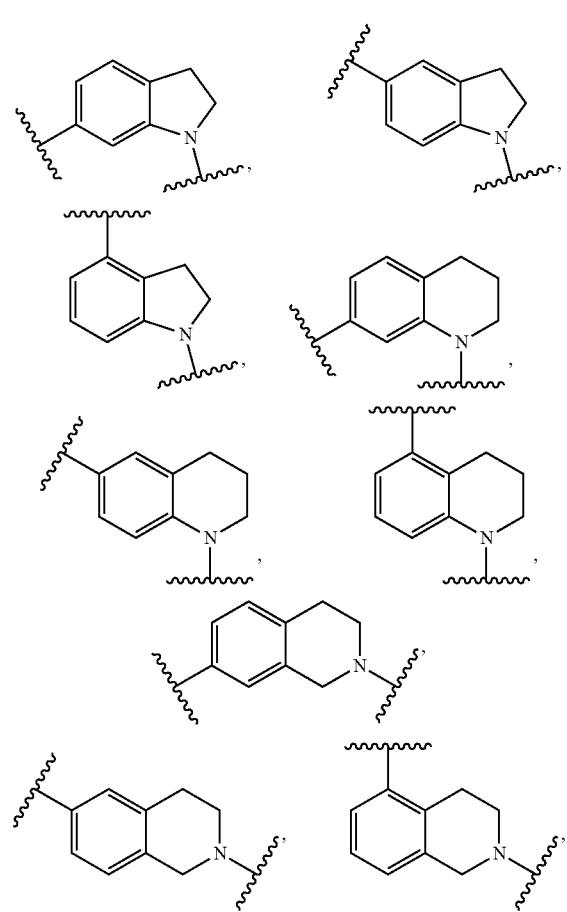

In some embodiments, $L^2$ is absent, —O—, —$CH_2$—O—, —C(=O)—, —C(=O)$NR^6$—, —$NR^6$C(=O)—, —$NR^6$—, or —$CH_2$—C(=O)$NR^6$—. In some embodiments, $L^2$ is absent, —O—, —$CH_2$—O—, —C(=O)—, —C(=O)$NR^6$—, —$NR^6$—, or —$CH_2$—C(=O)$NR^6$—.

In some embodiments, Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, Q is substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, $L^2$ is —C(=O)$NR^6$—, or —$CH_2$—C(=O)$NR^6$—; Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, the compound of Formula (I) has the structure of Formula (IV), or a pharmaceutically acceptable salt thereof:

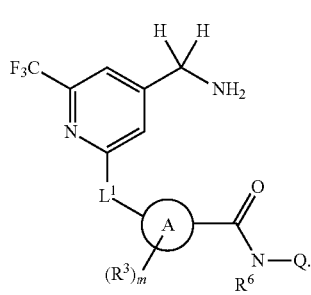

Formula (IV)

In some embodiments, -$L^2$-Q is —C(=O)$NR^6$-Q; Q and $R^6$ are taken together with the N atom to which they are attached to form a ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, Q and $R^6$ are taken together with the N atom to which they are attached to form a ring B, wherein ring B is a substituted or unsubstituted aziridinyl, substituted or unsubstituted azetidinyl, substituted or unsubstituted pyrrolidinyl, substituted or unsubstituted pyrrolidinonyl, substituted or unsubstituted piperidinyl, substituted or unsubstituted piperidinonyl, substituted or unsubstituted morpholinyl, substituted or unsubstituted thiomorpholinyl, substituted or unsubstituted piperazinyl, substituted or unsubstituted piperazinonyl, substituted or unsubstituted indolinyl, substituted or unsubstituted indolinonyl, substituted or unsubstituted 1,2,3,4-tetrahydroquinolinyl, substituted or unsubstituted 1,2,3,4-tetrahydroisoquinolinyl, substituted or unsubstituted 3,4-dihydro-2(1H)-quinolinonyl, wherein if ring B is substituted then ring B is substituted with 1-3 $R^8$.

In some embodiments, the compound of Formula (I) has the structure of Formula (V), or a pharmaceutically acceptable salt thereof:

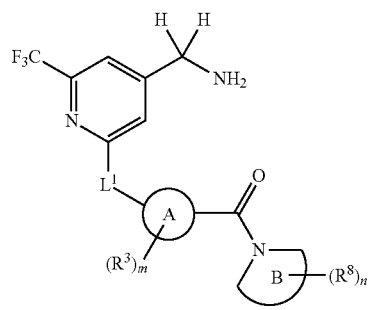

Formula (V)

wherein,
ring B is a monocyclic N-containing heterocycle or a bicyclic N-containing heterocycle;
n is 0, 1, 2, or 3.

In some embodiments,

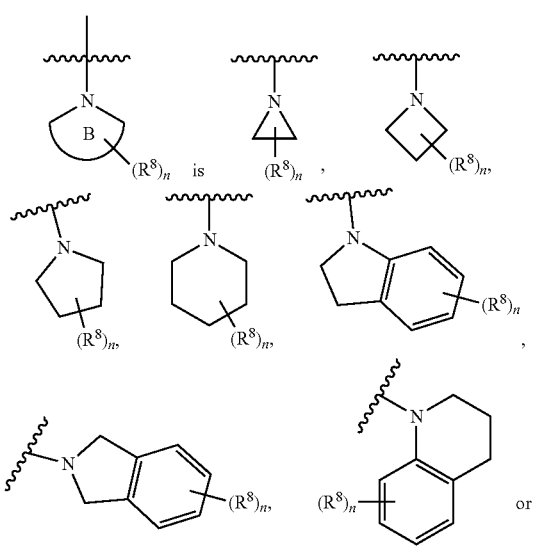

and n is 0, 1, or 2.

In some embodiments, (R⁸)ₙ is

In some embodiments, the compound of Formula (I) has the structure of Formula (VI), or a pharmaceutically acceptable salt thereof:

Formula (VI)

wherein,
L¹ is absent, —O— or —O—CH₂—;
L² is absent, —O—, —CH₂—O—, —C(=O)—, —C(=O)NR⁶—, —NR⁶—, or —CH₂—C(=O)NR⁶—.

In some embodiments, the compound of Formula (I) has the structure of Formula (VII), or a pharmaceutically acceptable salt thereof:

Formula (VII)

In some embodiments, L² is absent, —O—, —C(=O)NR⁶—, or —CH₂—C(=O)NR⁶—.

In some embodiments, the compound of Formula (I) has the structure of Formula (VIII), or a pharmaceutically acceptable salt thereof:

Formula (VIII)

In some embodiments, the compound of Formula (I) has the structure of Formula (IX), or a pharmaceutically acceptable salt thereof:

Formula (IX)

In some embodiments, L² is absent, —O—, —C(=O)NR⁶—, or —CH₂—C(=O)NR⁶—.

In some embodiments, the compound of Formula (I) has the structure of Formula (X), or a pharmaceutically acceptable salt thereof:

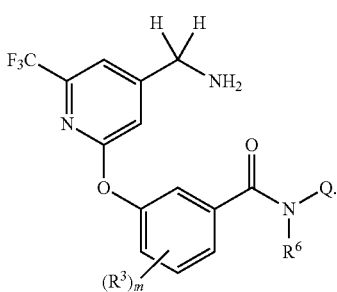

Formula (X)

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In one aspect, described herein is a method of treating a disease or condition in a mammal that would benefit from the inhibition or reduction of Lysyl oxidase like-2 (LOXL2) activity comprising administering a substituted trifluoromethylpyridinylmethylamine compound, or pharmaceutically acceptable salt, or solvate thereof, to the mammal in need thereof. In some embodiments, the disease or condition is fibrosis or cancer. In some embodiments, the fibrosis comprises lung fibrosis, liver fibrosis, kidney fibrosis, cardiac fibrosis, peritoneal fibrosis, ocular fibrosis or cutaneous fibrosis. In some embodiments, the fibrosis is myelofibrosis. In some embodiments, the substituted trifluoromethylpyridinylmethylamine compound, or pharmaceutically acceptable salt, or solvate thereof, is a Lysyl oxidase like-2 (LOXL2) inhibitor. In some embodiments, the substituted 2-(trifluoromethyl)pyridin-4-ylmethylamine compound In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of fibrosis in a mammal comprising administering a therapeutically effective amount of a compound described herein, or a pharmaceutically acceptable salt, or solvate thereof, to the mammal in need thereof. In other embodiments, the fibrosis is amenable to treatment with a LOXL2 inhibitor. In some embodiments, the fibrosis is lung fibrosis. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) t administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I) described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of LOXL2, or for the treatment, prevention or amelioration of one or more symptoms of a disease or condition that would benefit from inhibition or reduction of the LOXL2 activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Lysyl oxidase like-2 (LOXL2) is a member of the lysyl oxidase (LOX) family, which comprises $Cu^{2+}$ and lysine tyrosylquinone (LTQ)-dependent amine oxidases. The family comprises five genes: lox (LOX), loxl1 (lysyl oxidase like-1, LOXL1), loxl2 (LOXL2), loxl3 (lysyl oxidase like-3, LOXL3), and loxl4 (lysyl oxidase like-4, LOXL4). The LOX family is known for catalyzing the oxidative deamination of the ε-amino group of lysines and hydroxylysines in collagen and elastin to promote crosslinking of these molecules. Crosslinking of collagen and elastin is essential for maintaining tensile strength of the extracellular matrix.

LOXL2 has been demonstrated to have intracellular functions aside from its role in remodeling of the extracellular matrix. LOXL2 positively regulates the epithelial-to-mesenchymal transition (EMT) transducer, Snail1, by promoting Snail1 stability and functional activity. LOXL2 contributes positively to the activation of the focal adhesion kinase (FAK) signaling pathway and participates in the organization of focal adhesion complexes. Silencing of LOXL2 gene leads to reacquisition of epithelial cell polarity and decreases the migratory and invasive ability of mammary cell lines. The modulation of cell adhesion and cell polarity has been reported to be mediated by intracellular LOXL2. LOXL2 transcriptionally represses E-cadherin as well as tight junction and cell polarity genes by Snail1-dependent and Snail1-independent mechanisms. LOXL2 has been more recently described to be associated with chromatin and reported to be involved in histone H2 deamination, a function that is dependent on the LOXL2 catalytic domain.

In some embodiments, the methods disclosed herein are methods for inhibiting intracellular LOXL2. In some embodiments, the methods disclosed herein are methods for inhibiting extracellular (secreted) LOXL2. In some embodiments, the methods disclosed herein are methods for inhibiting extracellular and intracellular LOXL2.

Fibrosis

LOXL2 has been shown to be involved in fibrotic processes. Fibrotic processes include an excessive deposition of extracellular matrix components, such as collagen, which alters the physical, biochemical and biomechanical matrix properties leading to defective organ function and organ failure. Tissue fibrosis is also associated with cancer progression by direct promotion of cellular transformation and metastasis. Tumors are typically stiffer than normal tissue and tumor rigidity influences tumor metastasis.

Excessive LOXL2 enzyme activity has been implicated in the increased stiffness of tumors. Elevated LOXL2 is also associated with fibrotic lesions from livers of patients suffering from Wilson disease and primary biliary cirrhosis. Additionally, the administration of a LOXL2-specific monoclonal antibody AB0023 was efficacious in reducing disease in a model of fibrosis. AB0023 was shown to inhibit the production of growth factors and of crosslinked collagenous matrix and TGF-beta signaling.

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, the fibrosis comprises lung fibrosis, liver fibrosis, kidney fibrosis, cardiac fibrosis, peritoneal fibrosis, ocular fibrosis or cutaneous fibrosis. In some embodiments, the fibrosis comprises lung fibrosis. In some embodiments, the fibrosis comprises liver fibrosis. In some embodiments, the fibrosis comprises kidney fibrosis. In some embodiments, the fibrosis comprises cardiac fibrosis. In some embodiments, the fibrosis comprises peritoneal fibrosis. In some embodiments, the fibrosis comprises ocular fibrosis. In some embodiments, the fibrosis comprises cutaneous fibrosis.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is a fibrotic condition of the lung.

In some embodiments, the fibrotic condition is a fibrotic condition of the liver.

In some embodiments, the fibrotic condition is a fibrotic condition of the heart.

In some embodiments, the fibrotic condition is a fibrotic condition of the kidney.

In some embodiments, the fibrotic condition is a fibrotic condition of the skin.

In some embodiments, the fibrotic condition is a fibrotic condition of the eye.

In some embodiments, the fibrotic condition is a fibrotic condition of the gastrointestinal tract.

In some embodiments, the fibrotic condition is a fibrotic condition of the bone marrow.

In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, disclosed herein is a method for the treatment or prevention of fibrosis in a mammal comprising administering a LOXL2 inhibitor described herein, or a pharmaceutically acceptable salt thereof, to the mammal in need thereof.

In some embodiments, disclosed herein is a method of improving lung function in a mammal comprising administering a LOXL2 inhibitor described herein, or a pharmaceutically acceptable salt thereof, to the mammal in need thereof. In some embodiments, the mammal has been diagnosed as having lung fibrosis.

In some embodiments, disclosed herein is a method of treating idopathic pulmonary fibrosis in a mammal comprising administering a LOXL2 inhibitor described herein, or a pharmaceutically acceptable salt thereof, to the mammal in need thereof.

In some embodiments, disclosed herein is a method of controlling an abnormal accumulation or activation of cells, fibronectin, collagen or increased fibroblast recruitment in a tissue of a mammal comprising administering a LOXL2 inhibitor described herein, or a pharmaceutically acceptable salt thereof, to the mammal in need thereof. In some embodiments, the abnormal accumulation or activation of cells, fibronectin, collagen or increased fibroblast recruitment in the tissue results in fibrosis.

In some embodiments, disclosed herein is a method for the treatment or prevention of scleroderma in a mammal comprising administering a LOXL2 inhibitor described herein, or a pharmaceutically acceptable salt thereof, to the mammal in need thereof.

In some embodiments, disclosed herein is a method for reducing undesired or abnormal dermal thickening in a mammal comprising administering to mammal in need thereof a LOXL2 inhibitor described herein, or a pharmaceutically acceptable salt thereof. In some embodiments, the dermal thickening is associated with scleroderma.

In some embodiments, described herein is a method of controlling an abnormal accumulation or activation of cells, fibronectin, collagen or increased fibroblast recruitment in tissues of a mammal comprising administering to mammal in need thereof a LOXL2 inhibitor described herein, or a pharmaceutically acceptable salt thereof. In some embodiments, the abnormal accumulation or activation of cells, fibronectin, collagen or increased fibroblast recruitment in the dermal tissues results in fibrosis. In some embodiments, described herein is a method of reducing hydroxyproline content in tissues of a mammal with fibrosis comprising administering to mammal in need thereof a LOXL2 inhibitor described herein, or a pharmaceutically acceptable salt thereof.

Cancer

LOXL2 has been shown to be involved in signaling related to cancer cell growth, adhesion, motility and invasion. Specifically, LOXL2 induces epithelial-to-mesenchymal transition (EMT) of cells to promote tumor invasion. LOXL2 is also upregulated in hypoxic tumor environments which leads to enhanced invasion of tumor cells. LOXL2 has also been shown to promote angiogenesis in hypoxic tumor environments.

Increased LOXL2 expression is associated with poor prognosis in patients with colon, esophageal tumors, oral squamous cell carcinomas, laryngeal squamous cell carcinomas, and head and neck squamous cell carcinomas. LOXL2 has been proposed to participate in cancers of the breast, colon, gastric, head and neck, lung, and melanoma.

In some embodiments, disclosed herein are methods of treating cancer with a compound disclosed herein.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Compounds

Compounds described herein, including pharmaceutically acceptable salts, prodrugs, active metabolites and pharmaceutically acceptable solvates thereof, are LOXL2 inhibitors.

In one aspect, described herein is a compound of Formula (I), or a pharmaceutically acceptable salt thereof:

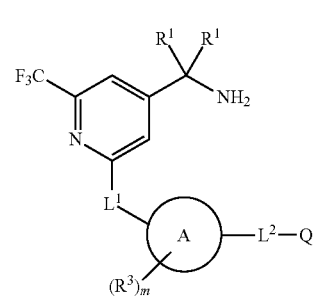

Formula (I)

wherein,
each $R^1$ is independently H, D, or F;
$L^1$ is absent, $X^1$, $X^1$—$C_1$-$C_6$alkylene, or $C_1$-$C_6$alkylene;
  $X^1$ is —O—, —S—, —S(=O)—, —S(=O)$_2$—, —C(=O)—, —C(=O)O—, —C(=O)NR$^2$—, —NR$^2$C(=O)—, or —NR$^2$—;
$R^2$ is H, substituted or unsubstituted $C_1$-$C_6$alkyl, $C_1$-$C_6$fluoroalkyl, or $C_1$-$C_6$deuteroalkyl;
each $R^3$ is independently H, D, halogen, —CN, —OR$^5$, —SR$^5$, —S(=O)R$^4$, —S(=O)$_2$R$^4$, —S(=O)$_2$N(R$^5$)$_2$, —NR$^2$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^2$C(=O)R$^4$, —NR$^2$C(=O)OR$^4$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
m is 0, 1, or 2;
each $R^4$ is independently selected from $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl;
each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl; or two $R^5$ on the same N atom are taken together with the N atom to which they are attached to a substituted or unsubstituted N-containing heterocycle;
Ring A is monocyclic carbocycle, bicyclic carbocycle, monocyclic heterocycle, or bicyclic heterocycle;
$L^2$ is absent, —$X^2$—, or —$C_1$-$C_6$alkylene-$X^2$—;
  $X^2$ is —O—, —S—, —S(=O)—, —S(=O)$_2$—, —S(=O)$_2$NR$^6$—, —C(=O)—, —C(=O)O—, —C(=O)NR$^6$—, —C(=O)NR$^6$—, —NR$^6$C(=O)—, —NR$^6$S(=O)$_2$—, or —NR$^6$—;
$R^6$ is H, $C_1$-$C_6$alkyl, $C_1$-$C_6$fluoroalkyl, or $C_1$-$C_6$deuteroalkyl;
Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, —$C_1$-$C_4$alkylene-(substituted or unsubstituted $C_3$-$C_8$cycloalkyl), substituted or unsubstituted $C_2$-$C_8$heterocycloalkyl, —$C_1$-$C_4$alkylene-(substituted or unsubstituted $C_2$-$C_8$heterocycloalkyl), substituted or unsubstituted aryl, —$C_1$-$C_4$alkylene-(substituted or unsubstituted aryl), substituted or unsubstituted heteroaryl, or —$C_1$-

C$_4$alkylene-(substituted or unsubstituted heteroaryl); wherein if Q is substituted then Q is substituted with one or more R$^8$;

or Q and R$^6$ are taken together with the N atom to which they are attached to form ring B, wherein ring B is a substituted or unsubstituted N-containing heterocycle, wherein if ring B is substituted then ring B is substituted with 1-3 R$^8$;

each R$^8$ is independently D, halogen, CN, —OR$^5$, —SR$^5$, —S(=O)R$^4$, —S(=O)$_2$R$^4$, —S(=O)$_2$N(R$^5$)$_2$, NR$^5$S(=O)$_2$R$^4$, C(=O)R$^4$, OC(=O)R$^4$, CO$_2$R$^5$, OCO$_2$R$^4$, N(R$^4$)$_2$, OC(=O)N(R$^5$)$_2$, —NHC(=O)R$^4$, —NHC(=O)OR$^4$, C$_1$-C$_6$alkyl, C$_1$-C$_6$alkenyl, C$_1$-C$_6$alkynyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl; or two R$^8$ groups attached to the same carbon atom are taken together with carbon atom to which they are attached to form either a substituted or unsubstituted carbocycle or substituted or unsubstituted heterocycle.

For any and all of the embodiments, substituents are selected from among a subset of the listed alternatives. For example, in some embodiments, each R$^1$ is independently H, D, or F. In some other embodiments, each R$^1$ is independently H, or F. In other embodiments, each R$^1$ is H. In some embodiments, each R$^1$ is D. In some embodiments, each R$^1$ is F.

In some embodiments, each R$^1$ is H; L$^1$ is absent, X$^1$, or X$^1$—C$_1$-C$_6$alkylene.

In some embodiments, L$^1$ is absent, X$^1$, X$^1$—CH$_2$—, or —CH$_2$—;

In some embodiments, L$^1$ is absent, —O—, —S—, —S(=O)—, —S(=O)$_2$—, —C(=O)—, —C(=O)O—, —C(=O)NR$^2$—, —NR$^2$C(=O)—, —NR$^2$—, —O—CH$_2$—, —S—CH$_2$—, —S(=O)—CH$_2$—, —S(=O)$_2$—CH$_2$—, —C(=O)—CH$_2$—, —C(=O)O—CH$_2$—, —C(=O)NR$^2$—CH$_2$—, —NR$^2$C(=O)—CH$_2$—, —NR$^2$—CH$_2$—, or —CH$_2$—.

In some embodiments, L$^1$ is absent, —O—, —S—, —S(=O)$_2$—, —C(=O)—, —C(=O)O—, —C(=O)NR$^2$—, —NR$^2$C(=O)—, —NR$^2$—, —O—CH$_2$—, —S—CH$_2$—, —NR$^2$—CH$_2$—, or —CH$_2$—.

In some embodiments, X$^1$ is —O—.

In some embodiments, L$^1$ is absent, X$^1$, X$^1$—CH$_2$—, or —CH$_2$—;

In some embodiments, L$^1$ is absent, —O—, or —O—CH$_2$—.

In some embodiments, the compound of Formula (I) has the structure of Formula (II), or a pharmaceutically acceptable salt thereof:

Formula (II)

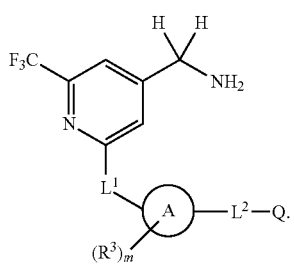

In some embodiments, L$^1$ is —O—, or —O—CH$_2$—.

In some embodiments, the compound of Formula (I) has the structure of Formula (III), or a pharmaceutically acceptable salt thereof:

Formula (III)

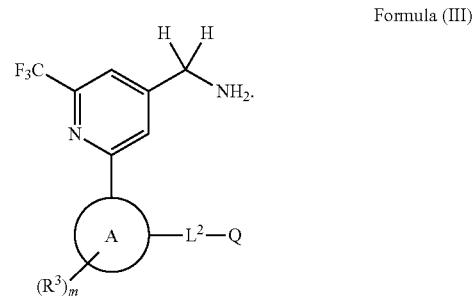

In some embodiments, Ring A is monocyclic C$_3$-C$_6$carbocycle, bicyclic C$_5$-C$_{12}$carbocycle, monocyclic C$_1$-C$_5$heterocycle, bicyclic C$_5$-C$_{10}$heterocycle.

In some embodiments, Ring A is monocyclic C$_3$-C$_6$carbocycle, bicyclic C$_9$-C$_{10}$carbocycle, monocyclic C$_1$-C$_5$heterocycle, bicyclic C$_6$-C$_9$heterocycle.

In some embodiments, Ring A is monocyclic C$_3$-C$_6$carbocycle.

In some embodiments, Ring A is phenyl, cyclopropyl, cyclobutyl, cyclopentyl, or cyclohexyl.

In some embodiments, Ring A is phenyl.

In some embodiments, Ring A is

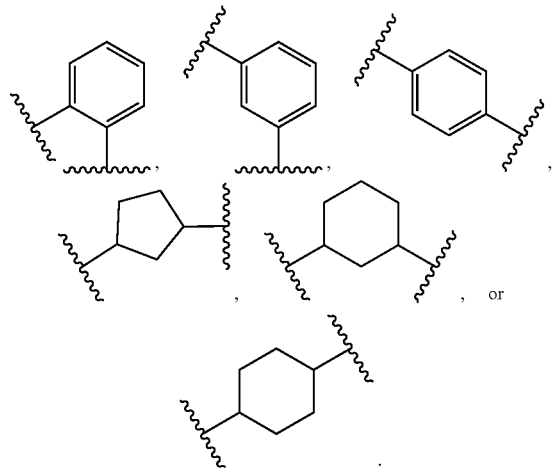

In some embodiments, Ring A is

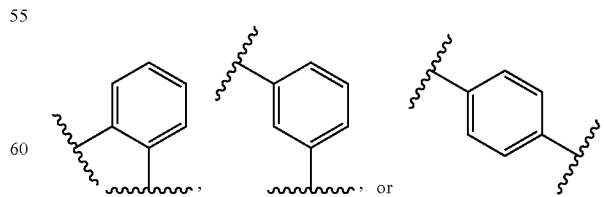

In some embodiments, Ring A is a bicyclic C$_5$-C$_{12}$carbocycle. In some embodiments, Ring A is a bicyclic C$_5$-C$_{12}$carbocycle that is a fused C$_5$-C$_{12}$carbocycle, bridged C$_5$-C$_{12}$carbocycle, or spirocyclic C$_5$-C$_{12}$carbocycle.

In some embodiments, Ring A is bicyclic $C_9$-$C_{10}$carbocycle.

In some embodiments, Ring A is naphthyl, indanyl, indenyl, or tetrahyodronaphthyl.

In some embodiments, Ring A is a bridged bicyclic $C_5$-$C_{12}$carbocycle that is

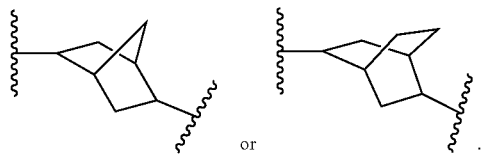 [SMILES: *C1CC2CC1CC2* ; *C1CC2CCC1CC2*]

or

In some embodiments, Ring A is a monocyclic heterocycle containing 1-4 N atoms and 0 or 1 O or S atom, monocyclic heterocycle containing 0-4 N atoms and 1 O or S atoms, bicyclic heterocycle containing 1-4 N atoms and 0 or 1 O or S atoms, or bicyclic heterocycle containing 0-4 N atoms and 1 O or S atoms.

In some embodiments, Ring A is pyrrolidinyl, pyrrolidinonyl, tetrahydrofuranyl, tetrahydrofuranonyl, dihydrofuranonyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, indolinyl, indolinonyl, 1,2,3,4-tetrahydroquinolinyl, 1,2,3,4-tetrahydroisoquinolinyl, 3,4-dihydro-2(1H)-quinolinonyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is pyrrolidinyl, pyrrolidinonyl, piperidinyl, piperazinyl, indolinyl, indolinonyl, 1,2,3,4-tetrahydroquinolinyl, 1,2,3,4-tetrahydroisoquinolinyl, 3,4-dihydro-2(1H)-quinolinonyl, pyrrolyl, imidazolyl, pyrazolyl, pyridinyl, pyrimidinyl, pyrazinyl, pyridazinyl, indolyl, indazolyl, or benzimidazolyl.

In some embodiments, Ring A

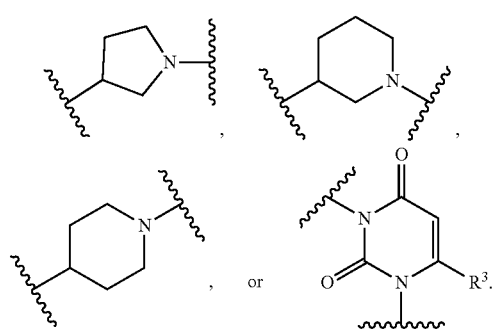

or

In some embodiments, Ring A is a bicyclic $C_5$-$C_{10}$heterocycle containing 1-4 N atoms and 0 or 1 O or S atoms, or bicyclic heterocycle containing 0-4 N atoms and 1 O or S atoms that is a fused bicyclic $C_5$-$C_{10}$heterocycle, bridged bicyclic $C_5$-$C_{10}$ heterocycle, or spiro bicyclic $C_5$-$C_{10}$heterocycle.

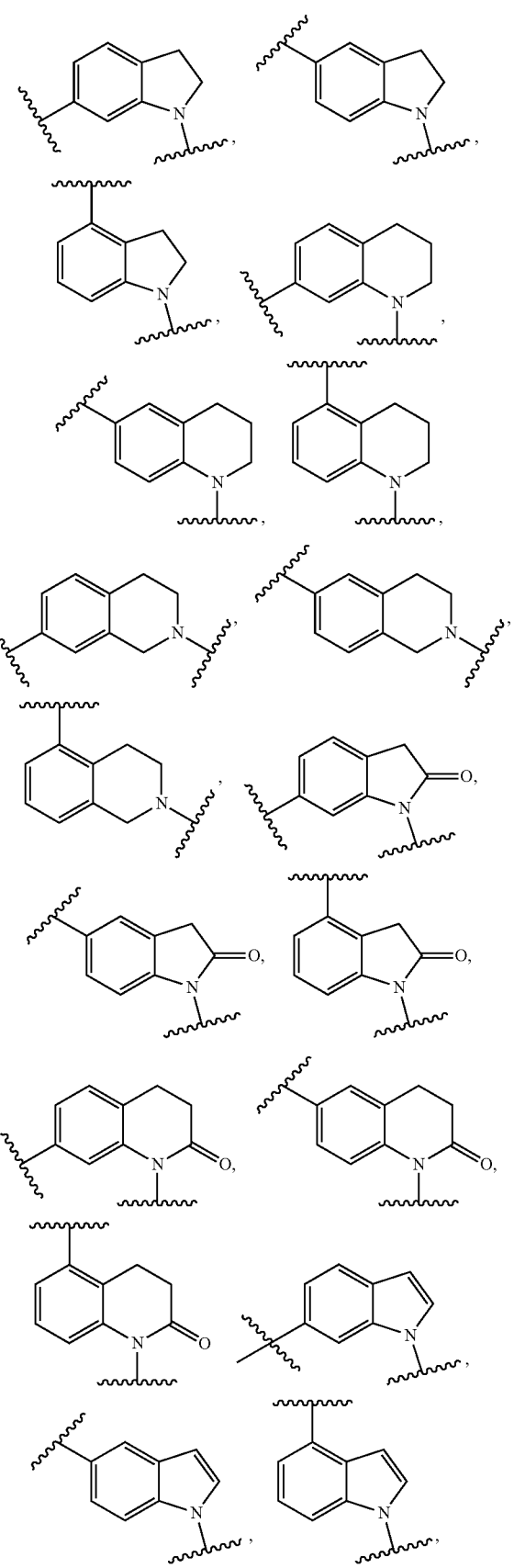

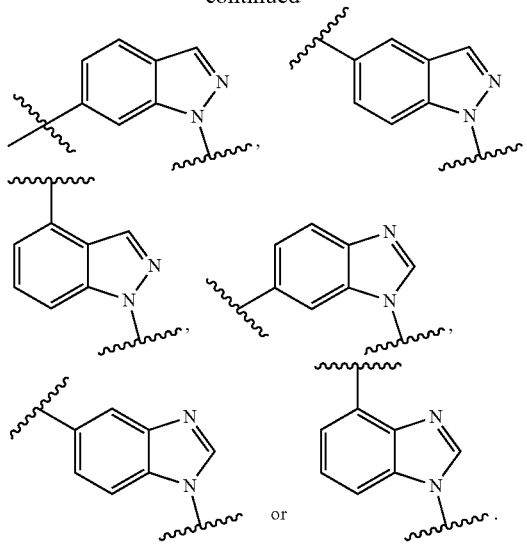

In some embodiments, Ring A is a bicyclic heterocycle containing 1-4 N atoms and 0 or 1 O or S atoms, or bicyclic heterocycle containing 0-4 N atoms and 1 O or S atoms.

In some embodiments, Ring A is a bicyclic $C_5$-$C_{10}$heterocycloalkyl containing 1-4 N atoms and 0 or 1 O or S atoms, or bicyclic heterocycle containing 0-4 N atoms and 1 O or S atoms that is a fused bicyclic $C_5$-$C_{10}$heterocycloalkyl, bridged bicyclic $C_5$-$C_{10}$heterocycloalkyl, or spiro bicyclic $C_5$-$C_{10}$heterocycloalkyl.

In some embodiments, Ring A is a bridged bicyclic $C_5$-$C_{10}$heterocycloalkyl that is

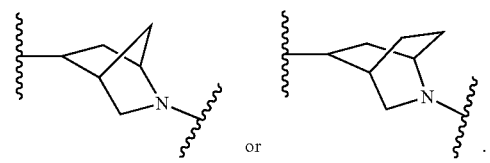 [SMILES: *C1CC2CC1CN2* ; *C1CC2CCC1CN2*]

In some embodiments, Ring A is spiro bicyclic $C_5$-$C_{10}$heterocycloalkyl that is

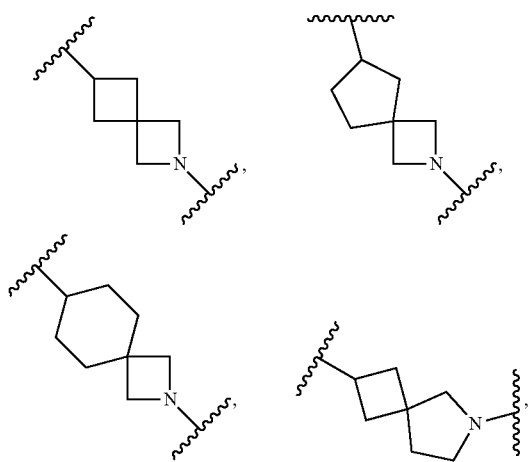

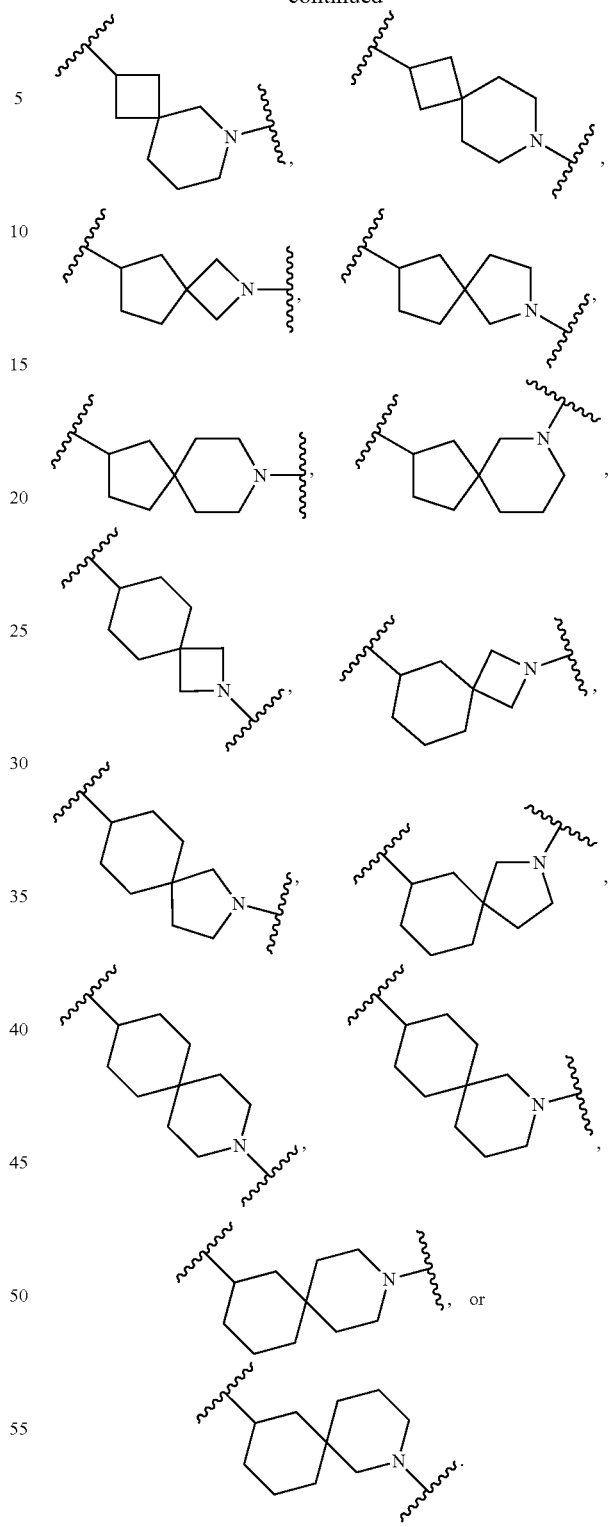

In some embodiments, $L^2$ is absent, —O—, —CH$_2$—O—, —C(=O)—, —C(=O)NR$^6$—, —NR$^6$C(=O)—, —NR$^6$—, or —CH$_2$—C(=O)NR$^6$—. In some embodiments, $L^2$ is absent, —O—, —CH$_2$—O—, —C(=O)—, —C(=O)NR$^6$—, —NR$^6$—, or —CH$_2$—C(=O)NR$^6$—.

In some embodiments, Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, Q is substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, $L^2$ is —C(=O)$NR^6$—, or —$CH_2$—C(=O)$NR^6$—; Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_6$cycloalkyl, —$C_1$-$C_2$alkylene-(substituted or unsubstituted $C_3$-$C_6$cycloalkyl), substituted or unsubstituted $C_2$-$C_8$heterocycloalkyl, —$C_1$-$C_2$alkylene-(substituted or unsubstituted $C_2$-$C_8$heterocycloalkyl), substituted or unsubstituted phenyl, —$C_1$-$C_2$alkylene-(substituted or unsubstituted phenyl), substituted or unsubstituted heteroaryl, or —$C_1$-$C_2$alkylene-(substituted or unsubstituted heteroaryl); wherein if Q is substituted then Q is substituted with one or more $R^8$; or Q and $R^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, the compound of Formula (I) has the structure of Formula (IV), or a pharmaceutically acceptable salt thereof:

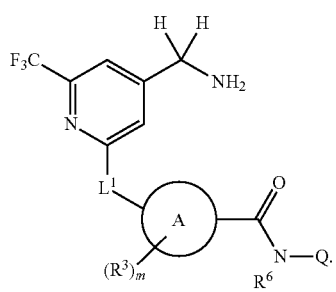

Formula (IV)

In some embodiments, -$L^2$-Q is —C(=O)$NR^6$-Q; Q and $R^6$ are taken together with the N atom to which they are attached to form a ring B, wherein ring B is a substituted or unsubstituted monocyclic N-containing heterocycle, or a substituted or unsubstituted bicyclic N-containing heterocycle, wherein if ring B is substituted then ring B is substituted with 1-3 $R^8$.

In some embodiments, —$NR^6$Q is

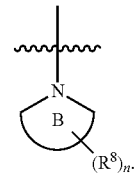

In some embodiments, Q and $R^6$ are taken together with the N atom to which they are attached to form a ring B, wherein ring B is a substituted or unsubstituted aziridinyl, substituted or unsubstituted azetidinyl, substituted or unsubstituted pyrrolidinyl, substituted or unsubstituted pyrrolidinonyl, substituted or unsubstituted piperidinyl, substituted or unsubstituted piperidinonyl, substituted or unsubstituted morpholinyl, substituted or unsubstituted thiomorpholinyl, substituted or unsubstituted piperazinyl, substituted or unsubstituted piperazinonyl, substituted or unsubstituted indolinyl, substituted or unsubstituted indolinonyl, substituted or unsubstituted 1,2,3,4-tetrahydroquinolinyl, substituted or unsubstituted 1,2,3,4-tetrahydroisoquinolinyl, substituted or unsubstituted 3,4-dihydro-2(1H)-quinolinonyl, wherein if ring B is substituted then ring B is substituted with 1-3 $R^8$.

In some embodiments, the compound of Formula (I) has the structure of Formula (V), or a pharmaceutically acceptable salt thereof:

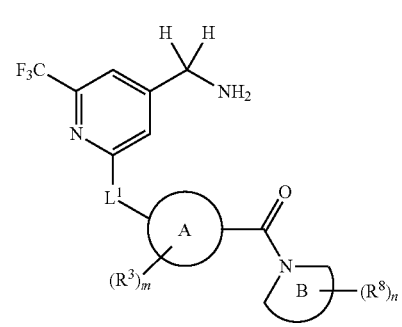

Formula (V)

wherein,
ring B is a monocyclic N-containing heterocycle or a bicyclic N-containing heterocycle;
n is 0, 1, 2, or 3.

In some embodiments, —$NR^6$Q is

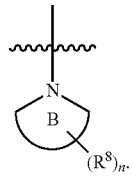

In some embodiments,
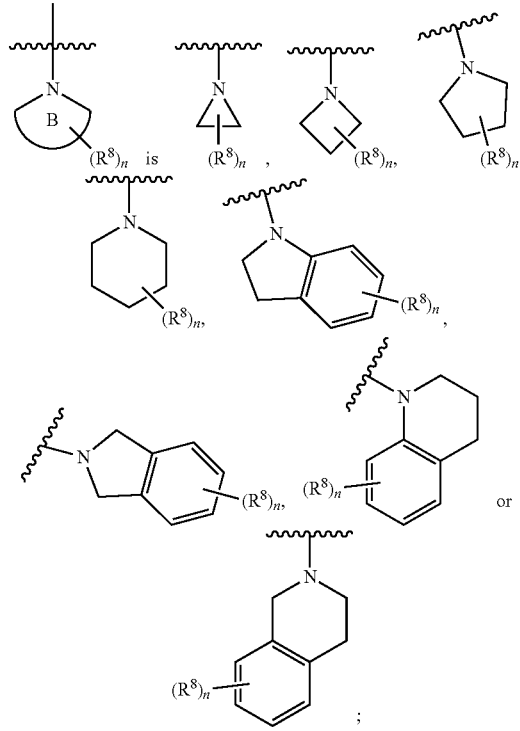
and n is 0, 1, or 2. In some embodiments,
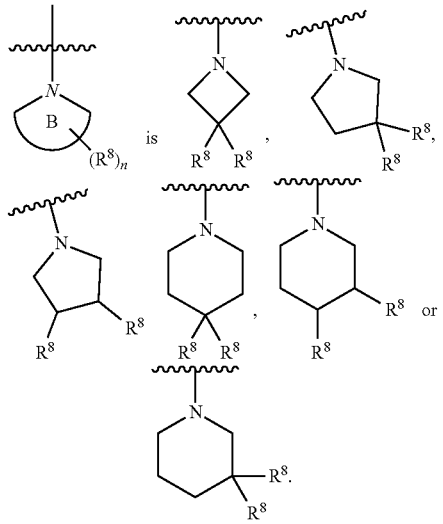
In some embodiments,
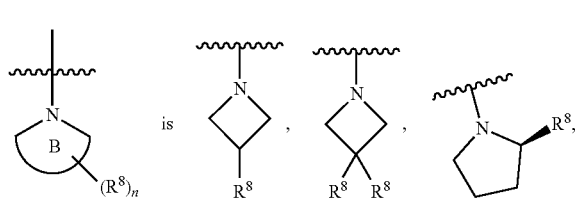
-continued
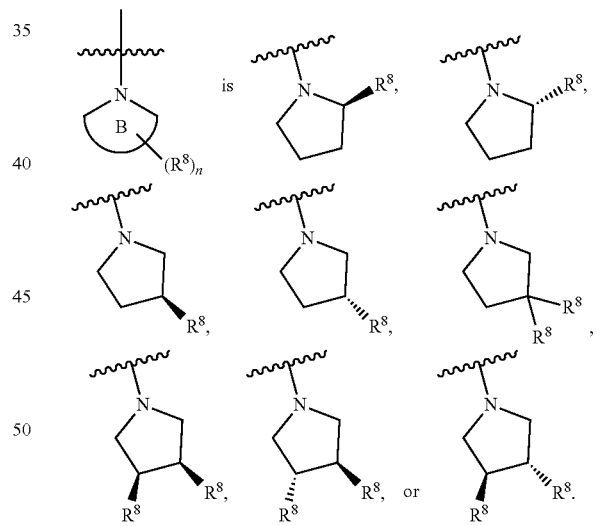
In some embodiments,
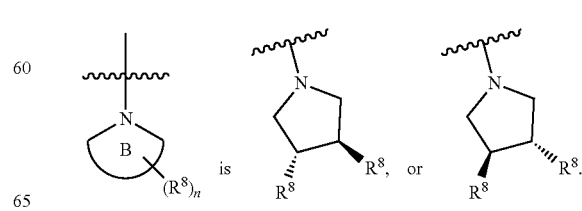

In some embodiments,

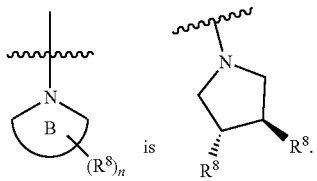 is

In some embodiments,

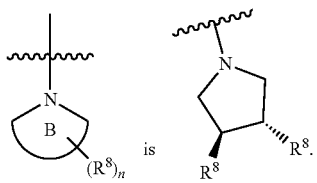 is

In some embodiments, each $R^8$ is independently D, F, Cl, CN, —OH, —OCH$_3$, —OCH$_2$CH$_3$, —S(=O)$_2$CH$_3$, —S(=O)$_2$NH$_2$, —S(=O)$_2$N(CH$_3$)$_2$, —C(=O)CH$_3$, OC(=O)CH$_3$, —CO$_2$H, —CO$_2$CH$_3$, —CO$_2$CH$_2$CH$_3$, —CO$_2$CH(CH$_3$)$_2$, —CO$_2$C(CH$_3$)$_3$, —NH$_2$, —N(CH$_3$)$_2$, —CH$_3$, —CH$_2$CH$_3$, —C≡CH, —CF$_3$, —CH$_2$CF$_3$, or —OCH$_2$OH.

In some embodiments, each $R^8$ is independently D, F, Cl, CN, —OH, —OCH$_3$, —OCH$_2$CH$_3$, —NH$_2$, —N(CH$_3$)$_2$, —CH$_3$, —CH$_2$CH$_3$, —CF$_3$, —CH$_2$CF$_3$, or —OCH$_2$OH.

In some embodiments, two $R^8$ groups attached to the same carbon atom are taken together with carbon atom to which they are attached to form either a substituted or unsubstituted monocyclic 3 to 6 membered carbocycle or substituted or unsubstituted monocyclic 3 to 6 membered heterocycle.

In some embodiments, the compound of Formula (I) has the structure of Formula (VI), or a pharmaceutically acceptable salt thereof:

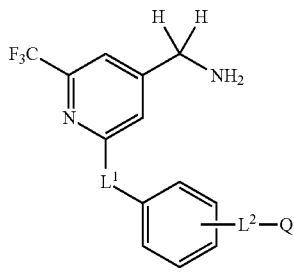

Formula (VI)

wherein,
$L^1$ is absent, —O— or —O—CH$_2$—;
$L^2$ is absent, —O—, —CH$_2$—O—, —C(=O)—, —C(=O)NR$^6$—, —NR$^6$—, or —CH$_2$—C(=O)NR$^6$—.

In some embodiments, the compound of Formula (I) has the structure of Formula (VII), or a pharmaceutically acceptable salt thereof:

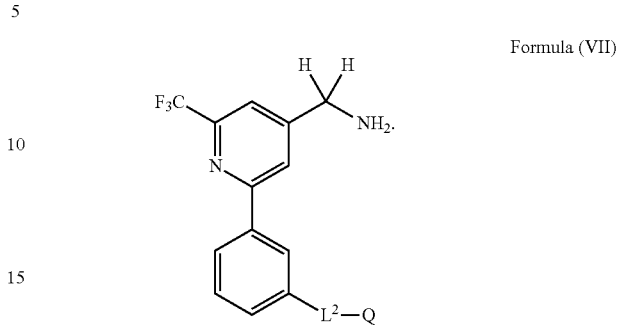

Formula (VII)

In some embodiments, $L^2$ is absent, —O—, —C(=O)NR$^6$—, or —CH$_2$—C(=O)NR$^6$—.

In some embodiments, the compound of Formula (I) has the structure of Formula (VIII), or a pharmaceutically acceptable salt thereof:

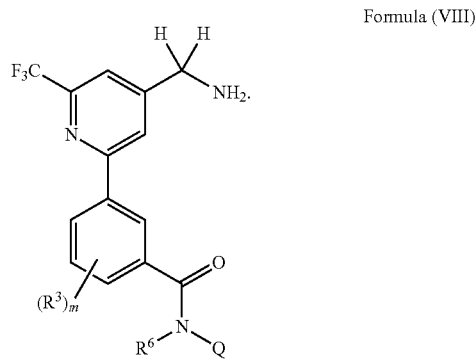

Formula (VIII)

In some embodiments, the compound of Formula (I) has the structure of Formula (IX), or a pharmaceutically acceptable salt thereof:

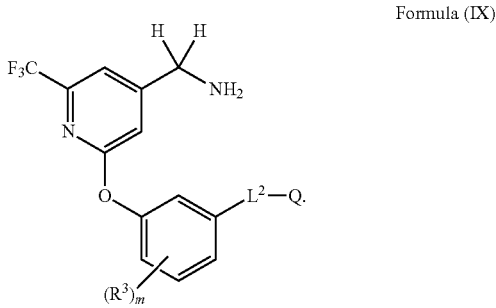

Formula (IX)

In some embodiments, $L^2$ is absent, —O—, —C(=O)NR$^6$—, or —CH$_2$—C(=O)NR$^6$—.

In some embodiments, the compound of Formula (I) has the structure of Formula (X), or a pharmaceutically acceptable salt thereof:

Formula (X)

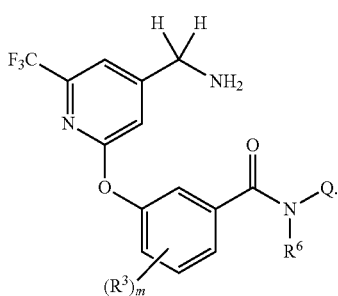

In some embodiments, the compound of Formula (I) has the following structure:

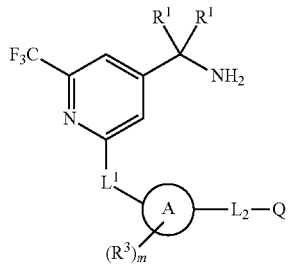

or a pharmaceutically acceptable salt thereof.

In some instances, $R^1$ is as described in Table 1. In some instances, $-L^1-$ is as described in Table 1. In some instances,

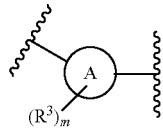

is as described in Table 1. In some instances, $-L^2-Q$ is as described in Table 1. In some instances, $R^1$, $-L^1-$, and $-L^2-Q$ are as described in Table 1. In some instances, $R^1$, $-L^1-$,

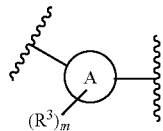

and $-L^2-Q$ are as described in Table 1.

In some embodiments, compounds of Formula (I) include, but are not limited to, those described in Table 1.

TABLE 1

| Compound Number | $R^1$ | $-L^1-$ | ![A ring with (R³)ₘ] | $-L_2-Q$ |
|---|---|---|---|---|
| 1-1 | H | — | ![3-pyridyl] | — |
| 1-2 | H | —O— | ![phenyl meta-substituted] | ![phenyl] |

TABLE 1-continued
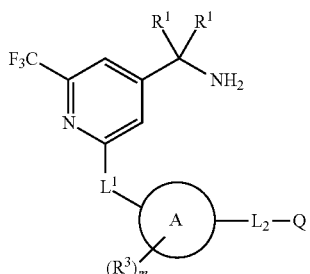
| Compound Number | R¹ | —L¹— | 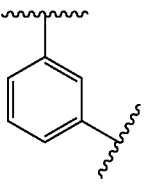 | —L₂—Q |
|---|---|---|---|---|
| 1-3 | H | —O— | 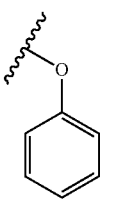 [SMILES: *Oc1ccccc1] | 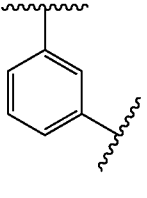 |
| 1-4 | H | —O— | 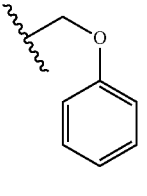 [SMILES: *COc1ccccc1] | 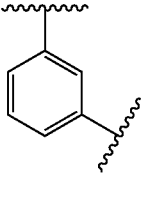 |
| 1-5 | H | —O— | 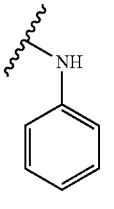 [SMILES: *Nc1ccccc1] | 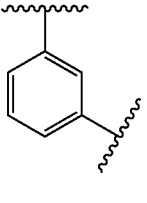 |
| 1-6 | H | —O— | 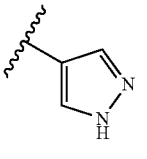 [SMILES: *c1cn[nH]c1] | 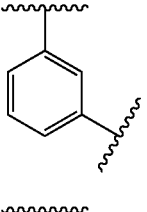 |
| 1-7 | H | —O— | 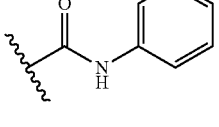 | 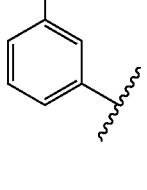 |
| 1-8 | D | —O— | 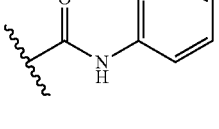 | |

TABLE 1-continued
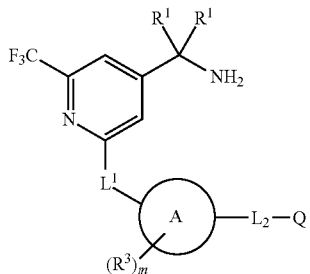
| Compound Number | R¹ | —L¹— | (R³)ₘ | —L₂—Q |
|---|---|---|---|---|
| 1-9 | H | —O— | 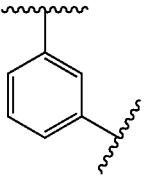 | 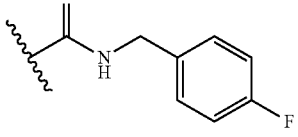 |
| 1-10 | H | —O— | 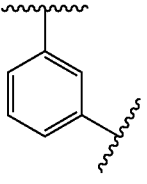 | 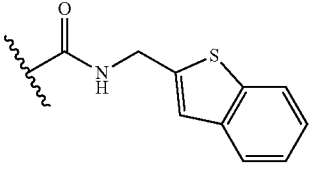 [SMILES: *C(=O)NCc1cc2ccccc2s1] |
| 1-11 | H | —O— | 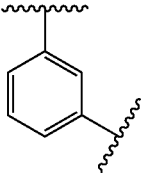 | 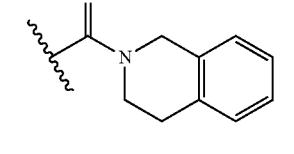 |
| 1-12 | H | —O— | 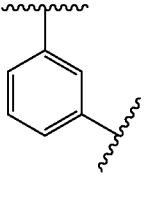 | 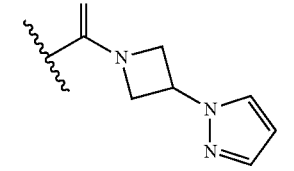 |
| 1-13 | H | —O— | 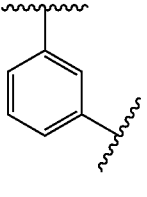 | 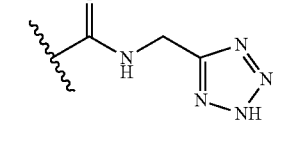 |
| 1-14 | H | —O— | 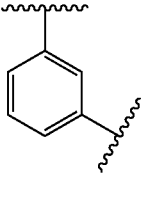 | 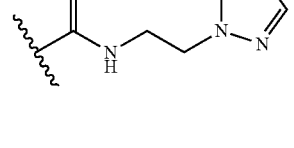 |

TABLE 1-continued
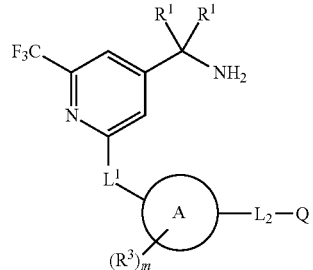
| Compound Number | R¹ | —L¹— | (R³)ₘ | —L₂—Q |
|---|---|---|---|---|
| 1-15 | H | —O— | 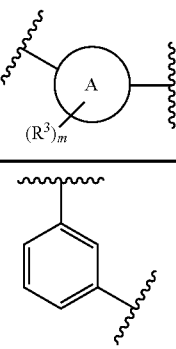 | 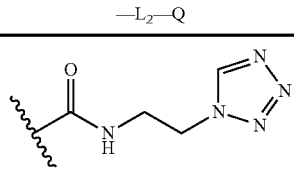 |
| 1-16 | H | —O— | 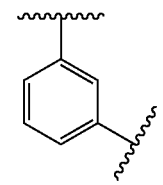 | 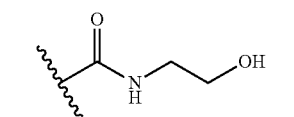 [SMILES: *C(=O)NCCO] |
| 1-17 | H | —O— | 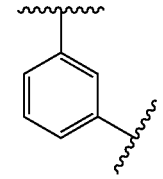 | 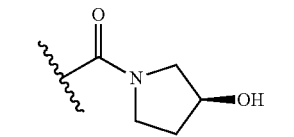 [SMILES: *C(=O)N1CC[C@H](O)C1] |
| 1-18 | H | —O— | 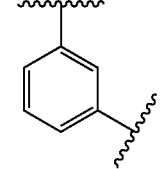 | 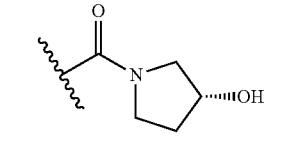 [SMILES: *C(=O)N1CC[C@@H](O)C1] |
| 1-19 (racemic trans) | H | —O— | 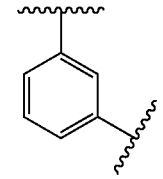 | 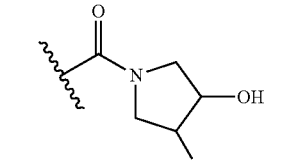 |
| 1-20 | H | —O— | 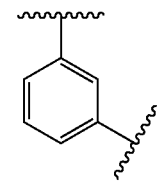 | 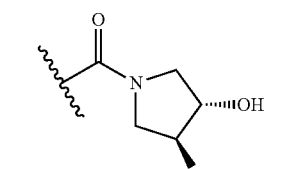 |

TABLE 1-continued
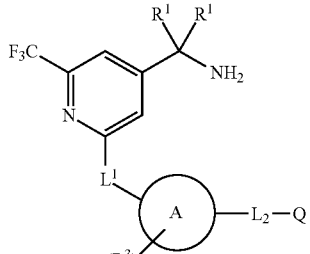
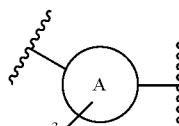
| Compound Number | R¹ | —L¹— | (R³)ₘ | —L₂—Q |
|---|---|---|---|---|
| 1-21 | H | —O— | 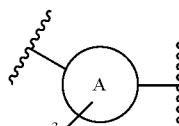 | 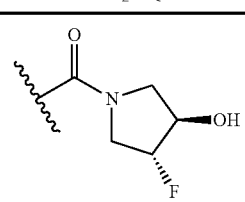 |
| 1-22 | H | —O— | 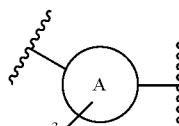 | 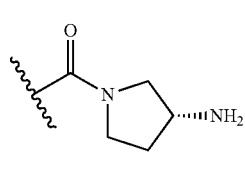 [SMILES: *C(=O)N1CC[C@@H](N)C1] |
| 1-23 (racemic trans) | H | —O— | 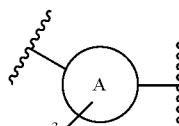 | 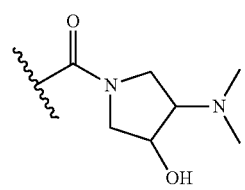 [SMILES: *C(=O)N1CC(O)C(N(C)C)C1] |
| 1-24 | H | —O— | 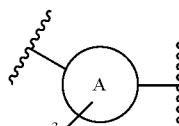 | 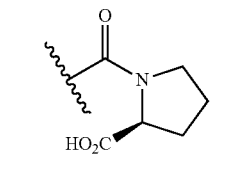 [SMILES: *C(=O)N1CCC[C@H]1C(=O)O] |
| 1-25 | H | —O— | 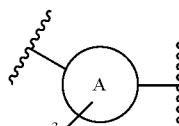 | 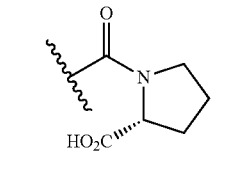 [SMILES: *C(=O)N1CCC[C@@H]1C(=O)O] |
| 1-26 | H | —O— | 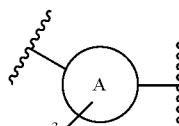 | 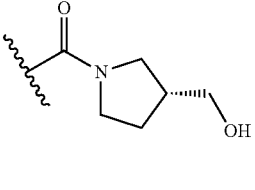 [SMILES: *C(=O)N1CC[C@@H](CO)C1] |

TABLE 1-continued
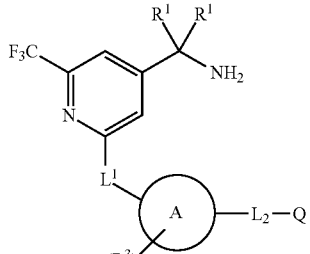
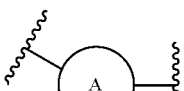
| Compound Number | R¹ | —L¹— | (R³)ₘ | —L₂—Q |
|---|---|---|---|---|
| 1-27 | H | —O— | 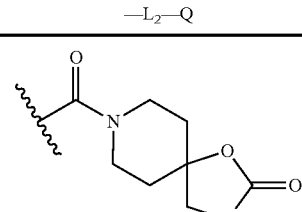 | 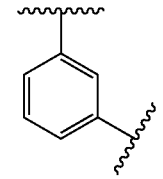 |
| 1-28 | H | —O— | 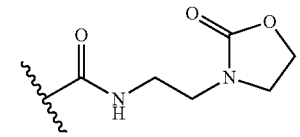 [SMILES: *C(=O)NCCN1CCOC1=O] | 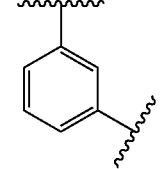 |
| 1-29 (racemic) | H | —O— | 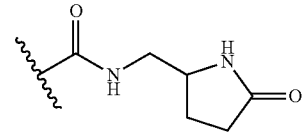 [SMILES: *C(=O)NCC1CCC(=O)N1] | 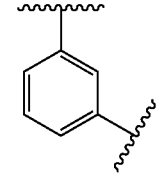 |
| 1-30 | H | —O— | 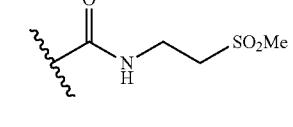 | 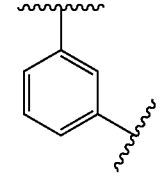 |
| 1-31 | H | —O— | 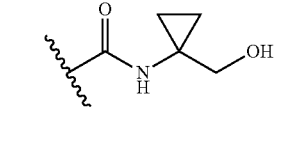 [SMILES: *C(=O)NC1(CO)CC1] | 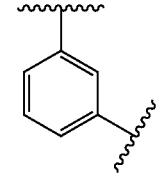 |
| 1-32 | H | —O— | 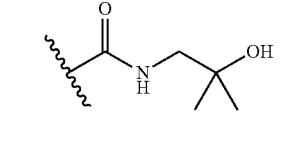 [SMILES: *C(=O)NCC(C)(C)O] | |

TABLE 1-continued
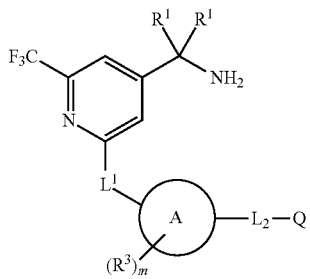
| Compound Number | R¹ | —L¹— | (R³)ₘ | —L₂—Q |
|---|---|---|---|---|
| 1-33 | H | —O— | 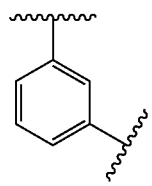 | 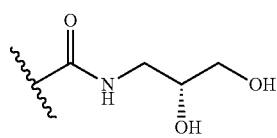 [SMILES: *C(=O)NC[C@@H](O)CO] |
| 1-34 | H | —O— | 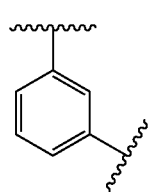 | 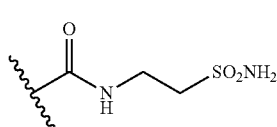 [SMILES: *C(=O)NCCS(N)(=O)=O] |
| 1-35 | H | —O— | 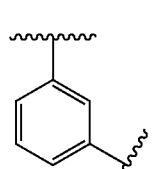 | 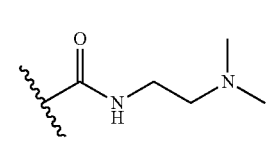 [SMILES: *C(=O)NCCN(C)C] |
| 1-36 (racemic trans) | H | —OCH₂— | 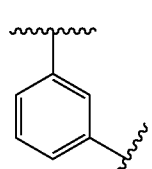 | 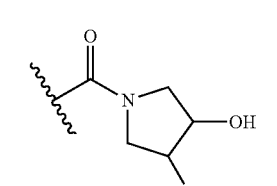 |
| 1-37 | H | —O— | 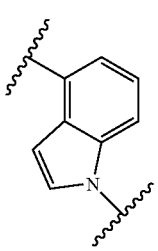 | 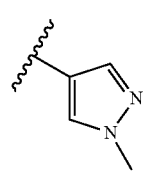 [SMILES: *c1cnn(C)c1] |

TABLE 1-continued
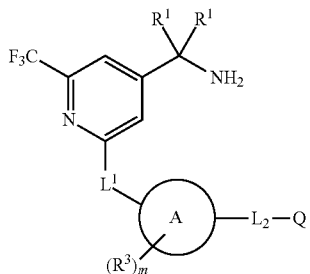
| Compound Number | R¹ | —L¹— | (R³)ₘ on A | —L₂—Q |
|---|---|---|---|---|
| 1-38 | H | —O— | 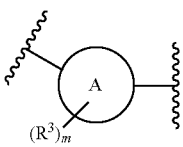 | 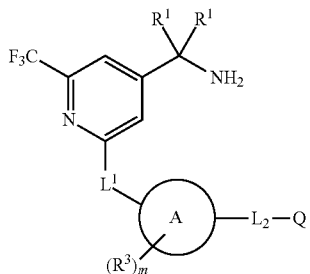 |
| 1-39 | H | —O— | 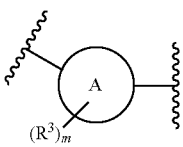 |  |
| 1-40 | H | —O— |  | 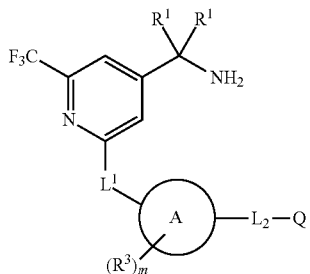 |
| 1-41 | H | —O— | 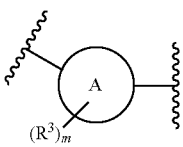 |  |
| 1-42 | H | —OCH₂— |  | 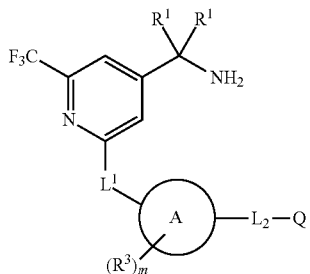 |
| 1-43 | H | —O— | 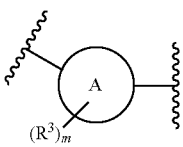 |  |

TABLE 1-continued
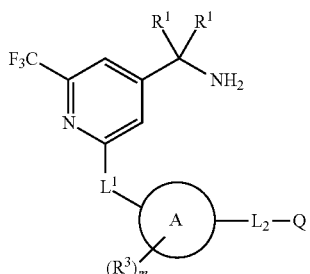
| Compound Number | R¹ | —L¹— | (R³)ₘ with A ring | —L₂—Q |
|---|---|---|---|---|
| 1-44 | H | —O— | 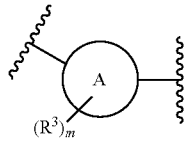 | 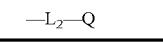 |
| 1-45 | H | —OCH₂— | 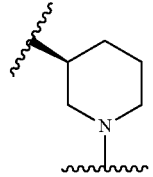 [SMILES: *[C@H]1CCCN(*)C1] | 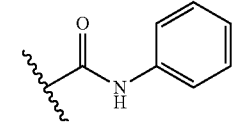 [SMILES: *C(=O)Nc1ccccc1] |
| 1-46 | H | —O— | 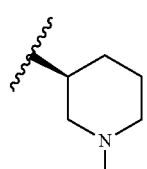 | 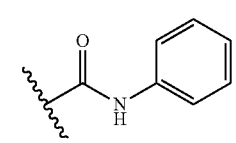 [SMILES: *C(=O)Nc1ccccc1] |
| 1-47 | H | —O— | 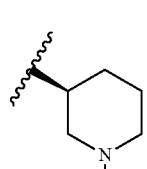 | 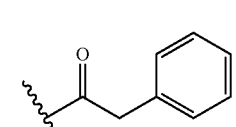 |
| 1-48 | H | —O— | 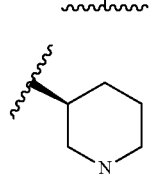 | 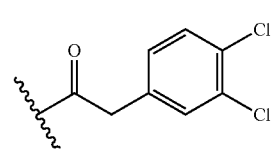 [SMILES: *C(=O)Cc1ccc(Cl)c(Cl)c1] |
| 1-49 | H | —O— | 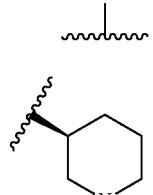 | 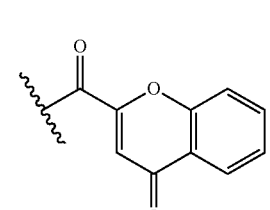 |

TABLE 1-continued
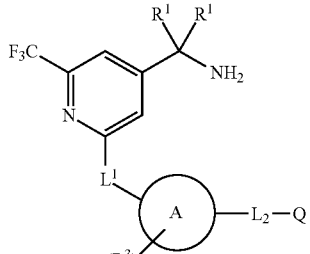
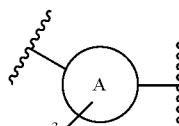
| Compound Number | R¹ | —L¹— | (R³)ₘ | —L₂—Q |
|---|---|---|---|---|
| 1-50 | H | —O— | 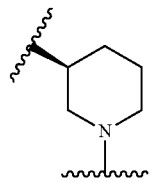 [SMILES: *[C@H]1CCCN(*)C1] | 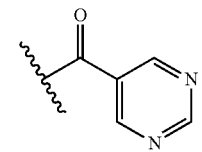 [SMILES: *C(=O)c1cncnc1] |
| 1-51 | H | —O— | 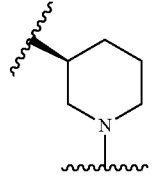 [SMILES: *[C@H]1CCCN(*)C1] | 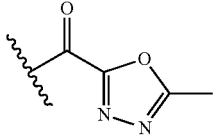 [SMILES: *C(=O)c1nnc(C)o1] |
| 1-52 | H | —O— | 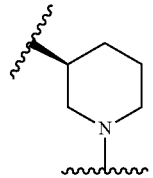 [SMILES: *[C@H]1CCCN(*)C1] | 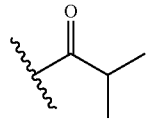 [SMILES: *C(=O)C(C)C] |
| 1-53 | H | —O— | 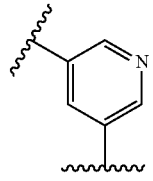 [SMILES: *c1cncc(*)c1] | 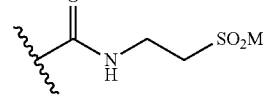 |
| 1-54 | H | —O— | 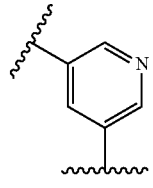 [SMILES: *c1cncc(*)c1] | 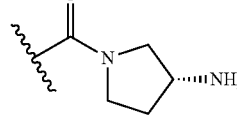 |
| 1-55 (racemic trans) | H | —O— | 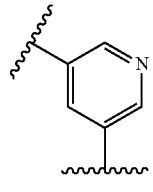 [SMILES: *c1cncc(*)c1] | 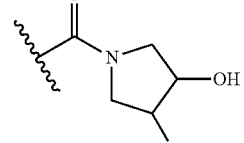 |

TABLE 1-continued
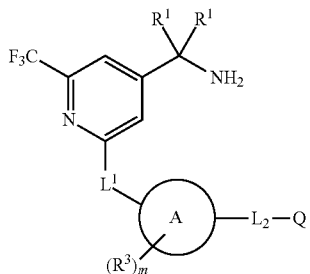
| Compound Number | R¹ | —L¹— | (R³)ₘ | —L₂—Q |
|---|---|---|---|---|
| 1-56 | H | —O— | 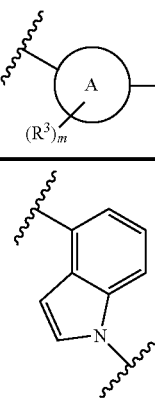 | 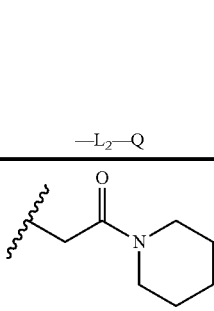 |
| 1-57 | H | —O— | 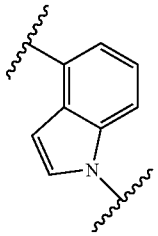 [SMILES: *c1cccc2c1ccn2*] | 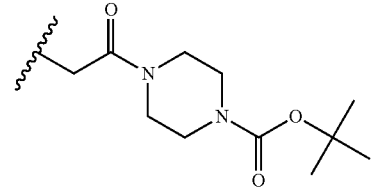 [SMILES: *CC(=O)N1CCN(C(=O)OC(C)(C)C)CC1] |
| 1-58 | H | —O— | 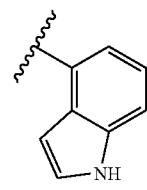 [SMILES: *c1cccc2[nH]ccc12] | — |
| 1-59 | H | —O— | 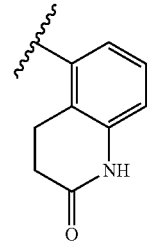 [SMILES: *c1cccc2c1CCC(=O)N2] | — |
| 1-60 | H | —O— | 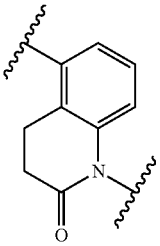 [SMILES: *c1cccc2c1CCC(=O)N2*] | 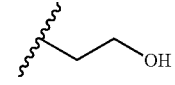 [SMILES: *CCO] |

TABLE 1-continued

| Compound Number | R¹ | —L¹— | (R³)ₘ | —L₂—Q |
|---|---|---|---|---|
| 1-61 | H | —O— | 5-linked 3,4-dihydroquinolin-2(1H)-one (N-linked) | —(CH₂)₃SO₂Me |
| 1-62 | H | —O— | 5-linked 3,4-dihydroquinolin-2(1H)-one (N-linked) | —(CH₂)₃-1,2,4-triazol-1-yl |
| 1-63 | H | —O— | 5-linked 3,4-dihydroquinolin-2(1H)-one (N-linked) | —(CH₂)₂C(O)-piperidin-1-yl |
| 1-64 | H | —O— | 5-linked 3,4-dihydroquinolin-2(1H)-one (N-linked) | —(CH₂)₂-pyridin-2-yl |

TABLE 1-continued
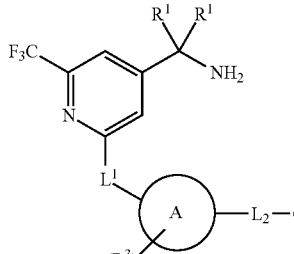
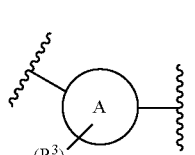
| Compound Number | R¹ | —L¹— | (R³)ₘ | —L₂—Q |
|---|---|---|---|---|
| 1-65 | H | —O— | 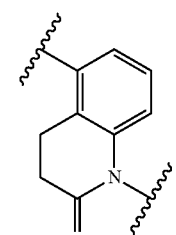 |  |
| 1-66 | H | —O— | 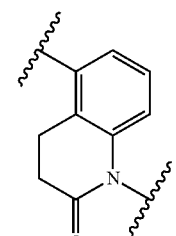 | 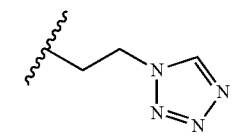 |
| 1-67 | H | —O— | 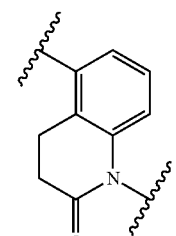 | 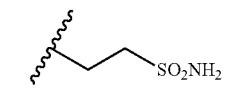 |
| 1-68 | H | —S— | 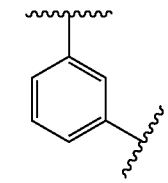 | 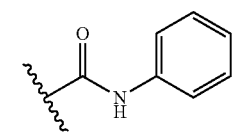 [SMILES: *C(=O)Nc1ccccc1] |
| 1-69 | H | —S— | 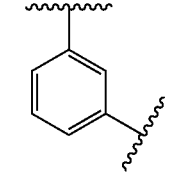 | 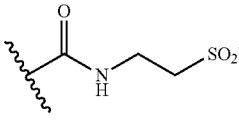 |

TABLE 1-continued
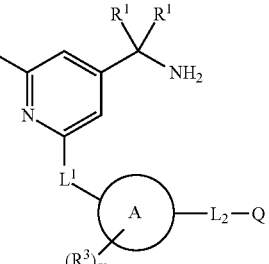
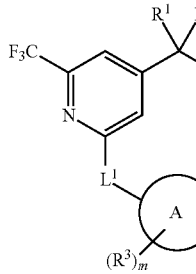
| Compound Number | R[1] | —L[1]— | (R[3])$_m$ | —L$_2$—Q |
|---|---|---|---|---|
| 1-70 | H | —S— | 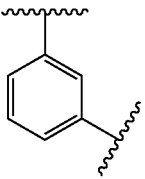 | 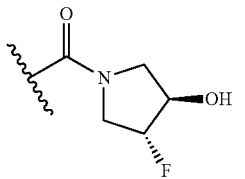 [SMILES: *C(=O)N1C[C@@H](O)[C@H](F)C1] |
| 1-71 | H | —S— | 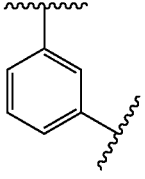 [SMILES: *c1cccc(*)c1] | 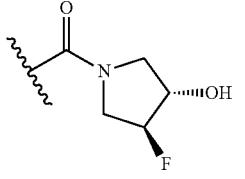 [SMILES: *C(=O)N1C[C@H](O)[C@@H](F)C1] |
| 1-72 | H | —S— | 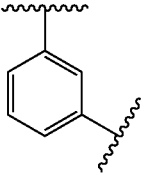 | 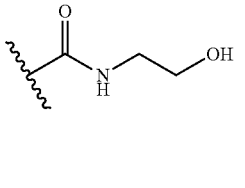 [SMILES: *C(=O)NCCO] |
| 1-73 | H | —S— | 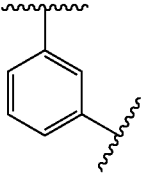 | 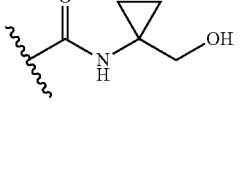 |
| 1-74 | H | —S— | 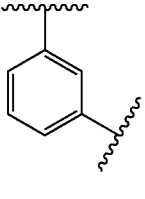 | 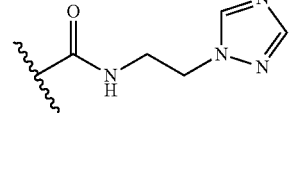 |
| 1-75 | H | —S— | 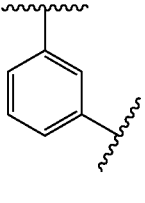 | 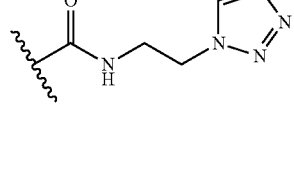 |

TABLE 1-continued
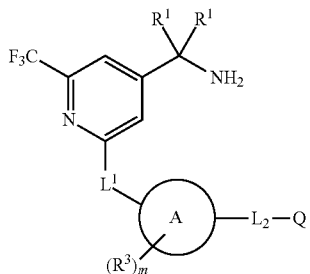
| Compound Number | R¹ | —L¹— | (R³)ₘ | —L₂—Q |
|---|---|---|---|---|
| 1-76 | H | —S— | 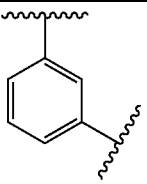 | 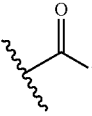 |
| 1-77 | H | —S— | 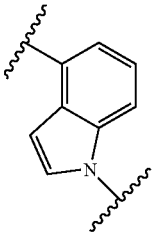 [SMILES: *c1cccc2c1ccn2*] | 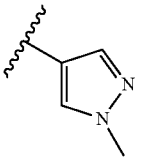 [SMILES: *c1cnn(C)c1] |
| 1-78 | H | —S— | 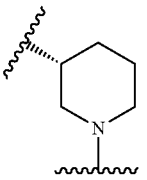 [SMILES: *[C@@H]1CCCN(*)C1] | 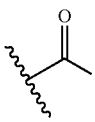 |
| 1-79 | H | —S— | 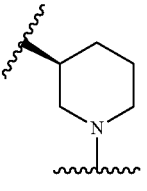 [SMILES: *[C@H]1CCCN(*)C1] | 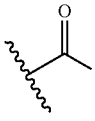 |
| 1-80 | H | —S— | 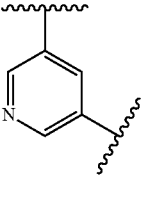 [SMILES: *c1cncc(*)c1] |  |
| 1-81 | H | —SCH₂— | 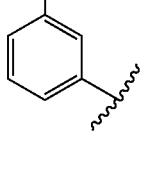 | 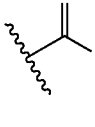 |

TABLE 1-continued
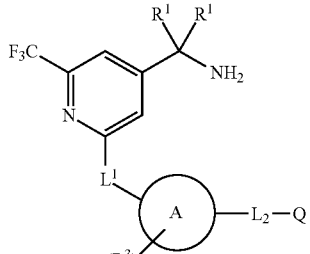
| Compound Number | R¹ | —L¹— | (R³)ₘ | —L₂—Q |
|---|---|---|---|---|
| 1-82 | H | —SCH₂— | 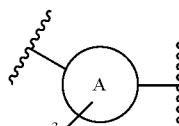 | 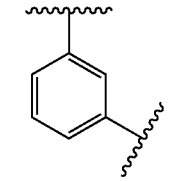 [SMILES: *c1cccc(*)c1] |
| 1-83 | H | —SCH₂— | 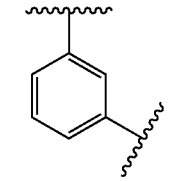 [SMILES: *c1cccc(*)c1] | 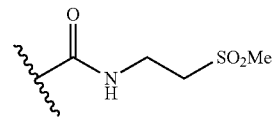 [SMILES: *C(=O)NCCS(C)(=O)=O] |
| 1-84 | H | —SCH₂— | 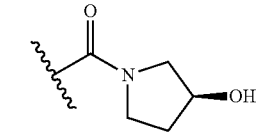 | 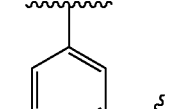 |
| 1-85 | H | —SCH₂— | 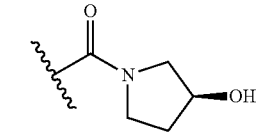 | 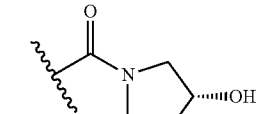 |
| 1-86 | H | —SCH₂— | 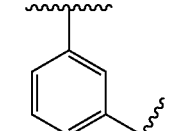 | 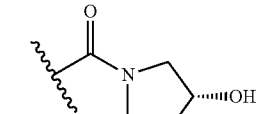 |
| 1-87 | H | —SCH₂— | 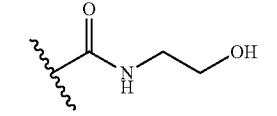 [SMILES: *C(=O)NCCO] | 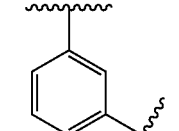 |

TABLE 1-continued
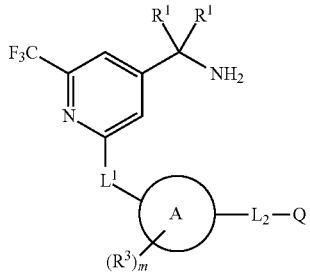
| Compound Number | R¹ | —L¹— | (R³)ₘ | —L₂—Q |
|---|---|---|---|---|
| 1-88 | H | —SCH₂— | 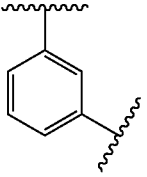 | 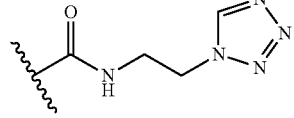 |
| 1-89 | H | —SCH₂— | 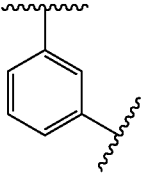 | 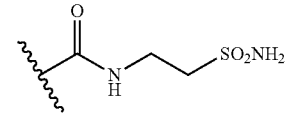 [SMILES: *C(=O)NCCS(N)(=O)=O] |
| 1-90 | H | —SCH₂— | 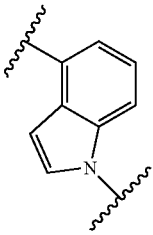 [SMILES: *c1cccc2c1ccn2*] | 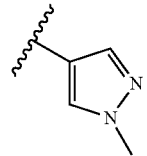 [SMILES: *c1cnn(C)c1] |
| 1-91 | H | —SCH₂— | 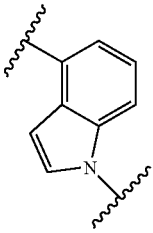 [SMILES: *c1cccc2c1ccn2*] | 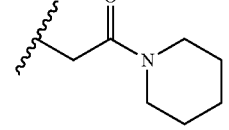 |
| 1-92 | H | —NH— | 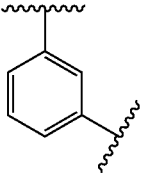 | 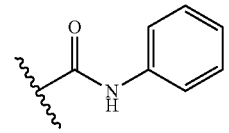 [SMILES: *C(=O)Nc1ccccc1] |

TABLE 1-continued
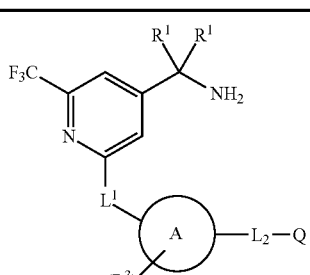
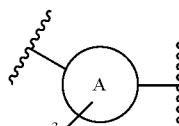
| Compound Number | R¹ | —L¹— | (R³)ₘ | —L₂—Q |
|---|---|---|---|---|
| 1-93 | H | —NH— | 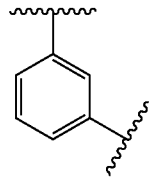 | 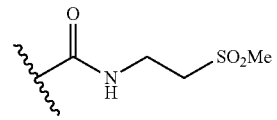 [SMILES: *C(=O)NCCS(C)(=O)=O] |
| 1-94 | H | —NH— | 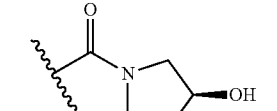 | 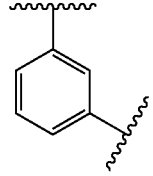 |
| 1-95 | H | —NH— | 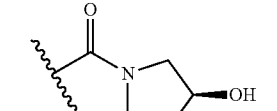 | 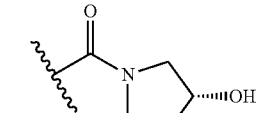 |
| 1-96 | H | —NH— | 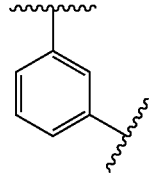 | 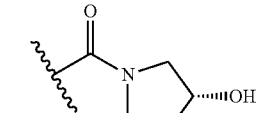 |
| 1-97 | H | —NH— | 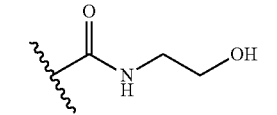 [SMILES: *C(=O)NCCO] | 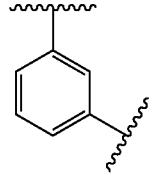 |
| 1-98 | H | —NH— | 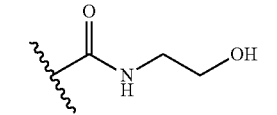 [SMILES: *C(=O)NCCO] | 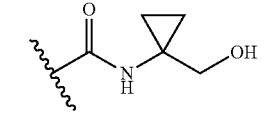 [SMILES: *C(=O)NC1(CO)CC1] |

TABLE 1-continued
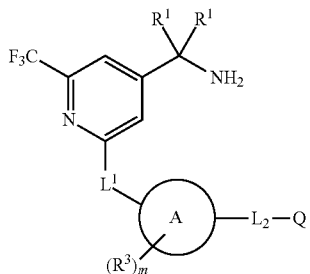
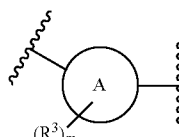
| Compound Number | R¹ | —L¹— | (R³)ₘ | —L₂—Q |
|---|---|---|---|---|
| 1-99 | H | —NH— | 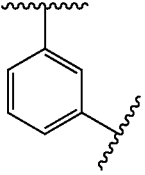 | 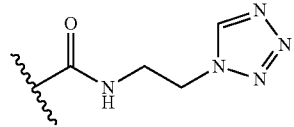 [SMILES: *C(=O)NCCn1cnnn1] |
| 1-100 | H | —NH— | 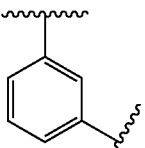 | 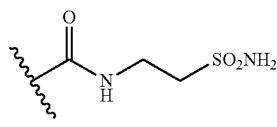 [SMILES: *C(=O)NCCS(N)(=O)=O] |
| 1-101 | H | —NH— | 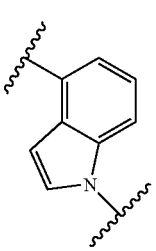 [SMILES: *c1cccc2c1ccn2*] | 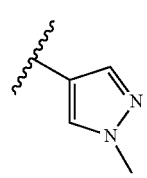 [SMILES: *c1cnn(C)c1] |
| 1-102 | H | —NH— | 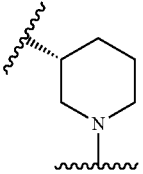 | 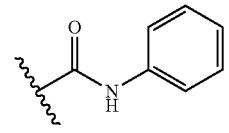 [SMILES: *C(=O)Nc1ccccc1] |
| 1-103 | H | —NH— | 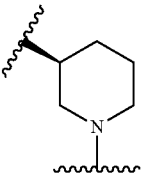 [SMILES: *[C@H]1CCCN(*)C1] | 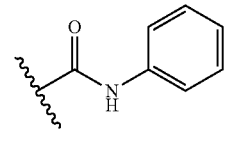 [SMILES: *C(=O)Nc1ccccc1] |
| 1-104 | H | —NH— | 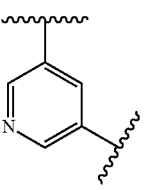 [SMILES: *c1cncc(*)c1] | 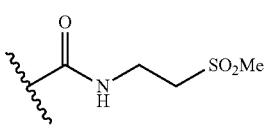 |

TABLE 1-continued
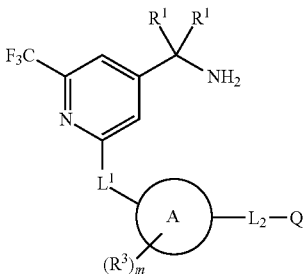
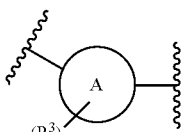
| Compound Number | R¹ | —L¹— | (R³)ₘ | —L₂—Q |
|---|---|---|---|---|
| 1-105 | H | —NHCH₂— | phenyl (meta) | C(=O)NH-phenyl |
| 1-106 | H | —NHCH₂— | phenyl (meta) | C(=O)NHCH₂CH₂SO₂Me |
| 1-107 | H | —NHCH₂— | phenyl (meta) | C(=O)-pyrrolidinyl(3-OH,4-F) |
| 1-108 | H | —NHCH₂— | phenyl (meta) | C(=O)-pyrrolidinyl(3-OH,4-F) |
| 1-109 | H | —NHCH₂— | phenyl (meta) | C(=O)NHCH₂CH₂OH |
| 1-110 | H | —NHCH₂— | phenyl (meta) | C(=O)NH-C(cyclopropyl)(CH₂OH) |

TABLE 1-continued
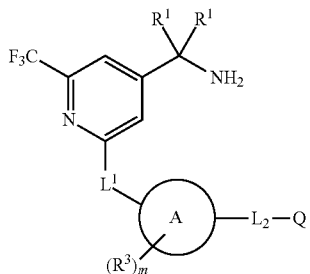
| Compound Number | R¹ | —L¹— | (R³)ₘ | —L₂—Q |
|---|---|---|---|---|
| 1-111 | H | —NHCH₂— | 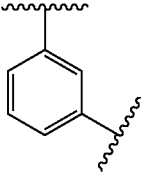 | 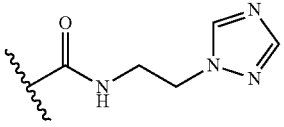 [SMILES: *C(=O)NCCn1cncn1] |
| 1-112 | H | —NHCH₂— | 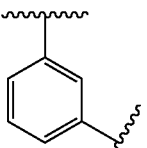 | 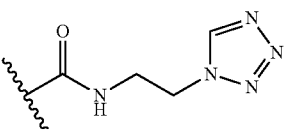 [SMILES: *C(=O)NCCn1cnnn1] |
| 1-113 | H | —NHCH₂— | 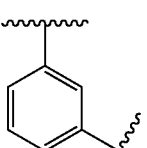 | 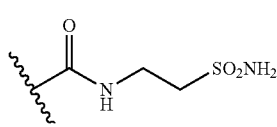 [SMILES: *C(=O)NCCS(N)(=O)=O] |
| 1-114 | H | —NHCH₂— | 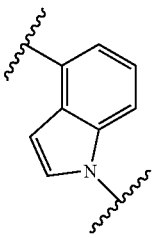 [SMILES: *c1cccc2c1ccn2*] | 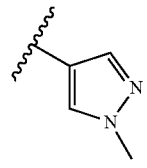 [SMILES: *c1cnn(C)c1] |
| 1-115 | H | —NHCH₂— | 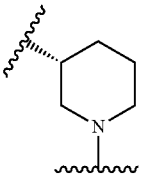 [SMILES: *[C@@H]1CCCN(*)C1] | 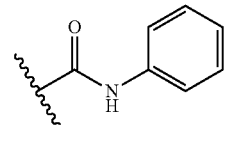 [SMILES: *C(=O)Nc1ccccc1] |
| 1-116 | H | —NHCH₂— | 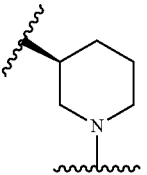 [SMILES: *[C@H]1CCCN(*)C1] | 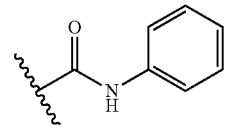 [SMILES: *C(=O)Nc1ccccc1] |

TABLE 1-continued
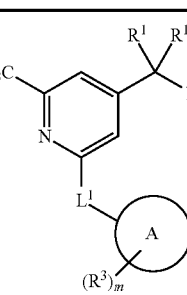
| Compound Number | R¹ | —L¹— | (R³)ₘ | —L₂—Q |
|---|---|---|---|---|
| 1-117 | H | —NHCH₂— | pyridine-3,5-diyl | —C(O)NHCH₂CH₂SO₂Me |
| 1-118 | H | —N(Me)— | phenyl-1,3-diyl | —C(O)NHCH₂CH₂SO₂Me |
| 1-119 | H | —N(CH₂CH₂F)— | phenyl-1,3-diyl | —C(O)NHCH₂CH₂SO₂Me |
| 1-120 | H | —N(CH₂CH₂OH)— | phenyl-1,3-diyl | —C(O)NHCH₂CH₂SO₂Me |
| 1-121 | H | —N(CH₂CH₂-pyrazol-1-yl)— | phenyl-1,3-diyl | —C(O)NHCH₂CH₂SO₂Me |
| 1-122 | H | —N(CH₂Ph)— | phenyl-1,3-diyl | —C(O)NHCH₂CH₂SO₂Me |

TABLE 1-continued
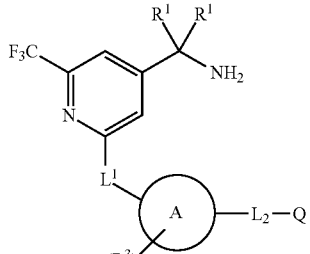
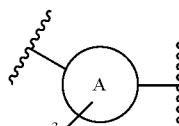
| Compound Number | R¹ | —L¹— | (R³)ₘ | —L₂—Q |
|---|---|---|---|---|
| 1-123 | H | —CH₂— | 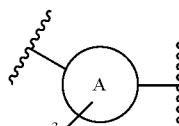 | 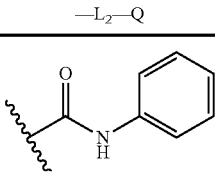 |
| 1-124 | H | —CH₂— | 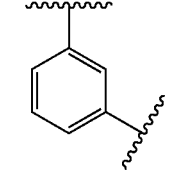 | 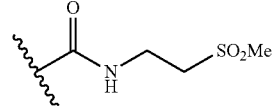 [SMILES: *C(=O)NCCS(C)(=O)=O] |
| 1-125 | H | —CH₂— | 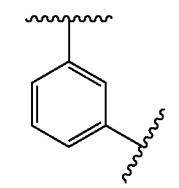 | 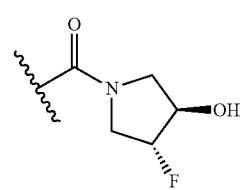 [SMILES: *C(=O)N1C[C@@H](O)[C@H](F)C1] |
| 1-126 | H | —CH₂— | 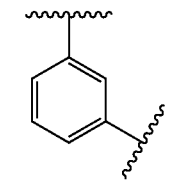 | 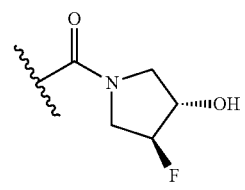 [SMILES: *C(=O)N1C[C@H](O)[C@@H](F)C1] |
| 1-127 | H | —CH₂— | 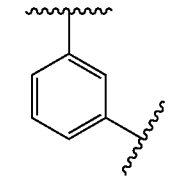 | 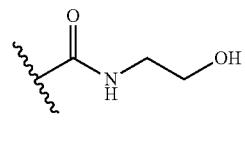 [SMILES: *C(=O)NCCO] |
| 1-128 | H | —CH₂— | 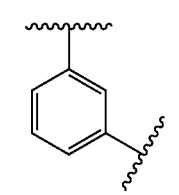 | 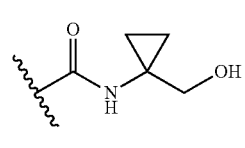 [SMILES: *C(=O)NC1(CO)CC1] |

TABLE 1-continued
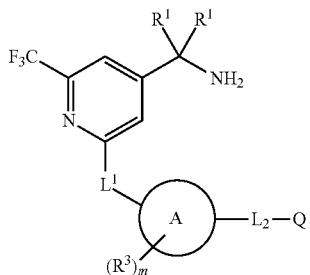
| Compound Number | R¹ | —L¹— | (R³)ₘ on A | —L₂—Q |
|---|---|---|---|---|
| 1-129 | H | —CH₂— | 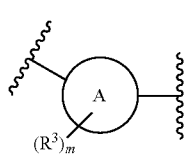 | 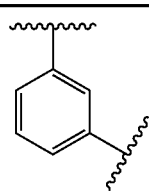 |
| 1-130 | H | —CH₂— | 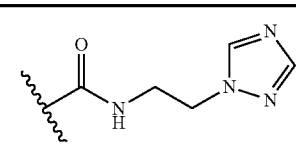 | 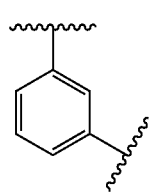 |
| 1-131 | H | —CH₂— | 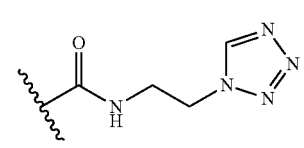 [SMILES: *C(=O)NCCn1cnnn1] | 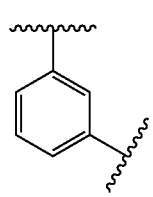 |
| 1-132 | H | —CH₂— | 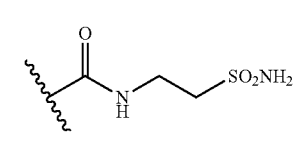 [SMILES: *C(=O)NCCS(N)(=O)=O] | 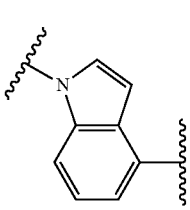 [SMILES: *c1cccc2c1ccn2*] |
| 1-133 | H | —CH₂— | 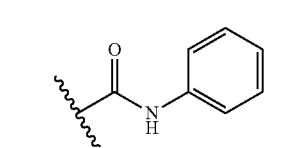 [SMILES: *C(=O)Nc1ccccc1] | 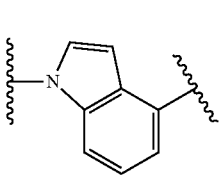 [SMILES: *c1cccc2c1ccn2*] |
| 1-134 | H | —CH₂— | 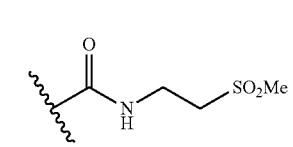 | 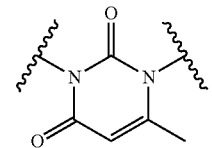 [SMILES: *n1c(C)cc(=O)n(*)c1=O] |

TABLE 1-continued
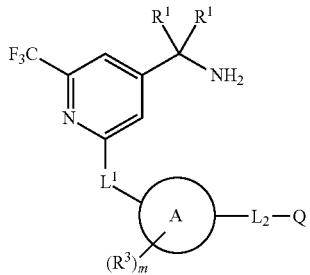
| Compound Number | R¹ | —L¹— | 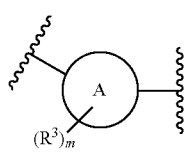 | —L₂—Q |
|---|---|---|---|---|
| 1-135 | H | —CH₂— | 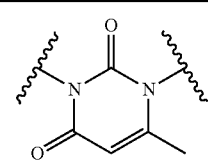 | 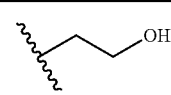 |
| 1-136 | H | —SO₂— | 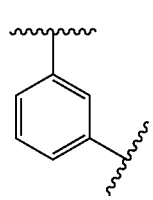 | 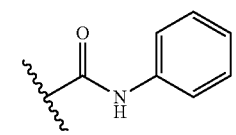 [SMILES: *C(=O)Nc1ccccc1] |
| 1-137 | H | —SO₂— | 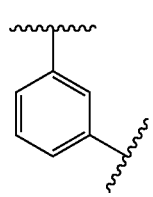 | 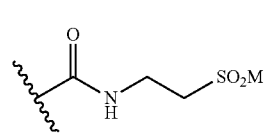 |
| 1-138 | H | —SO₂— | 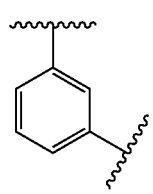 | 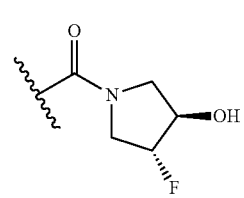 [SMILES: *C(=O)N1C[C@@H](O)[C@H](F)C1] |
| 1-139 | H | —SO₂— | 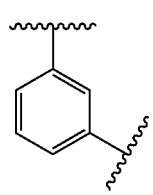 | 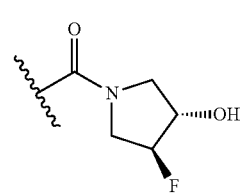 [SMILES: *C(=O)N1C[C@H](O)[C@@H](F)C1] |
| 1-140 | H | —SO₂— | 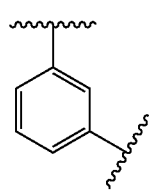 | 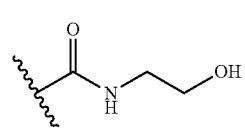 [SMILES: *C(=O)NCCO] |

US 11,072,585 B2
TABLE 1-continued
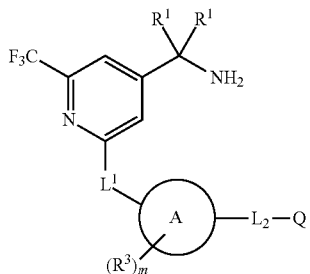
| Compound Number | R¹ | —L¹— | (R³)ₘ | —L₂—Q |
|---|---|---|---|---|
| 1-141 | H | —SO₂— | 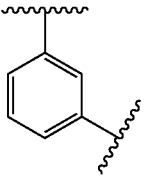 | 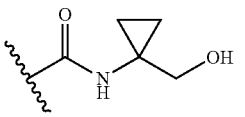 [SMILES: *C(=O)NC1(CO)CC1] |
| 1-142 | H | —SO₂— | 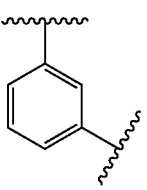 | 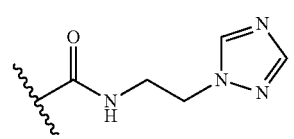 [SMILES: *C(=O)NCCn1cncn1] |
| 1-143 | H | —SO₂— | 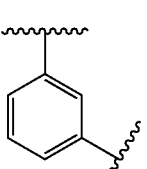 | 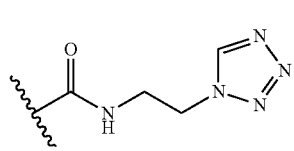 [SMILES: *C(=O)NCCn1cnnn1] |
| 1-144 | H | —SO₂— | 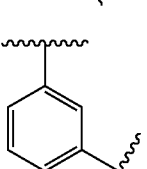 | 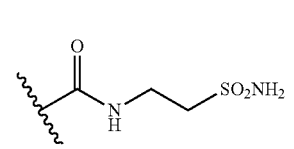 [SMILES: *C(=O)NCCS(N)(=O)=O] |
| 1-145 | H | —SO₂— | 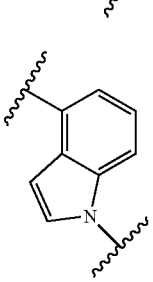 | 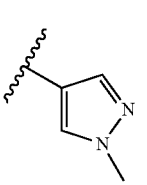 [SMILES: *c1cnn(C)c1] |
| 1-146 | H | —SO₂— | 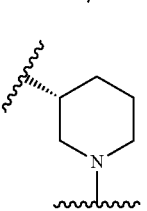 | 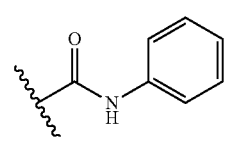 [SMILES: *C(=O)Nc1ccccc1] |

TABLE 1-continued
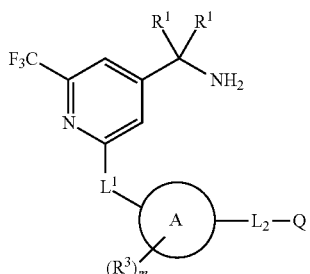
| Compound Number | R¹ | —L¹— | (R³)ₘ 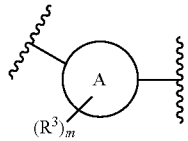 | —L₂—Q |
|---|---|---|---|---|
| 1-147 | H | —SO₂— | 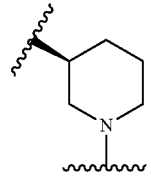 [SMILES: *[C@H]1CCCN(*)C1] | 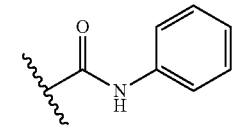 [SMILES: *C(=O)Nc1ccccc1] |
| 1-148 | H | —C(=O)NH— | 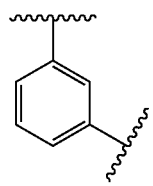 | 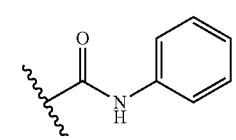 [SMILES: *C(=O)Nc1ccccc1] |
| 1-149 | H | C(=O)NH | 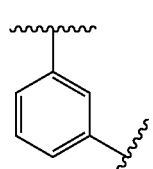 | 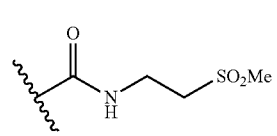 |
| 1-150 | H | —C(=O)NH— | 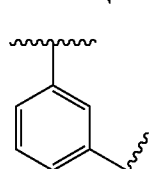 | 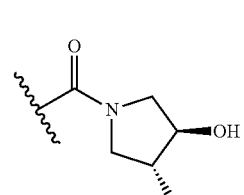 |
| 1-151 | H | —C(=O)NH— | 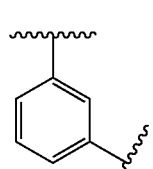 | 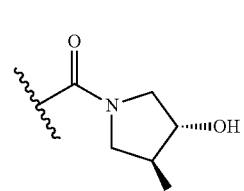 |
| 1-152 | H | —C(=O)NH— | 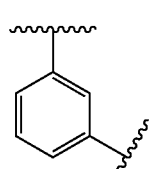 | 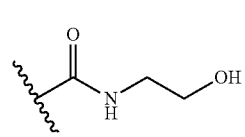 [SMILES: *C(=O)NCCO] |

TABLE 1-continued
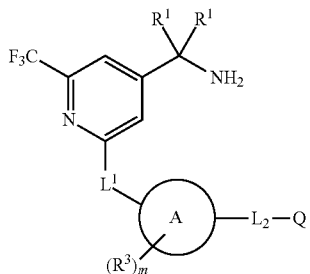
| Compound Number | R¹ | —L¹— | 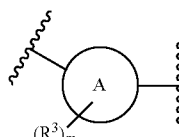 | —L₂—Q |
|---|---|---|---|---|
| 1-153 | H | —C(=O)NH— | 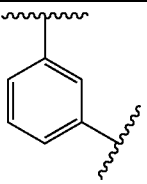 | 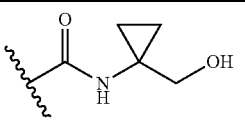 |
| 1-154 | H | —C(=O)NH— | 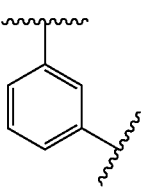 | 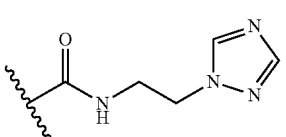 [SMILES: *C(=O)NCCn1cncn1] |
| 1-155 | H | —C(=O)NH— | 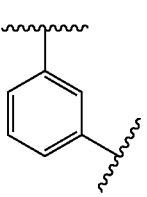 | 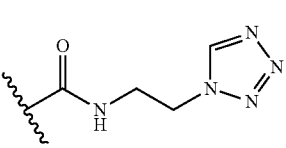 [SMILES: *C(=O)NCCn1cnnn1] |
| 1-156 | H | —C(=O)NH— | 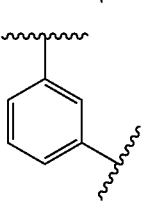 | 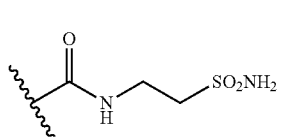 [SMILES: *C(=O)NCCS(N)(=O)=O] |
| 1-157 | H | —C(=O)NH | 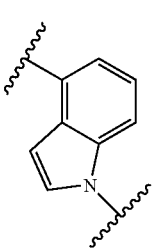 [SMILES: *c1cccc2c1ccn2*] | 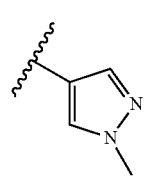 |
| 1-158 | H | —C(=O)NH— | 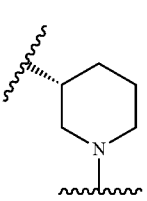 [SMILES: *[C@@H]1CCCN(*)C1] | 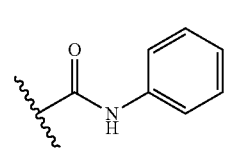 [SMILES: *C(=O)Nc1ccccc1] |

85 86
TABLE 1-continued
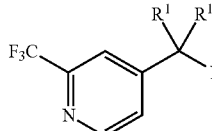
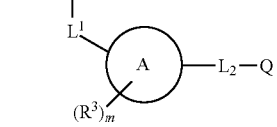
| Compound Number | R¹ | —L¹— | (R³)ₘ | —L₂—Q |
|---|---|---|---|---|
| 1-159 | H | —C(=O)NH— |  | 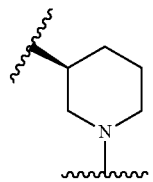 [SMILES: *[C@H]1CCCN(*)C1] |
| 1-160 | H | —C(=O)NH— | 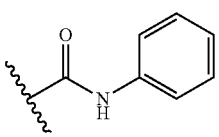 [SMILES: *C(=O)Nc1ccccc1] | 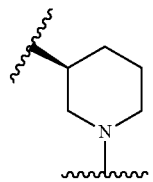 [SMILES: *[C@H]1CCCN(*)C1] |
| 1-161 | H | — | 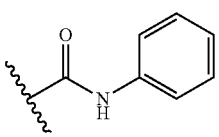 [SMILES: *C(=O)Nc1ccccc1] | — |
| 1-162 | H | — | 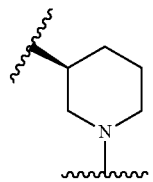 [SMILES: *[C@H]1CCCN(*)C1] | — |
| 1-163 | H | — | 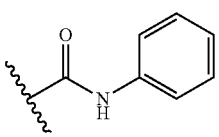 [SMILES: *C(=O)Nc1ccccc1] | — |
| 1-164 | H | — | 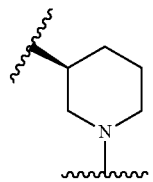 [SMILES: *[C@H]1CCCN(*)C1] | — |

TABLE 1-continued
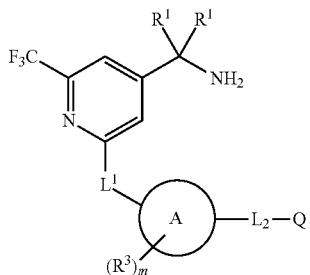
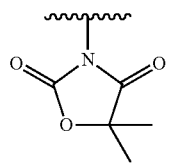 [SMILES: *N1C(=O)OC(C)(C)C1=O]
| Compound Number | R¹ | —L¹— | (R³)ₘ on A | —L₂—Q |
|---|---|---|---|---|
| 1-165 | H | — | 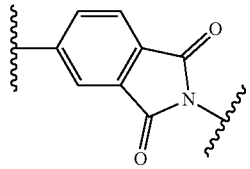 [SMILES: *c1ccc2c(c1)C(=O)N(*)C2=O] | — |
| 1-166 | H | O | 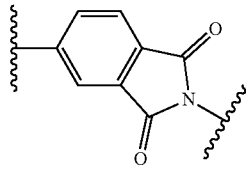 [SMILES: *c1ccc2c(c1)C(=O)N(*)C2=O] | Me |
| 1-167 | H | —O— | 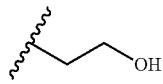 [SMILES: *CCO] | 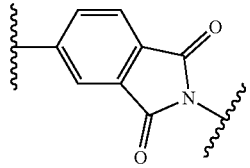 [SMILES: *c1ccc2c(c1)C(=O)N(*)C2=O] |
| 1-168 | H | —O— | 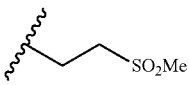 | 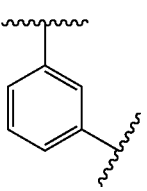 |
| 1-169 | H | —O— | 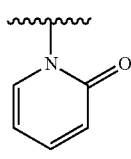 | 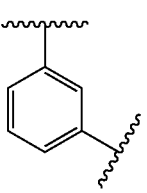 |
| 1-170 | H | —O— | 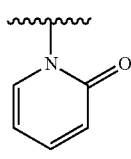 | 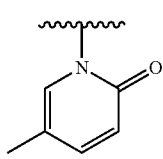 [SMILES: *n1cc(C)ccc1=O] |

TABLE 1-continued
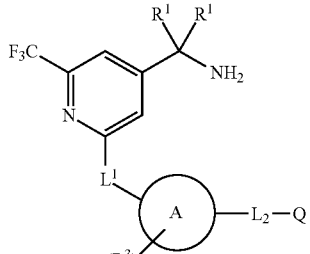
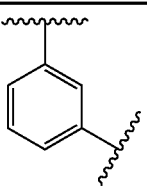
| Compound Number | R¹ | —L¹— | (R³)ₘ | —L₂—Q |
|---|---|---|---|---|
| 1-171 | H | —O— | 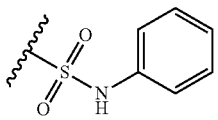 [SMILES: *S(=O)(=O)Nc1ccccc1] | 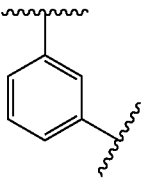 |
| 1-172 | H | —O— | 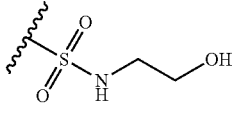 [SMILES: *S(=O)(=O)NCCO] | 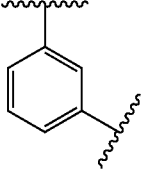 |
| 1-173 | H | —O— | 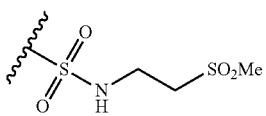 [SMILES: *S(=O)(=O)NCCS(C)(=O)=O] | 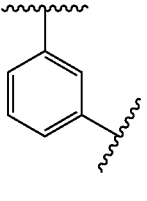 |
| 1-174 | H | —O— | 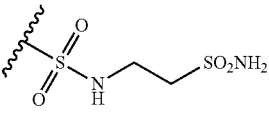 [SMILES: *S(=O)(=O)NCCS(N)(=O)=O] | 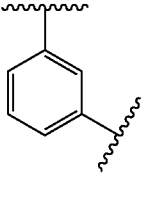 |
| 1-175 | H | —O— | 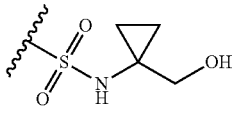 [SMILES: *S(=O)(=O)NC1(CO)CC1] | 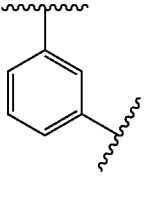 |
| 1-176 | H | —O— | 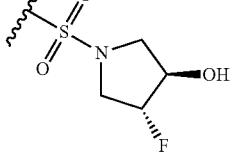 | |

TABLE 1-continued
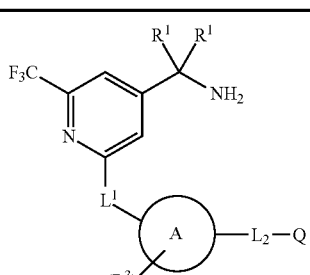
| Compound Number | R¹ | —L¹— | (R³)ₘ (A ring) | —L₂—Q |
|---|---|---|---|---|
| 1-177 | H | —O— | 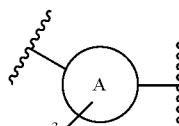 | 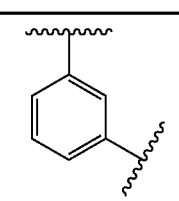 |
| 1-178 | H | —O— | 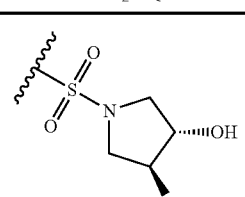 | 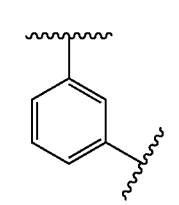 |
| 1-179 | H | —O— | 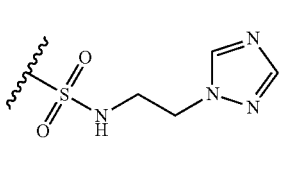 [SMILES: *S(=O)(=O)NCCn1cncn1] | 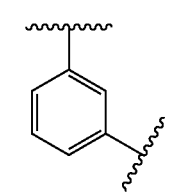 |
| 1-180 | H | —O— | 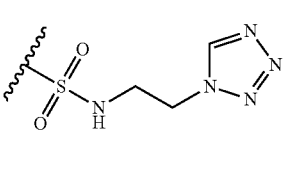 [SMILES: *S(=O)(=O)NCCn1cnnn1] | 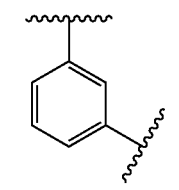 |
| 1-181 | H | —O— | 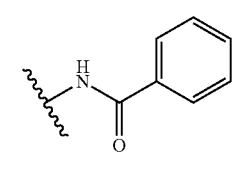 [SMILES: *NC(=O)c1ccccc1] | 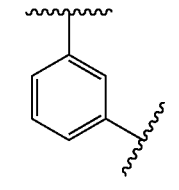 |
| 1-182 | H | —O— | 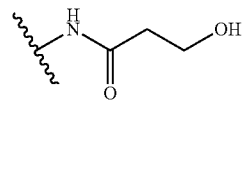 [SMILES: *NC(=O)CCO] | 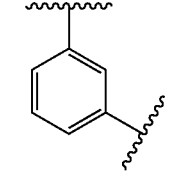 |

TABLE 1-continued
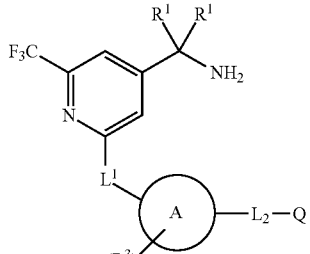
| Compound Number | R¹ | —L¹— | (R³)ₘ on A | —L₂—Q |
|---|---|---|---|---|
| 1-183 | H | —O— | 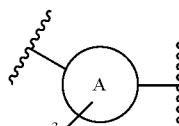 | 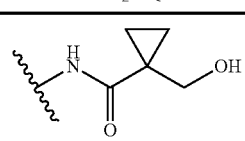 |
| 1-184 | H | —O— | 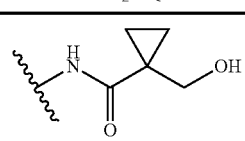 | 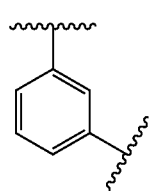 |
| 1-185 | H | —O— | 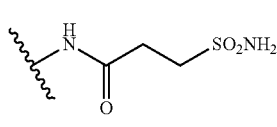 [SMILES: *NC(=O)CCS(N)(=O)=O] | 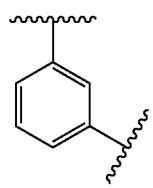 |
| 1-186 | H | —O— | 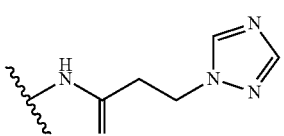 | 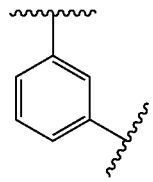 |
| 1-187 | H | —O— | 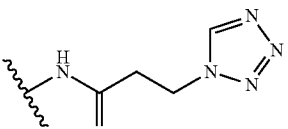 | 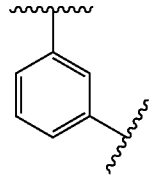 |
| 1-188 | H | —O— | 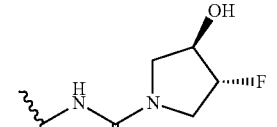 | 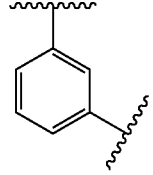 |

TABLE 1-continued
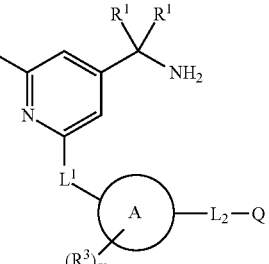
| Compound Number | R¹ | —L¹— | (R³)ₘ | —L₂—Q |
|---|---|---|---|---|
| 1-189 | H | —O— | 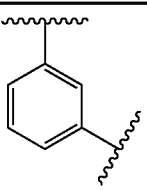 | 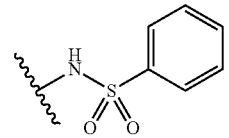 [SMILES: *NS(=O)(=O)c1ccccc1] |
| 1-190 | H | —O— | 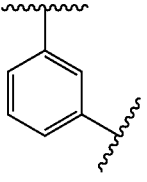 | 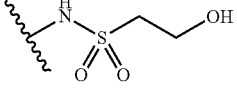 |
| 1-191 | H | —O— | 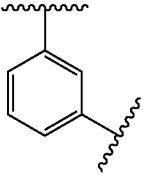 | 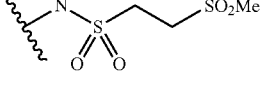 |
| 1-192 | H | —Ov | 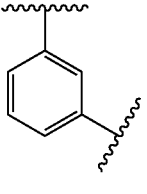 | 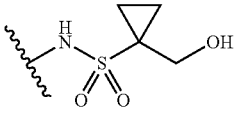 [SMILES: *NS(=O)(=O)C1(CO)CC1] |
| 1-193 | H | —O— | 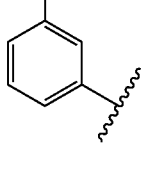 | 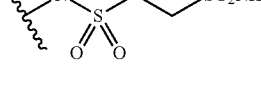 |
| 1-194 | H | —O— | 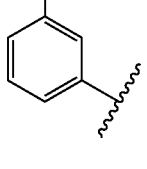 | 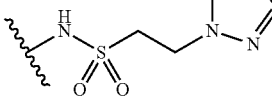 |

TABLE 1-continued

| Compound Number | R¹ | —L¹— | (R³)ₘ | —L₂—Q |
|---|---|---|---|---|
| 1-195 | H | —O— | phenyl (meta) | —NHSO₂CH₂CH₂-(tetrazol-1-yl) |
| 1-196 | H | —O— | phenyl (meta) | —NHSO₂-N(3-fluoro-4-hydroxypyrrolidinyl) |
| 1-197 | H | —O— | phenyl (meta) | —NHSO₂-N(3-fluoro-4-hydroxypyrrolidinyl) |
| 1-198 | H | —O— | phenyl (meta) | —C(O)NHCH₂CH₂CN |
| 1-199 | H | —O— | phenyl (meta) | —C(O)-N(3-cyanoazetidinyl) |
| 1-200 | H | —O— | phenyl (meta) | —C(O)NH-(oxetan-3-yl) |

TABLE 1-continued
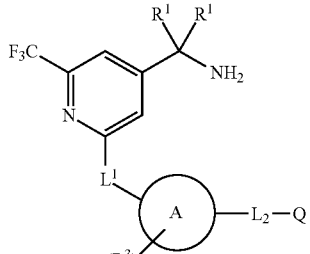
| Compound Number | R¹ | —L¹— | (R³)ₘ | —L₂—Q |
|---|---|---|---|---|
| 1-201 | H | —O— | 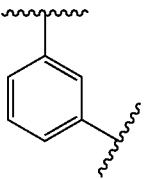 | 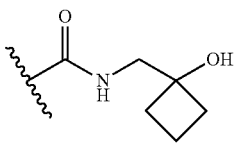 [SMILES: *C(=O)NCC1(O)CCC1] |
| 1-202 | H | —O— | 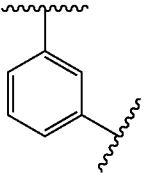 | 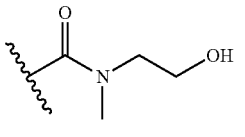 [SMILES: *C(=O)N(C)CCO] |
| 1-203 | H | —O— | 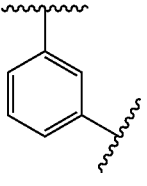 | 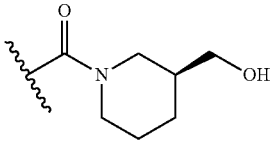 [SMILES: *C(=O)N1CCC[C@H](CO)C1] |
| 1-204 | H | —O— | 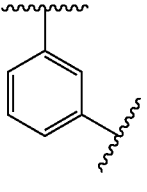 | 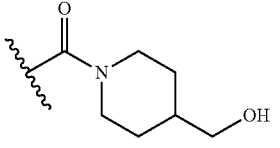 [SMILES: *C(=O)N1CCC(CO)CC1] |
| 1-205 | H | —O— | 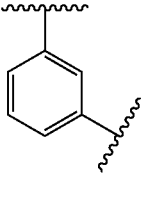 | 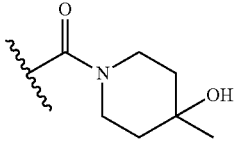 [SMILES: *C(=O)N1CCC(C)(O)CC1] |
| 1-206 | H | —O— | 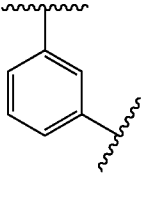 | 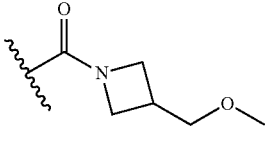 [SMILES: *C(=O)N1CC(COC)C1] |

TABLE 1-continued
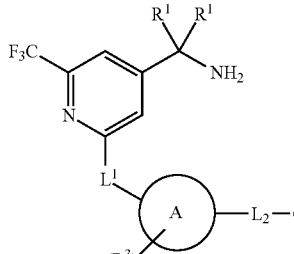
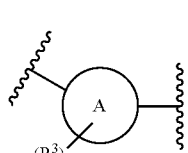
| Compound Number | R¹ | —L¹— | (R³)ₘ | —L₂—Q |
|---|---|---|---|---|
| 1-207 | H | —O— | 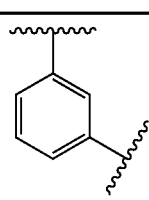 | 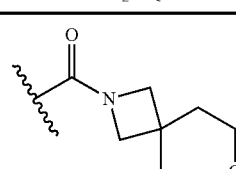 |
| 1-208 | H | —O— | 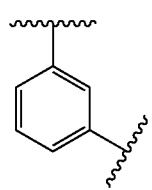 | 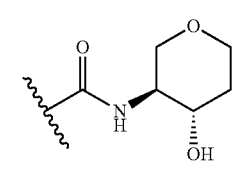 [SMILES: *C(=O)N[C@H]1COCC[C@@H]1O] |
| 1-209 | H | —O— | 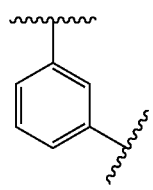 | 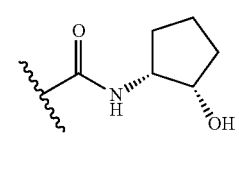 |
| 1-210 | H | —O— | 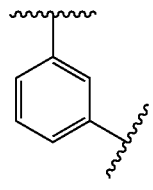 | 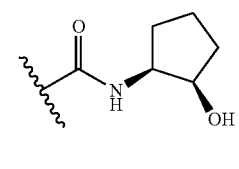 [SMILES: *C(=O)N[C@H]1CCC[C@H]1O] |
| 1-211 (racemic cis) | H | —O— | 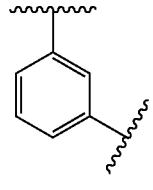 | 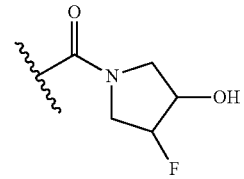 [SMILES: *C(=O)N1CC(O)C(F)C1] |
| 1-212 | H | —O— | 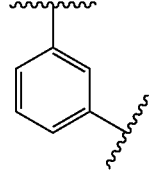 | 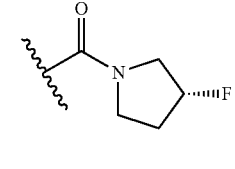 [SMILES: *C(=O)N1CC[C@@H](F)C1] |

TABLE 1-continued
| Compound Number | R¹ | —L¹— | (R³)ₘ | —L₂—Q |
|---|---|---|---|---|
| 1-213 | H | —O— | 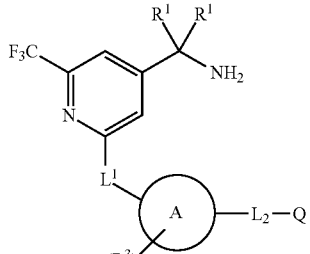 | 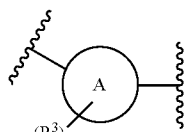 |
| 1-214 | H | —O— | 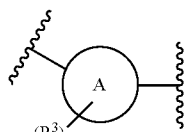 | 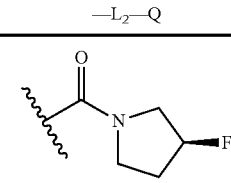 |
| 1-215 | H | —O— | 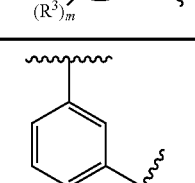 | 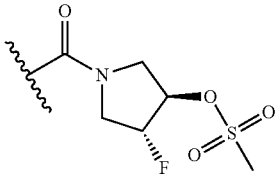 [SMILES: *C(=O)N1C[C@@H](F)[C@H](OS(C)(=O)=O)C1] |
| 1-216 | H | —O— | 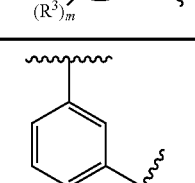 | 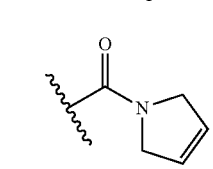 |
| 1-217 | H | —O— | 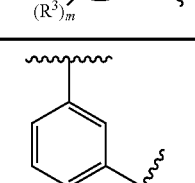 | 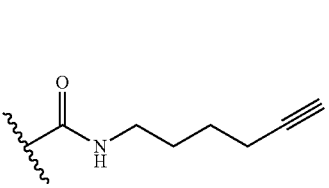 [SMILES: *C(=O)NCCCCC#C] |
| 1-218 | H | —O— | 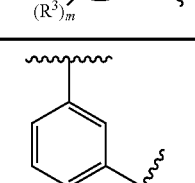 | 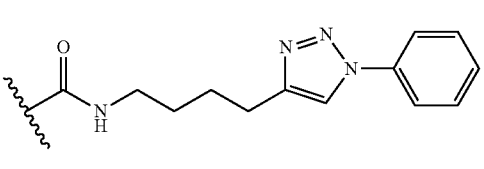 [SMILES: *C(=O)NCCCCc1cn(-c2ccccc2)nn1] |

TABLE 1-continued
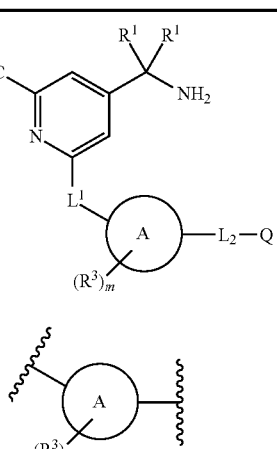
| Compound Number | R¹ | —L¹— | (R³)ₘ | —L₂—Q |
|---|---|---|---|---|
| 1-219 | H | —O— |  | 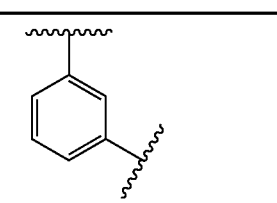 |
| 1-220 | H | —O— | 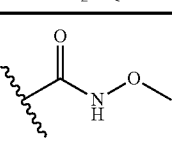 | 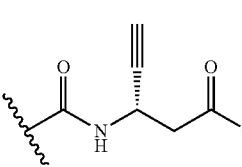 |
| 1-221 | H | —O— | 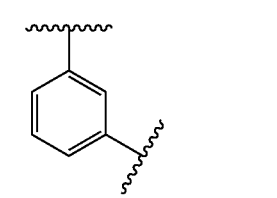 [SMILES: *c1cccc(*)c1] | 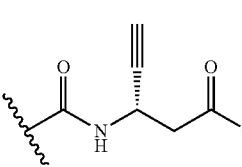 |
| 1-222 | H | —O— | 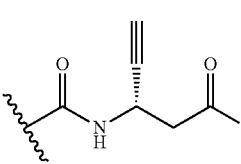 | 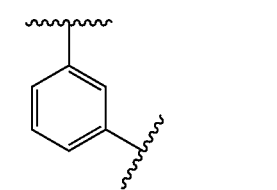 [SMILES: *c1cccc(*)c1] |
| 1-223 | H | —O— | 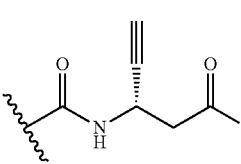 | 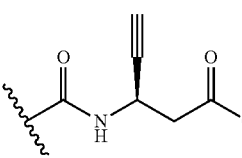 |
| 1-224 | H | —O— | 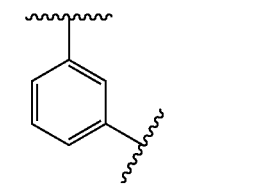 [SMILES: *c1cccc(*)c1] | 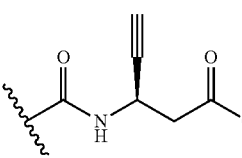 |

TABLE 1-continued
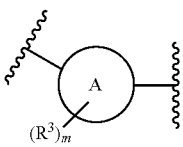
| Compound Number | R¹ | —L¹— | (R³)ₘ | —L₂—Q |
|---|---|---|---|---|
| 1-225 | H | —O— | 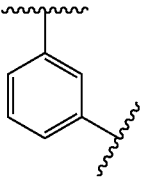 [SMILES: *c1cccc(*)c1] | 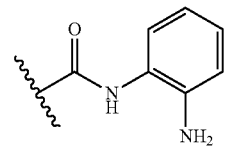 [SMILES: *C(=O)Nc1ccccc1N] |
| 1-226 | H | —O— | 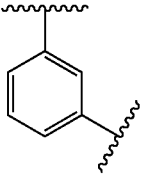 |  |
| 1-227 | H | —O— | 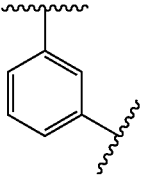 [SMILES: *c1cccc(*)c1] | 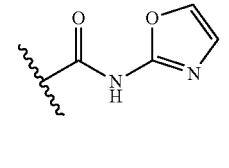 [SMILES: *C(=O)Nc1ncco1] |
| 1-228 | H | —O | 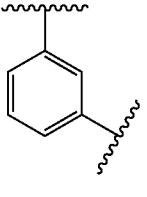 [SMILES: *c1cccc(*)c1] | 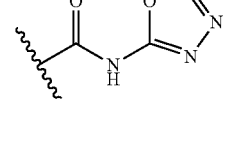 |
| 1-229 (racemic-trans) | H | —O— | 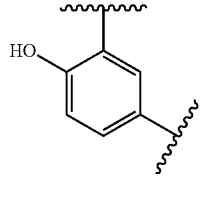 [SMILES: *c1ccc(O)c(*)c1] | 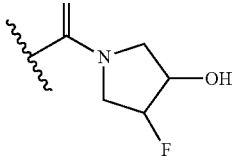 |
| 1-230 (racemic-trans) | H | —O— | 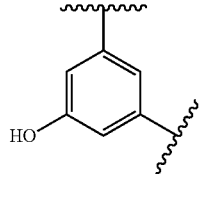 [SMILES: *c1cc(*)cc(O)c1] | 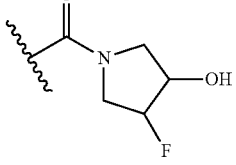 |

TABLE 1-continued
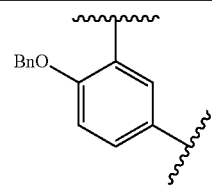
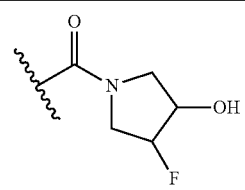
| Compound Number | R¹ | —L¹— | (R³)ₘ | —L₂—Q |
|---|---|---|---|---|
| 1-231 (racemic-trans) | H | —O— | 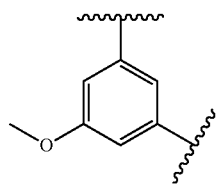 [SMILES: *c1cc(*)cc(OC)c1] | 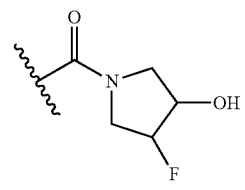 [SMILES: *C(=O)N1CC(O)C(F)C1] |
| 1-232 (racemic-trans) | H | —O— | 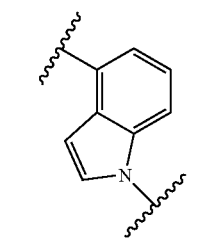 [SMILES: *c1cccc2c1ccn2*] | 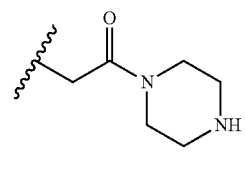 [SMILES: *CC(=O)N1CCNCC1] |
| 1-233 | H | —O— | 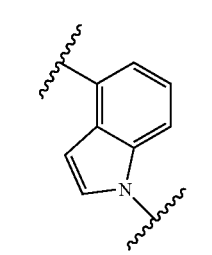 [SMILES: *c1cccc2c1ccn2*] | 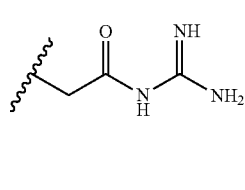 [SMILES: *CC(=O)NC(=N)N] |
| 1-234 | H | —O— | 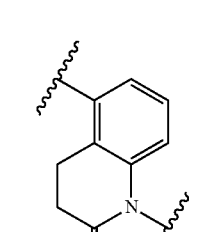 | 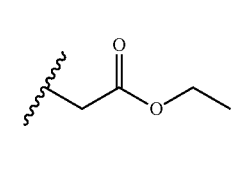 [SMILES: *CC(=O)OCC] |
| 1-235 | H | —O— | | |

//
US 11,072,585 B2
TABLE 1-continued
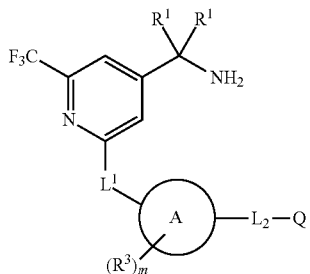
| Compound Number | R¹ | —L¹— | (R³)ₘ | —L₂—Q |
|---|---|---|---|---|
| 1-236 | H | —O— | 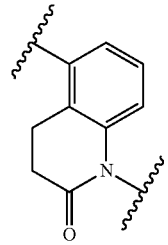 [SMILES: *c1cccc2c1CCC(=O)N2*] | 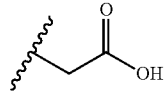 |
| 1-237 | H | —NHCH₂— | 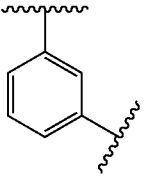 | 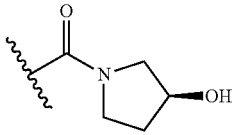 [SMILES: *C(=O)N1CC[C@H](O)C1] |
| 1-238 | H | —NHC(=O)— | 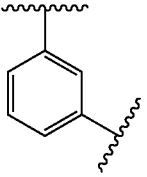 | 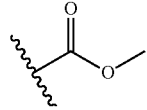 [SMILES: *C(=O)OC] |
| 1-239 | H | —NHC(=O)— | 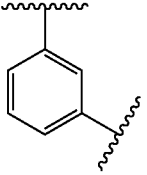 | 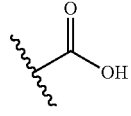 [SMILES: *C(=O)O] |
| 1-240 | H | —NHC(=O)— | 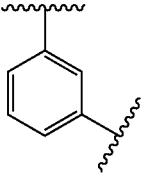 | 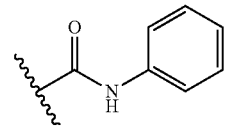 [SMILES: *C(=O)Nc1ccccc1] |
| 1-241 | H | —NHC(=O)— | 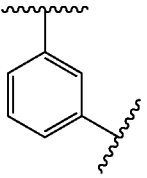 | 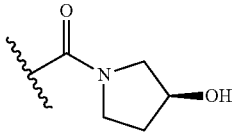 [SMILES: *C(=O)N1CC[C@H](O)C1] |

TABLE 1-continued
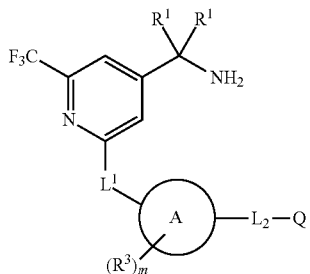
| Compound Number | R¹ | —L¹— | (R³)ₘ | —L₂—Q |
|---|---|---|---|---|
| 1-242 | H | —NHC(=O)— | 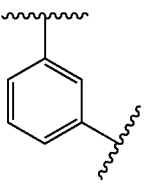 | 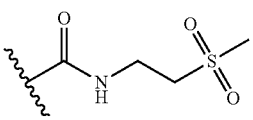 [SMILES: *C(=O)NCCS(C)(=O)=O] |
| 1-243 | H | —CH₂— | 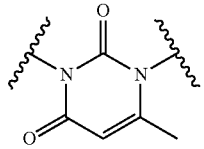 [SMILES: *n1c(C)cc(=O)n(*)c1=O] | 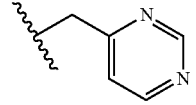 [SMILES: *Cc1ccncn1] |
| 1-244 | H | —O— | 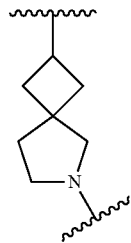 [SMILES: *C1CC2(CCN(*)C2)C1] | 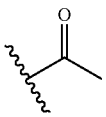 |
| 1-245 | H | —O— | 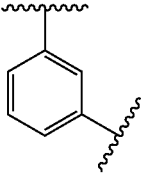 | 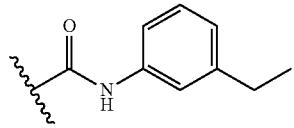 [SMILES: *C(=O)Nc1cccc(CC)c1] |
| 1-246 | H | —O— | 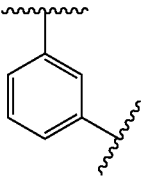 | 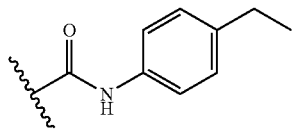 [SMILES: *C(=O)Nc1ccc(CC)cc1] |
| 1-247 | H | —O— | 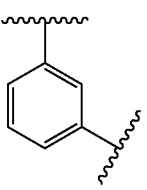 | 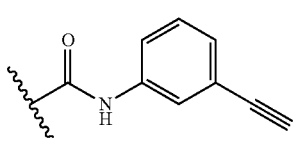 [SMILES: *C(=O)Nc1cccc(C#C)c1] |

TABLE 1-continued

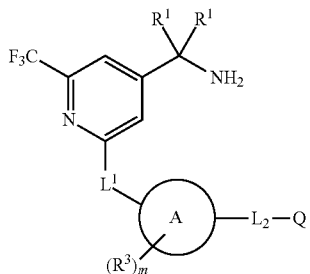

| Compound Number | R¹ | —L¹— | (R³)ₘ | —L₂—Q |
|---|---|---|---|---|
| 1-248 | H | —O— | 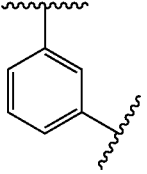 | 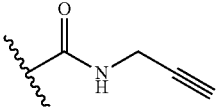 [SMILES: *C(=O)NCC#C] |
| 1-249 | H | —O— | 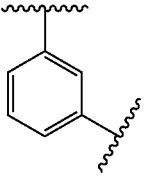 | 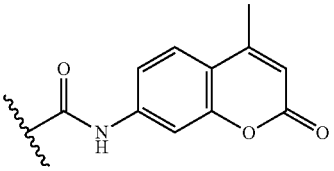 [SMILES: *C(=O)Nc1ccc2c(C)cc(=O)oc2c1] |
| 1-250 (cis Enant-1) | H | —O— | 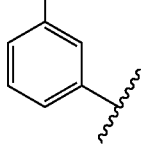 | 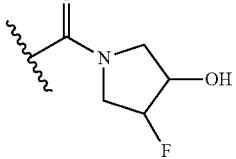 |
| 1-251 (cis Enant-2) | H | —O— | 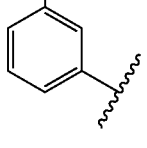 | 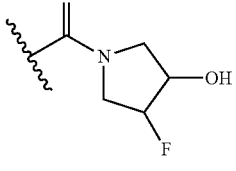 |
| 1-252 | H | —O— | 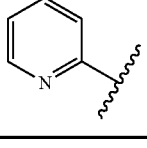 | 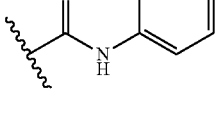 |

In some embodiments, compounds of Formula (I) include, but are not limited to:

(6-(Trifluoromethyl)-[2,3'-bipyridin]-4-yl)methanamine (Compound 1-1);
(2-([1,1'-Biphenyl]-3-yloxy)-6-(trifluoromethyl)pyridin-4-yl)methanamine (Compound 1-2);
(2-(3-Phenoxyphenoxy)-6-(trifluoromethyl)pyridin-4-yl)methanamine (Compound 1-3);
(2-(3-(Phenoxymethyl)phenoxy)-6-(trifluoromethyl)pyridin-4-yl)methanamine (Compound 1-4);
3-((4-(Aminomethyl)-6-(trifluoromethyl)pyridin-2-yl)oxy)-N-phenylaniline (Compound 1-5);
(2-(3-(1H-Pyrazol-4-yl)phenoxy)-6-(trifluoromethyl)pyridin-4-yl)methanamine (Compound 1-6);
3-((4-(Aminomethyl)-6-(trifluoromethyl)pyridin-2-yl)oxy)-N-phenylbenzamide (Compound 1-7);

3-((4-(Aminomethyl-d$_2$)-6-(trifluoromethyl)pyridin-2-yl)oxy)-N-phenylbenzamide (Compound 1-8);

3-((4-(Aminomethyl)-6-(trifluoromethyl)pyridin-2-yl)oxy)-N-(4-fluorobenzyl)benzamide (Compound 1-9);

3-((4-(Aminomethyl)-6-(trifluoromethyl)pyridin-2-yl)oxy)-N-(benzo[b]thiophen-2-ylmethyl)benzamide (Compound 1-10);

(3-((4-(Aminomethyl)-6-(trifluoromethyl)pyridin-2-yl)oxy)phenyl)(3,4-dihydroisoquinolin-2(1H)-yl)methanone (Compound 1-11);

(3-(1H-Pyrazol-1-yl)azetidin-1-yl)(3-((4-(aminomethyl)-6-(trifluoromethyl)pyridin-2-yl)oxy)phenyl)methanone (Compound 1-12);

N-((2H-Tetrazol-5-yl)methyl)-3-((4-(aminomethyl)-6-(trifluoromethyl)pyridin-2-yl)oxy)benzamide (Compound 1-13);

N-(2-(1H-1,2,4-Triazol-1-yl)ethyl)-3-((4-(aminomethyl)-6-(trifluoromethyl)pyridin-2-yl)oxy)benzamide (Compound 1-14);

N-(2-(1H-Tetrazol-1-yl)ethyl)-3-((4-(aminomethyl)-6-(trifluoromethyl)pyridin-2-yl)oxy)benzamide (Compound 1-15);

3-((4-(Aminomethyl)-6-(trifluoromethyl)pyridin-2-yl)oxy)-N-(2-hydroxyethyl)benzamide (Compound 1-16);

(S)-(3-((4-(Aminomethyl)-6-(trifluoromethyl)pyridin-2-yl)oxy)phenyl)(3-hydroxypyrrolidin-1-yl)methanone (Compound 1-17);

(R)-(3-((4-(Aminomethyl)-6-(trifluoromethyl)pyridin-2-yl)oxy)phenyl)(3-hydroxypyrrolidin-1-yl)methanone (Compound 1-18);

Racemic-trans-(3-((4-(aminomethyl)-6-(trifluoromethyl)oxy)phenyl)(3-fluoro-4-hydroxypyrrolidin-1-yl)methanone (Compound 1-19);

(S,S)-trans-(3-((4-(Aminomethyl)-6-(trifluoromethyl)pyridin-2-yl)oxy)phenyl)(3-fluoro-4-hydroxypyrrolidin-1-yl)methanone (Compound 1-20);

(R,R)-trans-(3-((4-(Aminomethyl)-6-(trifluoromethyl)pyridin-2-yl)oxy)phenyl)(3-fluoro-4-hydroxypyrrolidin-1-yl)methanone (Compound 1-21);

(R)-(3-((4-(Aminomethyl)-6-(trifluoromethyl)pyridin-2-yl)oxy)phenyl)(3-aminopyrrolidin-1-yl)methanone (Compound 1-22);

Racemic-trans-(3-((4-(aminomethyl)-6-(trifluoromethyl)pyridin-2-yl)oxy)phenyl)(-3-(dimethylamino)-4-hydroxypyrrolidin-1-yl)methanone (Compound 1-23);

(S)-1-(3-((4-(Aminomethyl)-6-(trifluoromethyl)pyridin-2-yl)oxy)benzoyl)pyrrolidine-2-carboxylic acid (Compound 1-24);

(R)-1-(3-((4-(Aminomethyl)-6-(trifluoromethyl)pyridin-2-yl)oxy)benzoyl)pyrrolidine-2-carboxylic acid (Compound 1-25);

(R)-(3-((4-(Aminomethyl)-6-(trifluoromethyl)pyridin-2-yl)oxy)phenyl)(3-(hydroxymethyl)pyrrolidin-1-yl)methanone (Compound 1-26);

8-(3-((4-(Aminomethyl)-6-(trifluoromethyl)pyridin-2-yl)oxy)benzoyl)-1-oxa-3,8-diazaspiro[4.5]decan-2-one (Compound 1-27);

3-((4-(Aminomethyl)-6-(trifluoromethyl)pyridin-2-yl)oxy)-N-(2-(2-oxooxazolidin-3-yl)ethyl)benzamide (Compound 1-28);

Racemic-3-((4-(aminomethyl)-6-(trifluoromethyl)pyridin-2-yl)oxy)-N-((5-oxopyrrolidin-2-yl)methyl)benzamide (Compound 1-29);

3-((4-(Aminomethyl)-6-(trifluoromethyl)pyridin-2-yl)oxy)-N-(2-(methylsulfonyl)ethyl)benzamide (Compound 1-30);

3-((4-(Aminomethyl)-6-(trifluoromethyl)pyridin-2-yl)oxy)-N-(1-(hydroxymethyl)cyclopropyl)benzamide (Compound 1-31);

3-((4-(Aminomethyl)-6-(trifluoromethyl)pyridin-2-yl)oxy)-N-(2-hydroxy-2-methylpropyl)benzamide (Compound 1-32);

(R)-3-((4-(Aminomethyl)-6-(trifluoromethyl)pyridin-2-yl)oxy)-N-(2,3-dihydroxypropyl)benzamide (Compound 1-33);

3-((4-(Aminomethyl)-6-(trifluoromethyl)pyridin-2-yl)oxy)-N-(2-sulfamoylethyl)benzamide (Compound 1-34);

3-((4-(Aminomethyl)-6-(trifluoromethyl)pyridin-2-yl)oxy)-N-(2-(dimethylamino)ethyl)benzamide (Compound 1-35);

Racemic-trans-(3-(((4-(aminomethyl)-6-(trifluoromethyl)pyridin-2-yl)oxy)methyl)phenyl)(3-fluoro-4-hydroxypyrrolidin-1-yl)methanone (Compound 1-36);

(2-((1-(1-Methyl-1H-pyrazol-4-yl)-1H-indol-4-yl)oxy)-6-(trifluoromethyl)pyridin-4-yl) methanamine (Compound 1-37);

2-(4-((4-(Aminomethyl)-6-(trifluoromethyl)pyridin-2-yl)oxy)-1H-indol-1-yl)-N-methyl-N-phenylacetamide (Compound 1-38);

(R)-3-((4-(Aminomethyl)-6-(trifluoromethyl)pyridin-2-yl)oxy)-N-phenylpyrrolidine-1-carboxamide (Compound 1-39);

(S)-3-((4-(Aminomethyl)-6-(trifluoromethyl)pyridin-2-yl)oxy)-N-phenylpyrrolidine-1-carboxamide (Compound 1-40);

4-((4-(Aminomethyl)-6-(trifluoromethyl)pyridin-2-yl)oxy)-N-phenylpiperidine-1-carboxamide (Compound 1-41);

4-(((4-(Aminomethyl)-6-(trifluoromethyl)pyridin-2-yl)oxy)methyl)-N-phenylpiperidine-1-carboxamide (Compound 1-42);

(R)-3-((4-(Aminomethyl)-6-(trifluoromethyl)pyridin-2-yl)oxy)-N-phenylpiperidine-1-carboxamide (Compound 1-43);

(S)-3-((4-(Aminomethyl)-6-(trifluoromethyl)pyridin-2-yl)oxy)-N-phenylpiperidine-1-carboxamide (Compound 1-44);

(S)-3-(((4-(Aminomethyl)-6-(trifluoromethyl)pyridin-2-yl)oxy)methyl)-N-phenylpiperidine-1-carboxamide (Compound 1-45);

(5)-1-(3-((4-(Aminomethyl)-6-(trifluoromethyl)pyridin-2-yl)oxy)piperidin-1-yl)-2-phenylethanone (Compound 1-46);

(S)-1-(3-((4-(Aminomethyl)-6-(trifluoromethyl)pyridin-2-yl)oxy)piperidin-1-yl)-2-(3,4-dichlorophenyl)ethanone (Compound 1-47);

(S)-2-(3-((4-(Aminomethyl)-6-(trifluoromethyl)pyridin-2-yl)oxy)piperidine-1-carbonyl)-4H-chromen-4-one (Compound 1-48);

(S)-(3-((4-(Aminomethyl)-6-(trifluoromethyl)pyridin-2-yl)oxy)piperidin-1-yl)(pyridin-3-yl)methanone (Compound 1-49);

(S)-(3-((4-(Aminomethyl)-6-(trifluoromethyl)pyridin-2-yl)oxy)piperidin-1-yl)(pyrimidin-5-yl)methanone (Compound 1-50);

(S)-(3-((4-(Aminomethyl)-6-(trifluoromethyl)pyridin-2-yl)oxy)piperidin-1-yl)(5-methyl-1,3,4-oxadiazol-2-yl)methanone (Compound 1-51);

(S)-1-(3-((4-(Aminomethyl)-6-(trifluoromethyl)pyridin-2-yl)oxy)piperidin-1-yl)-2-methylpropan-1-one (Compound 1-52);

5-((4-(Aminomethyl)-6-(trifluoromethyl)pyridin-2-yl)oxy)-N-(2-(methylsulfonyl)ethyl)nicotinamide (Compound 1-53);

(R)-(5-((4-(Aminomethyl)-6-(trifluoromethyl)pyridin-2-yl)oxy)pyridin-3-yl)(3-aminopyrrolidin-1-yl)methanone (Compound 1-54);

Racemic-trans-(5-((4-(aminomethyl)-6-(trifluoromethyl)pyridin-2-yl)oxy)pyridin-3-yl)(-3-fluoro-4-hydroxypyrrolidin-1-yl)methanone (Compound 1-55);

2-(4-((4-(Aminomethyl)-6-(trifluoromethyl)pyridin-2-yl)oxy)-1H-indol-1-yl)-1-(piperidin-1-yl)ethanone (Compound 1-56);

tert-Butyl 4-(2-(4-((4-(aminomethyl)-6-(trifluoromethyl)pyridin-2-yl)oxy)-1H-indol-1-yl)acetyl)piperazine-1-carboxylate (Compound 1-57);

(2-((1H-Indol-4-yl)oxy)-6-(trifluoromethyl)pyridin-4-yl)methanamine (Compound 1-58);

5-((4-(Aminomethyl)-6-(trifluoromethyl)pyridin-2-yl)oxy)-3,4-dihydroquinolin-2(1H)-one (Compound 1-59);

5-((4-(Aminomethyl)-6-(trifluoromethyl)pyridin-2-yl)oxy)-1-(2-hydroxyethyl)-3,4-dihydroquinolin-2(1H)-one (Compound 1-60);

3-((4-(Aminomethyl)-6-(trifluoromethyl)pyridin-2-yl)thio)-N-phenylbenzamide (Compound 1-68);

3-(((4-(Aminomethyl)-6-(trifluoromethyl)pyridin-2-yl)amino)methyl)-N-phenylbenzamide (Compound 1-105);

3-(((4-(Aminomethyl)-6-(trifluoromethyl)pyridin-2-yl)amino)methyl)-N-(2-(methylsulfonyl)ethyl)benzamide (Compound 1-106);

3-((4-(Aminomethyl)-6-(trifluoromethyl)pyridin-2-yl)methyl)-1-benzyl-6-methylpyrimidine-2,4(1H,3H)-dione (Compound 1-134);

3-((4-(Aminomethyl)-6-(trifluoromethyl)pyridin-2-yl)methyl)-1-(2-hydroxyethyl)-6-methylpyrimidine-2,4(1H,3H)-dione (Compound 1-135);

4'-(Aminomethyl)-6'-(trifluoromethyl)-2H-[1,2'-bipyridin]-2-one (Compound 1-161);

1-(3-((4-(Aminomethyl)-6-(trifluoromethyl)pyridin-2-yl)oxy)phenyl)pyridin-2(1H)-one
(Compound 1-169);

3-((4-(Aminomethyl)-6-(trifluoromethyl)pyridin-2-yl)oxy)-N-(2-cyanoethyl)benzamide (Compound 1-198);

1-(3-((4-(Aminomethyl)-6-(trifluoromethyl)pyridin-2-yl)oxy)benzoyl)azetidine-3-carbonitrile (Compound 1-199);

3-((4-(Aminomethyl)-6-(trifluoromethyl)pyridin-2-yl)oxy)-N-(oxetan-3-yl)benzamide (Compound 1-200);

3-((4-(Aminomethyl)-6-(trifluoromethyl)pyridin-2-yl)oxy)-N-((1-hydroxycyclobutyl)methyl)benzamide (Compound 1-201);

3-((4-(Aminomethyl)-6-(trifluoromethyl)pyridin-2-yl)oxy)-N-(2-hydroxyethyl)-N-methylbenzamide (Compound 1-202);

(S)-(3-((4-(Aminomethyl)-6-(trifluoromethyl)pyridin-2-yl)oxy)phenyl)(3-(hydroxymethyl)piperidin-1-yl)methanone (Compound 1-203);

(3-((4-(Aminomethyl)-6-(trifluoromethyl)pyridin-2-yl)oxy)phenyl)(4-(hydroxymethyl)piperidin-1-yl)methanone (Compound 1-204);

(3-((4-(Aminomethyl)-6-(trifluoromethyl)pyridin-2-yl)oxy)phenyl)(4-hydroxy-4-methylpiperidin-1-yl)methanone (Compound 1-205);

(3-((4-(Aminomethyl)-6-(trifluoromethyl)pyridin-2-yl)oxy)phenyl)(3-(methoxymethyl)azetidin-1-yl)methanone (Compound 1-206);

(3-((4-(Aminomethyl)-6-(trifluoromethyl)pyridin-2-yl)oxy)phenyl)(7-oxa-2-azaspiro[3.5]nonan-2-yl)methanone (Compound 1-207);

3-(((4-(Aminomethyl)-6-(trifluoromethyl)pyridin-2-yl)oxy)-N-((3S,4S)-4-hydroxytetrahydro-2H-pyran-3-yl)benzamide (Compound 1-208);

3-((4-(Aminomethyl)-6-(trifluoromethyl)pyridin-2-yl)oxy)-N-((1R,2S)-2-hydroxycyclopentyl)benzamide (Compound 1-209);

3-((4-(Aminomethyl)-6-(trifluoromethyl)pyridin-2-yl)oxy)-N-((1S,2R)-2-hydroxycyclopentyl)benzamide (Compound 1-210);

Racemic-cis-(3-((4-(aminomethyl)-6-(trifluoromethyl)pyridin-2-yl)oxy)phenyl)(3-fluoro-4-hydroxypyrrolidin-1-yl)methanone (Compound 1-211);

(R)-(3-((4-(Aminomethyl)-6-(trifluoromethyl)pyridin-2-yl)oxy)phenyl)(3-fluoropyrrolidin-1-yl)methanone (Compound 1-212);

(S)-(3-((4-(Aminomethyl)-6-(trifluoromethyl)pyridin-2-yl)oxy)phenyl)(3-fluoropyrrolidin-1-yl)methanone (Compound 1-213);

(3R,4R)-1-(3-((4-(Aminomethyl)-6-(trifluoromethyl)pyridin-2-yl)oxy)benzoyl)-4-fluoropyrrolidin-3-yl-methanesulfonate (Compound 1-214);

(3-((4-(Aminomethyl)-6-(trifluoromethyl)pyridin-2-yl)oxy)phenyl)(2,5-dihydro-1H-pyrrol-1-yl)methanone (Compound 1-215);

3-((4-(Aminomethyl)-6-(trifluoromethyl)pyridin-2-yl)oxy)-N-(hex-5-yn-1-yl)benzamide (Compound 1-216);

3-((4-(Aminomethyl)-6-(trifluoromethyl)pyridin-2-yl)oxy)-N-(4-(1-phenyl-1H-1,2,3-triazol-4-yl)butyl)benzamide (Compound 1-217);

3-((4-(Aminomethyl)-6-(trifluoromethyl)pyridin-2-yl)oxy)-N-hydroxybenzamide (Compound 1-218);

3-((4-(Aminomethyl)-6-(trifluoromethyl)pyridin-2-yl)oxy)-N-methoxybenzamide (Compound 1-219);

Methyl (S)-3-(3-((4-(aminomethyl)-6-(trifluoromethyl)pyridin-2-yl)oxy)benzamido)pent-4-ynoate (Compound 1-220);

(S)-3-(3-((4-(Aminomethyl)-6-(trifluoromethyl)pyridin-2-yl)oxy)benzamido)pent-4-ynoic acid (Compound 1-221);

Methyl (R)-3-(3-((4-(aminomethyl)-6-(trifluoromethyl)pyridin-2-yl)oxy)benzamido)pent-4-ynoate (Compound 1-222);

(R)-3-(3-((4-(Aminomethyl)-6-(trifluoromethyl)pyridin-2-yl)oxy)benzamido)pent-4-ynoic acid (Compound 1-223);

3-((4-(Aminomethyl)-6-(trifluoromethyl)pyridin-2-yl)oxy)benzoic acid (Compound 1-224);

3-((4-(Aminomethyl)-6-(trifluoromethyl)pyridin-2-yl)oxy)-N-(2-aminophenyl)benzamide (Compound 1-225);

3-((4-(Aminomethyl)-6-(trifluoromethyl)pyridin-2-yl)oxy)-N-(pyrimidin-5-yl)benzamide (Compound 1-226);

3-((4-(Aminomethyl)-6-(trifluoromethyl)pyridin-2-yl)oxy)-N-(oxazol-2-yl)benzamide (Compound 1-227);

3-((4-(Aminomethyl)-6-(trifluoromethyl)pyridin-2-yl)oxy)-N-(1,3,4-oxadiazol-2-yl)benzamide (Compound 1-228);

Racemic-trans-(3-((4-(aminomethyl)-6-(trifluoromethyl)pyridin-2-yl)oxy)-4-hydroxyphenyl)(3-fluoro-4-hydroxypyrrolidin-1-yl)methanone (Compound 1-229);

Racemic-trans-(3-((4-(aminomethyl)-6-(trifluoromethyl)pyridin-2-yl)oxy)-5-hydroxyphenyl)(3-fluoro-4-hydroxypyrrolidin-1-yl)methanone (Compound 1-230);

Racemic-trans-(3-((4-(aminomethyl)-6-(trifluoromethyl)pyridin-2-yl)oxy)-4-(benzyloxy)phenyl)(3-fluoro-4-hydroxypyrrolidin-1-yl)methanone (Compound 1-231);

Racemic-trans-(3-((4-(aminomethyl)-6-(trifluoromethyl)pyridin-2-yl)oxy)-5-methoxyphenyl)(3-fluoro-4-hydroxypyrrolidin-1-yl)methanone (Compound 1-232);

2-(4-((4-(Aminomethyl)-6-(trifluoromethyl)pyridin-2-yl)oxy)-1H-indol-1-yl)-1-(piperazin-1-yl)ethan-1-one (Compound 1-233);

2-(4-((4-(Aminomethyl)-6-(trifluoromethyl)pyridin-2-yl)oxy)-1H-indol-1-yl)-N-carbamimidoylacetamide (Compound 1-234);

Ethyl 2-(5-((4-(aminomethyl)-6-(trifluoromethyl)pyridin-2-yl)oxy)-2-oxo-3,4-dihydroquinolin-1(2H)-yl)acetate (Compound 1-235);

2-(5-((4-(Aminomethyl)-6-(trifluoromethyl)pyridin-2-yl)oxy)-2-oxo-3,4-dihydroquinolin-1(2H)-yl)acetic acid (Compound 1-236);

(S)-(3-(((4-(Aminomethyl)-6-(trifluoromethyl)pyridin-2-yl)amino)methyl)phenyl)(3-hydroxypyrrolidin-1-yl)methanone (Compound 1-237);

Methyl 3-((4-(aminomethyl)-6-(trifluoromethyl)pyridin-2-yl)carbamoyl)benzoate (Compound 1-238);

3-((4-(Aminomethyl)-6-(trifluoromethyl)pyridin-2-yl)carbamoyl)benzoic acid (Compound 1-239);

$N^1$-(4-(Aminomethyl)-6-(trifluoromethyl)pyridin-2-yl)-$N^3$-phenylisophthalamide (Compound 1-240);

(S)—N-(4-(Aminomethyl)-6-(trifluoromethyl)pyridin-2-yl)-3-(3-hydroxypyrrolidine-1-carbonyl)benzamide (Compound 1-241);

$N^1$-(4-(Aminomethyl)-6-(trifluoromethyl)pyridin-2-yl)-$N^3$-(2-(methylsulfonyl)ethyl)isophthalamide (Compound 1-242);

3-((4-(Aminomethyl)-6-(trifluoromethyl)pyridin-2-yl)methyl)-6-methyl-1-(pyrimidin-4-ylmethyl)pyrimidine-2,4(1H,3H)-dione (Compound 1-243);

1-(2-((4-(Aminomethyl)-6-(trifluoromethyl)pyridin-2-yl)oxy)-6-azaspiro[3.4]octan-6-yl)ethanone (Compound 1-244);

3-((4-(Aminomethyl)-6-(trifluoromethyl)pyridin-2-yl)oxy)-N-(3-ethylphenyl)benzamide (Compound 1-245);

3-((4-(Aminomethyl)-6-(trifluoromethyl)pyridin-2-yl)oxy)-N-(4-ethylphenyl)benzamide (Compound 1-246);

3-((4-(Aminomethyl)-6-(trifluoromethyl)pyridin-2-yl)oxy)-N-(3-ethynylphenyl)benzamide (Compound 1-247);

3-((4-(Aminomethyl)-6-(trifluoromethyl)pyridin-2-yl)oxy)-N-(prop-2-yn-1-yl)benzamide (Compound 1-248);

3-((4-(Aminomethyl)-6-(trifluoromethyl)pyridin-2-yl)oxy)-N-(4-methyl-2-oxo-2H-chromen-7-yl)benzamide (Compound 1-249);

(R,S) or (S,R)-cis-(3-((4-(Aminomethyl)-6-(trifluoromethyl)oxy)phenyl)(3-fluoro-4-hydroxypyrrolidin-1-yl)methanone (Compound 1-250);

(R,S) or (S,R)-cis-(3-((4-(Aminomethyl)-6-(trifluoromethyl)oxy)phenyl)(3-fluoro-4-hydroxypyrrolidin-1-yl)methanone (Compound 1-251);

4-((4-(Aminomethyl)-6-(trifluoromethyl)pyridin-2-yl)oxy)-N-phenylpicolinamide (Compound 1-252);

or a pharmaceutically acceptable salt thereof.

Any combination of the groups described above for the various variables is contemplated herein. Throughout the specification, groups and substituents thereof are chosen by one skilled in the field to provide stable moieties and compounds.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (-L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (-L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Pyridines are prepared using well known synthetic routes (see Allais et al Chem. Rev., 2014, 114, p 10829-10868 and references cited) and these are further functionalized to provide 2-substituted pyridines using a variety of methods. In some embodiments, 2-chloropyridines are obtained from direct chlorination of a pyridine using a suitable chlorination reagent. In some embodiments, the chlorination reagent is $Cl_2$. In some embodiments, 2-chloropyridines are prepared from the treatment of 2-hydroxypyridines with $POCl_3$. In other embodiments, 2-chloropyridines are prepared by the chlorination of a pyridine-N-oxide with a suitable chlorination reagent. In some embodiments, the chorination reagent is $POCl_3$, phosgene or triphosgene. 2-Aminopyridines are prepared by a variety of methods. In some embodiments, 2-aminopyridines are converted to 2-halopyridines using the Sandmeyer reaction. In other embodiments, 2-aminopyridines are prepared from the reaction of the corresponding N-oxide via treatment with t-butyl amine/$Ts_2O$ followed by in situ deprotection (see Yin et al, J. Org. Chem., 2007, 72, p 4554-4557 and references cited). 2-Trifluoromethyl substituted pyridines are prepared by a variety of routes. In some embodiments, 2-iodopyridine is reacted with (trifluoromethyl)copper to afford 2-trifluoromethylpyridine (see Cottet and Schlosser Eur. J. Org. Chem., 2002, 2, p 327-330).

In some embodiments, the O-linked compounds of Formula (I) having the general structure 1-2 are prepared as shown in Scheme 1.

Scheme 1

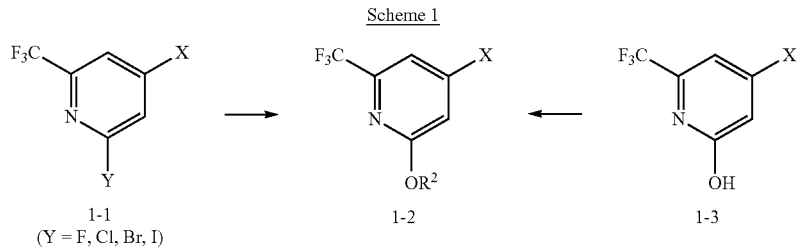

In some embodiments, 4-substituted-2-halo pyridine 1-1 is treated with an appropriately substituted alcohol $R^2OH$ in the presence of a strong base using a suitable polar solvent to provide 1-2. In some embodiments, the strong base is $KO^tBu$. In some embodiments, the polar solvent is DMF. In some embodiments, if $R^2$ is aryl or heteroaryl, a suitable milder base may be employed. In some embodiments, the milder base is $Cs_2CO_3$. In other embodiments, 1-2 is prepared from 2-hydroxypyridine (2-pyridone) 1-3. In some embodiments, o-alkylation is performed with suitable base and an alkylating agent in an appropriate organic solvent provides 1-2. In some embodiments, the suitable base is $Ag_2CO_3$. In other embodiments, the suitable alkylating agent is $R^2$—Br or $R^2$—I. In other embodiments, Mitsunobu conditions are used to achieve the same transformation.

In some embodiments, 2-thioalkylpyridines/2-thioarylpyridines 2-2 (compounds of Formula (I) containing a sulfur linkage), are prepared by treatment of the corresponding 2-halopyridine 2-1 with the appropriate thiol $R^2SH$ and a suitable base in a suitable solvent (Scheme 2). In some embodiments, the suitable base is $Cs_2CO_3$. In some embodiments, the suitable solvent is DMF.

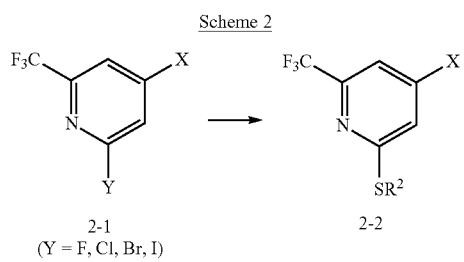

Scheme 2

2-1
(Y = F, Cl, Br, I)

2-2

In some embodiments, compounds of Formula (I) in which there is an amine linking group ($Y=NR^2R^{2'}$) are synthesized according to Scheme 3.

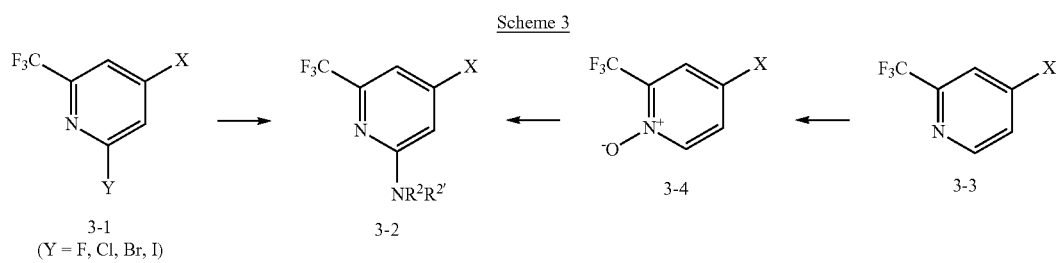

Scheme 3

3-1
(Y = F, Cl, Br, I)

3-2

3-4

3-3

In some embodiments, nucleophilic displacement of a 2-halopyridine 3-1 using an amine $NHR^2R^{2'}$ and a suitable base in a suitable organic solvent provides 3-2. In some embodiments, heat and pressure facilitate the reaction. In some embodiments, the suitable base is $KO^tBu$. In some embodiments, the suitable organic solvent is DMF. In some embodiments, a palladium or a copper catalyst is also used. In some embodiments, pyridines of general structure 3-3 are oxidized to the N-oxide (3-4) using a suitable oxidant. In some embodiments, the suitable oxidant is mCPBA. In some embodiments, treatment of the N-oxide with an amine $NHR^2R^{2'}$ in the presence of bromotripyrrolidinophosphonium hexafluorophosphate (PyBroP) and a suitable organic base in a solvent yields 3-2 (see Londregan Org. Lett., 2010, 12, p 5254-5257). In some embodiments, the suitable organic base is $^iPrEt_2N$. In some embodiments, the suitable solvent is $CH_2Cl_2$.

In some embodiments, the compounds of Formula (I) containing an amide linkage (4-) are prepared as shown in Scheme 4.

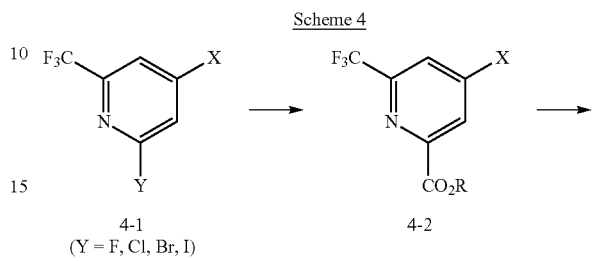

Scheme 4

4-1
(Y = F, Cl, Br, I)

4-2

4-3

4-4

In some embodiments, 2-halopyridine 4-1 may be treated with CO in the presence of a suitable palladium catalyst, a suitable base in a suitable organic solvent to afford the ester 4-2. In some embodiments, the palladium catalyst is $PdCl_2$ $(PPh_3)_4$. In some embodiments, the base is NaOAc. In some embodiments, the organic solvent is MeOH. In some embodiments, the ester is hydrolyzed using aqueous LiOH with a suitable organic solvent to afford acid 4-3. In some embodiments, the organic solvent is MeOH or THF. In some embodiments, standard peptide coupling reaction conditions with an appropriately substituted amine HNR'R" are used to yield amide 4-4.

In some embodiments, the compounds of Formula (I) containing a methyleneoxy or a methylene linkage are prepared as shown in Scheme 5.

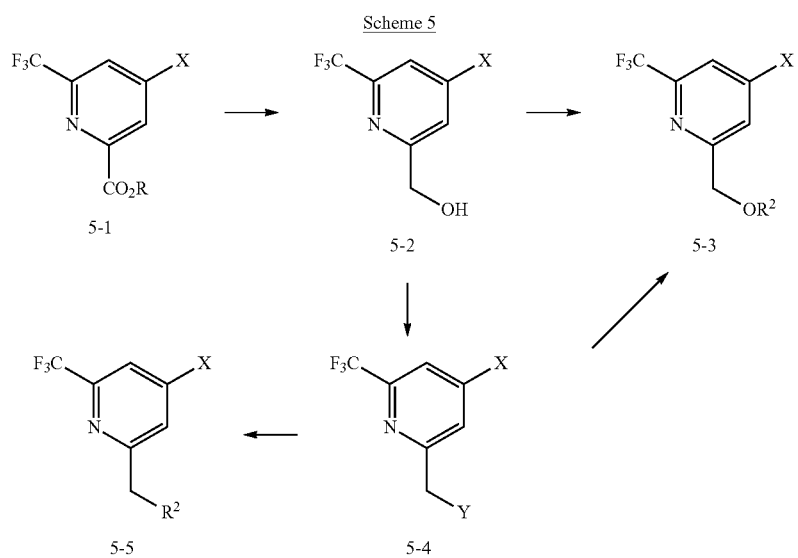

Scheme 5

In some embodiments, ester 5-1 is reduced to the alcohol 5-2 using a suitable reducing agent in an appropriate solvent. In some embodiments, the suitable reducing agent is NaBH$_4$. In some embodiments, the appropriate solvent is MeOH. In some embodiments, alcohol 5-2 is converted to ether 5-3 using the Mitsunobu reaction protocol. In other embodiments, alcohol 5-2 is converted into halogenated 5-4 using an appropriate halogenating reagent. In some embodiments, Y=Br in 5-4. In some embodiments the halogenating reagent is TPP or CBr$_4$. In some embodiments, displacement of the leaving group on 5-4 with an alcohol or phenol yields 5-3. In other embodiments compound 5-4 is reacted with other nucleophiles in the presence of a suitable base and suitable solvent to provide the methylene linked compound 5-5. In some embodiments, the base is NaH. In some embodiments, the suitable solvent is THF.

In some embodiments, the compounds of Formula (I) that contain a bond to an aryl (or heteroaryl) substituent are prepared as described in Scheme 6.

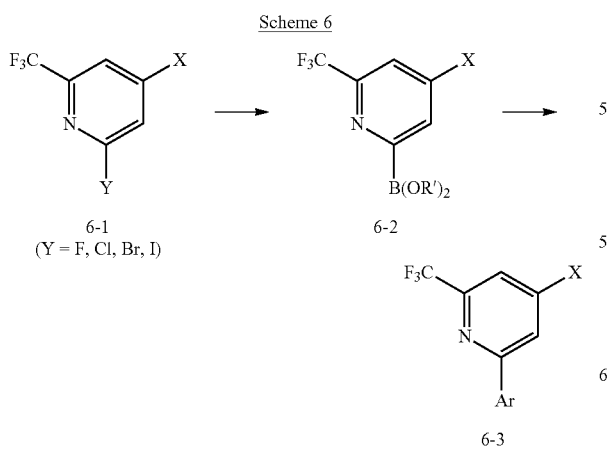

Scheme 6

In some embodiments, 2-halopyridine compound of general structure 6-1 is converted to the corresponding 2-boronic acid or 2-boronate ester derivative 6-2 using standard methodologies, such as those described in Liu et al, ARKIVOC, 2013, (i) p 135-153. In some embodiments, a Suzuki reaction employing 6-2 and an appropriately substituted aryl (or heteroaryl) bromide or iodide using a palladium catalyst in the presence of a suitable base and a suitable solvent affords compound 6-3. In some embodiments, the palladium catalyst is Pd(OAc)$_2$ or Pd(PPh$_3$)$_4$. In other embodiments, the suitable base is K$_2$CO$_3$. In other embodiments, the solvent is DMF. In other embodiments, compound 6-1 is coupled with an aryl (or heteroaryl) boronic acid/ester using standard conditions for the Suzuki reaction to afford 6-3 directly.

4-Aminomethylpyridines are prepared using a number of routes known to one skilled in the art. In some embodiments, 4-aminomethylpyridines are prepared as described in Scheme 7.

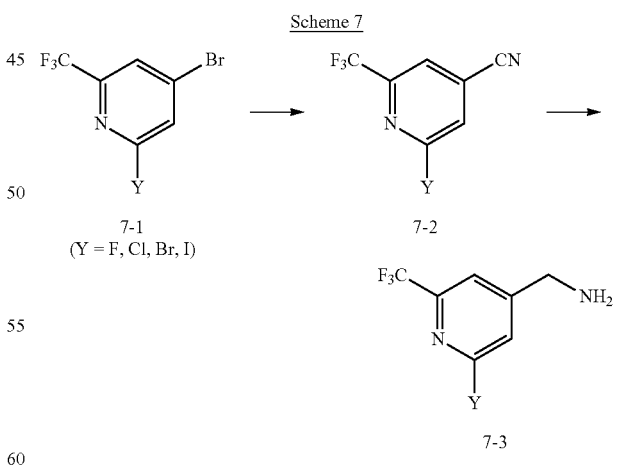

Scheme 7

In some embodiments, 4-bromo-2-picolinic ester derivative 7-1 (Scheme 7) is converted into the 4-cyano analog 7-2 with Zn(CN)$_2$ in the presence of a suitable palladium catalyst. In some embodiments, the suitable palladium catalyst is Pd(PPh$_3$)$_4$. In some embodiments, reduction of the nitrile with a suitable reducing agent affords the methyl amine 7-3.

In some embodiments, the reducing agent is CoCl$_2$ and NaBH$_4$. In some embodiments, the use of NaBD$_4$ in place of NaBH$_4$ allows for the preparation of the corresponding deuteromethyamine.

In some embodiments, pyridine compounds containing a 4-aminomethyl substituent are prepared as shown in Scheme 8.

Scheme 8

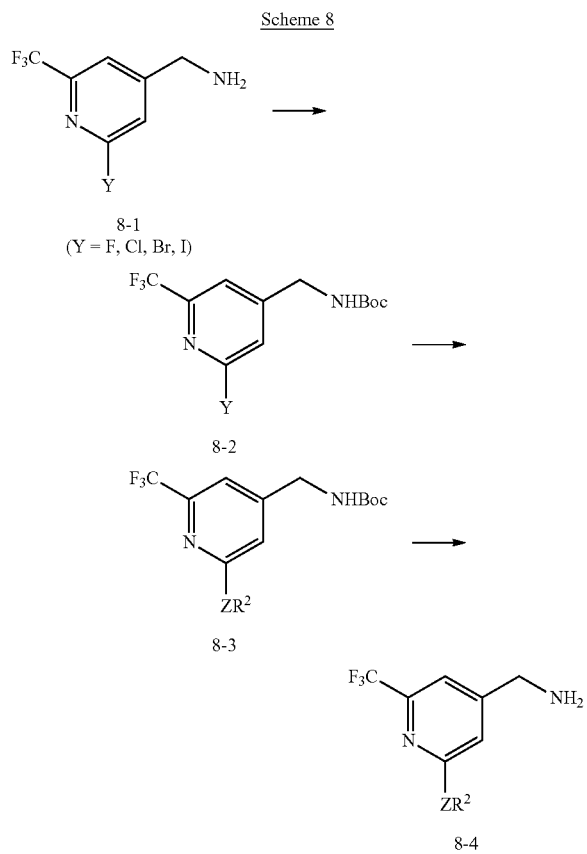

In some embodiments, the appropriately functionalized 4-aminomethyl pyridine 8-1 is treated with Boc$_2$O to afford 8-2. In some embodiments, 8-2 is transformed into 8-3 using the procedures described herein to install the appropriate substituent —ZR$^2$. In some embodiments, deprotection of the amine with TFA or HCl provides 8-4 as the corresponding salt.

In some embodiments, the compounds of Formula (I) containing an amide linkage (9-3) are prepared as shown in Scheme 9.

Scheme 9

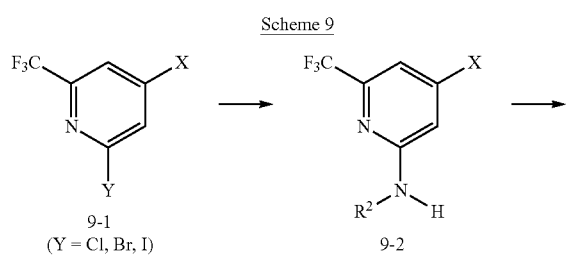

-continued

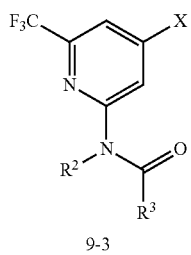

In some embodiments, 2-halopyridine 9-1 is treated with an amine NH$_2$R$^2$ in the presence of a suitable base and in an organic solvent to afford 9-2. In some embodiments, the suitable base is KO$^t$Bu. In some embodiments, the suitable organic solvent is DMF. In some embodiments, standard peptide coupling reaction conditions with an appropriately substituted carboxylic acid R$^3$CO$_2$H affords amide 9-3.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, C$_1$-C$_x$ includes C$_1$-C$_2$, C$_1$-C$_3$ ... C$_1$-C$_x$. By way of example only, a group designated as "C$_1$-C$_4$" indicates that there are one to four carbon atoms in the moiety, i.e. groups containing 1 carbon atom, 2 carbon atoms, 3 carbon atoms or 4 carbon atoms. Thus, by way of example only, "C$_1$-C$_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a C$_1$-C$_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a C$_1$-C$_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a C$_1$-C$_6$alkylene. In other embodiments, an alkylene is a C$_1$-C$_4$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. In some embodiments, bicyclic carbocycles are fused, bridged or spirocyclic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a C$_6$-C$_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a C$_3$-C$_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a C$_1$-C$_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a C$_1$-C$_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. In some embodiments, bicyclic heterocycles are fused, bridged or spirocyclic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring. In some embodiments, bicyclic heterocycloalkyls are fused, bridged or spirocyclic.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch.

The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of LOXL2 activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, hormone blocking therapy, radiation therapy, monoclonal antibodies, or combinations thereof.

Chemotherapy includes the use of anti-cancer agents.

In one aspect, the compound described herein, or a pharmaceutically acceptable salt thereof, is administered or formulated in combination with one or more anti-cancer agents.

EXAMPLES

The following examples are provided for illustrative purposes only and not to limit the scope of the claims provided herein.

Synthesis of Int-A

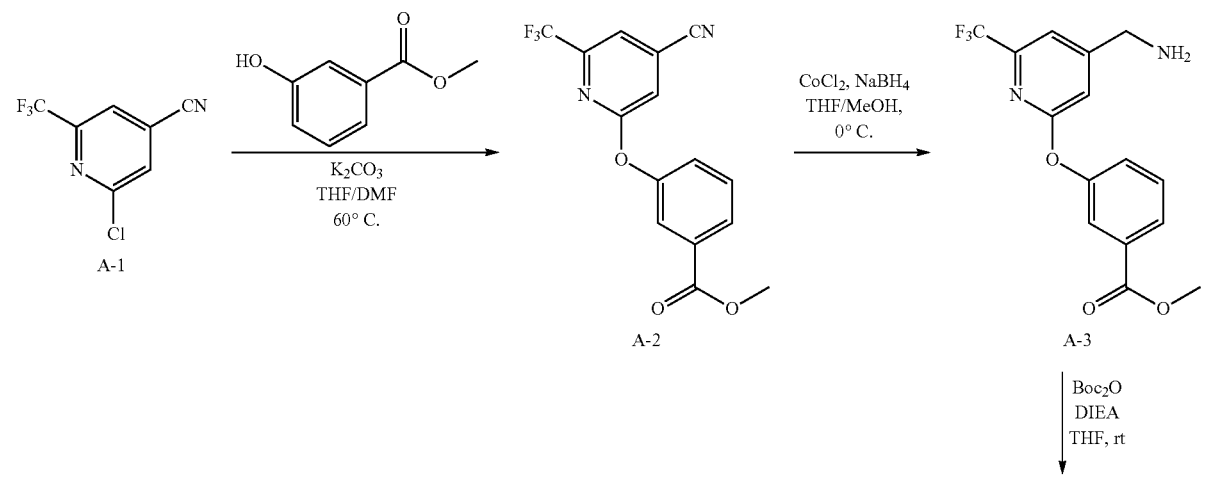

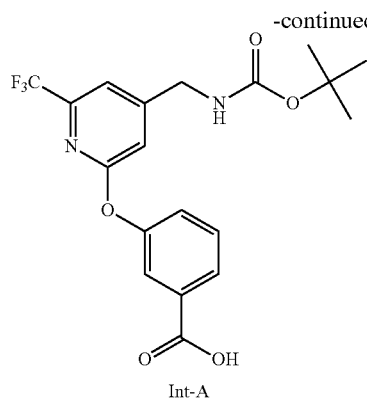

Int-A

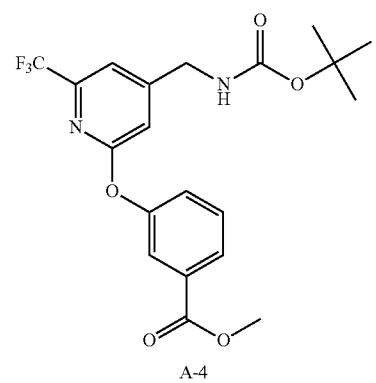

A-4

Step 1: Methyl 3-((4-cyano-6-(trifluoromethyl)pyridin-2-yl)oxy)benzoate (A-2)

To a solution of 2-chloro-6-(trifluoromethyl)isonicotinonitrile A-1 (4.0 g, 19.4 mmol) and methyl 3-hydroxybenzoate (3.24 g, 21.3 mmol) in a mixture of THF/DMF (4:1, 55 ml), was added potassium carbonate (8.0 g, 58 mmol). The reaction mixture was heated at 60° C. for 2 h.

The THF was evaporated under reduced pressure and the remaining reaction mixture was partitioned between water (200 mL) and ethyl acetate (100 mL). The organic layer was separated and the aqueous layer was re-extracted with EtOAc (1×100 ml). The combined organic layers were dried (Na$_2$SO$_4$), filtered, and then concentrated under reduced pressure. The crude residue was purified (silica gel; eluting with 0-50% EtOAc in hexanes), to afford compound A-2 as a light yellow solid (5.63 g, 91%). $^1$H NMR (300 MHz, DMSO-d$_6$): δ 8.21 (m, 1H), 8.07 (m, 1H), 7.87 (m, 1H), 7.77 (m, 1H), 7.64 (m, 1H), 7.55 (m, 1H), 3.85 (s, 3H); LCMS Mass: 323.0 (M$^+$+1).

Step 2: Methyl 3-((4-(aminomethyl)-6-(trifluoromethyl)pyridin-2-yl)oxy)benzoate (A-3)

To a stirred solution of methyl 3-((4-cyano-6-(trifluoromethyl)pyridin-2-yl)oxy)benzoate A-2 (1.5 g, 4.65 mmol) in THF/MeOH (1:1, 140 mL) at 0° C., was added portion-wise CoCl$_2$ (1.8 g, 13.98 mmol) followed by NaBH$_4$ (1.77 g, 46.5 mmol). The reaction mixture was stirred at 0° C. for 20 minutes. The mixture was diluted with EtOAc (100 mL) and filtered through celite. The filtrate was concentrated and the resulting residue was partitioned between water (200 mL) and EtOAc (200 mL). The water-organic layer was filtered through celite and the organic layer was separated, dried (Na$_2$SO$_4$), filtered, and then concentrated under reduced pressure to obtain compound A-3 as an amber oil (1.38 g, 92%) which did not require further purification. $^1$H NMR (300 MHz, DMSO-d$_6$): δ 7.83 (m, 1H), 7.67 (m, 1H), 7.65 (br m, 1H), 7.60 (m, 1H), 7.47 (m, 1H), 7.33 (br m, 1H), 3.80-3.83 (m, 5H); LCMS Mass: 327.0 (M$^+$+1).

Step 3: Methyl 3-((4-(((tert-butoxycarbonyl)amino)methyl)-6-(trifluoromethyl)pyridin-2-yl)oxy)benzoate (A-4)

To a stirred solution of ester A-3 (1.38 g, 4.24 mmol) in THF (25 mL) at 0° C., was added di-tert-butyl dicarbonate (1.29 g, 5.94 mmol) and DIEA (2.21 mL, 12.74 mmol). The mixture was warmed to RT and stirred for a further 4 h. The mixture was concentrated and the residue partitioned between EtOAc (50 mL) and water (50 mL). The organic layer was separated, dried (Na$_2$SO$_4$), filtered, and concentrated in vacuo. The residue was purified (silica gel; 0-60% EtOAc in hexanes), to afford compound A-4 as an amber oil (1.42 g, 78%). $^1$H NMR (300 MHz, DMSO-d$_6$): δ 7.85 (m, 1H), 7.69 (m, 1H), 7.58-7.62 (m, 2H), 7.48-7.51 (m, 2H), 7.13 (br m, 1H), 4.20 (m, 2H), 3.84 (s, 3H), 1.36 (s, 9H); LCMS Mass: 427.0 (M$^+$+1).

Step 4: 3-((4-(((tert-Butoxycarbonyl)amino)methyl)-6-(trifluoromethyl)pyridin-2-yl)oxy)benzoic acid (Int-A)

To a stirred solution of ester A-4 (1.42 g, 3.34 mmol) in a mixture of THF/H$_2$O (6:1, 21 mL) was added aqueous 4M LiOH (17 mL, 68 mmol). The mixture was stirred at RT for 16 h, then diluted with water (30 ml) and acidified to pH 3-4 using aq. sat. citric acid. The mixture was extracted with EtOAc (2×50 mL), and the combined organic layers were dried (Na$_2$SO$_4$), filtered, and concentrated under reduced pressure to afford Int-A as an off white solid (1.2 g, 87%). $^1$H NMR (300 MHz, DMSO-d$_6$): δ 13.17 (br s, 1H), 7.83 (m, 1H), 7.66 (br m, 1H), 7.53-7.62 (m, 2H), 7.44-7.51 (m, 2H), 7.12 (br m, 1H), 4.25 (m, 2H), 1.36 (s, 9H); LCMS Mass: 413.0 (M$^+$+1).

Synthesis of Int-B

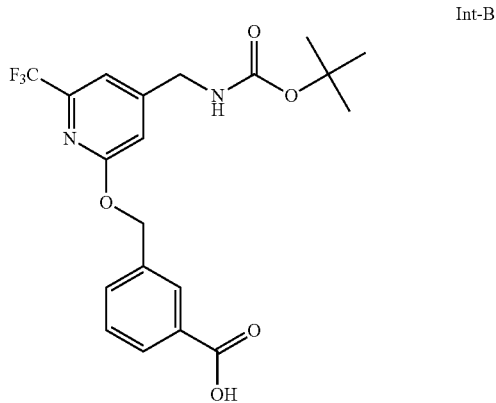 [SMILES: CC(C)(C)OC(=O)NCc1cc(OCc2cccc(C(=O)O)c2)nc(C(F)(F)F)c1]

Int-B 3-(((4-(((tert-Butoxycarbonyl)amino)methyl)-6-(trifluoromethyl)pyridin-2-yl)oxy)methyl)benzoic acid (Int-B)

The title compound (Int-B) was prepared using the procedure described for Int-A, using 3-(hydroxymethy)benzoic acid methyl ester in Step 1. ¹H NMR (300 MHz, DMSO-d₆): δ 12.99 (s, 1H), 8.04 (s, 1H), 7.88 (m, 1H), 7.70 (m, 1H), 7.45-7.60 (m, 2H), 7.35 (m, 1H), 6.99 (m, 1H), 5.42 (s, 2H), 4.15-4.22 (m, 2H), 1.36 (s, 9H); LCMS Mass: 427.0 (M⁺+1).
Synthesis of Int-C

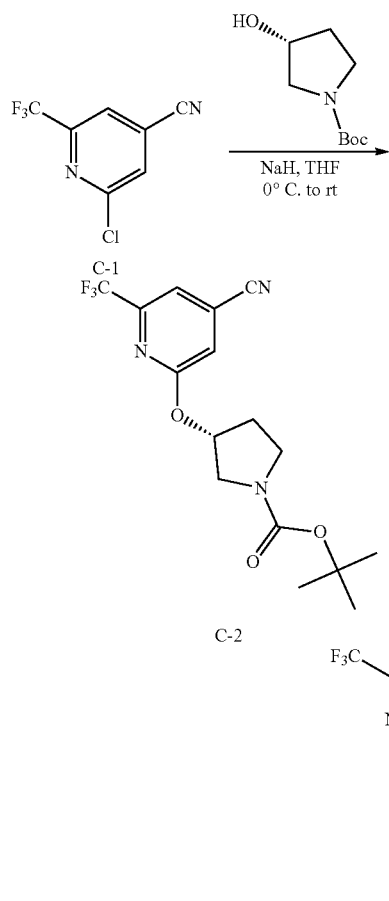

Step 1: (R)-tert-Butyl 3-((4-cyano-6-(trifluoromethyl)pyridin-2-yl)oxy)pyrrolidine-carboxylate (C-2)

To a stirred solution of (R)-1-N-boc-3-hydroxypyrrolidine (250 mg, 1.34 mmol) in THF (4 mL) at 0° C., was added NaH (64 mg of a 60% dispersion in mineral oil, 1.60 mmol). The mixture was stirred at 0° C. for 20 min. A solution of 2-chloro-6-(trifluoromethyl)isonicotinonitrile C-1 (276 mg, 1.34 mmol) in THF (3 mL) was added, and the mixture was warmed to RT and stirred for 6 h. The mixture was concentrated under reduced pressure and the residue partitioned between DCM (50 mL) and water (50 mL). The organic layer was separated, dried (MgSO₄), filtered, and then concentrated in vacuo. The crude residue was purified (silica gel; eluting with 0-30% EtOAc in hexanes), to afford compound C-2 as a colorless oil (317 mg, 66%). ¹H NMR (300 MHz, DMSO-d₆): δ 8.04 (s, 1H), 7.81 (s, 1H), 5.49 (m, 1H), 3.58 (m, 1H), 3.20-3.45 (m, 3H), 2.18 (m, 1H), 2.09 (m, 1H); LCMS Mass: 258.0 (M⁺+1–Boc).

Step 2: (R)-2-(Pyrrolidin-3-yloxy)-6-(trifluoromethyl)isonicotinonitrile hydrochloride (Int-C)

To a stirred solution of C-2 (313 mg, 0.876 mmol) in DCM (3 mL) at RT, was added 2M HCl in Et₂O (3 mL, 6.0 mmol). The mixture was stirred at RT for 18 h. The mixture was concentrated under reduced pressure to afford compound Int-C (229 mg, 89%) as a white solid. ¹H NMR (300 MHz, DMSO-d₆): δ 9.45 (br s, 2H), 8.09 (s, 1H), 7.80 (s, 1H), 5.58 (m, 1H), 3.53 (m, 1H), 3.30-3.40 (m, 3H), 2.10-2.40 (m, 2H); LCMS Mass: 258.0 (M⁺+1).
Synthesis of Int-D

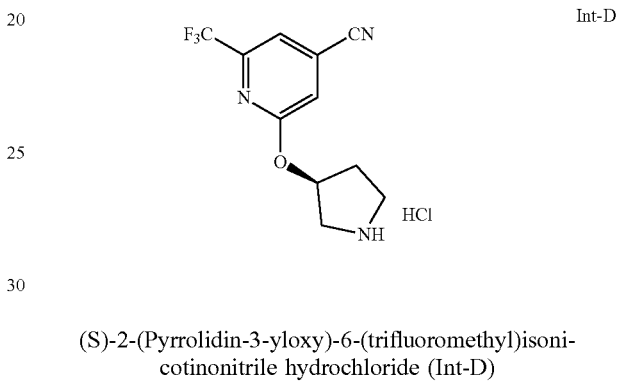

(S)-2-(Pyrrolidin-3-yloxy)-6-(trifluoromethyl)isonicotinonitrile hydrochloride (Int-D)

The title compound (Int-D) was prepared using the procedure described for Int-C, using (S)-1-N-boc-3-hydroxypyrrolidine in Step 1. ¹H NMR (300 MHz, DMSO-d₆): δ 9.40 (br s, 2H), 8.10 (s, 1H), 7.80 (s, 1H), 5.58 (m, 1H), 3.51 (m, 1H), 3.30-3.40 (m, 3H), 2.10-2.40 (m, 2H); LCMS Mass: 258.0 (M⁺+1).
Synthesis of Int-E

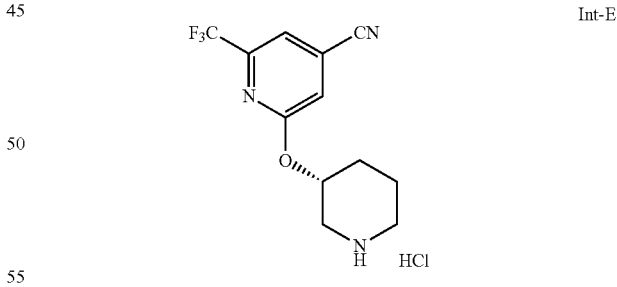

(R)-2-(Piperidin-3-yloxy)-6-(trifluoromethyl)isonicotinonitrile hydrochloride (Int-E)

The title compound (Int-E) was prepared using the procedure described for Int-C, using (R)-1-N-boc-3-hydroxypiperidine in Step 1. ¹H NMR (300 MHz, DMSO-d₆): δ 9.28 (br s, 1H), 8.94 (br s, 1H), 8.08 (s, 1H), 7.75 (s, 1H), 5.31 (m, 1H), 3.20-3.50 (m, 2H), 3.00-3.10 (m, 2H), 1.80-2.00 (m, 3H), 1.70 (m, 1H); LCMS Mass: 272.0 (M⁺+1).

Synthesis of Int-F

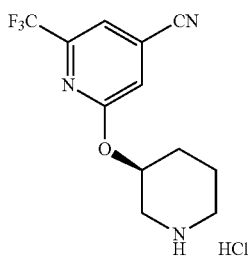

Int-F (S)-2-(Piperidin-3-yloxy)-6-(trifluoromethyl)isonicotinonitrile hydrochloride (Int-F)

The title compound (Int-F) was prepared using the procedure described for Int-C, using (S)-1-N-boc-3-hydroxypiperidine in Step 1. $^1$H NMR (300 MHz, DMSO-$d_6$): δ 9.26 (br s, 1H), 8.90 (br s, 1H), 8.08 (s, 1H), 7.74 (s, 1H), 5.30 (m, 1H), 3.20-3.50 (m, 2H), 3.00-3.10 (m, 2H), 1.80-2.00 (m, 3H), 1.71 (m, 1H); LCMS Mass: 272.0 (M$^+$+1).

Synthesis of Int-G

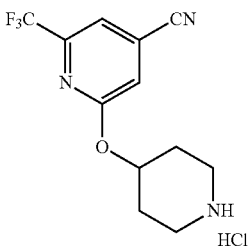

Int-G 2-(Piperidin-4-yloxy)-6-(trifluoromethyl)isonicotinonitrile hydrochloride (Int-G)

The title compound (Int-G) was prepared using the procedure described for Int-C, using 1-boc-4-hydroxypiperidine in Step 1. $^1$H NMR (300 MHz, DMSO-$d_6$): δ 8.89 (br s, 2H), 8.04 (s, 1H), 7.81 (s, 1H), 5.24 (m, 1H), 3.05-3.30 (m, 4H), 2.10-2.25 (m, 2H), 1.85-2.00 (m, 2H); LCMS Mass: 272.0 (M$^+$+1).

Synthesis of Int-H

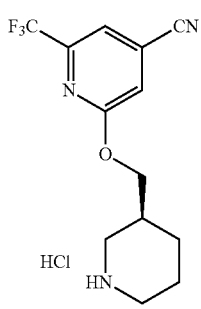

Int-H (S)-2-(Piperidin-3-ylmethoxy)-6-(trifluoromethyl)isonicotinonitrile hydrochloride (Int-H)

The title compound (Int-H) was prepared using the procedure described for Int-C, using (S)—N-boc-3-piperidinemethanol in Step 1. $^1$H NMR (300 MHz, DMSO-$d_6$): δ 9.02 (br s, 1H), 8.85 (br s, 1H), 8.05 (s, 1H), 7.81 (s, 1H), 4.16-4.35 (m, 2H), 3.23 (m, 1H), 2.65-2.80 (m, 2H), 2.24 (m, 1H), 1.60-1.90 (m, 3H), 1.25-1.40 (m, 2H); LCMS Mass: 286.0 (M$^+$+1).

Synthesis of Int-I

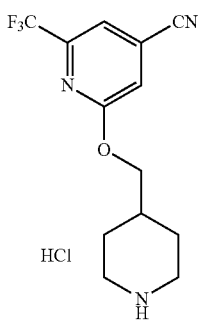

Int-I 2-(Piperidin-4-ylmethoxy)-6-(trifluoromethyl)isonicotinonitrile hydrochloride (Int-I)

The title compound (Int-I) was prepared using the procedure described for Int-C, using 1-boc-4-(hydroxymethyl)piperidine in Step 1. $^1$H NMR (300 MHz, DMSO-$d_6$): δ 8.96 (br s, 1H), 8.63 (br s, 1H), 8.04 (s, 1H), 7.78 (s, 1H), 4.15-4.25 (m, 2H), 3.20-3.30 (m, 2H), 2.80-2.95 (m, 2H), 2.06 (m, 1H), 1.80-1.95 (m, 2H), 1.40-1.60 (m, 2H); LCMS Mass: 286.0 (M$^+$+1).

Synthesis of Int-J

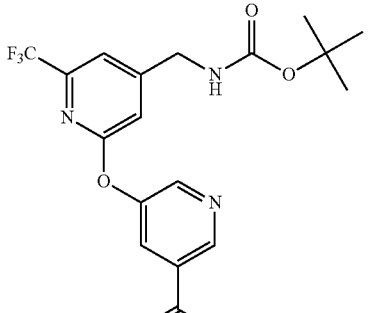

Int-J 5-((4-(((tert-Butoxycarbonyl)amino)methyl)-6-(trifluoromethyl)pyridin-2-yl)oxy)nicotinic acid (Int-J)

The title compound (Int-J) was prepared using the procedure described for Int-A, using 5-hydroxy-nicotinic acid methyl ester in Step 1. $^1$H NMR (300 MHz, DMSO-$d_6$): δ 8.92 (m, 1H), 8.70 (m, 1H), 8.05 (m, 1H), 7.61 (m, 1H), 7.55 (s, 1H), 7.21 (s, 1H), 4.24-4.29 (m, 2H), 1.39 (s, 9H); LCMS Mass: 414.0 (M$^+$+1).

Synthesis of Int-K

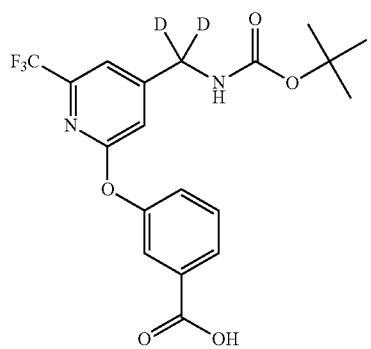

Int-K

3-((4-(((tert-Butoxycarbonyl)amino)methyl-d₂)-6-(trifluoromethyl)pyridin-2-yl)oxy)benzoic acid (Int-K)

The title compound (Int-K) was prepared using the procedure described for Int-A, using NaBD₄, THF-d₈, and MeOH-d₄ in Step 2. ¹H NMR (300 MHz, DMSO-d₆): δ 13.00 (br s, 1H), 7.82 (m, 1H), 7.66 (m, 1H), 7.55-7.60 (m, 2H), 7.43-7.52 (m, 2H), 7.12 (m, 1H), 1.36 (s, 9H); LCMS Mass: 415.0 (M⁺+1).

Synthesis of Int-L

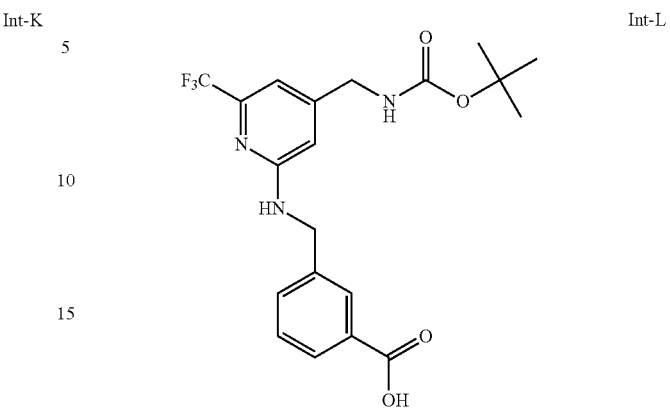

Int-L

3-(((4-(((tert-Butoxycarbonyl)amino)methyl)-6-(trifluoromethyl)pyridin-2-yl)amino)methyl)benzoic acid (Int-L)

The title compound (Int-L) was prepared using the procedure described for Int-A, using methyl 3-(aminomethyl)benzoate hydrochloride in Step 1. ¹H NMR (500 MHz, DMSO-d₆): δ 12.82 (br s, 1H), 7.92 (s, 1H), 7.79 (m, 1H), 7.71 (m, 1H), 7.55 (m, 1H), 7.41 (m, 2H), 6.79 (s, 1H), 6.59 (s, 1H), 4.51 (m, 2H), 4.04 (m, 2H), 1.37 (s, 9H); LCMS Mass: 426.0 (M⁺+1).

Synthesis of Int-M

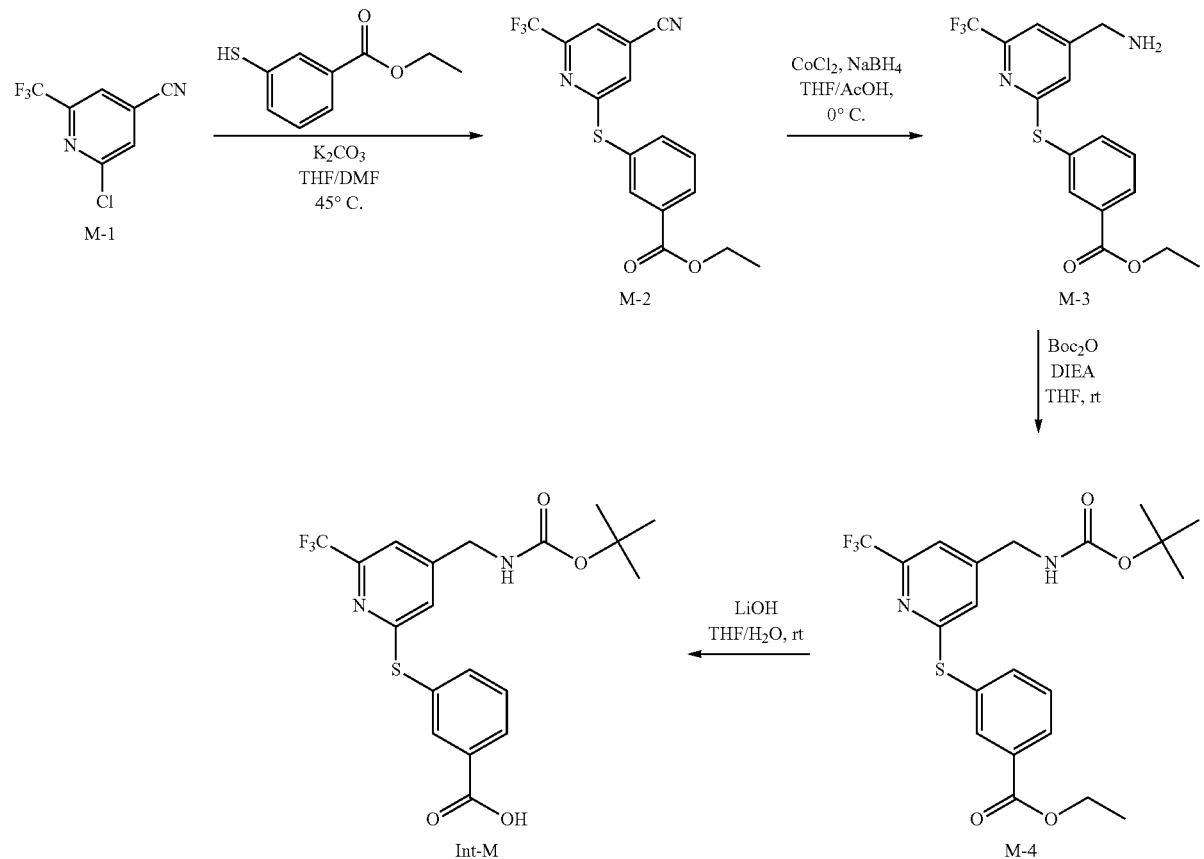

Step 1: Ethyl 3-((4-cyano-6-(trifluoromethyl)pyridin-2-yl)thio)benzoate (M-2)

The title compound (M-2) (680 mg, 100%) was prepared from 2-chloro-6-(trifluoromethyl)isonicotinonitrile (M-1) and ethyl 3-sulfanylbenzoate, using the procedure described for Int-A, Step 1. LCMS Mass: 353.0 (M$^+$+1).

Step 2: Ethyl 3-((4-(aminomethyl)-6-(trifluoromethyl)pyridin-2-yl)thio)benzoate (M-3)

To a stirred solution of compound M-2 (680 mg, 1.93 mmol) in THF (10 mL) and acetic acid (6 mL) at 0° C., was added portion-wise CoCl$_2$ (626 mg, 4.82 mmol) followed by NaBH$_4$ (365 mg, 9.65 mmol). The reaction mixture was stirred at 0° C. for 20 minutes then warmed to RT and stirred for 10 min. The mixture was diluted with EtOAc (30 mL) and filtered through celite. The filtrate was concentrated and the resulting residue was partitioned between water and EtOAc, and stirred for 15 min. The water-organic layer was filtered through celite and the organic layer was separated, washed with brine, dried (Na$_2$SO$_4$), filtered, and then concentrated under reduced pressure to obtain compound M-3 (565 mg) which was used without further purification. LCMS Mass: 357.0 (M$^+$+1).

Step 3: Ethyl 3-((4-(((tert-butoxycarbonyl)amino)methyl)-6-(trifluoromethyl)pyridin-2-yl)thio)benzoate (M-4)

The title compound (M-4) (410 mg, 57%) was prepared from compound M-1 using the procedure described for Int-A, Step 3. LCMS Mass: 457.0 (M$^+$+1).

Step 4: 3-((4-(((tert-Butoxycarbonyl)amino)methyl)-6-(trifluoromethyl)pyridin-2-yl)thio)benzoic acid (Int-M)

The title compound (Int-M) (340 mg, 88%) was prepared from compound M-4 using the procedure described for Int-A, Step 4. $^1$H NMR (300 MHz, DMSO-d$_6$): δ 8.00-8.10 (m, 2H), 7.82 (m, 1H), 7.64 (m, 1H), 7.51 (m, 1H), 7.44 (m, 1H), 7.03 (m, 1H), 4.09-4.18 (m, 2H), 1.30 (s, 9H); LCMS Mass: 429.0 (M$^+$+1).

Synthesis of Int-N

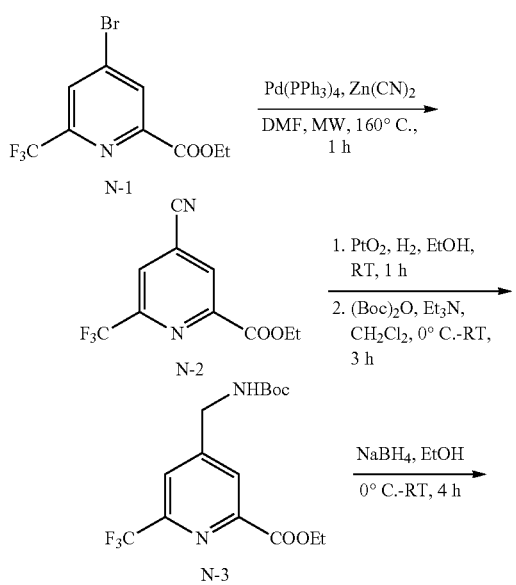

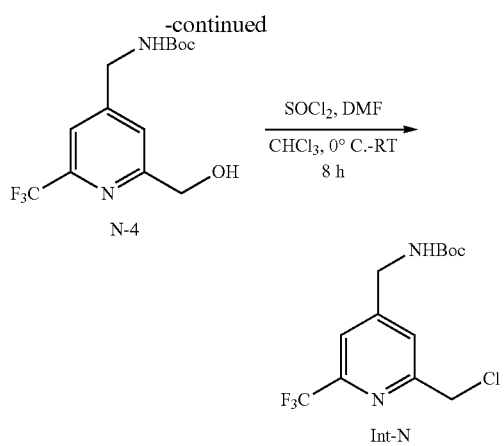

Step 1: Ethyl 4-cyano-6-(trifluoromethyl)picolinate (N-2)

To a stirred solution of ethyl 4-bromo-6-(trifluoromethyl)picolinate N-1 (1 g, 3.35 mmol) in DMF (10 mL) at RT, were added Zn(CN)$_2$ (589 mg, 5.03 mmol) followed by Pd(PPh$_3$)$_4$ (387 mg, 0.33 mmol). The mixture was degassed under argon for 10 min. The reaction mixture was placed in a Biotage microwave synthesizer and stirred at 160° C. for 1 h. The reaction mixture was cooled to RT, diluted with water (30 mL) and extracted with EtOAc (2×50 mL). The combined organic extracts were washed with brine (25 mL), dried (Na$_2$SO$_4$), filtered, and concentrated under reduced pressure. The residue was purified (silica gel; eluting with 4% EtOAc in hexanes), to afford compound N-2 (400 mg, 49%) as white solid. $^1$H NMR (500 MHz, CDCl$_3$): δ 8.51 (s, 1H), 8.07 (d, J=1.2 Hz, 1H), 4.54 (q, J=7.2 Hz, 2H), 1.47 (t, J=7.2 Hz, 3H).

Step 2: Ethyl 4-(((tert-butoxycarbonyl)amino)methyl)-6-(trifluoromethyl)picolinate (N-3)

To a stirred solution of compound N-2 (250 mg, 1.02 mmol) in ethanol (10 mL) at RT, was added PtO$_2$ (25 mg). The reaction mixture was stirred at RT under hydrogen (1 atmosphere pressure) for 1 h. The reaction mixture was filtered through a pad of celite and the celite was washed with ethanol (10 mL). The combined filtrate was concentrated under reduced pressure to obtain the desired amine.

The amine was dissolved in CH$_2$Cl$_2$ (10 mL), cooled to 0° C., and to this were added di-tert-butyl-dicarbonate (0.35 mL, 1.54 mmol) followed by TEA (0.43 mL, 3.07 mmol). The reaction mixture was warmed to RT and stirred for 3 h. The mixture was diluted with water (20 mL) and extracted with EtOAc (2×30 mL). The combined organic extracts were washed with brine (20 mL), dried (Na$_2$SO$_4$), filtered, and concentrated under reduced pressure. The residue was purified (silica gel; eluting with 15% EtOAc in hexanes), to afford compound N-3 (180 mg, 50%) as pale yellow oil. $^1$H NMR (500 MHz, CDCl$_3$): δ 8.20 (s, 1H), 7.77 (s, 1H), 5.11 (br s, 1H), 4.46-4.54 (m, 4H), 1.50 (s, 9H), 1.46 (t, J=7.1 Hz, 3H); LCMS Mass: 349.1 (M$^+$+1).

Step 3: tert-Butyl ((2-(hydroxymethyl)-6-(trifluoromethyl)pyridin-4-yl)methyl)carbamate (N-4)

To a stirred solution of compound N-3 (180 mg, 0.52 mmol) in ethanol (10 mL) at 0° C. under an inert atmosphere, was added NaBH$_4$ (79 mg, 2.07 mmol) portion-wise. The reaction mixture was warmed to RT and stirred for 4 h. The reaction mixture was quenched with saturated aq. NH$_4$Cl solution (15 mL) and extracted with EtOAc (2×20 mL). The combined organic extracts were washed with brine (15 mL), dried (Na$_2$SO$_4$), filtered, and concentrated under reduced pressure. The residue was purified (silica gel; eluting with 30% EtOAc in hexanes) to afford compound N-4 (100 mg, 63%) as colorless viscous syrup. $^1$H NMR (400 MHz, CDCl$_3$): δ 7.50 (s, 1H), 7.40 (s, 1H), 5.02 (br s, 1H), 4.82 (d, J=5.3 Hz, 2H), 4.41 (br d, J=6.3 Hz, 2H), 3.19 (t, J=5.4 Hz, 1H), 1.47 (s, 9H); LCMS Mass: 306.9 (M$^+$+1).

Step 4: tert-Butyl ((2-(chloromethyl)-6-(trifluoromethyl)pyridin-4-yl)methyl)carbamate (Int-N)

To a stirred solution of tert-butyl ((2-(hydroxymethyl)-6-(trifluoromethyl)pyridin-4-yl)methyl)carbamate N-4 (60 mg, 0.2 mmol) in CHCl$_3$ (5 mL) at 0° C., were added thionyl chloride (0.02 mL, 0.29 mmol) followed by DMF (cat), drop-wise. The reaction mixture was warmed to RT and stirred for 8 h. The reaction mixture was poured into ice-cold water (10 mL), basified with saturated aq. NaHCO$_3$ solution to pH ~8, and extracted with CH$_2$Cl$_2$ (2×10 mL). The combined organic extracts washed with brine (7 mL), dried (Na$_2$SO$_4$), filtered, and concentrated under reduced pressure to afford Int-N (45 mg) as pale yellow oil, which was used without further purification. $^1$H NMR (400 MHz, CDCl$_3$): δ 7.63 (s, 1H), 7.53 (s, 1H), 5.09 (br s, 1H), 4.72 (s, 2H), 4.42 (br d, J=5.9 Hz, 2H), 1.48 (br s, 9H); LCMS Mass: 325.2 (M$^+$+1).

Synthesis of Int-O

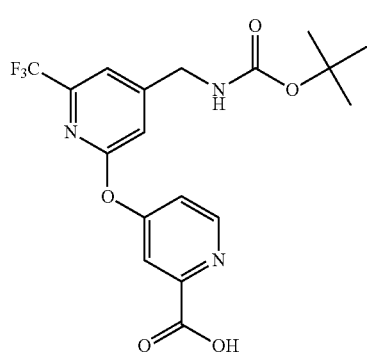

Int-O 4-((4-(((tert-Butoxycarbonyl)amino)methyl)-6-(trifluoromethyl)pyridin-2-yl)oxy)picolinic acid (Int-O)

The title compound (Int-O) was prepared using the procedure described for Int-A, using 4-hydroxy-pyridine-2-carboxylic acid methyl ester in Step 1. LCMS Mass: 414.0 (M$^+$+1).

Example 1: 3-((4-(Aminomethyl)-6-(trifluoromethyl)pyridin-2-yl)oxy)-N-phenylbenzamide hydrochloride (Compound 1-7)

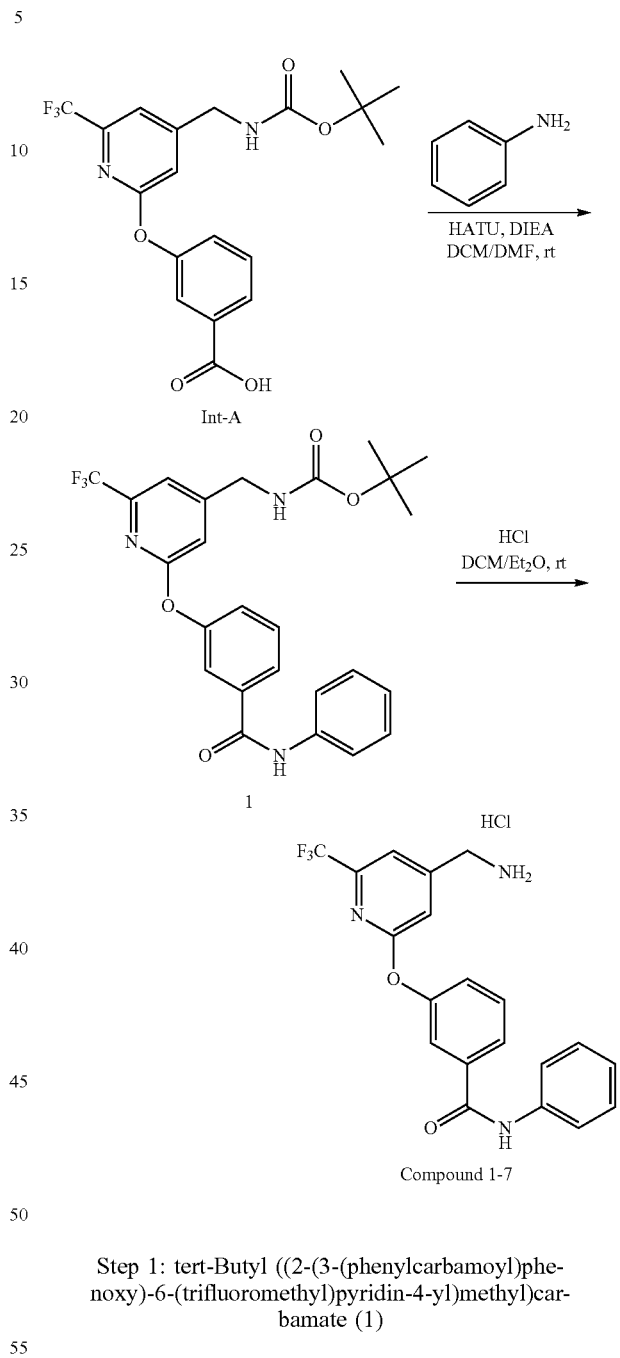

Step 1: tert-Butyl ((2-(3-(phenylcarbamoyl)phenoxy)-6-(trifluoromethyl)pyridin-4-yl)methyl)carbamate (1)

To a stirred solution of Int-A (750 mg, 1.82 mmol) in a mixture of DCM/DMF (3:1, 12 mL), was added HATU (1.04 g, 2.74 mmol) and the mixture was stirred at RT for 20 min. Aniline (219 mg, 2.35 mmol) and DIEA (702 mg, 5.44 mmol) were added and the mixture stirred at RT for 18 h. The DCM was evaporated under reduced pressure and the remaining reaction mixture was partitioned between water (100 mL) and EtOAc (100 mL). The organic layer was separated, dried (Na$_2$SO$_4$), filtered, and then concentrated under reduced pressure. The crude residue was purified (silica gel; eluting with 0-60% EtOAc in hexanes), to afford compound 1 (630 mg, 71%) as an off-white solid. $^1$H NMR (300 MHz, DMSO-d$_6$): δ 10.27 (s, 1H), 7.86 (m, 2H), 7.72-7.77 (m, 2H), 7.57-7.64 (m, 2H), 7.51 (m, 1H), 7.44 (m, 1H), 7.30-7.36 (m, 2H), 7.06-7.13 (m, 2H), 4.25 (m, 2H), 1.35 (s, 9H); LCMS Mass: 510.0 (M$^+$+Na) and 432.0 (MH$^+$–C$_4$H$_8$).

Step 2: 3-((4-(Aminomethyl)-6-(trifluoromethyl) pyridin-2-yl)oxy)-N-phenylbenzamide hydrochloride (Compound 1-7)

To a stirred mixture of amide 1 (630 mg, 1.29 mmol) in DCM (27 mL) at RT, was added 2 M HCl in Et$_2$O (9.69 mL, 19.38 mmol). The mixture was stirred at RT for 18 h. Additional 2 M HCl in Et$_2$O (9 mL, 18.0 mmol) was added and the mixture stirred for a further 2 h. The mixture was concentrated under reduced pressure to afford the title compound 1-7 (375 mg, 69%) as a white solid. $^1$H NMR (300 MHz, DMSO-d$_6$): δ 10.35 (s, 1H), 8.56 (br s, 3H), 7.84-7.90 (m, 2H), 7.74-7.79 (m, 3H), 7.65 (m, 1H), 7.52 (m, 1H), 7.45 (m, 1H), 7.31-7.38 (m, 2H), 7.09 (m, 1H), 4.23 (m, 2H); LCMS Mass: 388.0 (M$^+$+1).

Example 2: 3-((4-(Aminomethyl)-6-(trifluoromethyl)pyridin-2-yl)oxy)-N-(4-fluorobenzyl)benzamide hydrochloride (Compound 1-9)

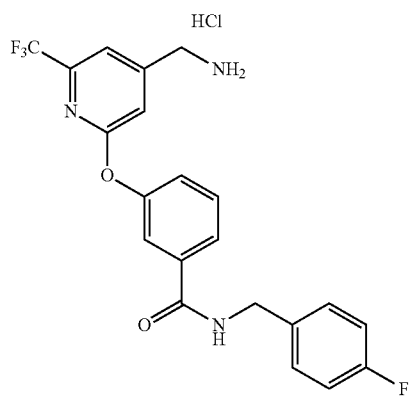 [SMILES: Cl ; NCc1cc(Oc2cccc(C(=O)NCc3ccc(F)cc3)c2)nc(C(F)(F)F)c1]

The title compound (1-9) was prepared using the procedure for Example 1, using 4-fluorobenzyl amine in Step 1. LCMS Mass: 420.0 (M$^+$+1).

Example 3: 3-((4-(Aminomethyl)-6-(trifluoromethyl)pyridin-2-yl)oxy)-N-(benzo[b]thiophen-2-ylmethyl)benzamide hydrochloride (Compound 1-10)

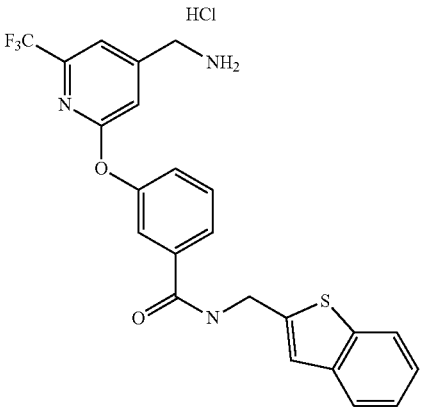 [SMILES: Cl ; NCc1cc(Oc2cccc(C(=O)NCc3cc4ccccc4s3)c2)nc(C(F)(F)F)c1]

The title compound (1-10) was prepared using the procedure for Example 1, using 1-benzothiophen-2yl-methyl-amine in Step 1. LCMS Mass: 458.0 (M$^+$+1).

Example 4: (3-((4-(Aminomethyl)-6-(trifluoromethyl)pyridin-2-yl)oxy)phenyl)(3,4-dihydroisoquinolin-2(1H)-yl)methanone hydrochloride (Compound 1-11)

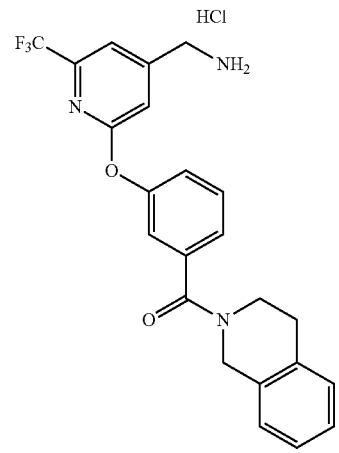 [SMILES: Cl ; NCc1cc(Oc2cccc(C(=O)N3CCc4ccccc4C3)c2)nc(C(F)(F)F)c1]

The title compound (1-11) was prepared using the procedure for Example 1, using 1,2,3,4-tetrahydroisoquinoline in Step 1. LCMS Mass: 428.0 (M$^+$+1).

Example 5: (3-(1H-Pyrazol-1-yl)azetidin-1-yl)(3-((4-(aminomethyl)-6-(trifluoromethyl)pyridin-2-yl)oxy)phenyl)methanone trifluoroacetate (Compound 1-12)

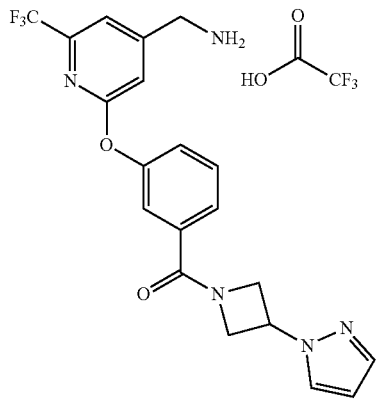

The title compound (1-12) was prepared using the procedure for Example 1, using 1-(azetidin-3-yl)-1H-pyrazole in Step 1. Compound 1-12 was purified via preparative HPLC (Waters XTerra® Prep MS C-18 OBD 5 μM 50×100 mm column; eluting with 10-90% ACN/H$_2$O containing 0.1% TFA, over 20 min). LCMS Mass: 418.0 (M$^+$+1).

Example 6: N-((2H-Tetrazol-5-yl)methyl)-3-((4-(aminomethyl)-6-(trifluoromethyl)pyridin-2-yl)oxy)benzamide hydrochloride (Compound 1-13)

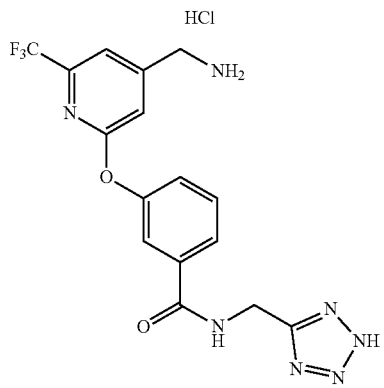 [SMILES: Cl ; NCc1cc(Oc2cccc(C(=O)NCc3nn[nH]n3)c2)nc(C(F)(F)F)c1]

The title compound (1-13) was prepared using the procedure for Example 1, using (2H-tetrazol-5-ylmethyl)amine hydrochloride in Step 1. LCMS Mass: 394.0 (M$^+$+1).

Example 7: N-(2-(1H-1,2,4-Triazol-1-yl)ethyl)-3-((4-(aminomethyl)-6-(trifluoromethyl)pyridin-2-yl)oxy)benzamide hydrochloride (Compound 1-14)

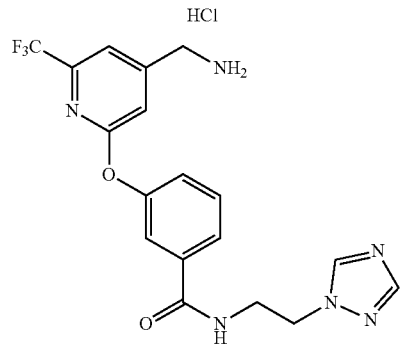 [SMILES: Cl ; NCc1cc(Oc2cccc(C(=O)NCCn3cncn3)c2)nc(C(F)(F)F)c1]

The title compound (1-14) was prepared using the procedure for Example 1, using 2-(1H-1,2,4-triazol-1-yl)ethanamine in Step 1. $^1$H NMR (300 MHz, DMSO-d$_6$): δ 8.65-8.80 (m, 5H), 8.08 (s, 1H), 7.85 (s, 1H), 7.72 (m, 1H), 7.51-7.60 (m, 3H), 7.35 (m, 1H), 4.37 (m, 2H), 4.21 (m, 2H), 3.62-3.66 (m, 2H); LCMS Mass: 407.0 (M$^+$+1).

Example 8: N-(2-(1H-Tetrazol-1-yl)ethyl)-3-((4-(aminomethyl)-6-(trifluoromethyl)pyridin-2-yl)oxy)benzamide hydrochloride (Compound 1-15)

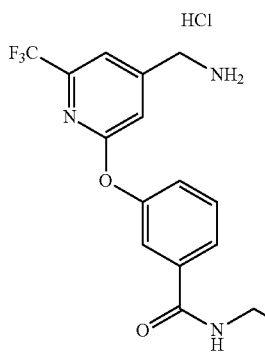

The title compound (1-15) was prepared using the procedure for Example 1, using 2-(1H-1,2,3,4-tetrazol-1-yl)ethanamine in Step 1. $^1$H NMR (300 MHz, DMSO-d$_6$): δ 9.39 (s, 1H), 8.75 (m, 1H), 8.55 (br s, 3H), 7.83 (s, 1H), 7.67 (m, 1H), 7.54-7.57 (m, 2H), 7.48 (m, 1H), 7.37 (m, 1H), 4.60-4.64 (m, 2H), 4.20-4.24 (m, 2H), 3.67-3.71 (m, 2H); LCMS Mass: 408.0 (M$^+$+1).

Example 9: 3-((4-(Aminomethyl)-6-(trifluoromethyl)pyridin-2-yl)oxy)-N-(2-hydroxyethyl)benzamide hydrochloride (Compound 1-16)

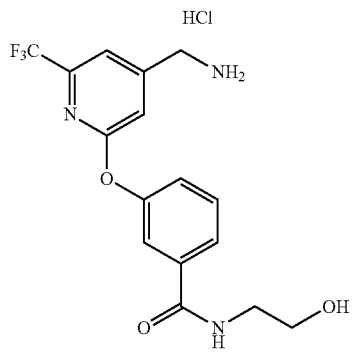 [SMILES: Cl ; NCc1cc(Oc2cccc(C(=O)NCCO)c2)nc(C(F)(F)F)c1]

The title compound (1-16) was prepared using the procedure for Example 1, using 2-aminoethanol in Step 1. $^1$H NMR (300 MHz, DMSO-d$_6$): δ 8.50-8.60 (br m, 4H), 7.83 (s, 1H), 7.78 (m, 1H), 7.65 (m, 1H), 7.54 (m, 1H), 7.48 (m, 1H), 7.34 (m, 1H), 4.74 (br s, 1H), 4.19-4.23 (m, 2H), 3.47-3.51 (m, 2H), 3.29-3.33 (m, 2H); LCMS Mass: 356.0 (M$^+$+1).

Example 10: (S)-(3-((4-(Aminomethyl)-6-(trifluoromethyl)pyridin-2-yl)oxy)phenyl)(3-hydroxypyrrolidin-1-yl)methanone hydrochloride (Compound 1-17)

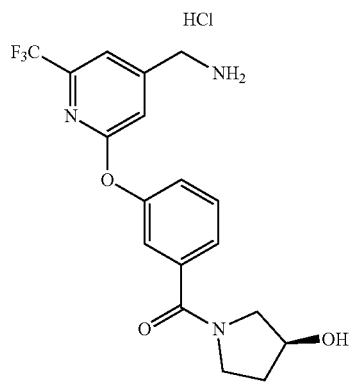 [SMILES: Cl ; NCc1cc(Oc2cccc(C(=O)N3CC[C@H](O)C3)c2)nc(C(F)(F)F)c1]

The title compound (1-17) was prepared using the procedure for Example 1, using (S)-3-pyrrolidinol hydrochloride in Step 1. $^1$H NMR (300 MHz, DMSO-d$_6$): δ 8.60 (br s, 3H), 7.83 (s, 1H), 7.49-7.52 (m, 2H), 7.39 (m, 1H), 7.25-7.33 (m, 2H), 4.18-4.31 (m, 3H), 3.20-3.60 (m, 5H), 1.70-2.00 (m, 2H); LCMS Mass: 382.0 (M$^+$+1).

Example 11: (R)-(3-((4-(Aminomethyl)-6-(trifluoromethyl)pyridin-2-yl)oxy)phenyl)(3-hydroxypyrrolidin-1-yl)methanone hydrochloride (Compound 1-18)

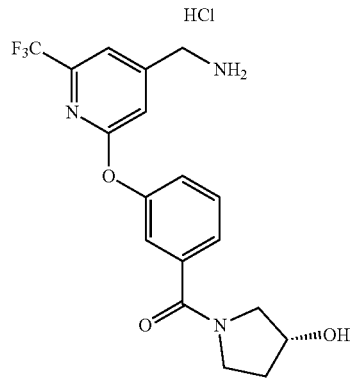 [SMILES: Cl ; NCc1cc(Oc2cccc(C(=O)N3CC[C@@H](O)C3)c2)nc(C(F)(F)F)c1]

The title compound (1-18) was prepared using the procedure for Example 1, using (R)-3-pyrrolidinol hydrochloride in Step 1. $^1$H NMR (300 MHz, DMSO-d$_6$): δ 8.63 (br s, 3H), 7.85 (s, 1H), 7.49-7.56 (m, 2H), 7.40 (m, 1H), 7.27-7.34 (m, 2H), 4.15-4.25 (m, 3H), 3.18-3.58 (m, 5H), 1.70-1.95 (m, 2H); LCMS Mass: 382.0 (M$^+$+1).

Example 12: Racemic-trans-(3-((4-(aminomethyl)-6-(trifluoromethyl)pyridin-2-yl)oxy)phenyl)(3-fluoro-4-hydroxypyrrolidin-1-yl)methanone hydrochloride (Compound 1-19)

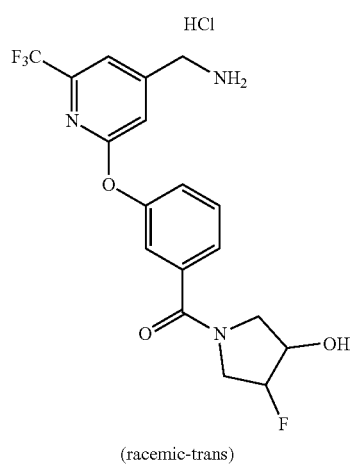 [SMILES: Cl ; NCc1cc(Oc2cccc(C(=O)N3CC(O)C(F)C3)c2)nc(C(F)(F)F)c1]

(racemic-trans)

The title compound (1-19) was prepared using the procedure for Example 1, using racemic-trans-4-fluoro-3-hydroxypyrrolidine hydrochloride in Step 1. $^1$H NMR (300 MHz, DMSO-d$_6$): δ 8.62 (br s, 3H), 7.86 (s, 1H), 7.51-7.57 (m, 2H), 7.41 (m, 1H), 7.30-7.40 (m, 2H), 5.62 (m, 1H), 4.95 (m, 1H), 4.12-4.30 (br m, 3H), 3.45-3.92 (m, 4H); LCMS Mass: 400.0 (M$^+$+1).

Example 13: (S,S)-trans-(3-((4-(Aminomethyl)-6-(trifluoromethyl)pyridin-2-yl)oxy)phenyl)(3-fluoro-4-hydroxypyrrolidin-1-yl)methanone hydrochloride (Compound 1-20)
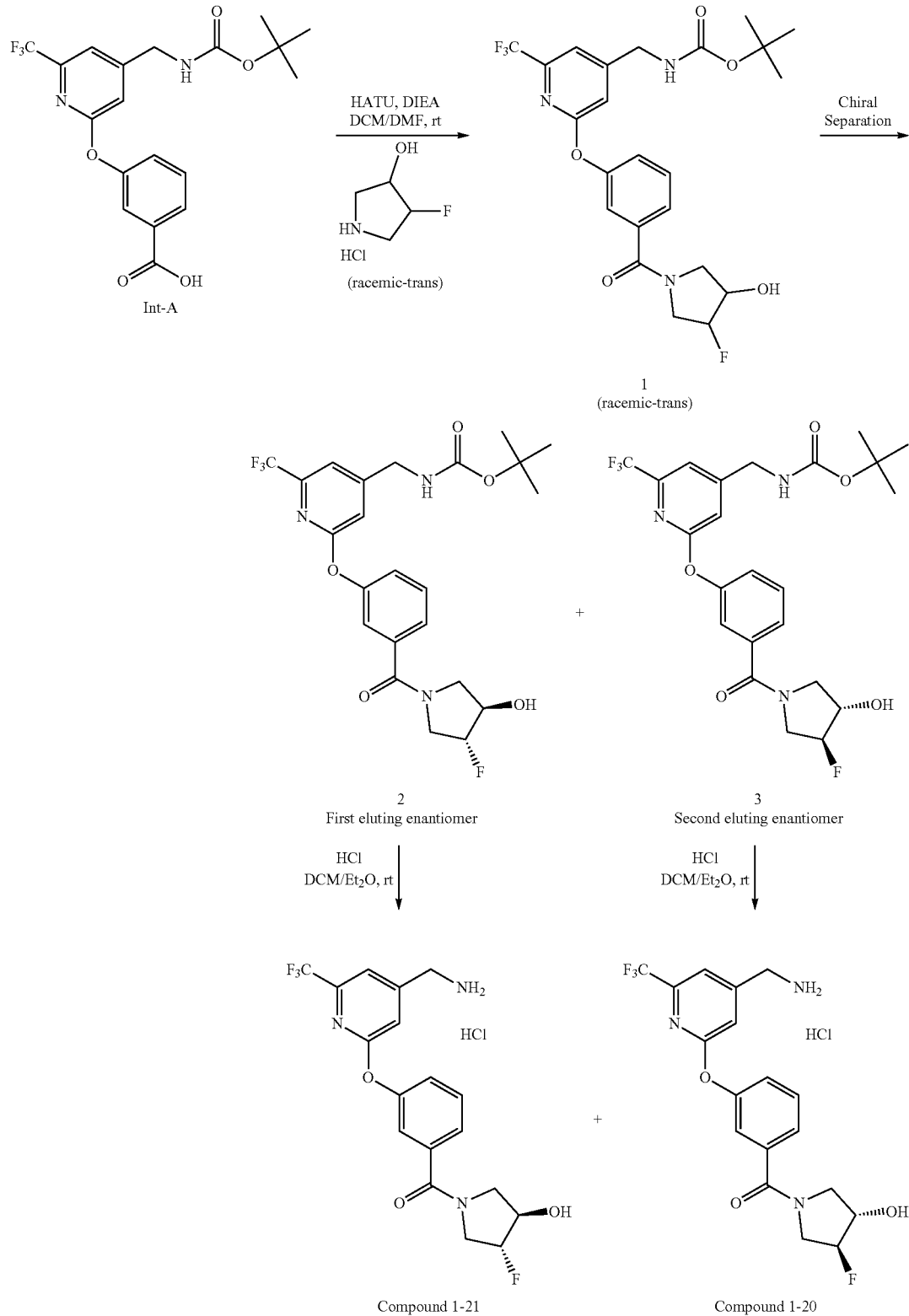

Two separate equal reaction batches were set up as follows: To a stirred solution of Int-A (750 mg, 1.82 mmol) in a mixture of DCM/DMF (3:1, 11 mL), was added HATU (1.0 g, 2.63 mmol) and the mixture was stirred at RT for 20 min. Racemic-trans-4-fluoro-3-hydroxypyrrolidine hydrochloride (304 mg, 2.14 mmol) and DIEA (938 mg, 7.27 mmol) were added and the mixture stirred at RT for 2.5 h. At this point both reaction batches were combined and the DCM was evaporated under reduced pressure. The remaining reaction mixture was partitioned between water (200 mL) and EtOAc (200 mL). The organic layer was separated, dried (Na$_2$SO$_4$), filtered, and then concentrated under reduced pressure. The crude residue was purified (silica gel; eluting with 10-100% EtOAc in hexanes), to afford compound 1 (1.58 g, 87%) as a white solid. $^1$H NMR (300 MHz, DMSO-d$_6$): δ 7.60 (m, 1H), 7.47-7.56 (m, 2H), 7.36-7.44 (m, 2H), 7.31 (m, 1H), 7.14 (s, 1H), 5.56 (m, 1H), 4.93 (m, 1H), 4.10-4.30 (m, 3H), 3.45-3.90 (m, 4H), 1.38 (s, 9H); LCMS Mass: 522.0 (M$^+$+Na).

Step 2: (R,R)-trans-tert-butyl ((2-(3-(3-fluoro-4-hydroxypyrrolidine-1-carbonyl)phenoxy)-6-(trifluoromethyl)pyridin-4-yl)methyl)carbamate (2) and (S,S)-trans-tert-butyl ((2-(3-(3-fluoro-4-hydroxypyrrolidine-1-carbonyl)phenoxy)-6-(trifluoromethyl)pyridin-4-yl)methyl)carbamate (3)

Compound 2 (102 mg) and compound 3 (88 mg) were both obtained from compound 1 (300 mg, 0.60 mmol) via chiral HPLC separation (Chiral Pak ADH, 250×20 mm, 5 μm column, eluting isocratically with 10% MeOH:isopropanol (1:1) and 90% hexanes (containing 0.1% DEA), flow rate 18 mL/min), wherein compound 2 was the first to elute and compound 3 was the second to elute.

Compound 2: $^1$H NMR (400 MHz, DMSO-d$_6$): δ 7.59 (m, 1H), 7.47-7.56 (m, 2H), 7.35-7.45 (m, 2H), 7.31 (m, 1H), 7.16 (s, 1H), 5.56 (m, 1H), 4.94 (m, 1H), 4.25-4.30 (m, 2H), 4.17 (m, 1H), 3.45-3.90 (m, 4H), 1.39 (s, 9H); LCMS Mass: 500.0 (M$^+$+1). Chiral HPLC analysis: R$_t$=11.84 min (Chiral Pak ADH, 250×4.6 mm, 5 μm column, eluting isocratically with 10% MeOH:EtOH (1:1) and 90% hexanes (containing 0.1% DEA) over 25 mins; flow rate 1.0 mL/min).

Compound 3: $^1$H NMR (400 MHz, DMSO-d$_6$): δ 7.59 (m, 1H), 7.47-7.56 (m, 2H), 7.35-7.45 (m, 2H), 7.31 (m, 1H), 7.16 (s, 1H), 5.56 (m, 1H), 4.95 (m, 1H), 4.25-4.30 (m, 2H), 4.17 (m, 1H), 3.45-3.90 (m, 4H), 1.39 (s, 9H); LCMS Mass: 500.0 (M$^+$+1). Chiral HPLC analysis: R$_t$=14.71 min (Chiral Pak ADH, 250×4.6 mm, 5 μm column, eluting isocratically with 10% MeOH:EtOH (1:1) and 90% hexanes (containing 0.1% DEA) over 25 mins; flow rate 1.0 mL/min).

Step 3: (S,S)-trans-(3-((4-(Aminomethyl)-6-(trifluoromethyl)pyridin-2-yl)oxy)phenyl)(3-fluoro-4-hydroxypyrrolidin-1-yl)methanone hydrochloride (Compound 1-20)

The title compound (1-20) (77 mg, 100%) was prepared from compound 3 (88 mg, 0.176 mmol) using the procedure for Example 1, Step 2. $^1$H NMR (300 MHz, DMSO-d$_6$): δ 8.61 (br s, 3H), 7.84 (s, 1H), 7.51-7.57 (m, 2H), 7.43 (m, 1H), 7.28-7.37 (m, 2H), 5.57 (br m, 1H), 4.95 (m, 1H), 4.12-4.30 (br m, 3H), 3.30-3.92 (m, 4H); LCMS Mass: 400.0 (M$^+$+1).

Example 14: (R,R)-trans-(3-((4-(Aminomethyl)-6-(trifluoromethyl)pyridin-2-yl)oxy)phenyl)(3-fluoro-4-hydroxypyrrolidin-1-yl)methanone hydrochloride (Compound 1-21)

The title compound (1-21) (89 mg, 100%) was prepared from compound 2 (102 mg, 0.204 mmol) (from Example 13, Step 2) using the procedure for Example 1, Step 2. $^1$H NMR (300 MHz, DMSO-d$_6$): δ 8.61 (br s, 3H), 7.84 (s, 1H), 7.51-7.57 (m, 2H), 7.43 (m, 1H), 7.28-7.37 (m, 2H), 5.62 (br m, 1H), 4.95 (m, 1H), 4.12-4.30 (br m, 3H), 3.30-3.92 (m, 4H); LCMS Mass: 400.0 (M$^+$+1).

Example 15: (R)-(3-((4-(Aminomethyl)-6-(trifluoromethyl)pyridin-2-yl)oxy)phenyl)(3-aminopyrrolidin-1-yl)methanone dihydrochloride (Compound 1-22)

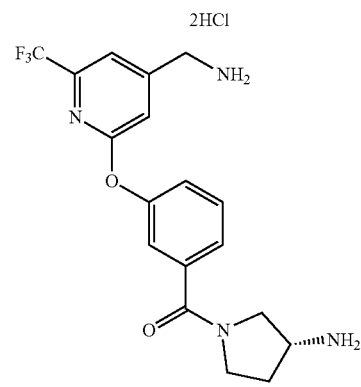 [SMILES: "2HCl" ; NCc1cc(Oc2cccc(C(=O)N3CC[C@@H](N)C3)c2)nc(C(F)(F)F)c1]

The title compound (1-22) was prepared using the procedure for Example 1, using (R)-tert-butyl pyrrolidin-3-ylcarbamate in Step 1. LCMS Mass: 381.0 (M$^+$+1).

Example 16: Racemic-trans-(3-((4-(aminomethyl)-6-(trifluoromethyl)pyridin-2-yl)oxy)phenyl)(-3-(dimethylamino)-4-hydroxypyrrolidin-1-yl)methanone hydrochloride (Compound 1-23)

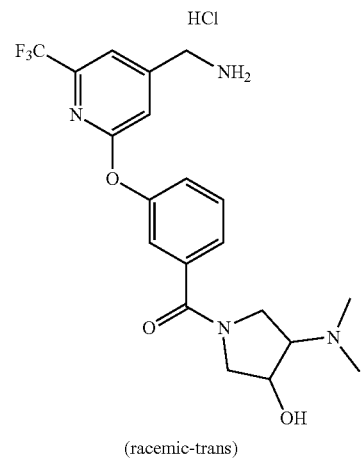 [SMILES: Cl ; CN(C)C1CN(C(=O)c2cccc(Oc3cc(CN)cc(C(F)(F)F)n3)c2)CC1O]

(racemic-trans)

The title compound (1-23) was prepared using the procedure for Example 1, using racemic-trans-4-(dimethylamino)-3-pyrrolidinol in Step 1. LCMS Mass: 425.0 (M$^+$+1).

Example 17: (S)-1-(3-((4-(Aminomethyl)-6-(trifluoromethyl)pyridin-2-yl)oxy)benzoyl)pyrrolidine-2-carboxylic acid hydrochloride (Compound 1-24)
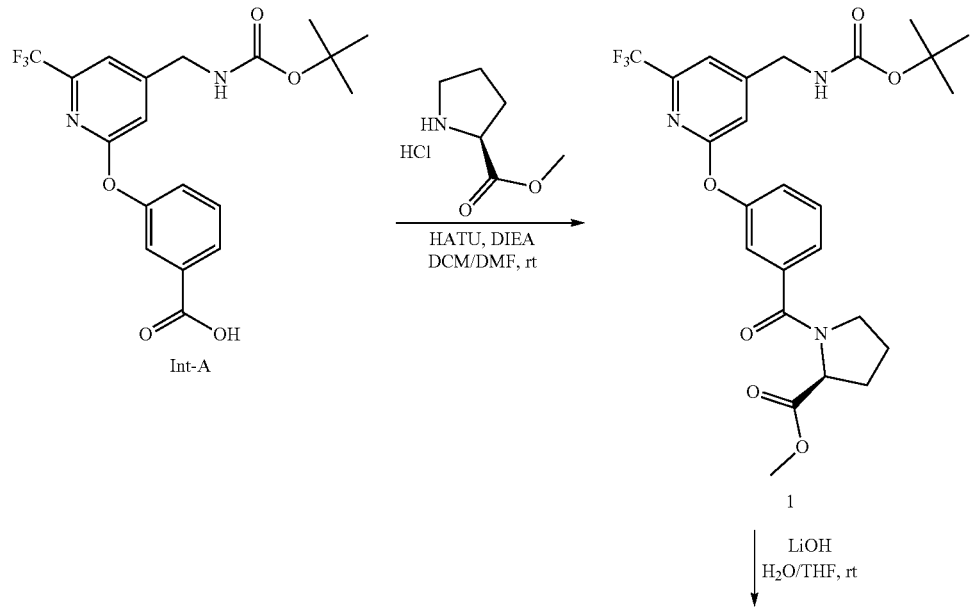
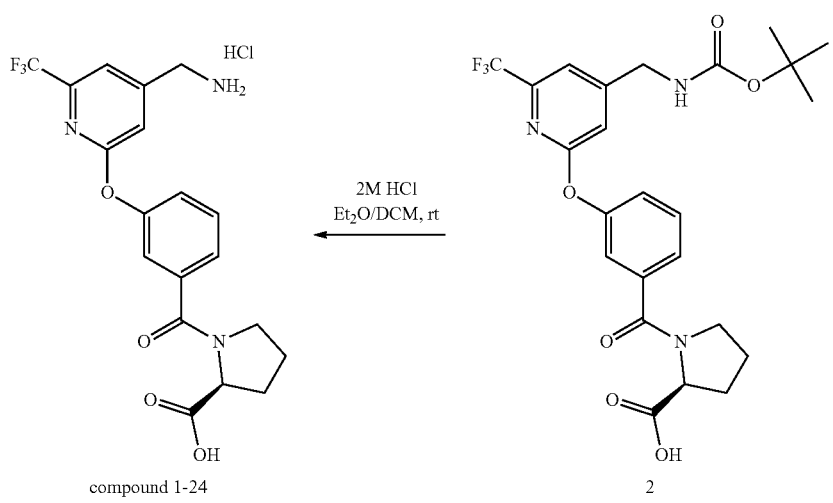

Step 1: (S)-Methyl 1-(3-((4-(((tert-butoxycarbonyl) amino)methyl)-6-(trifluoromethyl)pyridin-2-yl)oxy) benzoyl)pyrrolidine-2-carboxylate (1)

The title compound (1) (117 mg, 92%) was prepared from Int-A and (S)-methyl pyrrolidine-2-carboxylate hydrochloride, using the procedure for Example 1, Step 1. LCMS Mass: 546.0 (M$^+$+Na).

Step 2: (S)-1-(3-((4-(((tert-Butoxycarbonyl)amino) methyl)-6-(trifluoromethyl)pyridin-2-yl)oxy)benzoyl)pyrrolidine-2-carboxylic acid (2)

To a stirred solution of ester 1 (117 mg, 0.223 mmol) in a mixture of THF (1.5 mL) and water (0.75 mL) at RT, was added aq. 4M LiOH solution (1.1 mL, 4.4 mmol). The reaction mixture was stirred at RT for 16 h. The THF was removed under reduced pressure and the remaining mixture was diluted with water and acidified to pH 3-4 with sat. aq. citric acid solution. The precipitate was isolated via filtration and dried under high vacuum to afford compound 2 (87 mg, 77%) as an off-white solid. $^1$H NMR (300 MHz, DMSO-d$_6$): δ 7.47-7.64 (m, 3H), 7.41 (m, 1H), 7.31 (m, 1H), 7.13-7.25 (m, 2H), 4.35 (m, 1H), 4.20-4.25 (m, 2H), 3.45-3.53 (m, 2H), 2.22 (m, 1H), 1.75-1.90 (m, 3H), 1.25-1.37 (br m, 9H); LCMS Mass: 532.0 (M$^+$+Na).

Step 3: (S)-1-(3-((4-(Aminomethyl)-6-(trifluoromethyl)pyridin-2-yl)oxy)benzoyl)pyrrolidine-2-carboxylic acid hydrochloride (Compound 1-24)

The title compound (1-24) (31 mg, 41%) was prepared from acid 2, using the procedure for Example 1, Step 2. LCMS Mass: 410.0 (M$^+$+1).

Example 18: (R)-1-(3-((4-(Aminomethyl)-6-(trifluoromethyl)pyridin-2-yl)oxy)benzoyl)pyrrolidine-2-carboxylic acid hydrochloride (Compound 1-25)

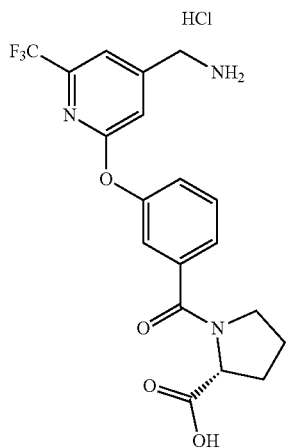 [SMILES: Cl ; NCc1cc(Oc2cccc(C(=O)N3CCC[C@@H]3C(=O)O)c2)nc(C(F)(F)F)c1]

The title compound (1-25) was prepared using the procedure for Example 17, using (R)-methyl pyrrolidine-2-carboxylate hydrochloride in Step 1. LCMS Mass: 410.0 (M$^+$+1).

Example 19: (R)-(3-((4-(Aminomethyl)-6-(trifluoromethyl)pyridin-2-yl)oxy)phenyl)(3-(hydroxymethyl)pyrrolidin-1-yl)methanone hydrochloride (Compound 1-26)

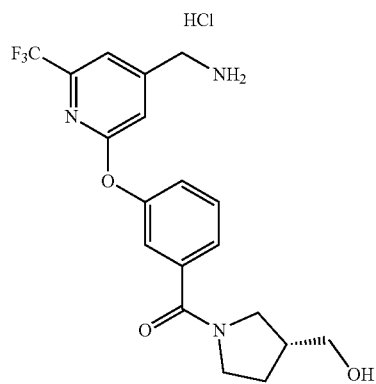 [SMILES: Cl ; NCc1cc(Oc2cccc(C(=O)N3CC[C@@H](CO)C3)c2)nc(C(F)(F)F)c1]

The title compound (1-26) was prepared using the procedure for Example 1, using (R)-pyrrolidin-3-ylmethanol hydrochloride in Step 1. $^1$H NMR (300 MHz, DMSO-d$_6$): δ 8.60 (br s, 3H), 7.83 (s, 1H), 7.48-7.55 (m, 2H), 7.39 (m, 1H), 7.25-7.34 (m, 2H), 4.19-4.24 (m, 2H), 3.17-3.60 (m, 6H), 2.28 (m, 1H), 1.85 (m, 1H), 1.61 (m, 1H); LCMS Mass: 396.0 (M$^+$+1).

Example 20: 8-(3-((4-(Aminomethyl)-6-(trifluoromethyl)pyridin-2-yl)oxy)benzoyl)-1-oxa-3,8-diazaspiro[4.5]decan-2-one hydrochloride (Compound 1-27)

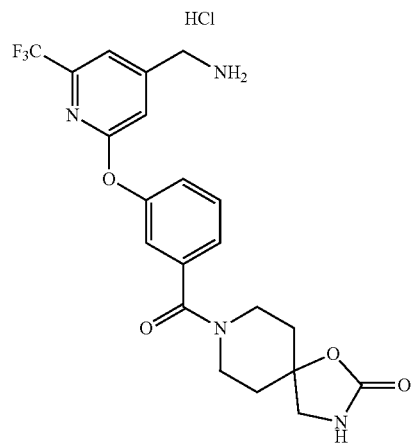 [SMILES: Cl ; NCc1cc(Oc2cccc(C(=O)N3CCC4(CC3)CNC(=O)O4)c2)nc(C(F)(F)F)c1]

The title compound (1-27) was prepared using the procedure for Example 1, using 1-oxa-3,8-diazaspiro[4.5]decan-2-one hydrochloride in Step 1. LCMS Mass: 451.0 (M$^+$+1).

Example 21: 3-((4-(Aminomethyl)-6-(trifluoromethyl)pyridin-2-yl)oxy)-N-(2-(2-oxooxazolidin-3-yl)ethyl)benzamide (Compound 1-28)

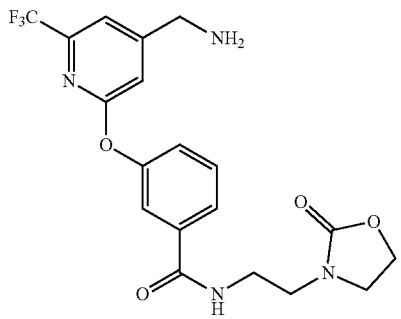 [SMILES: NCc1cc(Oc2cccc(C(=O)NCCN3CCOC3=O)c2)nc(C(F)(F)F)c1]

The title compound (1-28) was prepared using the procedure for Example 1, using 3-(2-aminoethyl)-1,3-oxazolidin-2-one hydrochloride in Step 1. LCMS Mass: 425.0 ($M^+$+1).

Example 22: Racemic-3-((4-(aminomethyl)-6-(trifluoromethyl)pyridin-2-yl)oxy)-N-((5-oxopyrrolidin-2-yl)methyl)benzamide hydrochloride (Compound 1-29)

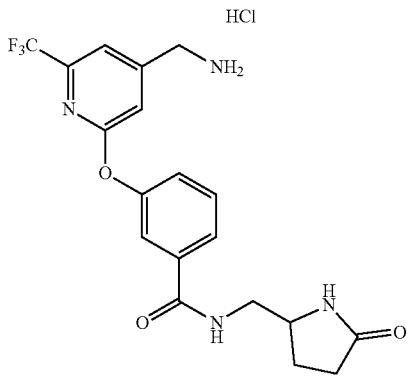 [SMILES: Cl ; NCc1cc(Oc2cccc(C(=O)NCC3CCC(=O)N3)c2)nc(C(F)(F)F)c1]

The title compound (1-29) was prepared using the procedure for Example 1, using racemic-5-(aminomethyl)-2-pyrrolidone in Step 1. LCMS Mass: 409.0 ($M^+$+1).

Example 23: 3-((4-(Aminomethyl)-6-(trifluoromethyl)pyridin-2-yl)oxy)-N-(2-(methylsulfonyl)ethyl)benzamide hydrochloride (Compound 1-30)

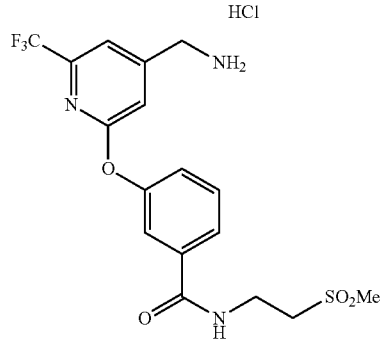 [SMILES: Cl ; CS(=O)(=O)CCNC(=O)c1cccc(Oc2cc(CN)cc(C(F)(F)F)n2)c1]

The title compound (1-30) was prepared using the procedure for Example 1, using 2-(methylsulfonyl)ethanamine hydrochloride in Step 1. $^1$H NMR (300 MHz, DMSO-$d_6$): δ 8.87 (m, 1H), 8.64 (br s, 3H), 7.85 (s, 1H), 7.76 (m, 1H), 7.51-7.64 (m, 3H), 7.37 (m, 1H), 4.21 (s, 2H), 3.60-3.64 (m, 2H), 3.33-3.37 (m, 2H), 3.01 (s, 3H); LCMS Mass: 418.0 ($M^+$+1).

Example 24: 3-((4-(Aminomethyl)-6-(trifluoromethyl)pyridin-2-yl)oxy)-N-(1-(hydroxymethyl)cyclopropyl)benzamide hydrochloride (Compound 1-31)

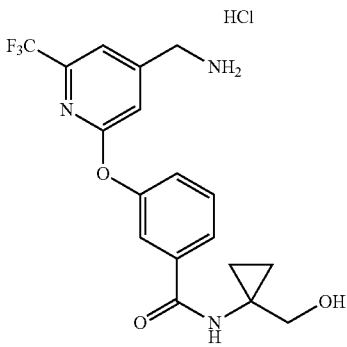 [SMILES: Cl ; NCc1cc(Oc2cccc(C(=O)NC3(CO)CC3)c2)nc(C(F)(F)F)c1]

The title compound (1-31) was prepared using the procedure for Example 1, using (1-aminocyclopropyl)methanol in Step 1. $^1$H NMR (300 MHz, DMSO-$d_6$): δ 8.74 (s, 1H), 8.59 (br s, 3H), 7.83 (s, 1H), 7.77 (m, 1H), 7.64 (m, 1H), 7.47-7.55 (m, 2H), 7.33 (m, 1H), 4.74 (m, 1H), 4.21 (s, 2H), 3.47-3.51 (m, 2H), 0.65-0.78 (m, 4H); LCMS Mass: 382.0 ($M^+$+1).

Example 25: 3-((4-(Aminomethyl)-6-(trifluoromethyl)pyridin-2-yl)oxy)-N-(2-hydroxy-2-methylpropyl)benzamide hydrochloride (Compound 1-32)

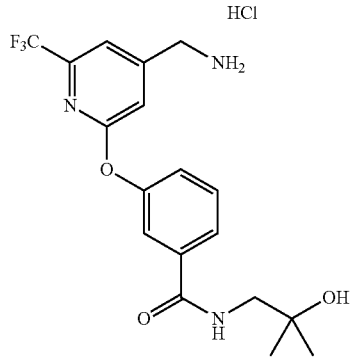 [SMILES: Cl ; CC(C)(O)CNC(=O)c1cccc(Oc2cc(CN)cc(C(F)(F)F)n2)c1]

The title compound (1-32) was prepared using the procedure for Example 1, using 1-amino-2-methylpropan-2-ol in Step 1. LCMS Mass: 384.0 (M$^+$+1).

Example 26: (R)-3-((4-(Aminomethyl)-6-(trifluoromethyl)pyridin-2-yl)oxy)-N-(2,3-dihydroxypropyl)benzamide hydrochloride (Compound 1-33)

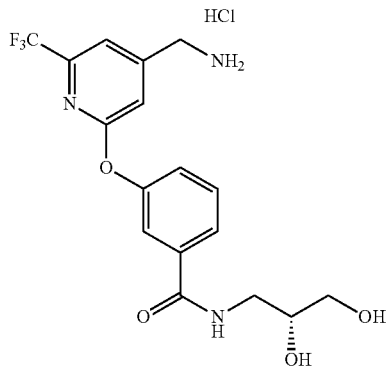 [SMILES: Cl ; NCc1cc(Oc2cccc(C(=O)NC[C@@H](O)CO)c2)nc(C(F)(F)F)c1]

The title compound (1-33) was prepared using the procedure for Example 1, using (R)-3-amino-1,2-propanediol in Step 1. LCMS Mass: 386.0 (M$^+$+1).

Example 27: 3-((4-(Aminomethyl)-6-(trifluoromethyl)pyridin-2-yl)oxy)-N-(2-sulfamoylethyl)benzamide hydrochloride (Compound 1-34)

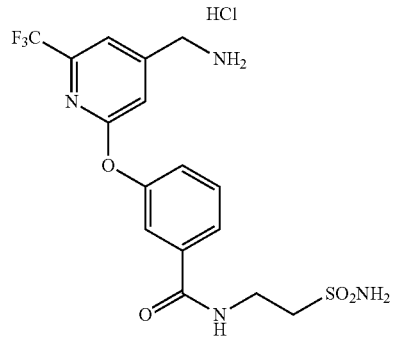 [SMILES: Cl ; NCc1cc(Oc2cccc(C(=O)NCCS(N)(=O)=O)c2)nc(C(F)(F)F)c1]

The title compound (1-34) was prepared using the procedure for Example 1, using 2-aminoethane-1-sulfonamide in Step 1. $^1$H NMR (300 MHz, DMSO-d$_6$): δ 8.76 (m, 1H), 8.54 (br s, 3H), 7.82 (s, 1H), 7.75 (m, 1H), 7.62 (m, 1H), 7.57 (m, 1H), 7.49 (m, 1H), 7.37 (m, 1H), 6.94 (s, 2H), 4.19-4.23 (m, 2H), 3.59-3.63 (m, 2H), 3.20-3.24 (m, 2H); LCMS Mass: 419.0 (M$^+$+1).

Example 28: 3-((4-(Aminomethyl)-6-(trifluoromethyl)pyridin-2-yl)oxy)-N-(2-(dimethylamino)ethyl)benzamide dihydrochloride (Compound 1-35)

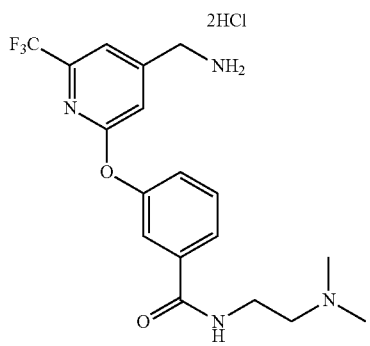 [SMILES: "2HCl" ; CN(C)CCNC(=O)c1cccc(Oc2cc(CN)cc(C(F)(F)F)n2)c1]

The title compound (1-35) was prepared using the procedure for Example 1, using 2-(dimethylamino)ethylamine in Step 1. LCMS Mass: 383.0 (M$^+$+1).

Example 29: Racemic-trans-(3-(((4-(aminomethyl)-6-(trifluoromethyl)pyridin-2-yl)oxy)methyl)phenyl)(3-fluoro-4-hydroxypyrrolidin-1-yl)methanone hydrochloride (Compound 1-36)

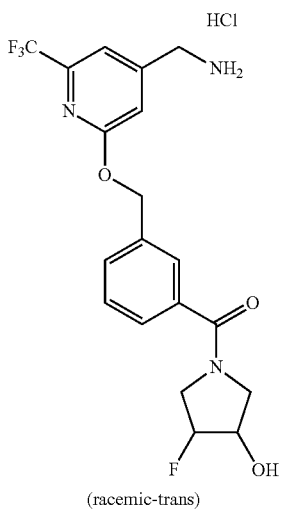 [SMILES: Cl ; NCc1cc(OCc2cccc(C(=O)N3CC(O)C(F)C3)c2)nc(C(F)(F)F)c1]

(racemic-trans)

The title compound (1-36) was prepared using the procedure for Example 1, using Int-B and racemic-trans-4-fluoro-3-hydroxypyrrolidine hydrochloride in Step 1. LCMS Mass: 414.0 (M⁺+1).

Example 30: 3-((4-(Aminomethyl-d₂)-6-(trifluoromethyl)pyridin-2-yl)oxy)-N-phenylbenzamide hydrochloride (Compound 1-8)

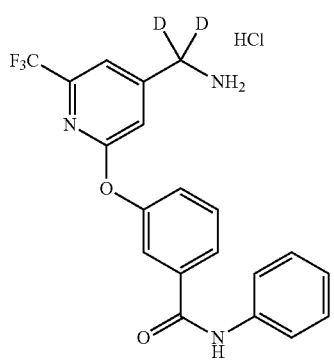 [SMILES: [2H]C([2H])(N)c1cc(Oc2cccc(C(=O)Nc3ccccc3)c2)nc(C(F)(F)F)c1 ; Cl]

The title compound (1-8) was prepared using the procedure for Example 1, using Int-K in Step 1. ¹H NMR (300 MHz, DMSO-d₆): δ 10.33 (s, 1H), 8.51 (br s, 3H), 7.84-7.91 (m, 2H), 7.72-7.79 (m, 3H), 7.62 (m, 1H), 7.51 (m, 1H), 7.43 (m, 1H), 7.31-7.38 (m, 2H), 7.09 (m, 1H); LCMS Mass: 390.0 (M⁺+1).

Example 31: (R)-3-((4-(Aminomethyl)-6-(trifluoromethyl)pyridin-2-yl)oxy)-N-phenylpyrrolidine-1-carboxamide trifluoroacetate (Compound 1-39)

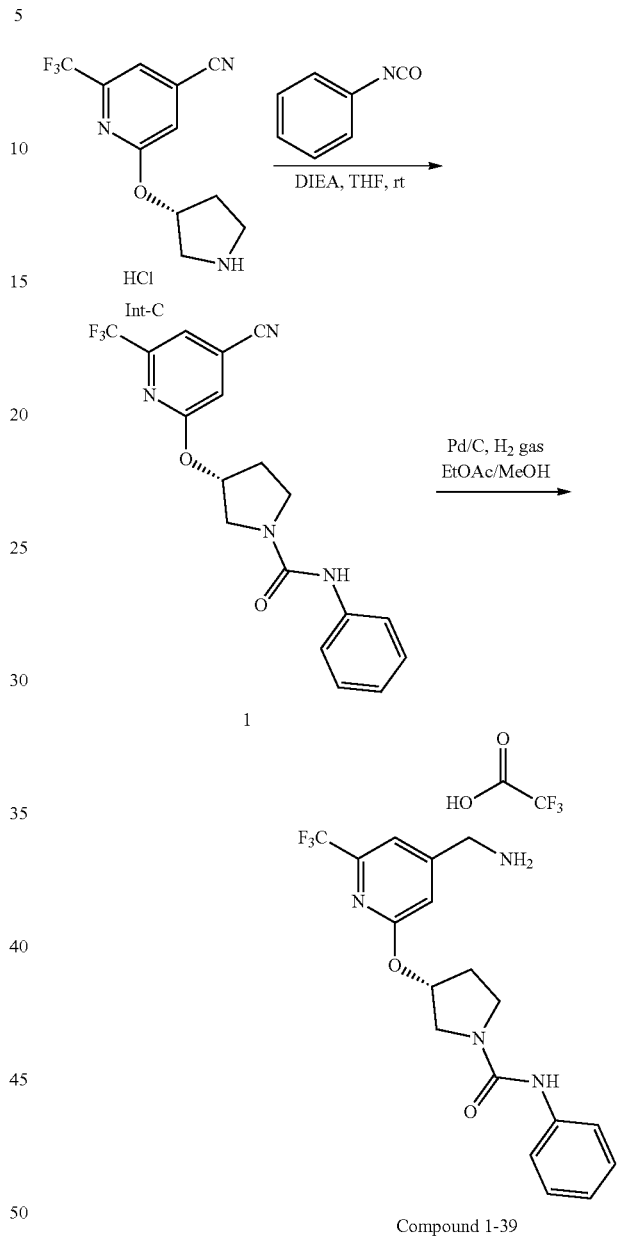

Compound 1-39

Step 1: (R)-3-((4-Cyano-6-(trifluoromethyl)pyridin-2-yl)oxy)-N-phenylpyrrolidine-1-carboxamide (1)

To a stirred solution of Int-C (225 mg, 0.766 mmol) and DIEA (248 mg, 1.92 mmol) in THF (4 mL) at RT, was added phenyl isocyanate (137 mg, 1.15 mmol). The mixture was stirred at RT for 3.5 h. The mixture was concentrated under reduced pressure and the residue purified (silica gel; eluting with 0-25% EtOAc in DCM), to afford compound 1 (288 mg, 100%) as a colorless oil. ¹H NMR (300 MHz, DMSO-d₆): δ 8.23 (s, 1H), 8.04 (s, 1H), 7.82 (s, 1H), 7.44-7.51 (m, 2H), 7.16-7.25 (m, 2H), 6.91 (m, 1H), 5.60 (m, 1H), 3.74 (m, 2H), 3.57-3.68 (m, 2H), 3.48 (m, 1H), 2.10-2.40 (m, 2H); LCMS Mass: 377.0 (M⁺+1).

Step 2: (R)-3-((4-(Aminomethyl)-6-(trifluoromethyl)pyridin-2-yl)oxy)-N-phenylpyrrolidine-1-carboxamide trifluoroacetate (Compound 1-39)

A mixture of carboxamide 1 (288 mg, 0.765 mmol), 10 wt % Pd on carbon (0.076 mmol), and EtOAc:MeOH (1:1, 6 mL), was stirred at RT under 1 atmosphere of H2 gas. After 3 h, the mixture was filtered through celite and the filtrate concentrated under reduced pressure. The residue was purified via preparative HPLC (Waters XTerra® Prep MS C-18 OBD 5 µM 50×100 mm column; eluting with 10-90% ACN/H$_2$O containing 0.1% TFA, over 20 min) to afford compound 1-39 (265 mg, 70%) as a white solid. $^1$H NMR (300 MHz, DMSO-d$_6$): δ 8.33 (br s, 3H), 8.24 (s, 1H), 7.63 (s, 1H), 7.45-7.51 (m, 2H), 7.17-7.25 (m, 3H), 6.92 (m, 1H), 5.57 (m, 1H), 4.10-4.22 (m, 2H), 3.41-3.78 (m, 4H), 2.10-2.40 (m, 2H); LCMS Mass: 381.0 (M$^+$+1).

Example 32: (S)-3-((4-(Aminomethyl)-6-(trifluoromethyl)pyridin-2-yl)oxy)-N-phenylpyrrolidine-1-carboxamide trifluoroacetate (Compound 1-40)

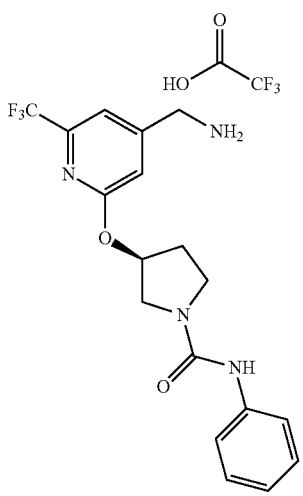

The title compound (1-40) was prepared using the procedure for Example 31, using Int-D in Step 1. LCMS Mass: 381.0 (M$^+$+1).

Example 33: (R)-3-((4-(Aminomethyl)-6-(trifluoromethyl)pyridin-2-yl)oxy)-N-phenylpiperidine-1-carboxamide trifluoroacetate (Compound 1-43)

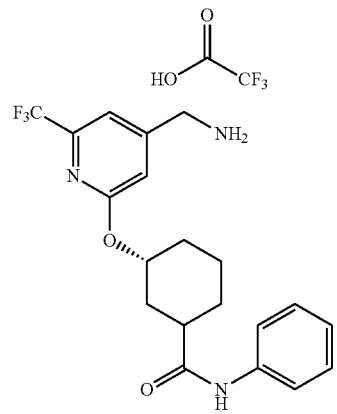

The title compound (1-43) was prepared using the procedure for Example 31, using Int-E in Step 1. LCMS Mass: 395.0 (M$^+$+1).

Example 34: (S)-3-((4-(Aminomethyl)-6-(trifluoromethyl)pyridin-2-yl)oxy)-N-phenylpiperidine-1-carboxamide trifluoroacetate (Compound 1-44)

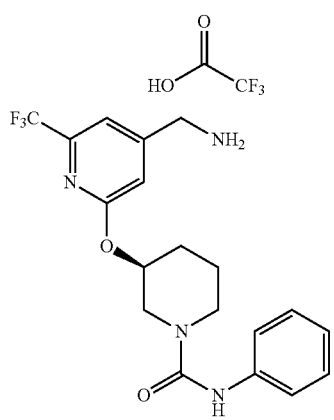

The title compound (1-44) was prepared using the procedure for Example 31, using Int-F in Step 1. LCMS Mass: 395.0 (M$^+$+1).

Example 35: (S)-1-(3-((4-(Aminomethyl)-6-(trifluoromethyl)pyridin-2-yl)oxy)piperidin-1-yl)-2-phenylethanone trifluoroacetate (Compound 1-46)

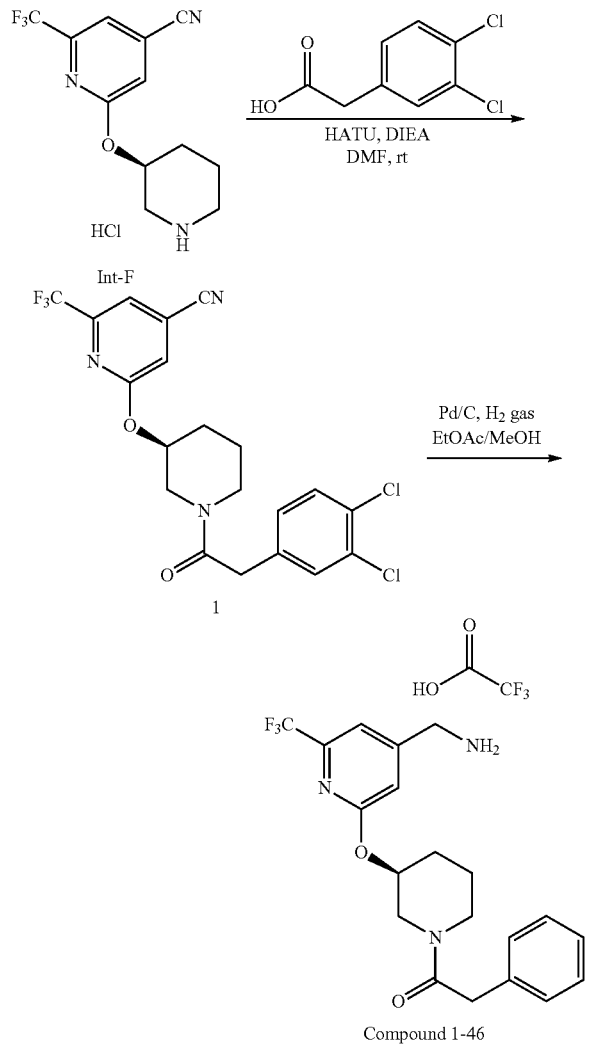

Step 1: (S)-2-((1-(2-(3,4-Dichlorophenyl)acetyl)piperidin-3-yl)oxy)-6-(trifluoromethyl)isonicotinonitrile (1)

A solution of 3,4-dichlorophenylacetic acid (150 mg, 0.731 mmol) and HATU (370 mg, 0.974 mmol) in DMF (3 mL) was stirred at RT for 20 min. Int-F (150 mg, 0.487 mmol) and DIEA (252 mg, 1.95 mmol) were added and the mixture stirred at RT for 18 h. Water (50 mL), brine (20 mL) and aq. 2M HCl solution (10 mL) were added and the mixture was extracted with EtOAc (4×10 mL). The combined organic layers were dried ($MgSO_4$), filtered, and then concentrated under reduced pressure. The crude residue was purified (silica gel; eluting with 0-50% EtOAc in hexanes), to afford compound 1 (180 mg, 81%) as a colorless oil. $^1$H NMR (300 MHz, DMSO-$d_6$): δ 8.02 (s, 1H), 7.67 (m, 1H), 7.37-7.60 (m, 2H), 7.16 (m, 1H), 5.05 (m, 1H), 3.30-4.00 (m, 6H), 1.96 (m, 1H), 1.85 (m, 1H), 1.65 (m, 1H), 1.51 (m, 1H); LCMS Mass: 458.0 ($M^+$+1).

Step 2: (S)-1-(3-((4-(Aminomethyl)-6-(trifluoromethyl)pyridin-2-yl)oxy)piperidin-1-yl)-2-phenylethanone trifluoroacetate (Compound 1-46)

The title compound (1-46) (68 mg, 34%) was prepared from (S)-2-((1-(2-(3,4-dichlorophenyl)acetyl)piperidin-3-yl)oxy)-6-(trifluoromethyl)isonicotinonitrile 1 using the procedure for Example 31, Step 2. $^1$H NMR (300 MHz, DMSO-$d_6$): δ 8.33 (br s, 3H), 7.61 (m, 1H), 7.07-7.37 (m, 6H), 5.03 (m, 1H), 4.10-4.22 (m, 2H), 3.30-4.00 (br m, 6H), 1.30-2.00 (br m, 4H); LCMS Mass: 394.0 ($M^+$+1).

Example 36: (S)-1-(3-((4-(Aminomethyl)-6-(trifluoromethyl)pyridin-2-yl)oxy)piperidin-1-yl)-2-(3,4-dichlorophenyl)ethanone trifluoroacetate (Compound 1-47)

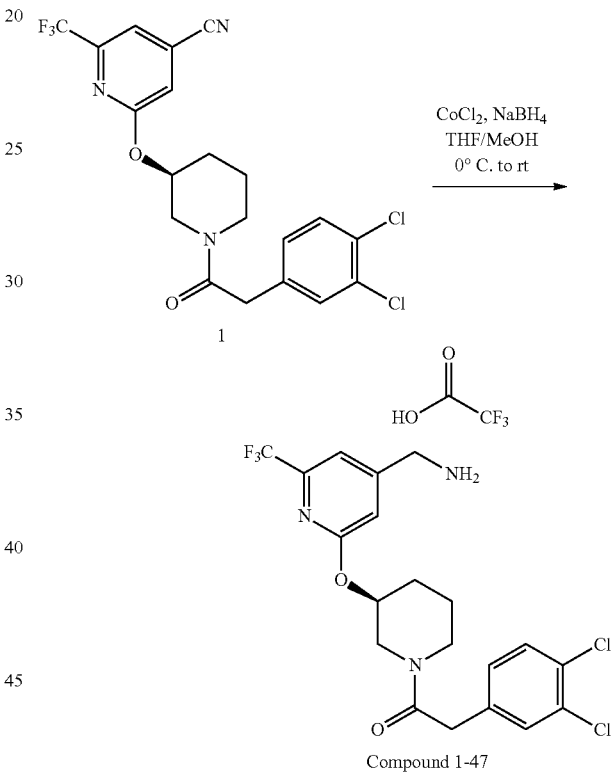

To a stirred solution of (S)-2-((1-(2-(3,4-dichlorophenyl)acetyl)piperidin-3-yl)oxy)-6-(trifluoromethyl)isonicotinonitrile 1 (75 mg, 0.164 mmol) (from Example 35, Step 1) in MeOH/THF (1:1, 2 mL) at 0° C., was added $CoCl_2$ (43 mg, 0.333 mmol) and $NaBH_4$ (62 mg, 1.64 mmol). The mixture was warmed to RT and stirred for a further 4 h. The mixture was partially concentrated then diluted with EtOAc (40 mL), before filtering through celite. The celite was rinsed with EtOAc (30 mL) and the combined filtrates washed with water (2×100 mL), dried ($MgSO_4$), filtered, and then concentrated under reduced pressure. The residue was purified via preparative HPLC (Waters XTerra® Prep MS C-18 OBD 5 μM 50×100 mm column; eluting 10-90% ACN/$H_2O$ containing 0.1% TFA, over 20 min) to afford compound 1-47 (36 mg, 38%) as a yellow oil. $^1$H NMR (300 MHz, DMSO-$d_6$): δ 8.35 (br s, 3H), 7.37-7.60 (m, 3H), 7.10-7.20 (m, 2H), 5.03 (m, 1H), 4.10-4.20 (m, 2H), 3.50-4.00 (m, 5H), 3.40 (m, 1H), 1.96 (m, 1H), 1.82 (m, 1H), 1.62 (m, 1H), 1.52 (m, 1H); LCMS Mass: 462.0 (M$^+$+1).

Example 37: (S)-2-(3-((4-(Aminomethyl)-6-(trifluoromethyl)pyridin-2-yl)oxy)piperidine-1-carbonyl)-4H-chromen-4-one trifluoroacetate (Compound 1-48)

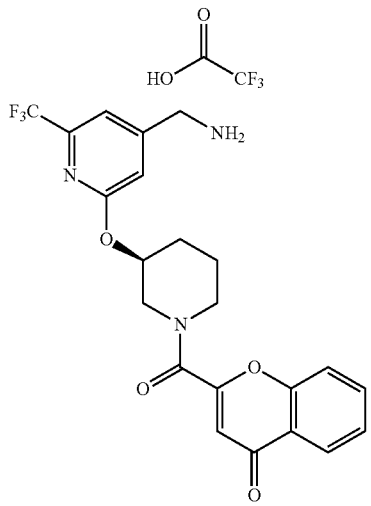

The title compound (1-48) was prepared using the procedure for Example 35, using 4-oxo-4H-chromene-2-carboxylic acid in Step 1. LCMS Mass: 448.0 (M$^+$+1).

Example 38: (S)-(3-((4-(Aminomethyl)-6-(trifluoromethyl)pyridin-2-yl)oxy)piperidin-1-yl)(pyridin-3-yl)methanone trifluoroacetate (Compound 1-49)

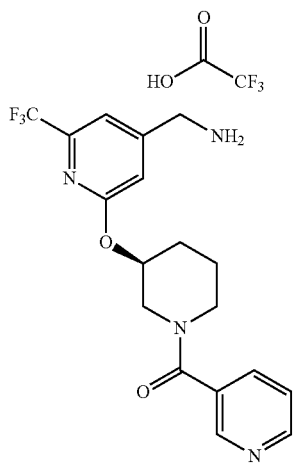

The title compound (1-49) was prepared using the procedure for Example 35, using nicotinic acid in Step 1. LCMS Mass: 381.0 (M$^+$+1).

Example 39: (S)-(3-((4-(Aminomethyl)-6-(trifluoromethyl)pyridin-2-yl)oxy)piperidin-1-yl)(pyrimidin-5-yl)methanone trifluoroacetate (Compound 1-50)

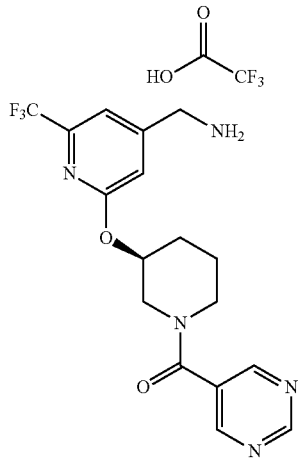

The title compound (1-50) was prepared using the procedure for Example 35, using pyrimidine-5-carboxylic acid in Step 1. LCMS Mass: 382.0 (M$^+$+1).

Example 40: (S)-(3-((4-(Aminomethyl)-6-(trifluoromethyl)pyridin-2-yl)oxy)piperidin-1-yl)(5-methyl-1,3,4-oxadiazol-2-yl)methanone trifluoroacetate (Compound 1-51)

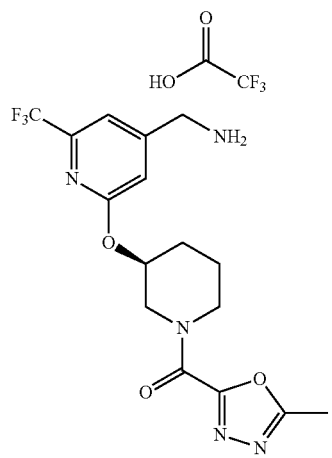

The title compound (1-51) was prepared using the procedure for Example 35, using 5-methyl-1,3,4-oxadiazole-2-carboxylic acid in Step 1. LCMS Mass: 386.0 (M$^+$+1).

Example 41: (S)-1-(3-((4-(Aminomethyl)-6-(trifluoromethyl)pyridin-2-yl)oxy)piperidin-1-yl)-2-methylpropan-1-one trifluoroacetate (Compound 1-52)

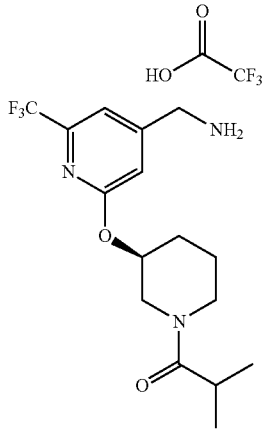

The title compound (1-52) was prepared using the procedure for Example 35, using isobutyric acid in Step 1. LCMS Mass: 346.0 (M$^+$+1).

Example 42: (S)-3-(((4-(Aminomethyl)-6-(trifluoromethyl)pyridin-2-yl)oxy)methyl)-N-phenylpiperidine-1-carboxamide trifluoroacetate (Compound 1-45)

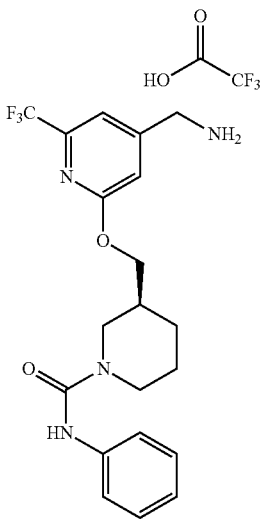

The title compound (1-45) was prepared using the procedure for Example 31, using Int-H in Step 1. LCMS Mass: 409.0 (M$^+$+1).

Example 43: 4-((4-(Aminomethyl)-6-(trifluoromethyl)pyridin-2-yl)oxy)-N-phenylpiperidine-1-carboxamide trifluoroacetate (Compound 1-41)

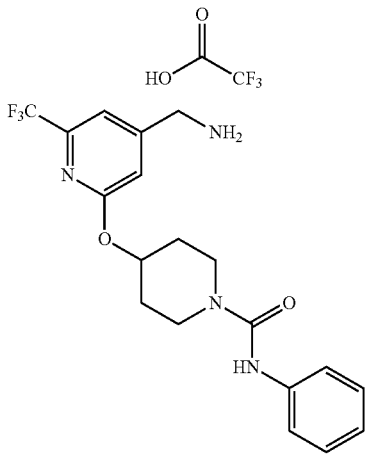

The title compound (1-41) was prepared using the procedure for Example 31, using Int-G in Step 1. LCMS Mass: 395.0 (M$^+$+1).

Example 44: 4-(((4-(Aminomethyl)-6-(trifluoromethyl)pyridin-2-yl)oxy)methyl)-N-phenylpiperidine-1-carboxamide trifluoroacetate (Compound 1-42)

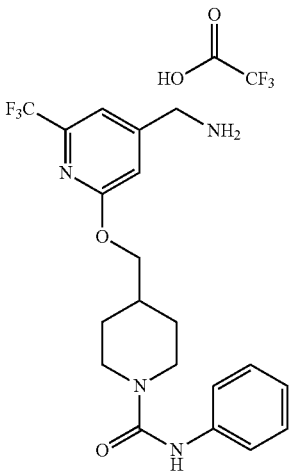

The title compound (1-42) was prepared using the procedure for Example 31, using Int-I in Step 1. LCMS Mass: 409.0 (M$^+$+1).

Example 45: 5-((4-(Aminomethyl)-6-(trifluoromethyl)pyridin-2-yl)oxy)-N-(2-(methylsulfonyl)ethyl)nicotinamide hydrochloride (Compound 1-53)

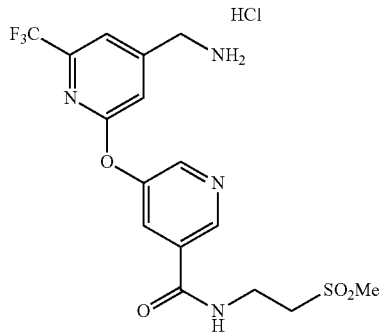 [SMILES: Cl ; CS(=O)(=O)CCNC(=O)c1cncc(Oc2cc(CN)cc(C(F)(F)F)n2)c1]

The title compound (1-53) was prepared using the procedure for Example 1, using Int-J and 2-(methylsulfonyl)ethanamine hydrochloride in Step 1. LCMS Mass: 419.0 ($M^+$+1).

Example 46: (R)-(5-((4-(Aminomethyl)-6-(trifluoromethyl)pyridin-2-yl)oxy)pyridin-3-yl)(3-aminopyrrolidin-1-yl)methanone dihydrochloride (Compound 1-54)

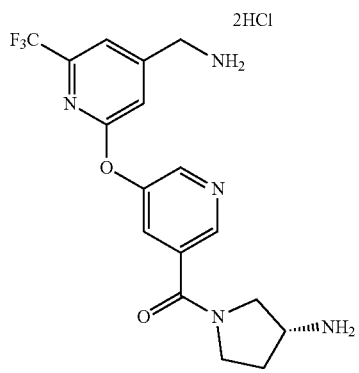 [SMILES: "2HCl" ; NCc1cc(Oc2cncc(C(=O)N3CC[C@@H](N)C3)c2)nc(C(F)(F)F)c1]

The title compound (1-54) was prepared using the procedure for Example 1, using Int-J and (R)-tert-butyl pyrrolidin-3-ylcarbamate in Step 1. LCMS Mass: 382.0 ($M^+$+1).

Example 47: Racemic-trans-(5-((4-(aminomethyl)-6-(trifluoromethyl)pyridin-2-yl)oxy)pyridin-3-yl)(-3-fluoro-4-hydroxypyrrolidin-1-yl)methanone hydrochloride (Compound 1-55)

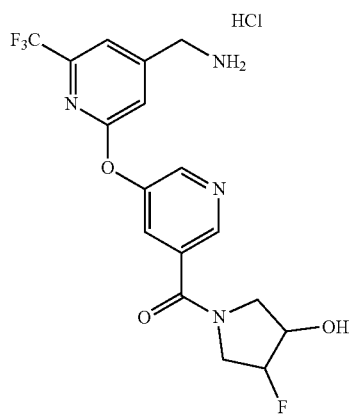

(Racemic-Trans)

The title compound (1-55) was prepared using the procedure for Example 1, using Int-J and racemic-trans-4-fluoro-3-hydroxypyrrolidine hydrochloride in Step 1. LCMS Mass: 401.0 ($M^+$+1).

Example 48: (2-((1H-Indol-4-yl)oxy)-6-(trifluoromethyl)pyridin-4-yl)methanamine (Compound 1-58)

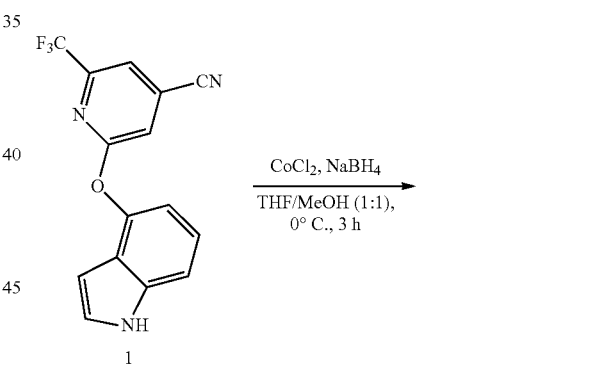

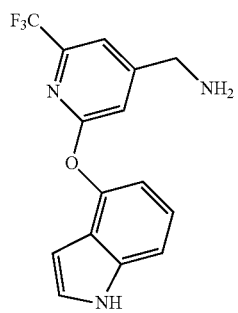

Compound 1-58

To a stirred solution of 2-((1H-indol-4-yl)oxy)-6-(trifluoromethyl)isonicotinonitrile 1 (100 mg, 0.33 mmol) (from Example 49, Step 1) in THF/MeOH (1:1, 4 mL) at 0° C. were added $CoCl_2$ (85 mg, 0.66 mmol) and $NaBH_4$ (125 mg, 3.3 mmol) under inert atmosphere, and the mixture stirred at 0° C. for 3 h. The reaction mixture was quenched with water (10 mL) and filtered through celite. The filtrate was extracted with 10% MeOH/CH$_2$Cl$_2$ (2×10 mL). The organic layer was washed with brine (15 mL), dried (Na$_2$SO$_4$), filtered and concentrated under reduced pressure. The crude was purified by preparative HPLC to afford compound 1-58 (25 mg, 24%) as an off-white solid. $^1$H NMR (400 MHz, DMSO-d$_6$): δ 11.31 (br s, 1H), 7.60 (s, 1H), 7.33-7.28 (m, 2H), 7.16 (s, 1H), 7.11 (t, J=7.9 Hz, 1H), 6.79 (d, J=7.1 Hz, 1H), 6.12-6.09 (m, 1H), 3.79 (s, 2H), 2.02 (br s, 2H); m/z 308.3 (M+H$^+$).

Example 49: (2-((1-(1-Methyl-1H-pyrazol-4-yl)-1H-indol-4-yl)oxy)-6-(trifluoromethyl)pyridin-4-yl) methanamine hydrochloride (Compound 1-37)

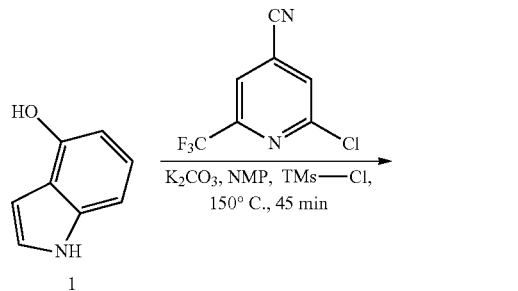

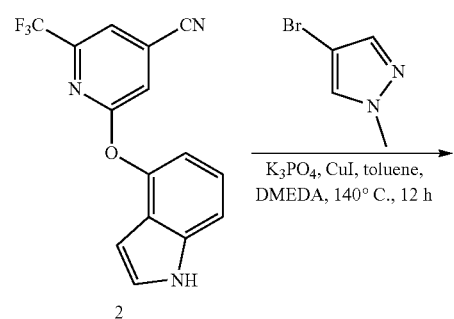

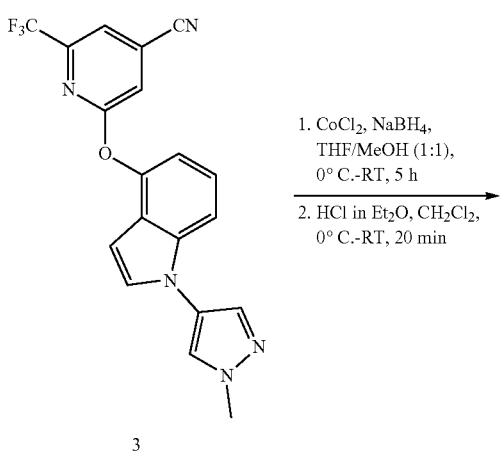

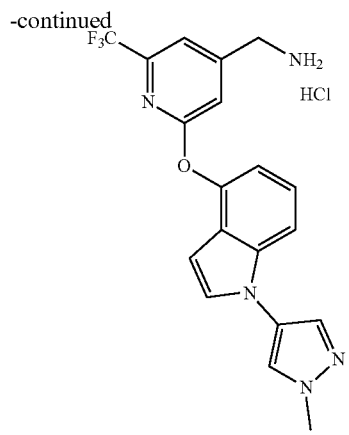

Compound 1-37

Step 1: 2-((1H-Indol-4-yl)oxy)-6-(trifluoromethyl) isonicotinonitrile (2)

To a stirred solution of 1H-indol-4-ol 1 (500 mg, 3.76 mmol) in N-methyl-2-pyrrolidone (12.5 mL) were added 2-chloro-6-(trifluoromethyl) isonicotinonitrile (774 mg, 3.76 mmol), K$_2$CO$_3$ (1.04 g, 7.52 mmol) and TMS-C$_1$ (0.5 mL, 3.76 mmol). The reaction mixture was heated to 150° C. in a microwave synthesizer for 45 min. The reaction mixture was quenched with water (40 mL) and extracted with Et$_2$O (2×50 mL). The combined organic extracts were washed with brine (20 mL), dried (Na$_2$SO$_4$), filtered and concentrated under reduced pressure. The crude was purified (silica gel; eluting 4% EtOAc/hexanes) to afford compound 2 (180 mg, 16%) as an off-white solid. $^1$H NMR (400 MHz, DMSO-d$_6$): δ 11.37 (br s, 1H), 8.16 (d, J=0.7 Hz, 1H), 7.90 (s, 1H), 7.37-7.32 (m, 2H), 7.14 (t, J=7.9 Hz, 1H), 6.86 (dd, J=7.6, 0.6 Hz, 1H), 6.14-6.13 (m, 1H); LC-MS (ESI): 72.74%; m/z 303.9 (M+H$^+$).

Step 2: 2-((1-(1-Methyl-1H-pyrazol-4-yl)-1H-indol-4-yl) oxy)-6-(trifluoromethyl) isonicotinonitrile (3)

To a stirred solution of compound 2 (100 mg, 0.33 mmol) in toluene (5 mL) were added 4-bromo-1-methyl-1H-pyrazole (68 mg, 0.36 mmol), N,N'-dimethylethylenediamine (0.014 mL, 0.13 mmol), potassium phosphate (176 mg, 0.82 mmol) and CuI (6.2 mg, 0.03 mmol). The reaction mixture was degassed under Ar for 30 min at RT, and then heated to 140° C. for 12 h. The mixture was diluted with EtOAc (30 mL) and filtered through celite. The filtrate was concentrated under reduced pressure and the crude was purified (silica gel; using 20% EtOAc/hexanes) to afford compound 3 (65 mg, 51%) as sticky solid. $^1$H NMR (500 MHz, DMSO-d$_6$): δ 8.26 (s, 1H), 8.20 (s, 1H), 8.01 (s, 1H), 7.85 (s, 1H), 7.52 (d, J=3.5 Hz, 1H), 7.44 (d, J=8.1 Hz, 1H), 7.25 (t, J=8.0 Hz, 1H), 6.98 (d, J=7.5 Hz, 1H), 6.38 (d, J=2.9 Hz, 1H), 3.92 (s, 3H); LC-MS (ESI): 97.13%; m/z 383.9 (M+H$^+$).

Step 3: (2-((1-(1-Methyl-1H-pyrazol-4-yl)-1H-indol-4-yl) oxy)-6-(trifluoromethyl) pyridin-4-yl) methanamine hydrochloride (Compound 1-37)

To a stirred solution of compound 3 (65 mg, 0.17 mmol) in THF/MeOH (1:1, 4 mL) at 0° C. were added CoCl$_2$ (44 mg, 0.33 mmol) and NaBH$_4$ (64 mg, 1.7 mmol) portion wise under inert atmosphere. The reaction was warmed to RT and stirred for 5 h. The reaction mixture was filtered through a pad of celite and the residue was washed with 10% MeOH/CH$_2$Cl$_2$ (20 mL). The filtrate was washed with brine (10 mL), dried (Na$_2$SO$_4$), filtered and concentrated under reduced pressure to obtain the desired amine.

To this amine in CH$_2$Cl$_2$ (2 mL) was added 2M HCl in Et$_2$O (5 mL, 10 mmol) at 0° C. under inert atmosphere and stirred for 20 min. The obtained solid was filtered and dried under vacuum to afford compound 1-37 (20 mg, 30%) as pale yellow solid. $^1$H NMR (400 MHz, DMSO-d$_6$): δ 8.56 (br s, 3H), 8.24 (s, 1H), 7.82 (s, 2H), 7.51-7.38 (m, 3H), 7.23 (t, J=8.0 Hz, 1H), 6.91 (d, J=7.3 Hz, 1H), 6.30 (dd, J=3.2, 0.6 Hz, 1H), 4.21-4.16 (m, 2H), 3.91 (s, 3H); MS (Agilent 6310 Ion Trap): m/z 388.3 (M+H$^+$).

Example 50: 2-(4-((4-(Aminomethyl)-6-(trifluoromethyl)pyridin-2-yl)oxy)-1H-indol-1-yl)-N-methyl-N-phenylacetamide hydrochloride (Compound 1-38)

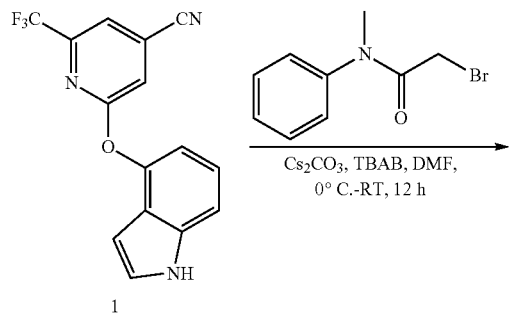

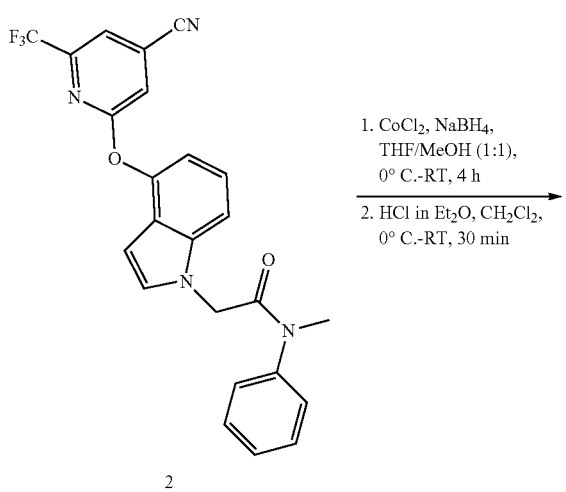

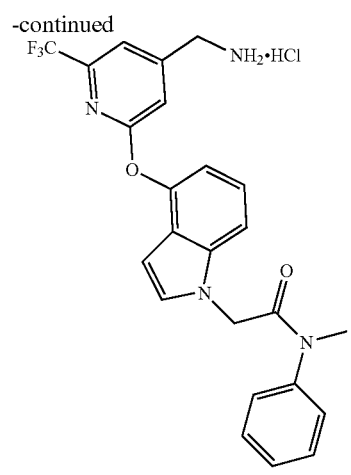

Compound 1-38

Step 1: 2-(4-((4-Cyano-6-(trifluoromethyl)pyridin-2-yl)oxy)-1H-indol-1-yl)-N-methyl-N-phenylacetamide (2)

To a stirred solution of 2-((1H-indol-4-yl) oxy)-6-(trifluoromethyl) isonicotinonitrile 1 (100 mg, 0.33 mmol) (from Example 49, Step 1) in DMF (3 mL) at 0° C., were added 2-bromo-N-methyl-N-phenylacetamide (113 mg, 0.49 mmol), Cs$_2$CO$_3$ (214 mg, 0.66 mmol) and n-Bu$_4$NBr (5.3 mg, 0.02 mmol). The mixture was warmed to RT and stirred for 12 h. The reaction mixture was quenched with water (20 mL) and extracted with EtOAc (2×30 mL). The combined organic extracts were washed with brine (15 mL), dried (Na$_2$SO$_4$), filtered and concentrated under reduced pressure. The crude was purified (silica gel; eluting 10-15% EtOAc/hexanes) to afford compound 2 (130 mg, 87%) as an off-white solid. $^1$H NMR (500 MHz, DMSO-d$_6$): δ 8.18 (s, 1H), 7.93 (s, 1H), 7.57-7.55 (m, 4H), 7.46-7.44 (m, 1H), 7.22-7.12 (m, 3H), 6.89 (d, J=7.8 Hz, 1H), 6.14 (br s, 1H), 4.78 (br s, 2H), 3.21 (br s, 3H); LC-MS (ESI): m/z 451.1 (M+H$^+$).

Step 2: 2-(4-((4-(Aminomethyl)-6-(trifluoromethyl)pyridin-2-yl)oxy)-1H-indol-1-yl)-N-methyl-N-phenylacetamide hydrochloride (Compound 1-38)

To a stirred solution of compound 2 (130 mg, 0.29 mmol) in THF/MeOH (1:1, 6 mL) at 0° C. were added cobalt (II) chloride (74 mg, 0.58 mmol) and NaBH$_4$ (109 mg, 2.88 mmol) portion wise under inert atmosphere. The mixture was warmed to RT and stirred for 4 h. The reaction mixture was filtered through a pad of celite and the celite was washed with 10% MeOH/CH$_2$Cl$_2$ (30 mL). The filtrate was washed with brine (10 mL), dried (Na$_2$SO$_4$), filtered and concentrated under reduced pressure to obtain the desired amine.

To this amine in CH$_2$Cl$_2$ (2 mL) was added 2 M HCl in Et$_2$O (3 mL, 6 mmol) at 0° C. under inert atmosphere and stirred for 30 min. The obtained solid was filtered and dried under vacuum to afford compound 1-38 (91 mg, 70%) as an off-white solid. $^1$H NMR (400 MHz, DMSO-d$_6$): δ 8.37 (br s, 3H), 7.78 (s, 1H), 7.59-7.47 (m, 5H), 7.40 (s, 1H), 7.24-7.13 (m, 3H), 6.84 (d, J=8.4 Hz, 1H), 6.11 (d, J=3.0 Hz, 1H), 4.78 (br s, 2H), 4.20 (br s, 2H), 3.22 (br s, 3H); MS (Agilent 6310 Ion Trap): m/z 455.3 (M+H$^+$).

Example 51: 2-(4-((4-(Aminomethyl)-6-(trifluoromethyl)pyridin-2-yl)oxy)-1H-indol-1-yl)-1-(piperidin-1-yl)ethanone (Compound 1-56)

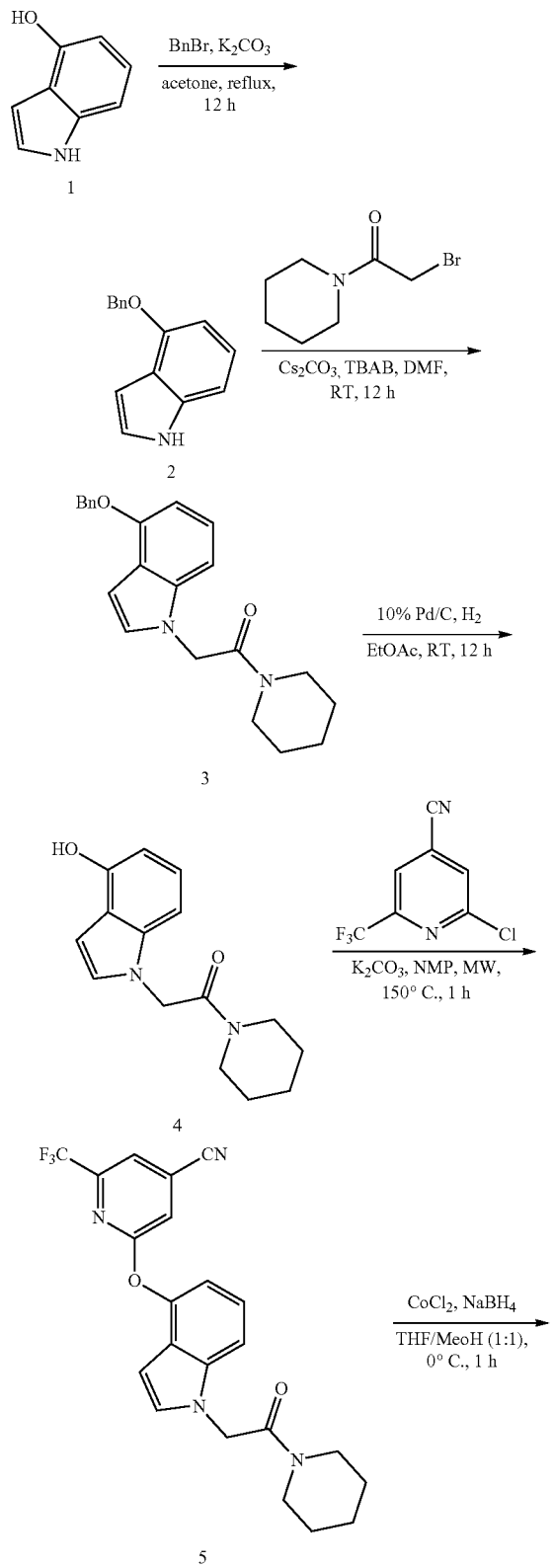

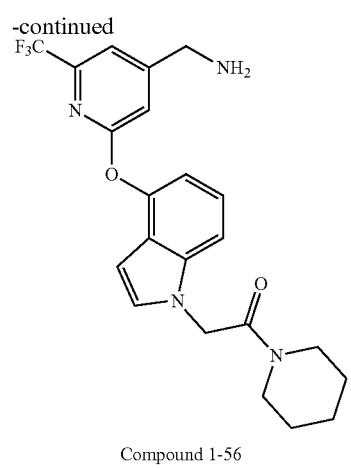

Compound 1-56

Step 1: 4-(Benzyloxy)-1H-indole (2)

To a stirred solution of 1H-indol-4-ol 1 (1 g, 7.52 mmol) in acetone (50 mL) were added benzyl bromide (1.54 g, 8.95 mmol) and $K_2CO_3$ (3.11 g, 22.56 mmol) at RT under inert atmosphere. The reaction mixture was heated to reflux temperature and stirred for 12 h. The mixture was diluted with water (60 mL) and extracted with EtOAc (2×60 mL). The combined organic extracts were washed with brine (20 mL), dried ($Na_2SO_4$), filtered, and concentrated under reduced pressure. The crude was purified (silica gel; eluting 1-6% EtOAc/hexanes) to afford compound 2 (650 mg, 41%) as colorless sticky solid. $^1$H NMR (500 MHz, DMSO-$d_6$): δ 11.08 (br s, 1H), 7.49 (d, J=7.5 Hz, 2H), 7.39 (t, J=7.5 Hz, 2H), 7.34-7.29 (m, 1H), 7.21 (t, J=2.6 Hz, 1H), 7.01-6.92 (m, 2H), 6.55 (d, J=7.2 Hz, 1H), 6.45-6.43 (m, 1H), 5.20 (s, 2H); LC-MS: m/z 224.3 (M+H$^+$).

Step 2: 2-(4-(Benzyloxy)-1H-indol-1-yl)-1-(piperidin-1-yl)ethan-1-one (3)

To a stirred solution of compound 2 (200 mg, 0.9 mmol) in DMF (10 mL) at RT were added 2-bromo-1-(piperidin-1-yl)ethan-1-one (277 mg, 1.34 mmol), $Cs_2CO_3$ (584 mg, 1.8 mmol) and n-$Bu_4$NBr (catalytic amount). The mixture was stirred at RT for 12 h. The mixture was diluted with water (30 mL), stirred well and filtered. The obtained solid was dissolved in $CH_2Cl_2$, dried ($Na_2SO_4$), filtered and concentrated under reduced pressure. The crude was purified (silica gel; eluting 30% EtOAc/hexanes) to afford compound 3 (150 mg, 48%) as an off-white solid. $^1$H NMR (500 MHz, DMSO-$d_6$): δ 7.64 (d, J=7.2 Hz, 2H), 7.54 (t, J=7.5 Hz, 2H), 7.49-7.44 (m, 1H), 7.29 (d, J=2.9 Hz, 1H), 7.15-7.05 (m, 2H), 6.73 (d, J=7.5 Hz, 1H), 6.60 (d, J=3.2 Hz, 1H), 5.36 (s, 2H), 5.24 (s, 2H), 3.64 (br t, J=4.9 Hz, 2H), 3.55 (t, J=5.2 Hz, 2H), 1.76-1.65 (m, 4H), 1.58-1.56 (m, 2H); LC-MS (ESI): m/z 349.0 (M+H$^+$).

Step 3: 2-(4-Hydroxy-1H-indol-1-yl)-1-(piperidin-1-yl)ethan-1-one (4)

To a stirred solution of compound 3 (150 mg, 0.43 mmol) in EtOAc (30 mL) and MeOH (5 mL) was added 10% Pd/C (50% wet, 50 mg) under inert atmosphere. The reaction mixture was evacuated and stirred under H2 atmosphere (balloon) at RT for 12 h. The reaction mixture was filtered through a pad of celite and washed with EtOAc (10 mL).

The filtrate was concentrated under reduced pressure to afford compound 4 (80 mg, 72%) as an off-white solid. $^1$H NMR (500 MHz, DMSO-$d_6$): δ 9.32 (s, 1H), 7.06 (d, J=3.2 Hz, 1H), 6.85 (t, J=7.8 Hz, 1H), 6.73 (d, J=8.1 Hz, 1H), 6.44 (d, J=2.9 Hz, 1H), 6.35 (d, J=7.5 Hz, 1H), 5.03 (s, 2H), 3.47 (t, J=5.2 Hz, 2H), 3.39 (t, J=4.9 Hz, 2H), 1.61-1.48 (m, 4H), 1.43-1.40 (m, 2H); LC-MS (ESI): m/z 258.9 (M+H$^+$).

Step 4: 2-((1-(2-Oxo-2-(piperidin-1-yl)ethyl)-1H-indol-4-yl)oxy)-6-(trifluoromethyl)isonicotinonitrile (5)

To a stirred solution of compound 4 (80 mg, 0.31 mmol) in N-methyl-2-pyrrolidone (3 mL) were added 2-chloro-6-(trifluoromethyl)isonicotinonitrile (77 mg, 0.37 mmol) and $K_2CO_3$ (86 mg, 0.62 mmol). The reaction mixture was heated to 150° C. in a microwave synthesizer for 1 h. The mixture was diluted with water (20 mL) and extracted with EtOAc (2×30 mL). The combined organic extracts were washed with brine (20 mL), dried ($Na_2SO_4$), filtered and concentrated under reduced pressure. The crude was purified (silica gel; eluting 30% EtOAc/hexanes) to afford compound 5 (30 mg, 23%) as an off-white solid. $^1$H NMR (500 MHz, DMSO-$d_6$): δ 8.19 (s, 1H), 7.94 (s, 1H), 7.30 (d, J=8.4 Hz, 1H), 7.27 (d, J=3.2 Hz, 1H), 7.15 (t, J=8.0 Hz, 1H), 6.89 (d, J=7.8 Hz, 1H), 6.16 (d, J=3.2 Hz, 1H), 5.19 (s, 2H), 3.53-3.50 (m, 2H), 3.43 (t, J=5.5 Hz, 2H), 1.64-1.53 (m, 4H), 1.46-1.42 (m, 2H); LC-MS (ESI): m/z 429.1 (M+H$^+$).

Step 5: 2-(4-((4-(Aminomethyl)-6-(trifluoromethyl) pyridin-2-yl)oxy)-1H-indol-1-yl)-1-(piperidin-1-yl) ethan-1-one (Compound 1-56)

To a stirred solution of compound 5 (30 mg, 0.07 mmol) in THF/MeOH (1:1, 8 mL) at 0° C. were added $CoCl_2$ (18 mg, 0.14 mmol) and $NaBH_4$ (27 mg, 0.7 mmol). The mixture was stirred at 0° C. for 1 h. The mixture was filtered, the filtrate was washed with water (15 mL) and extracted with EtOAc (2×20 mL). The combined organic layers were washed with brine (15 mL), dried ($Na_2SO_4$), filtered, and concentrated under reduced pressure. The crude was triturated with n-pentane (2×5 mL) and then purified by preparative HPLC to afford compound 1-56 (10 mg, 33%) as pale brown solid. $^1$H NMR (400 MHz, CD$_3$OD): δ 7.58 (s, 1H), 7.29-7.26 (m, 1H), 7.22 (t, J=7.8 Hz, 1H), 7.16-7.11 (m, 2H), 6.90 (dd, J=7.5, 0.7 Hz, 1H), 6.20 (dd, J=3.2, 0.7 Hz, 1H), 5.18 (s, 2H), 4.18 (s, 2H), 3.62-3.54 (m, 4H), 1.75-1.68 (m, 2H), 1.66-1.61 (m, 2H), 1.60-1.53 (m, 2H); LC-MS (ESI): m/z 433.1 (M+H$^+$).

Example 52: tert-Butyl 4-(2-(4-((4-(aminomethyl)-6-(trifluoromethyl)pyridin-2-yl)oxy)-1H-indol-1-yl) acetyl)piperazine-1-carboxylate (Compound 1-57)

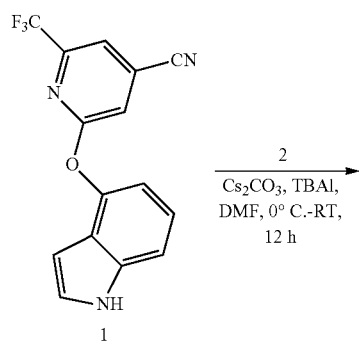

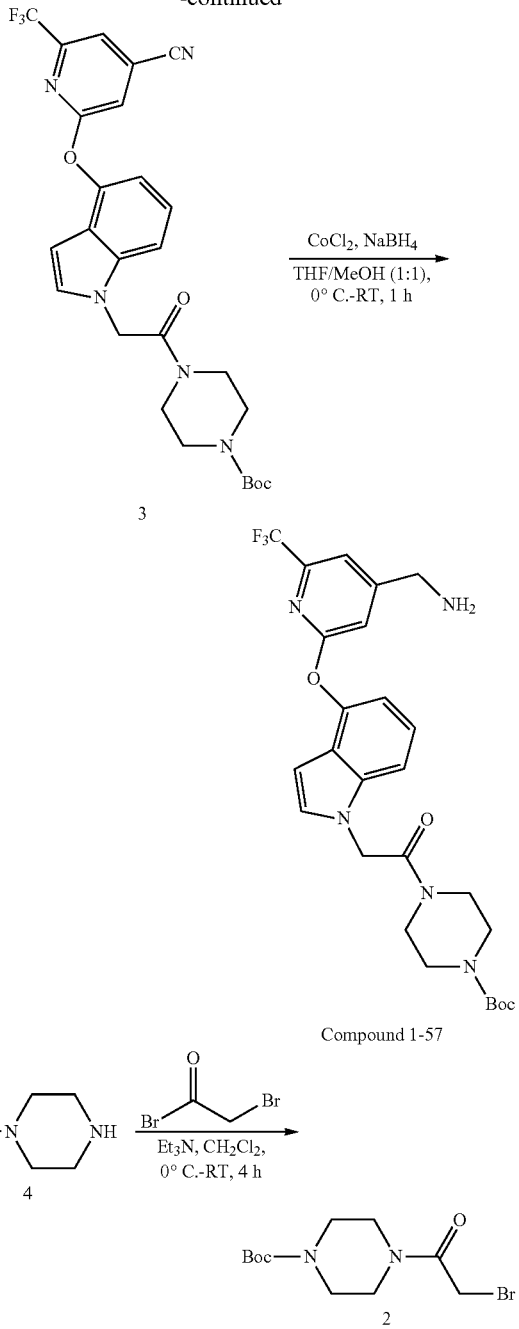

Step 1: tert-Butyl 4-(2-bromoacetyl)piperazine-1-carboxylate (2)

To a stirred solution of tert-butyl piperazine-1-carboxylate 4 (1 g, 5.38 mmol) in $CH_2Cl_2$ (15 mL) at 0° C., were added 2-bromoacetyl bromide (864 mg, 4.3 mmol) and TEA (1 mL, 7.53 mmol). The reaction mixture was warmed to RT and stirred for 4 h. The mixture was quenched with water (50 mL) and extracted with $CH_2Cl_2$ (2×40 mL). The combined organic extracts were washed with brine (20 mL), dried ($Na_2SO_4$), filtered and concentrated under reduced pressure. The crude was purified (silica gel; eluting 25% EtOAc/hexanes) to afford compound 2 (900 mg, 54%) as pale yellow solid. $^1$H NMR (500 MHz, DMSO-d$_6$): δ 4.16 (s, 2H), 3.47-3.42 (m, 4H), 3.38-3.35 (m, 2H), 3.31-3.29 (m, 2H), 1.41 (s, 9H); LC-MS (ESI): m/z 328.1 (M$^+$+Na).

Step 2: tert-Butyl 4-(2-(4-((4-cyano-6-(trifluoromethyl)pyridin-2-yl)oxy)-1H-indol-1-yl)acetyl)piperazine-1-carboxylate (3)

To a stirred solution of 2-((1H-indol-4-yl)oxy)-6-(trifluoromethyl)isonicotinonitrile 1 (150 mg, 0.5 mmol) (from Example 49, Step 1) in DMF (12 mL) at 0° C., were added tert-butyl 4-(2-bromoacetyl)piperazine-1-carboxylate 2 (228 mg, 0.74 mmol), Cs$_2$CO$_3$ (324 mg, 0.99 mmol) and n-Bu$_4$NBr (8 mg, 0.02 mmol). The reaction mixture was warmed to RT and stirred for 12 h. The mixture was quenched with water (30 mL) and extracted with EtOAc (2×30 mL). The combined organic extracts were washed with brine (20 mL), dried (Na$_2$SO$_4$), filtered and concentrated under reduced pressure to obtain the crude. The crude was triturated with Et$_2$O (2×10 mL) to afford compound 3 (150 mg, 57%) as white solid. $^1$H NMR (500 MHz, DMSO-d$_6$): δ 8.32 (s, 1H), 8.09 (s, 1H), 7.47 (d, J=8.1 Hz, 1H), 7.40 (d, J=3.2 Hz, 1H), 7.29 (t, J=8.0 Hz, 1H), 7.03 (d, J=7.8 Hz, 1H), 6.31 (d, J=3.2 Hz, 1H), 5.37 (s, 2H), 3.72-3.70 (m, 2H), 3.59-3.56 (m, 4H), 3.48-3.46 (m, 2H), 1.56 (s, 9H); LC-MS (ESI): m/z 474.0 (M$^+$-$^t$Bu).

Step 3: tert-Butyl 4-(2-(4-((4-(aminomethyl)-6-(trifluoromethyl)pyridin-2-yl)oxy)-1H-indol-1-yl)acetyl) piperazine-1-carboxylate (Compound 1-57)

To a stirred solution of compound 3 (100 mg, 0.19 mmol) in THF/MeOH (1:1, 10 mL) at 0° C. were added CoCl$_2$ (61 mg, 0.5 mmol) and NaBH$_4$ (36 mg, 0.94 mmol). The reaction was warmed to RT and stirred for 1 h. The mixture was filtered through a pad of celite. The filtrate was washed with water (20 mL) and extracted with EtOAc (2×30 mL). The combined organic layers were washed with brine (15 mL), dried (Na$_2$SO$_4$), filtered, and concentrated under reduced pressure. The crude was purified by preparative HPLC to afford compound 1-57 (23 mg, 15%) as white solid. $^1$H NMR (500 MHz, DMSO-d$_6$): δ 7.61 (s, 1H), 7.28 (d, J=8.1 Hz, 1H), 7.24-7.19 (m, 2H), 7.13 (t, J=8.0 Hz, 1H), 6.81 (d, J=7.5 Hz, 1H), 6.14 (d, J=3.2 Hz, 1H), 5.22 (s, 2H), 3.79 (s, 2H), 3.57-3.55 (m, 2H), 3.45-3.42 (m, 4H), 3.34-3.32 (m, 2H), 2.21 (b s, 2H), 1.42 (s, 9H); LC-MS (ESI): m/z 478.1 (M$^+$-$^t$Bu).

Example 53: 5-((4-(Aminomethyl)-6-(trifluoromethyl)pyridin-2-yl)oxy)-3,4-dihydroquinolin-2(1H)-one hydrochloride (Compound 1-59)

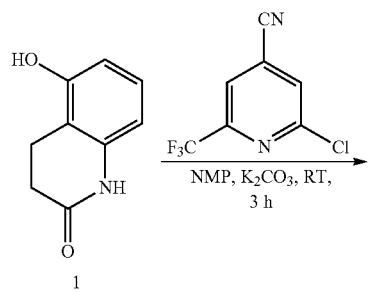

Step 1: 2-((2-Oxo-1,2,3,4-tetrahydroquinolin-5-yl)oxy)-6-(trifluoromethyl)isonicotinonitrile (2)

To a stirred solution of 5-hydroxy-3,4-dihydroquinolin-2 (1H)-one 1 (50 mg, 0.31 mmol) in N-methyl-2-pyrrolidone (3 mL) at RT, were added 2-chloro-6-(trifluoromethyl)isonicotinonitrile (63 mg, 0.31 mmol) and K$_2$CO$_3$ (85 mg, 0.61 mmol). The mixture was stirred at RT for 3 h. The mixture was diluted with water (10 mL) and extracted with EtOAC (2×15 mL). The combined organic extracts were washed with brine (10 mL), dried (Na$_2$SO$_4$), filtered, and concentrated under reduced pressure. The crude was triturated with Et$_2$O (2×5 mL) to afford compound 2 (50 mg, 49%) as white solid. $^1$H NMR (400 MHz, DMSO-d$_6$): δ 10.28 (s, 1H), 8.18 (s, 1H), 7.97 (s, 1H), 7.23 (t, J=8.0 Hz, 1H), 6.85-6.78 (m, 2H), 2.65 (t, J=7.6 Hz, 2H), 2.42-2.35 (m, 2H); LC-MS (ESI): m/z 332.1 (M−1).

Step 2: 5-((4-(Aminomethyl)-6-(trifluoromethyl) pyridin-2-yl)oxy)-3,4-dihydroquinolin-2(1H)-one hydrochloride (Compound 1-59)

To a stirred solution of compound 2 (50 mg, 0.15 mmol) in THF/MeOH (1:1, 6 mL) at 0° C. were added CoCl$_2$ (39 mg, 0.3 mmol) and NaBH$_4$ (57 mg, 1.5 mmol) under inert atmosphere; warmed to RT and stirred for 2 h. The mixture was diluted with EtOAc (20 mL), filtered through a pad of celite and the celite pad was washed with EtOAc (10 mL). The filtrate was washed with water (15 mL) and brine (10 mL). The organic layer was separated, dried (Na$_2$SO$_4$), filtered, and concentrated under reduced pressure. The crude was triturated with Et$_2$O (2×5 mL) to afford the desired amine as pale brown solid.

To this amine in CH$_2$Cl$_2$ (2 mL) was added 2M HCl in Et$_2$O (0.5 mL) at 0° C. The mixture was warmed to RT and

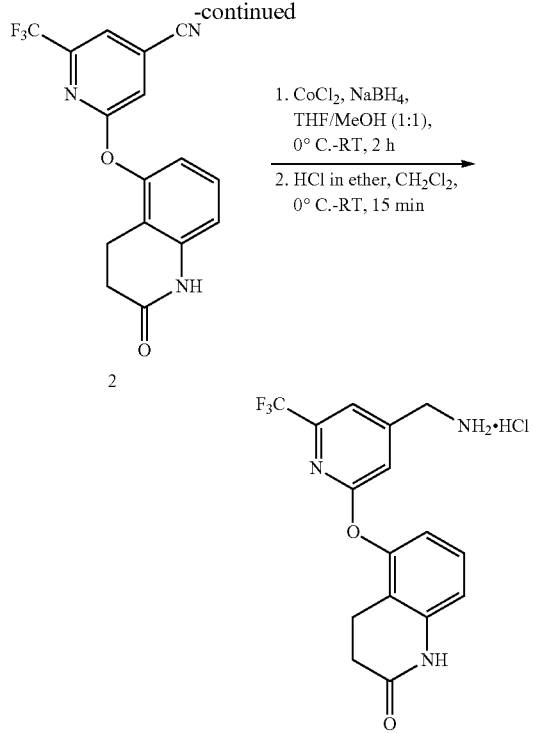

Compound 1-59 stirred for 15 min. The obtained solid was filtered and dried under vacuum to afford compound 1-59 (35 mg, 69%) as an off-white solid. $^1$H NMR (500 MHz, DMSO-d$_6$): δ 10.30 (s, 1H), 8.43 (br s, 2H), 7.77 (s, 1H), 7.36 (s, 1H), 7.22 (t, J=8.1 Hz, 1H), 6.81 (d, J=7.8 Hz, 1H), 6.75 (d, J=8.1 Hz, 1H), 4.19 (br s, 2H), 2.60 (t, J=6.9 Hz, 2H), 2.40-2.36 (m, 2H); MS (Agilent 6310 Ion Trap): m/z 338.2 (M+H$^+$).

Example 54: (6-(Trifluoromethyl)-[2,3'-bipyridin]-4-yl)methanamine trifluoroacetate (Compound 1-1)

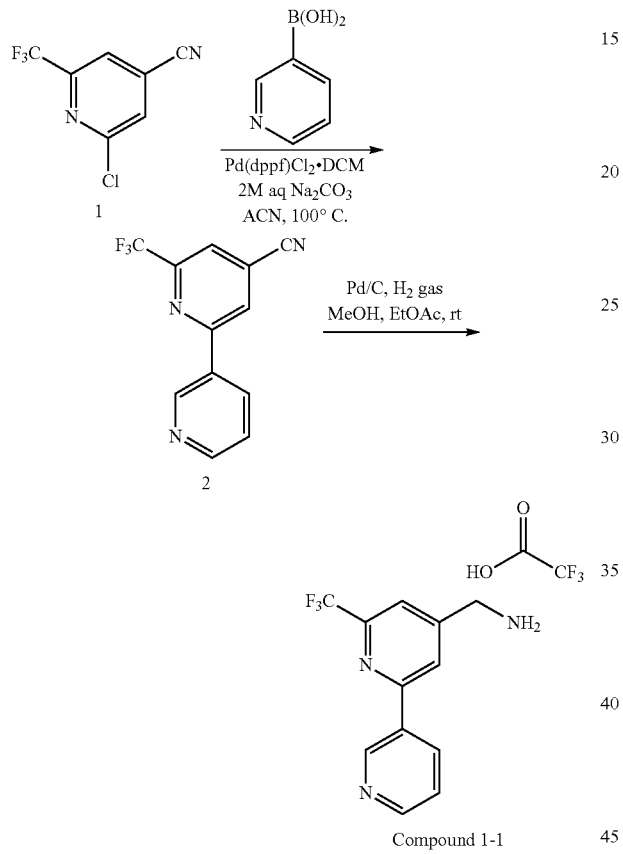

Step 1: 6-(Trifluoromethyl)-[2,3'-bipyridine]-4-carbonitrile (2)

A mixture of 2-chloro-6-(trifluoromethyl)isonicotinonitrile 1 (125 mg, 0.605 mmol), 3-pyridylboronic acid (90 mg, 0.738 mmol), 2M aq. Na$_2$CO$_3$ solution (0.6 mL), and ACN (3 mL) was purged with nitrogen at RT for 3 min. [1,1'-Bis(diphenylphosphino)ferrocene]dichloropalladium(II) complex with DCM (1:1) (5 mol %) was added, and the mixture heated at 100° C. for 4 h. The mixture was concentrated and purified via silica gel chromatography to afford compound 2 (114 mg, 76%) a as white solid. LCMS Mass: 250 (M$^+$+1).

Step 2: (6-(Trifluoromethyl)-[2,3'-bipyridin]-4-yl)methanamine trifluoroacetate (Compound 1-1)

The title compound (1-1) (121 mg, 72%) was prepared from 6-(trifluoromethyl)-[2,3'-bipyridine]-4-carbonitrile 2 using the procedure for Example 31, Step 2. $^1$H NMR (300 MHz, DMSO-d$_6$): δ 9.28 (m, 1H), 8.75 (m, 1H), 8.49 (m, 1H), 8.43 (br s, 3H), 8.05 (s, 1H), 7.65 (m, 1H), 4.26-4.34 (m, 2H); LCMS Mass: 254.0 (M$^+$+1).

Example 55: (2-([1,1'-Biphenyl]-3-yloxy)-6-(trifluoromethyl)pyridin-4-yl)methanamine trifluoroacetate (Compound 1-2)

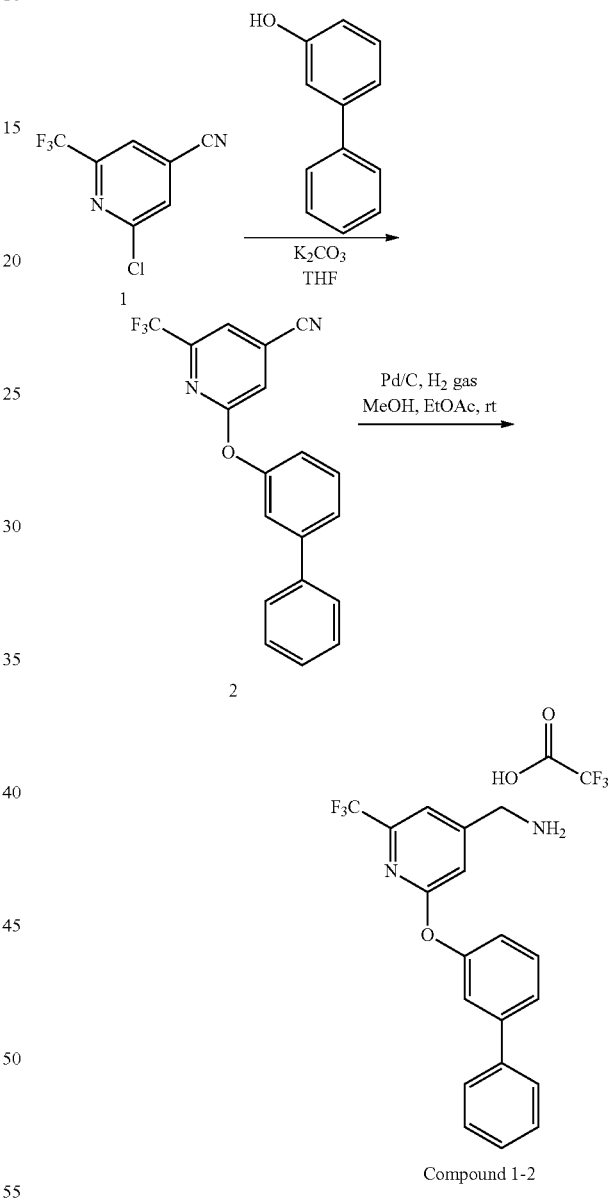

Step 1: 2-([1,1'-Biphenyl]-3-yloxy)-6-(trifluoromethyl)isonicotinonitrile (2)

A stirred mixture of 2-chloro-6-(trifluoromethyl)isonicotinonitrile 1 (75 mg, 0.363 mmol), [1,1'-biphenyl]-3-ol (75 mg, 0.435 mmol), K$_2$CO$_3$ (150 mg, 1.089 mmol), and THF (3 mL), was heated at 75° C. for 32 h. After cooling to RT, the mixture was concentrated and purified via silica gel chromatography to afford compound 2 (75 mg, 61%) as a colorless oil. $^1$H NMR (300 MHz, DMSO-d$_6$): δ 8.20 (m, 1H), 8.03 (m, 1H), 7.50-7.70 (m, 2H), 7.35-7.48 (m, 3H), 7.20 (m, 1H), 6.90-7.08 (m, 3H).

Step 2: (2-([1,1'-Biphenyl]-3-yloxy)-6-(trifluoromethyl)pyridin-4-yl)methanamine trifluoroacetate (Compound 1-2)

The title compound (1-2) (51 mg, 69%) was prepared from 2-([1,1'-biphenyl]-3-yloxy)-6-(trifluoromethyl)isonicotinonitrile 2 using the procedure for Example 31, Step 2. $^1$H NMR (300 MHz, DMSO-d$_6$): δ 8.36 (br s, 3H), 7.79 (m, 1H), 7.65-7.71 (m, 2H), 7.55-7.62 (m, 2H), 7.35-7.61 (m, 5H), 7.18 (m, 1H), 4.19-4.26 (m, 2H); LCMS Mass: 345.0 (M$^+$+1).

Example 56: (2-(3-Phenoxyphenoxy)-6-(trifluoromethyl)pyridin-4-yl)methanamine trifluoroacetate (Compound 1-3)

The title compound (1-3) was prepared using the procedure for Example 55, using 3-phenoxyphenol in Step 1. LCMS Mass: 361.0 (M$^+$+1).

Example 57: (2-(3-(Phenoxymethyl)phenoxy)-6-(trifluoromethyl)pyridin-4-yl)methanamine trifluoroacetate (Compound 1-4)

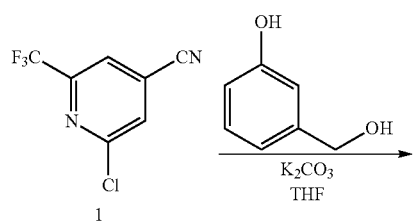

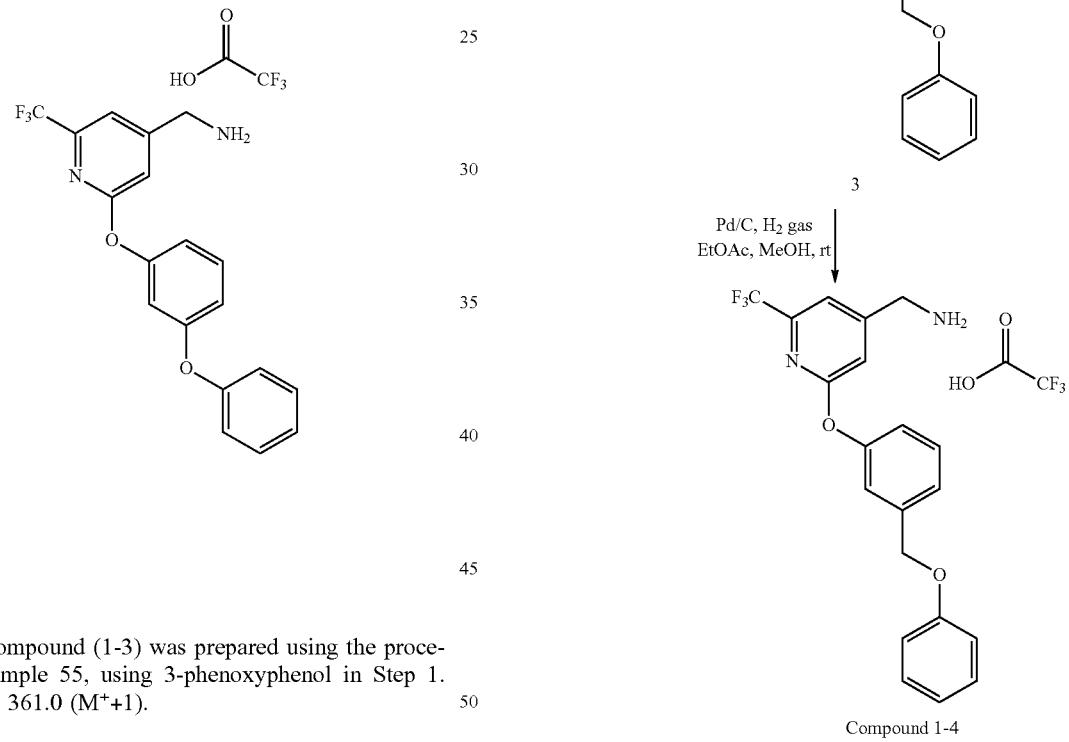

Compound 1-4

Step 1: 2-(3-(Hydroxymethyl)phenoxy)-6-(trifluoromethyl)isonicotinonitrile (2)

The title compound (2) (250 mg, 59%) was prepared using the procedure for Example 55, Step 1, using 3-(hydroxymethyl)phenol. $^1$H NMR (300 MHz, DMSO-d$_6$): δ 8.18 (s, 1H), 7.97 (s, 1H), 7.40 (m, 1H), 7.22 (m, 1H), 7.14 (m, 1H), 7.08 (m, 1H), 5.29 (m, 1H), 4.49-4.53 (m, 2H); LCMS Mass: 295.0 (M$^+$+1).

Step 2: 2-(3-(Phenoxymethyl)phenoxy)-6-(trifluoromethyl)isonicotinonitrile (3)

To a solution of Ph$_3$P (49 mg, 0.186 mmol) in THF (1 mL) at 0° C., was added diisopropyl azodicarboxylate (38 mg, 0.186 mmol). The mixture was warmed to RT and stirred for 15 min. 2-(3-(Hydroxymethyl)phenoxy)-6-(trifluoromethyl)isonicotinonitrile 2 (50 mg, 0.169 mmol) was added and the mixture stirred for a further 15 min. Phenol (16 mg, 0.169 mmol) was added and the mixture stirred at RT for 16 h. The mixture was partitioned between EtOAc (10 mL) and water (10 mL). The organic layer was separated, dried (Na$_2$SO$_4$), filtered, and then concentrated under reduced pressure. The residue was purified via silica gel chromatography to afford compound 3 (25 mg, 40%) as a colorless oil. LCMS Mass: 371.0 (M$^+$+1).

Example 59: (2-(3-(1H-Pyrazol-4-yl)phenoxy)-6-(trifluoromethyl)pyridin-4-yl)methanamine trifluoroacetate (Compound 1-6)

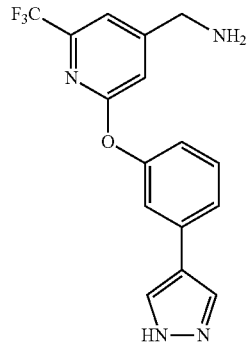

The title compound (1-6) was prepared using the procedure for Example 55, using 3-(1H-pyrazol-4-yl)phenol in Step 1. LCMS Mass: 335.0 (M$^+$+1).

Step 3: (2-(3-(Phenoxymethyl)phenoxy)-6-(trifluoromethyl)pyridin-4-yl)methanamine trifluoroacetate trifluoroacetate (Compound 1-4)

The title compound (1-4) (17 mg, 59%) was prepared from 2-(3-(phenoxymethyl)phenoxy)-6-(trifluoromethyl)isonicotinonitrile 3 using the procedure for Example 31, Step 2. $^1$H NMR (300 MHz, DMSO-d$_6$): δ 8.38 (br s, 3H), 7.77 (s, 1H), 7.25-7.55 (m, 6H), 7.18 (m, 1H), 6.90-7.00 (m, 3H), 5.12 (s, 2H), 4.18-4.22 (m, 2H); LCMS Mass: 375.0 (M$^+$+1).

Example 58: 3-((4-(Aminomethyl)-6-(trifluoromethyl)pyridin-2-yl)oxy)-N-phenylaniline (Compound 1-5)

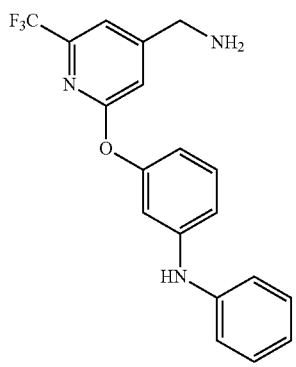 [SMILES: NCc1cc(Oc2cccc(Nc3ccccc3)c2)nc(C(F)(F)F)c1]

The title compound (1-5) was prepared using the procedure for Example 55, using 3-(phenylamino)phenol in Step 1. Compound 1-5 did not require HPLC purification, rather the obtained solid was triturated with Et$_2$O to afford pure 1-5. LCMS Mass: 360.0 (M$^+$+1).

Example 60: 3-((4-(Aminomethyl)-6-(trifluoromethyl)pyridin-2-yl)oxy)-N-(2-cyanoethyl)benzamide hydrochloride (Compound 1-198)

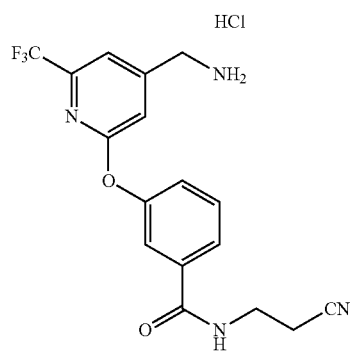 [SMILES: Cl ; N#CCCNC(=O)c1cccc(Oc2cc(CN)cc(C(F)(F)F)n2)c1]

The title compound (1-198) was prepared using the procedure for Example 1, using 3-aminopropionitrile in Step 1. LCMS Mass: 365.0 (M$^+$+1).

Example 61: 1-(3-((4-(Aminomethyl)-6-(trifluoromethyl)pyridin-2-yl)oxy)benzoyl)azetidine-3-carbonitrile trifluoroacetate (Compound 1-199)

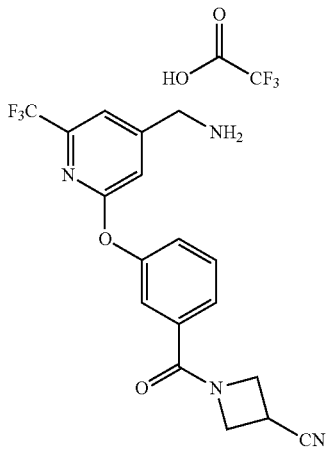

The title compound (1-199) was prepared using the procedure for Example 1, using 3-cyanoazetidine hydrochloride in Step 1. LCMS Mass: 377.0 (M$^+$+1).

Example 62: 3-((4-(Aminomethyl)-6-(trifluoromethyl)pyridin-2-yl)oxy)-N-(oxetan-3-yl)benzamide trifluoroacetate (Compound 1-200)

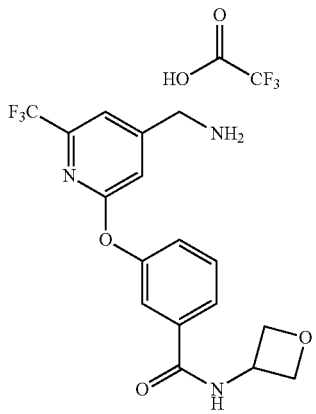

The title compound (1-200) was prepared using the procedure for Example 1, using oxetan-3-amine hydrochloride in Step 1, and trifluoroacetic acid in DCM in Step 2. $^1$H NMR (300 MHz, DMSO-d$_6$): δ 8.36 (br s, 3H), 7.74-7.81 (m, 2H), 7.58-7.63 (m, 2H), 7.39-7.45 (m, 2H), 4.49-4.57 (m, 2H), 4.32-4.40 (m, 2H), 4.20-4.27 (m, 2H), 3.54 (m, 1H).

Example 63: 3-((4-(Aminomethyl)-6-(trifluoromethyl)pyridin-2-yl)oxy)-N-((1-hydroxycyclobutyl)methyl)benzamide hydrochloride (Compound 1-201)

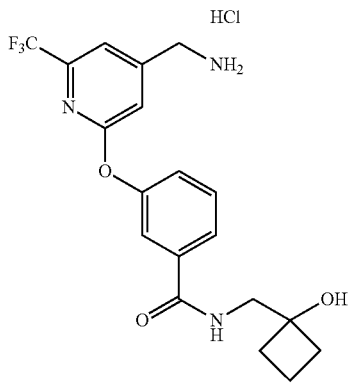 [SMILES: Cl ; NCc1cc(Oc2cccc(C(=O)NCC3(O)CCC3)c2)nc(C(F)(F)F)c1]

The title compound (1-201) was prepared using the procedure for Example 1, using 1-(aminomethyl)cyclobutanol in Step 1. LCMS Mass: 396.0 (M$^+$+1).

Example 64: 3-((4-(Aminomethyl)-6-(trifluoromethyl)pyridin-2-yl)oxy)-N-(2-hydroxyethyl)-N-methylbenzamide hydrochloride (Compound 1-202)

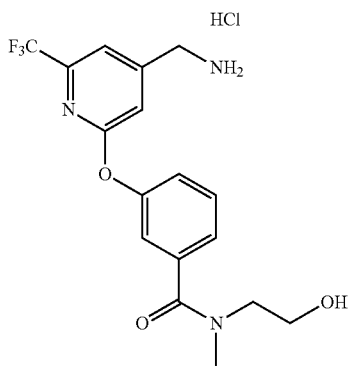 [SMILES: Cl ; CN(CCO)C(=O)c1cccc(Oc2cc(CN)cc(C(F)(F)F)n2)c1]

The title compound (1-202) was prepared using the procedure for Example 1, using 2-(methylamino)ethanol in Step 1. $^1$H NMR (300 MHz, DMSO-d$_6$): δ 8.73 (br s, 3H), 7.83-8.01 (m, 2H), 7.51-7.66 (m, 2H), 7.21-7.30 (m, 2H), 4.51 (m, 1H), 4.16-4.24 (m, 2H), 3.25-3.36 (m, 2H), 2.94 (s, 3H).

Example 65: (S)-(3-((4-(Aminomethyl)-6-(trifluoromethyl)pyridin-2-yl)oxy)phenyl)(3-(hydroxymethyl)piperidin-1-yl)methanone hydrochloride (Compound 1-203)

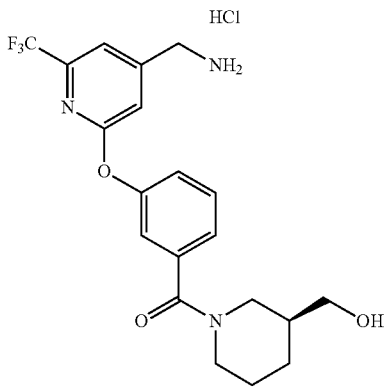 [SMILES: Cl ; NCc1cc(Oc2cccc(C(=O)N3CCC[C@H](CO)C3)c2)nc(C(F)(F)F)c1]

The title compound (1-203) was prepared using the procedure for Example 1, using (S)-piperidin-3-ylmethanol in Step 1. LCMS Mass: 410.0 (M$^+$+1).

Example 66: (3-((4-(Aminomethyl)-6-(trifluoromethyl)pyridin-2-yl)oxy)phenyl)(4-(hydroxymethyl)piperidin-1-yl)methanone hydrochloride (Compound 1-204)

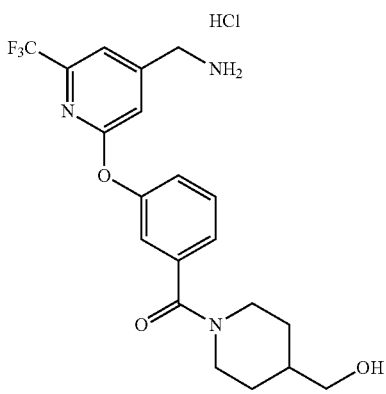 [SMILES: Cl ; NCc1cc(Oc2cccc(C(=O)N3CCC(CO)CC3)c2)nc(C(F)(F)F)c1]

The title compound (1-204) was prepared using the procedure for Example 1, using 4-hydroxymethylpiperidine hydrochloride in Step 1. LCMS Mass: 410.0 (M$^+$+1).

Example 67: (3-((4-(Aminomethyl)-6-(trifluoromethyl)pyridin-2-yl)oxy)phenyl)(4-hydroxy-4-methylpiperidin-1-yl)methanone hydrochloride (Compound 1-205)

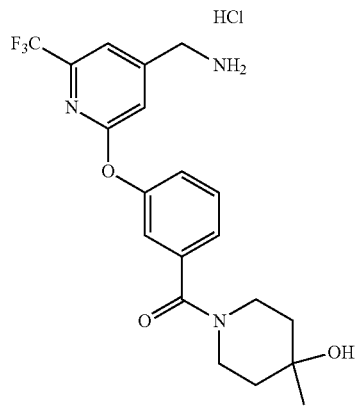 [SMILES: Cl ; CC1(O)CCN(C(=O)c2cccc(Oc3cc(CN)cc(C(F)(F)F)n3)c2)CC1]

The title compound (1-205) was prepared using the procedure for Example 1, using 4-hydroxy-4-methylpiperidine hydrochloride in Step 1. LCMS Mass: 410.0 (M$^+$+1).

Example 68: (3-((4-(Aminomethyl)-6-(trifluoromethyl)pyridin-2-yl)oxy)phenyl)(3-(methoxymethyl)azetidin-1-yl)methanone hydrochloride (Compound 1-206)

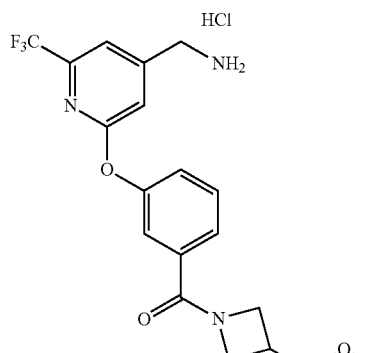

The title compound (1-206) was prepared using the procedure for Example 1, using 3-(methoxymethyl)azetidine hydrochloride in Step 1. $^1$H NMR (300 MHz, DMSO-d$_6$): δ 8.66 (br s, 3H), 7.85 (m, 1H), 7.78 (m, 1H), 7.66 (m, 1H), 7.51-7.59 (m, 2H), 7.39 (m, 1H), 4.20-4.24 (m, 2H), 3.68-3.72 (m, 2H), 3.28-3.48 (m, 4H), 3.24 (s, 3H), 2.27 (m, 1H).

Example 69: (3-((4-(Aminomethyl)-6-(trifluoromethyl)pyridin-2-yl)oxy)phenyl)(7-oxa-2-azaspiro[3.5]nonan-2-yl)methanone hydrochloride (Compound 1-207)

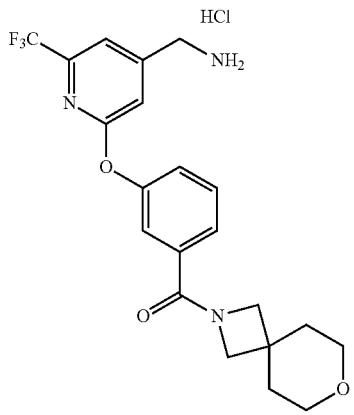 [SMILES: Cl ; NCc1cc(Oc2cccc(C(=O)N3CC4(CCOCC4)C3)c2)nc(C(F)(F)F)c1]

The title compound (1-207) was prepared using the procedure for Example 1, using 7-oxa-2-azaspiro[3.5]nonane hydrochloride in Step 1. LCMS Mass: 422.0 (M$^+$+1).

Example 70: 3-((4-(Aminomethyl)-6-(trifluoromethyl)pyridin-2-yl)oxy)-N-((3S,4S)-4-hydroxytetrahydro-2H-pyran-3-yl)benzamide hydrochloride (Compound 1-208)

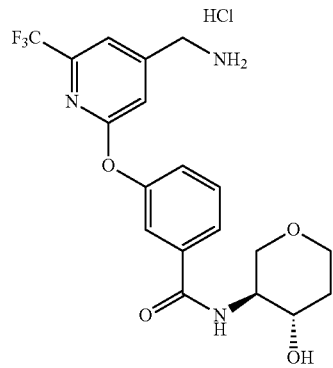 [SMILES: Cl ; NCc1cc(Oc2cccc(C(=O)N[C@H]3COCC[C@@H]3O)c2)nc(C(F)(F)F)c1]

The title compound (1-208) was prepared using the procedure for Example 1, using (3S,4S)-3-aminotetrahydro-2H-pyran-4-ol in Step 1. LCMS Mass: 412.0 (M$^+$+1).

Example 71: 3-((4-(Aminomethyl)-6-(trifluoromethyl)pyridin-2-yl)oxy)-N-((1R,2S)-2-hydroxycyclopentyl)benzamide hydrochloride (Compound 1-209)

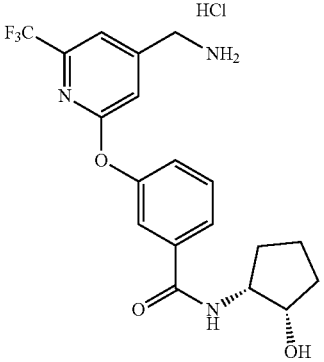 [SMILES: Cl ; NCc1cc(Oc2cccc(C(=O)N[C@@H]3CCC[C@@H]3O)c2)nc(C(F)(F)F)c1]

The title compound (1-209) was prepared using the procedure for Example 1, using (1S,2R)-2-aminocyclopentanol hydrochloride in Step 1. LCMS Mass: 396.0 (M$^+$+1).

Example 72: 3-((4-(Aminomethyl)-6-(trifluoromethyl)pyridin-2-yl)oxy)-N-((1S,2R)-2-hydroxycyclopentyl)benzamide hydrochloride (Compound 1-210)

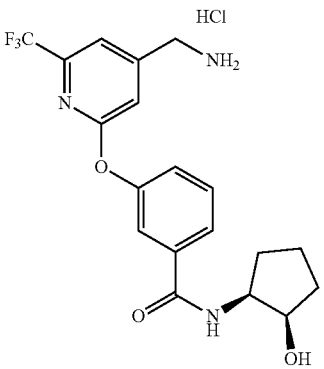 [SMILES: Cl ; NCc1cc(Oc2cccc(C(=O)N[C@H]3CCC[C@H]3O)c2)nc(C(F)(F)F)c1]

The title compound (1-210) was prepared using the procedure for Example 1, using (1R,2S)-2-aminocyclopentanol hydrochloride in Step 1. LCMS Mass: 396.0 (M$^+$+1).

Example 73: Racemic-cis-(3-((4-(aminomethyl)-6-(trifluoromethyl)pyridin-2-yl)oxy)phenyl)(3-fluoro-4-hydroxypyrrolidin-1-yl)methanone hydrochloride (Compound 1-211)

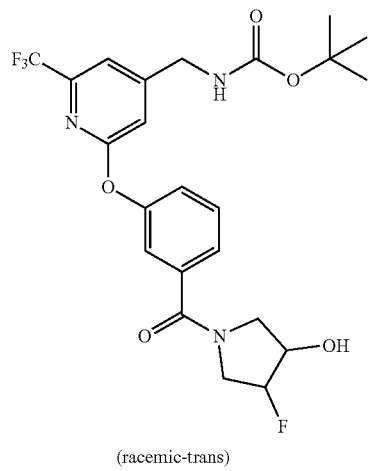
(racemic-trans)

DMP, DCM
0° C. to RT, 5 h

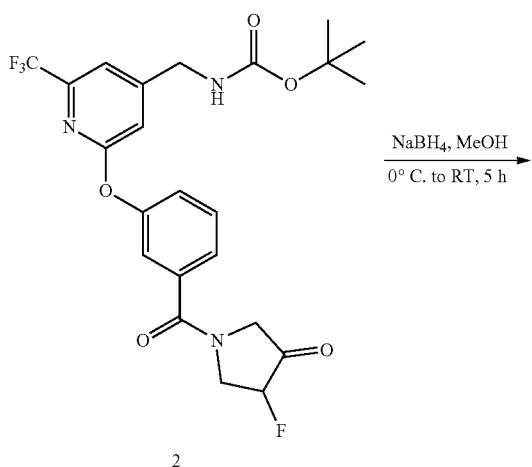
2

NaBH₄, MeOH
0° C. to RT, 5 h

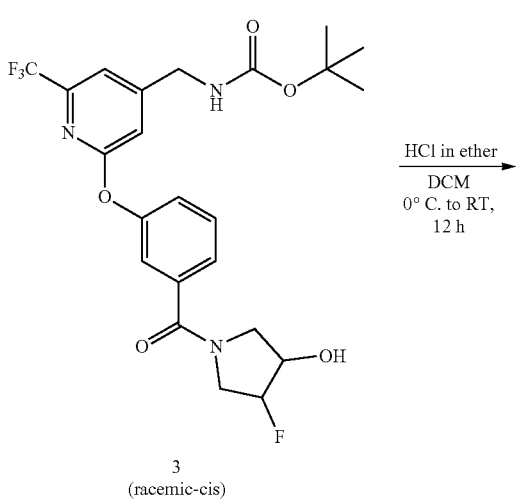
3
(racemic-cis)

HCl in ether
DCM
0° C. to RT,
12 h

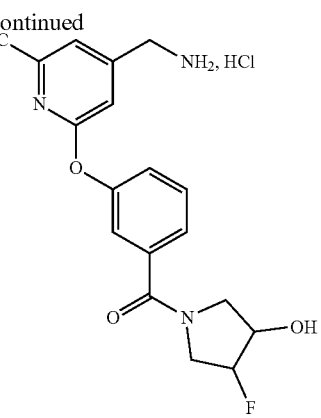
Compound 1-211
(racemic-cis)

Step 1: Racemic-tert-butyl ((2-(3-(3-fluoro-4-oxopyrrolidine-1-carbonyl)phenoxy)-6-(trifluoromethyl)pyridin-4-yl)methyl)carbamate (2)

To a stirred solution of compound 1 (400 mg, 0.8 mmol) (from Example 13, Step 1) in $CH_2Cl_2$ (15 mL) at 0° C. under an inert atmosphere, was added Dess-Martin periodinane (1.36 g, 3.21 mmol) portion wise. The reaction mixture was gradually warmed to RT and stirred for an additional 5 h. The mixture was diluted with $CH_2Cl_2$ (50 mL) and washed with ice cold sat. $NaHCO_3$ (20 mL). The organic layer was separated, washed with brine (15 mL), dried ($Na_2SO_4$), filtered and concentrated in vacuo to afford compound 2 (390 mg) as a pale brown solid, which was used without further purification.

Step 2: Racemic-cis-tert-butyl ((2-(3-(3-fluoro-4-hydroxypyrrolidine-1-carbonyl)phenoxy)-6-(trifluoromethyl)pyridin-4-yl)methyl)carbamate (3)

To a stirred solution of compound 2 (390 mg, crude) in MeOH (15 mL) at 0° C. under an inert atmosphere, was added $NaBH_4$ (119 mg, 3.14 mmol) portion wise. The reaction mixture was gradually warmed to RT and stirred for an additional 5 h. The volatiles were removed under reduced pressure (at 35° C.). The residue was dissolved in EtOAc (50 mL), washed with water (15 mE) and brine (15 mL). The organic layer was separated, dried ($Na_2SO_4$), filtered and concentrated. The residue was purified (silica gel; eluting 20-50% EtOAc/hexanes) to afford compound 3 (110 mg, 28% over two steps) as a pale brown solid. $^1$H NMR (500 MHz, DMSO-$d_6$): δ 7.59 (m, 1H), 7.49-7.55 (m, 2H), 7.29-7.43 (m, 3H), 7.15 (s, 1H), 5.48 (m, 1H), 4.87 (m, 1H), 4.15-4.34 (m, 3H), 3.46-3.82 (m, 3H), 3.26 (m, 1H), 1.39 (s, 9H). Chiral HPLC analysis: Observe two peaks; $R_t$=14.21 and 15.31 min (Chiral Pak ADH, 250×4.6 mm, 5 μm column, eluting isocratically with 10% MeOH:EtOH (1:1) and 90% hexanes (containing 0.1% DEA) over 25 mins; flow rate 1.0 mL/min).

Step 3: Racemic-cis-(3-((4-(aminomethyl)-6-(trifluoromethyl)pyridin-2-yl)oxy)phenyl)(3-fluoro-4-hydroxypyrrolidin-1-yl)methanone hydrochloride (Compound 1-211)

To a stirred solution of compound 3 (50 mg, 0.1 mmol) in $CH_2Cl_2$ (1 mL) at 0° C., was added 2M HCl in $Et_2O$ (1 mL, 2 mmol). The reaction mixture was gradually warmed to RT and stirred for an additional 12 h. Then the volatiles were removed, and the residue was triturated with Et$_2$O (2×2 mL) and dried under vacuum to afford compound 1-211 (30 mg, 77%) as a pale brown solid. $^1$H NMR (500 MHz, DMSO-d$_6$): δ 8.50 (br s, 3H), 7.83 (s, 1H), 7.56 (m, 1H), 7.50 (br s, 1H), 7.43 (m, 1H), 7.30-7.35 (m, 2H), 5.50 (m, 1H), 4.89 (m, 1H), 4.21-4.24 (m, 3H), 3.46-3.82 (m, 3H), 3.26 (m, 1H); LCMS Mass: 400.0 (M$^+$+1).

Example 74: (R)-(3-((4-(Aminomethyl)-6-(trifluoromethyl)pyridin-2-yl)oxy)phenyl)(3-fluoropyrrolidin-1-yl)methanone hydrochloride (Compound 1-212)

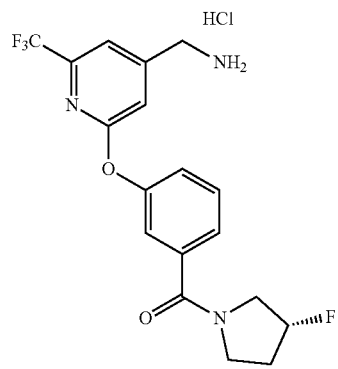 [SMILES: Cl ; NCc1cc(Oc2cccc(C(=O)N3CC[C@@H](F)C3)c2)nc(C(F)(F)F)c1]

The title compound (1-212) was prepared using the procedure for Example 1, using (R)-3-fluoropyrrolidine hydrochloride in Step 1. LCMS Mass: 384.0 (M$^+$+1).

Example 75: (S)-(3-((4-(Aminomethyl)-6-(trifluoromethyl)pyridin-2-yl)oxy)phenyl)(3-fluoropyrrolidin-1-yl)methanone hydrochloride (Compound 1-213)

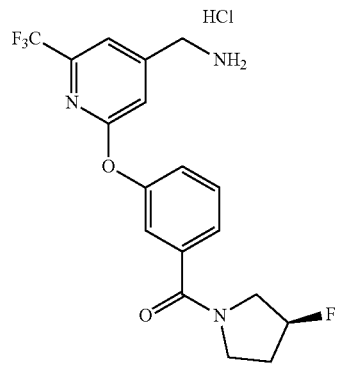 [SMILES: Cl ; NCc1cc(Oc2cccc(C(=O)N3CC[C@H](F)C3)c2)nc(C(F)(F)F)c1]

The title compound (1-213) was prepared using the procedure for Example 1, using (S)-3-fluoropyrrolidine hydrochloride in Step 1. LCMS Mass: 384.0 (M$^+$+1).

Example 76: (3R,4R)-1-(3-((4-(Aminomethyl)-6-(trifluoromethyl)pyridin-2-yl)oxy)benzoyl)-4-fluoropyrrolidin-3-ylmethanesulfonate hydrochloride (Compound 1-214)

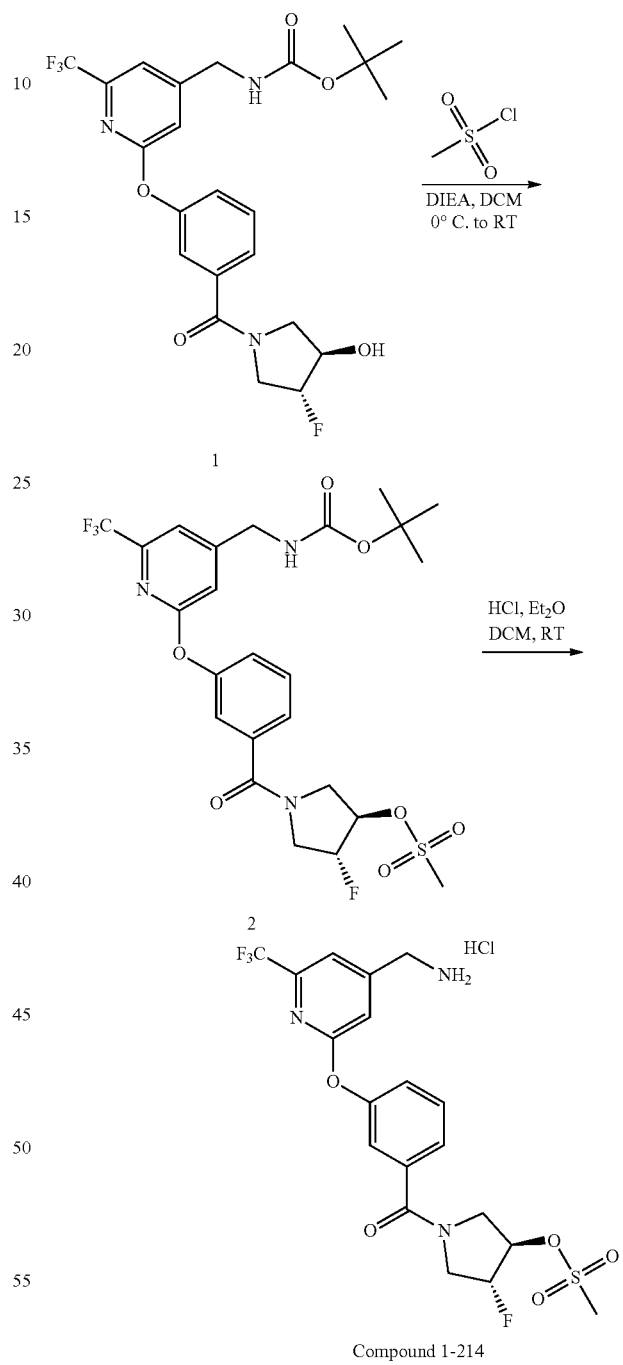

Compound 1-214

Step 1: (3R,4R)-1-(3-((4-(((tert-Butoxycarbonyl)amino)methyl)-6-(trifluoromethyl)pyridin-2-yl)oxy)benzoyl)-4-fluoropyrrolidin-3-yl methanesulfonate (2)

To a stirred solution of (R,R)-trans-tert-butyl ((2-(3-(3-fluoro-4-hydroxypyrrolidine-1-carbonyl)phenoxy)-6-(trifluoromethyl)pyridin-4-yl)methyl)carbamate 1 (58 mg, 0.116 mmol) (from Example 13, Step 2) and DIEA (30 mg, 0.232 mmol) in DCM (1 mL) at 0° C., was added methanesulfonyl chloride (14 mg, 0.118 mmol). The mixture was warmed to RT and stirred for 2 h. Additional methanesulfonyl chloride (5 mg, 0.039 mmol) was added, and the mixture stirred for 30 min. The mixture was concentrated under pressure and the residue purified (silica gel; eluting 0-100% EtOAc/hexanes) to afford compound 2 (53 mg, 79%) as an white solid. LCMS Mass: 578.0 ($M^+$+1).

Step 2: (3R,4R)-1-(3-((4-(Aminomethyl)-6-(trifluoromethyl)pyridin-2-yl)oxy)benzoyl)-4-fluoropyrrolidin-3-ylmethanesulfonate (Compound 1-214)

The title compound (1-214) (42 mg, 89%) was prepared from compound 2 using the procedure for Example 1, Step 2. $^1$H NMR (300 MHz, DMSO-$d_6$): δ 8.56 (br s, 3H), 7.82 (s, 1H), 7.30-7.60 (m, 5H), 5.20-5.50 (br m, 2H), 4.21 (s, 2H), 3.60-4.10 (m, 4H), 3.31 (s, 3H); LCMS Mass: 478.0 ($M^+$+1).

Example 77: (3-((4-(Aminomethyl)-6-(trifluoromethyl)pyridin-2-yl)oxy)phenyl)(2,5-dihydro-1H-pyrrol-1-yl)methanone hydrochloride (Compound 1-215)

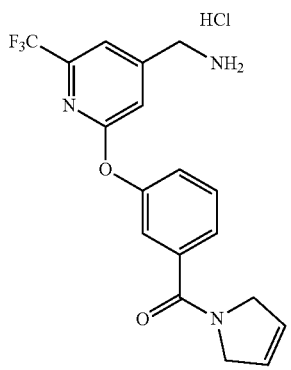 [SMILES: Cl ; NCc1cc(Oc2cccc(C(=O)N3CC=CC3)c2)nc(C(F)(F)F)c1]

The title compound (1-215) was prepared using the procedure for Example 1, using 2,5-dihydro-1H-pyrrole hydrochloride in Step 1. $^1$H NMR (300 MHz, DMSO-$d_6$): δ 8.62 (br s, 3H), 7.83 (m, 1H), 7.51-7.56 (m, 2H), 7.39-7.44 (m, 2H), 7.29 (m, 1H), 5.93 (m, 1H), 5.80 (m, 1H), 4.16-4.30 (m, 6H).

Example 78: 3-((4-(Aminomethyl)-6-(trifluoromethyl)pyridin-2-yl)oxy)-N-(hex-5-yn-1-yl)benzamide trifluoroacetate (Compound 1-216)

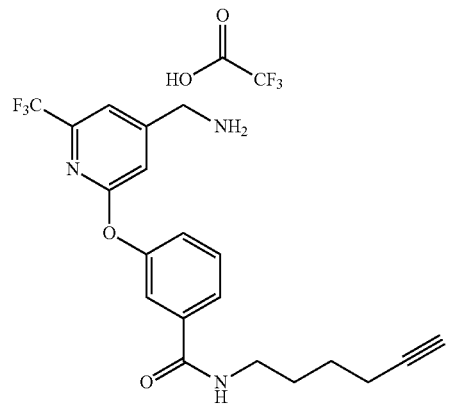

The title compound (1-216) was prepared using the procedure for Example 1, using hex-5-ynylamine hydrochloride in Step 1. LCMS Mass: 392.0 ($M^+$+1).

Example 79: 3-((4-(Aminomethyl)-6-(trifluoromethyl)pyridin-2-yl)oxy)-N-(4-(1-phenyl-1H-1,2,3-triazol-4-yl)butyl)benzamide hydrochloride (Compound 1-217)

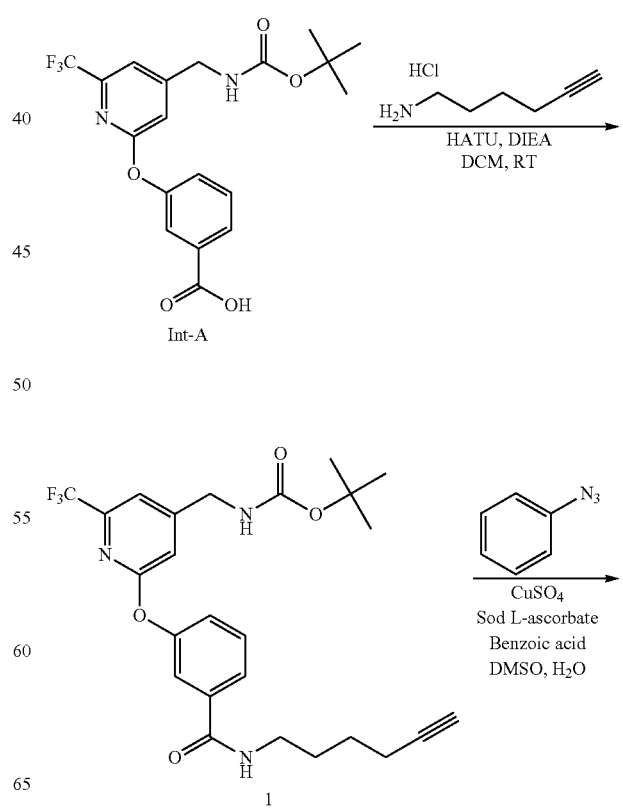

-continued

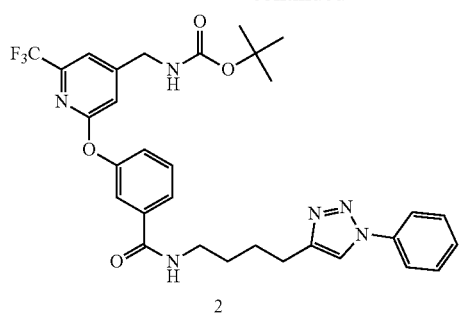

Step 3: 3-((4-(Aminomethyl)-6-(trifluoromethyl)pyridin-2-yl)oxy)-N-(4-(1-phenyl-H-1H-1, 2,3-triazol-4-yl)butyl)benzamide hydrochloride (Compound 1-217)

The title compound (1-217) was prepared from compound 2 (30 mg, 88%) using the procedure for Example 1, Step 2. $^1$H NMR (300 MHz, DMSO-$d_6$): δ 8.50-8.63 (m, 5H), 7.80-7.88 (m, 3H), 7.75 (m, 1H), 7.40-7.62 (m, 6H), 7.34 (m, 1H), 4.18-4.28 (m, 2H), 3.22-3.38 (m, 2H), 2.70-2.80 (m, 2H), 1.55-1.80 (m, 4H); LCMS Mass: 511.0 (M$^+$+1).

Example 80: 3-((4-(Aminomethyl)-6-(trifluoromethyl)pyridin-2-yl)oxy)-N-hydroxybenzamide hydrochloride (Compound 1-218)

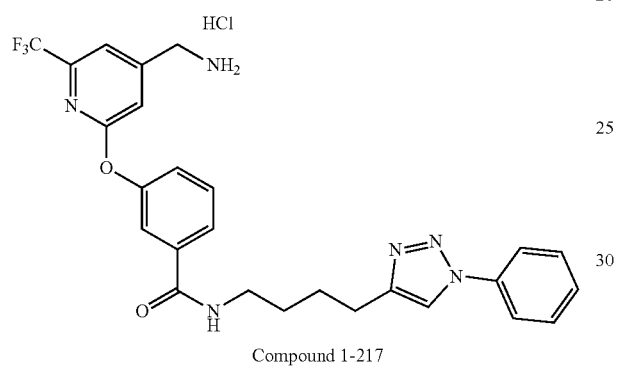

Compound 1-217

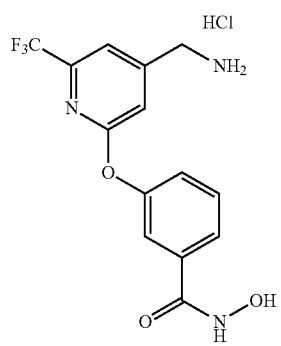 [SMILES: Cl ; NCc1cc(Oc2cccc(C(=O)NO)c2)nc(C(F)(F)F)c1]

Step 1: tert-Butyl ((2-(3-(hex-5-yn-1-ylcarbamoyl)phenoxy)-6-(trifluoromethyl)pyridin-4-yl)methyl)carbamate (1)

The title compound (1) (610 mg, 86%) was prepared following the procedure for Example 1, Step 1, using hex-5-ynylamine hydrochloride. LCMS Mass: 492.0 (M$^+$+1).

Step 2: tert-Butyl ((2-(3-((4-(1-phenyl-1H-1,2,3-triazol-4-yl)butyl)carbamoyl)phenoxy)-6-(trifluoromethyl)pyridin-4-yl)methyl)carbamate (2)

To a stirred solution of compound 1 (50 mg, 0.10 mmol) in DMSO (0.6 mL) and water (1.4 mL) at 0° C., were added azidobenzene (0.22 mL of a 0.5M solution in TBME, 0.11 mmol), CuSO$_4$ (13 mol %), sodium L-(+)-ascorbate (25 mol %), and benzoic acid (10 mol %). The mixture was warmed to RT and stirred for 20 h. The mixture was partitioned between water and EtOAc.

The organic layer was separated, dried (Na$_2$SO$_4$), and concentrated under reduced pressure. The residue was purified (silica gel; eluting 80% EtOAc/hexanes) to afford compound 2 (38 mg, 62%) as a white solid. LCMS Mass: 611.0 (M$^+$+1).

The title compound (1-218) was prepared using the procedure for Example 1, using hydroxylamine hydrochloride in Step 1. LCMS Mass: 328.0 (M$^+$+1).

Example 81: 3-((4-(Aminomethyl)-6-(trifluoromethyl)pyridin-2-yl)oxy)-N-methoxybenzamide hydrochloride (Compound 1-219)

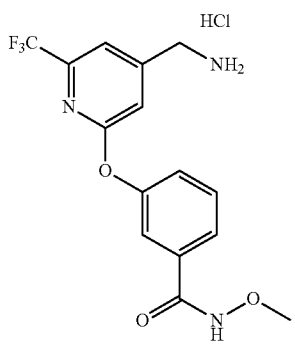 [SMILES: Cl ; CONC(=O)c1cccc(Oc2cc(CN)cc(C(F)(F)F)n2)c1]

The title compound (1-219) was prepared using the procedure for Example 1, using O— methylhydroxylamine in Step 1. LCMS Mass: 342.0 (M$^+$+1).

Examples 82 and 83: Methyl (S)-3-(3-((4-(aminomethyl)-6-(trifluoromethyl)pyridin-2-yl)oxy)benzamido)pent-4-ynoate (Compound 1-220) and (S)-3-(3-((4-(aminomethyl)-6-(trifluoromethyl)pyridin-2-yl)oxy)benzamido)pent-4-ynoic acid (Compound 1-221)

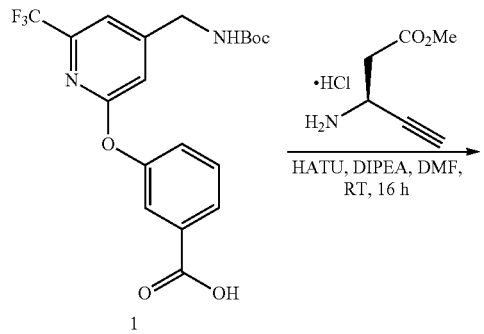

Step 1: Methyl (S)-3-(3-((4-(((tert-butoxycarbonyl)amino)methyl)-6-(trifluoromethyl)pyridin-2-yl)oxy)benzamido)pent-4-ynoate (2)

To a stirred solution of Int-A (200 mg, 0.48 mmol) in DMF (8 mL) at RT, were added methyl (S)-3-aminopent-4-ynoate hydrochloride (62 mg, 0.48 mmol) (prepared following procedures described in J. A. Zablocki et al, *J. Med. Chem.* 1995, 38, 2378), HATU (277 mg, 0.73 mmol), and DIEA (0.25 mL, 1.46 mmol), and the mixture was stirred at RT for 16 h. The mixture was quenched with water (20 mL) and extracted with EtOAc (2×20 mL). The combined organic extracts were washed with brine (10 mL), dried ($Na_2SO_4$), filtered and concentrated. The residue was purified (silica gel; eluting 30-35% EtOAc/hexanes) to afford compound 2 (60 mg, 24%) as an off-white sticky solid. $^1$H NMR (500 MHz, DMSO-$d_6$): δ 8.94 (br m, 1H), 7.75 (m, 1H), 7.64 (s, 1H), 7.53-7.59 (m, 2H), 7.50 (s, 1H), 7.38 (br m, 1H), 7.11 (s, 1H), 5.08 (m, 1H), 4.25 (br m, 2H), 3.59 (s, 3H), 3.25 (m, 1H), 2.77-2.88 (m, 2H), 1.37 (s, 9H); LCMS Mass: 544.1 ($M^+$+Na).

Step 2: Methyl (S)-3-(3-((4-(aminomethyl)-6-(trifluoromethyl)pyridin-2-yl)oxy)benzamido)pent-4-ynoate (Compound 1-220) & (S)-3-(3-((4-(aminomethyl)-6-(trifluoromethyl)pyridin-2-yl)oxy)benzamido)pent-4-ynoic acid (Compound 1-221)

To a stirred solution of compound 2 (60 mg, 0.11 mmol) in $CH_2Cl_2$ (1 mL) at 0° C. under an inert atmosphere, was added 2M HCl in $Et_2O$ (1 mL, 2 mmol). The reaction mixture was gradually warmed to RT and stirred for 16 h. The volatiles were removed, and the residue was triturated with n-pentane (2×2 mL), then $Et_2O$ (2×2 mL), and dried under vacuum to obtain a solid which was purified (via preparative HPLC) to afford compound 1-220 (7 mg, 14%) as a colorless oil, and compound 1-221 (6.5 mg, 14%) as a white solid.

Compound 1-220: $^1$H NMR (500 MHz, $CD_3OD$): δ 7.70 (m, 1H), 7.61 (m, 1H), 7.51-7.55 (m, 2H), 7.36 (m, 1H), 7.22 (s, 1H), 5.26 (m, 1H), 3.92 (s, 2H), 3.69 (s, 3H), 2.87 (m, 2H), 2.75 (m, 1H); LCMS Mass: 422.0 ($M^+$+1).

Compound 1-221: $^1$H NMR (500 MHz, $CD_3OD$): δ 7.74 (m, 1H), 7.63 (s, 1H), 7.54-7.58 (m, 2H), 7.39 (m, 1H), 7.30

(s, 1H), 5.11 (m, 1H), 4.16 (s, 2H), 2.67 (br m, 2H), 2.62 (m, 1H); LCMS Mass: 408.0 (M⁺+1).

Examples 84 and 85: Methyl (R)-3-(3-((4-(aminomethyl)-6-(trifluoromethyl)pyridin-2-yl)oxy)benzamido)pent-4-ynoate hydrochloride (Compound 1-222) and (R)-3-(3-((4-(aminomethyl)-6-(trifluoromethyl)pyridin-2-yl)oxy)benzamido)pent-4-ynoic acid hydrochloride (Compound 1-223))

Compound 1-222

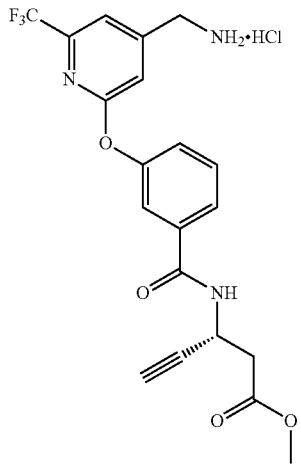

Compound 1-223

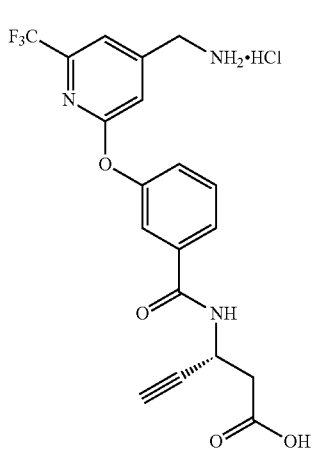

The title compounds (1-222 and 1-223) were prepared using the procedure for Examples 82 and 83, using methyl (R)-3-aminopent-4-ynoate hydrochloride (prepared following procedures described in J. A. Zablocki et al, *J. Med. Chem.* 1995, 38, 2378) in Step 1.

Compound 1-222: ¹H NMR (500 MHz, CD₃OD): δ 7.87 (br m, 1H), 7.77-7.79 (m, 2H), 7.71 (m, 1H), 7.48-7.55 (m, 2H), 5.41 (m, 1H), 4.45 (s, 2H), 3.84 (s, 3H), 3.03 (m, 2H), 2.91 (m, 1H); LCMS Mass: 421.9 (M⁺+1).

Compound 1-223: ¹H NMR (500 MHz, CD₃OD): δ 7.88 (m, 1H), 7.77-7.79 (m, 2H), 7.71 (m, 1H), 7.53 (m, 1H), 7.49

(s, 1H), 5.39 (m, 1H), 4.44 (s, 2H), 2.99 (m, 2H), 2.89 (m, 1H); LCMS Mass: 407.9 (M⁺+1).

Example 86: 3-((4-(Aminomethyl)-6-(trifluoromethyl)pyridin-2-yl)oxy)benzoic acid hydrochloride (Compound 1-224)

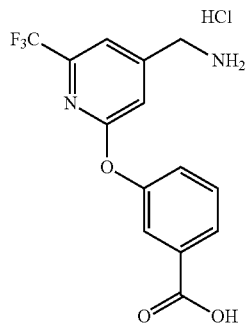 [SMILES: Cl ; NCc1cc(Oc2cccc(C(=O)O)c2)nc(C(F)(F)F)c1]

The title compound (1-224) was prepared from Int-A using the procedure for Example 1, Step 2. LCMS Mass: 313.0 (M⁺+1).

Example 87: 3-((4-(Aminomethyl)-6-(trifluoromethyl)pyridin-2-yl)oxy)-N-(2-aminophenyl)benzamide hydrochloride (Compound 1-225)

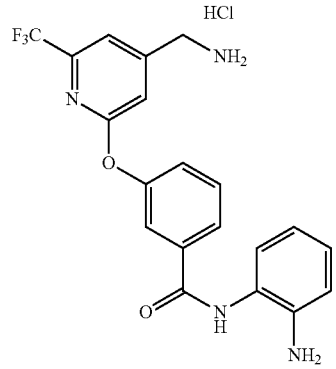 [SMILES: Cl ; NCc1cc(Oc2cccc(C(=O)Nc3ccccc3N)c2)nc(C(F)(F)F)c1]

The title compound (1-225) was prepared using the procedure for Example 1, using 5-aminopyrimidine in Step 1.
¹H NMR (300 MHz, DMSO-d₆): δ 10.42 (br s, 1H), 8.66 (br s, 3H), 8.00 (m, 1H), 7.84-7.89 (m, 2H), 7.63 (m, 1H), 7.56 (m, 1H), 7.41-7.48 (m, 2H), 7.16-7.30 (m, 3H), 4.20-4.24 (m, 2H).

Example 88: 3-((4-(Aminomethyl)-6-(trifluoromethyl)pyridin-2-yl)oxy)-N-(pyrimidin-5-yl)benzamide hydrochloride (Compound 1-226)

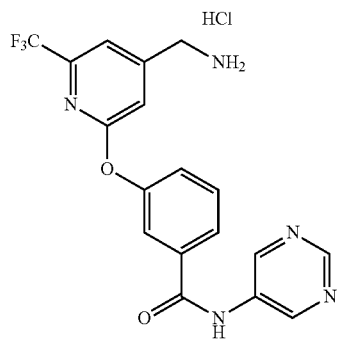 [SMILES: Cl ; NCc1cc(Oc2cccc(C(=O)Nc3cncnc3)c2)nc(C(F)(F)F)c1]

The title compound (1-226) was prepared using the procedure for Example 1, using 5-aminopyrimidine in Step 1. LCMS Mass: 390.0 (M$^+$+1).

Example 89: 3-((4-(Aminomethyl)-6-(trifluoromethyl)pyridin-2-yl)oxy)-N-(oxazol-2-yl)benzamide hydrochloride (Compound 1-227)

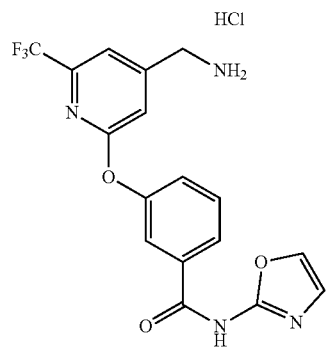 [SMILES: Cl ; NCc1cc(Oc2cccc(C(=O)Nc3ncco3)c2)nc(C(F)(F)F)c1]

The title compound (1-227) was prepared using the procedure for Example 1, using 2-aminooxazole in Step 1. LCMS Mass: 379.0 (M$^+$+1).

Example 90: 3-((4-(Aminomethyl)-6-(trifluoromethyl)pyridin-2-yl)oxy)-N-(1,3,4-oxadiazol-2-yl)benzamide hydrochloride (Compound 1-228)

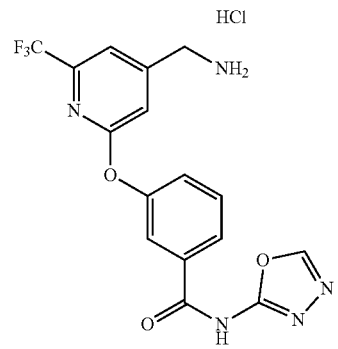 [SMILES: Cl ; NCc1cc(Oc2cccc(C(=O)Nc3nnco3)c2)nc(C(F)(F)F)c1]

The title compound (1-228) was prepared using the procedure for Example 1, using 1,3,4-oxadiazol-2-amine in Step 1. $^1$H NMR (300 MHz, DMSO-d$_6$): δ 8.74 (br s, 3H), 7.88 (m, 1H), 7.53-7.70 (m, 6H), 7.36 (m, 1H), 4.20-4.30 (m, 2H).

Example 91: Racemic-trans-(3-((4-(aminomethyl)-6-(trifluoromethyl)pyridin-2-yl)oxy)-4-hydroxyphenyl)(3-fluoro-4-hydroxypyrrolidin-1-yl)methanone hydrochloride (Compound 1-229)

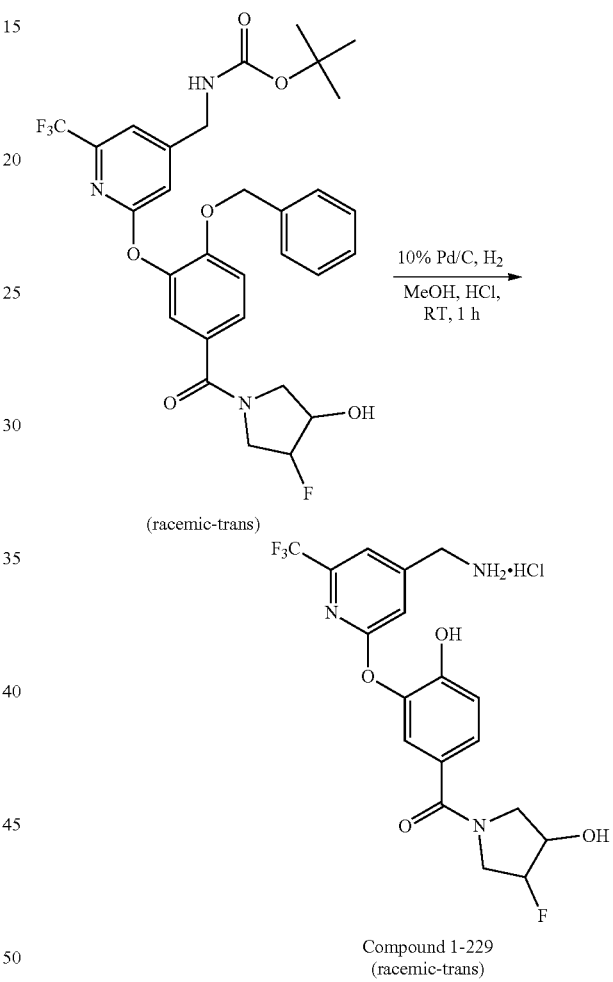

To a stirred solution of racemic-trans-tert-butyl ((2-(2-(benzyloxy)-5-(3-fluoro-4-hydroxypyrrolidine-1-carbonyl)phenoxy)-6-(trifluoromethyl)pyridin-4-yl)methyl)carbamate (20 mg, 0.04 mmol) (from Example 93, Step 6) in MeOH (10 mL) at RT, were added conc. HCl (1 drop) and 10% Pd/C (50% wet, 2 mg). The reaction mixture was stirred at RT under H2 (1 atmosphere) for 1 h. The mixture was filtered through celite washing with MeOH (8 mL). The filtrate was concentrated and the residue was triturated with Et$_2$O (2×1 mL) to afford compound 1-229 (15 mg, 91%) as an off-white solid. $^1$H NMR (400 MHz, CD$_3$OD): δ 7.61 (s, 1H), 7.34-7.40 (m, 3H), 7.04 (m, 1H), 4.95 (m, 1H), 4.37 (m, 1H), 4.30 (br s, 2H), 3.78-4.05 (m, 2H), 3.73 (m, 1H), 3.60 (m, 1H); LCMS Mass: 416.0 (M$^+$+1).

Example 92: Racemic-trans-(3-((4-(aminomethyl)-6-(trifluoromethyl)pyridin-2-yl)oxy)-5-hydroxyphenyl)(3-fluoro-4-hydroxypyrrolidin-1-yl)methanone hydrochloride (Compound 1-230)

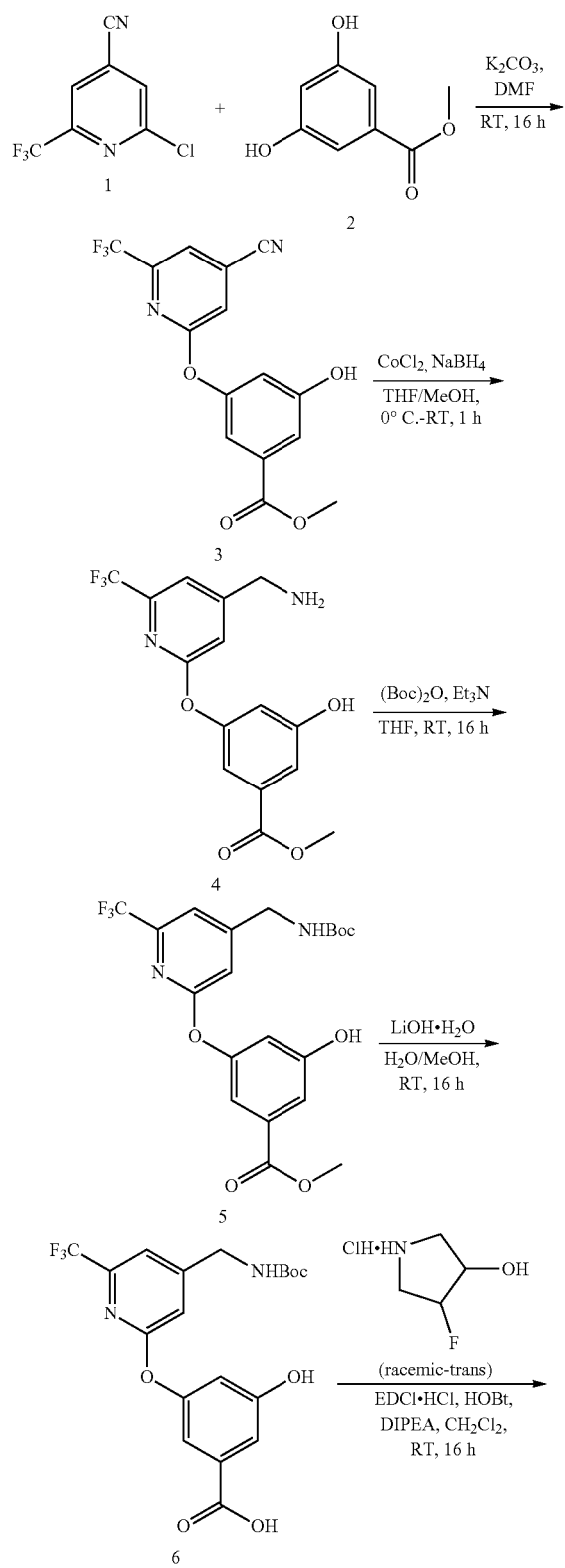

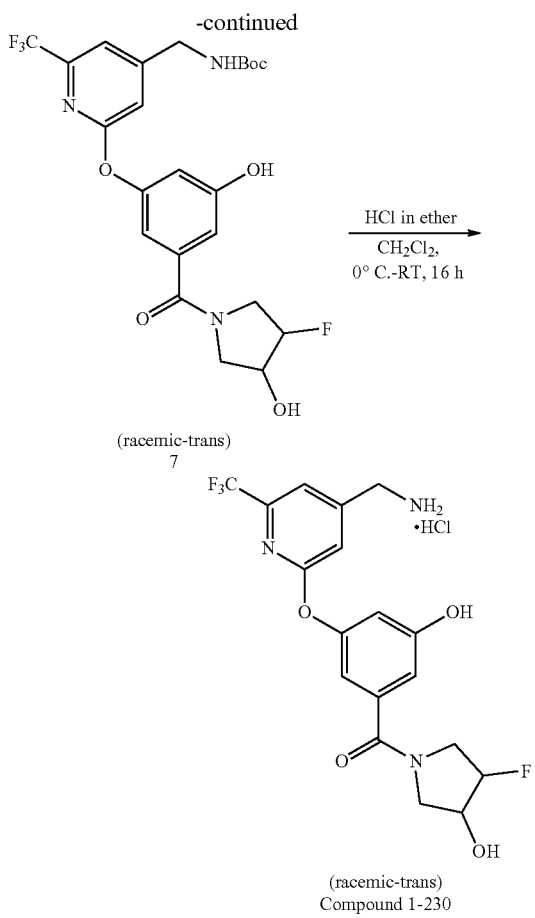

Step 1: Methyl 3-((4-cyano-6-(trifluoromethyl)pyridin-2-yl)oxy)-5-hydroxybenzoate (3)

To a stirred solution of methyl 3,5-dihydroxybenzoate 2 (163 mg, 0.97 mmol) in DMF (10 mL) at RT, were added $K_2CO_3$ (161 mg, 1.16 mmol) and 2-chloro-6-(trifluoromethyl)isonicotinonitrile 1 (200 mg, 0.97 mmol). The reaction mixture was stirred at RT for 16 h. The mixture was quenched with water (20 mL) and extracted with EtOAc (2×20 mL), and the combined organic extracts were washed with brine (10 mL), dried ($Na_2SO_4$), filtered and concentrated. The residue was purified (silica gel; eluting 20-25% EtOAc/hexanes) to afford compound 3 (110 mg, 34%) as a white solid. $^1$H NMR (500 MHz, $CDCl_3$): δ 7.59 (s, 1H), 7.41-7.44 (m, 2H), 7.36 (s, 1H), 6.90 (br s, 1H), 3.91 (s, 3H); LCMS Mass: 339.1 ($M^+$+1).

Step 2: Methyl 3-((4-(aminomethyl)-6-(trifluoromethyl)pyridin-2-yl)oxy)-5-hydroxybenzoate (4)

To a stirred solution of compound 3 (500 mg, 1.48 mmol) in THF (5 mL) and MeOH (10 mL) at ° 0 C under an inert atmosphere, were added $CoCl_2$ (572 mg, 4.44 mmol) and $NaBH_4$ (562 mg, 14.8 mmol) portion wise. The reaction mixture was gradually warmed to RT and stirred for 1 h. The mixture was quenched with ice cold water (20 mL) and filtered through a pad of celite. The filtrate was extracted with EtOAc (2×30 mL). The combined organic extracts were washed with brine (20 mL), dried ($Na_2SO_4$), filtered, and concentrated to afford compound 4 (415 mg) as an off white solid, which was used without further purification. $^1$H NMR (500 MHz, DMSO-$d_6$): δ 7.67 (s, 1H), 7.29 (s, 1H), 7.24 (m, 1H), 7.12 (m, 1H), 6.82 (m, 1H), 3.84 (s, 2H), 3.82 (s, 3H), 2.2 (br s, 2H); LCMS Mass: 342.9 (M$^+$+1).

Step 3: Methyl 3-((4-(((tert-butoxycarbonyl)amino) methyl)-6-(trifluoromethyl)pyridin-2-yl)oxy)-5-hydroxybenzoate (5)

To a stirred solution of compound 4 (410 mg, crude) in THF (10 mL) at RT, were added (Boc)$_2$O (0.33 mL, 1.44 mmol) and TEA (0.33 mL, 2.4 mmol). The mixture was stirred at RT for 16 h. The mixture was quenched with water (20 mL) and extracted with EtOAc (2×30 mL). The combined organic extracts were washed with brine (20 mL), dried (Na$_2$SO$_4$), filtered and concentrated. The residue was purified (silica gel; eluting 30-40% EtOAc/hexanes) to afford compound 5 (490 mg, 75% over two steps) as a white solid. $^1$H NMR (500 MHz, CDCl$_3$): δ 7.40 (m, 1H), 7.33 (m, 1H), 6.95-7.07 (m, 2H), 6.89 (m, 1H), 5.04 (br s, 1H), 4.37-4.41 (m, 2H), 3.90 (s, 3H), 1.47 (br s, 9H); LCMS Mass: 443.0 (M$^+$+1).

Step 4: 3-((4-(((tert-Butoxycarbonyl)amino)methyl)-6-(trifluoromethyl)pyridin-2-yl)oxy)-5-hydroxybenzoic acid (6)

To a stirred solution of compound 5 (245 mg, 0.55 mmol) in MeOH (3 mL) and water (3 mL) at RT, was added LiOH.H$_2$O (46 mg, 1.1 mmol), and the mixture was stirred at RT for 16 h. The MeOH was removed under reduced pressure and the mixture was quenched with water (15 mL), acidified with citric acid to pH ~3, and extracted with EtOAc (2×20 mL). The combined organic extracts were washed with brine (10 mL), dried (Na$_2$SO$_4$), filtered and concentrated to afford compound 6 (200 mg, 84%) as a pale yellow viscous oil. $^1$H NMR (500 MHz, DMSO-$d_6$): δ 12.99 (br s, 1H), 10.10 (s, 1H), 7.55 (m, 1H), 7.50 (s, 1H), 7.23 (m, 1H), 7.07 (m, 2H), 6.79 (m, 1H), 4.24 (m, 2H), 1.36 (s, 9H); LCMS Mass: 429.0 (M$^+$+1).

Step 5: Racemic-trans-tert-butyl ((2-(3-(3-fluoro-4-hydroxypyrrolidine-1-carbonyl)-5-hydroxyphenoxy)-6-(trifluoromethyl)pyridin-4-yl)methyl)carbamate (7)

To a stirred solution of compound 6 (200 mg, 0.47 mmol) in CH$_2$Cl$_2$ (5 mL) at RT, were added EDCI hydrochloride (178 mg, 0.93 mmol), HOBt (32 mg, 0.23 mmol), racemic-trans-4-fluoropyrrolidin-3-ol hydrochloride (99 mg, 0.7 mmol) and DIEA (0.16 mL, 0.93 mmol). The mixture was stirred at RT for 16 h. The mixture was quenched with water (20 mL) and extracted with CH$_2$Cl$_2$ (2×20 mL). The combined organic extracts were washed with brine (15 mE), dried (Na$_2$SO$_4$), filtered and concentrated. The residue was purified (silica gel; eluting 3-5% MeOH/CH$_2$Cl$_2$) to afford compound 7 (150 mg, 62%) as an off white solid. LCMS Mass: 538.0 (M$^+$+Na).

Step 6: Racemic-trans-(3-((4-(aminomethyl)-6-(trifluoromethyl)pyridin-2-yl)oxy)-5-hydroxyphenyl)(3-fluoro-4-hydroxypyrrolidin-1-yl)methanone hydrochloride (Compound 1-230)

To a stirred solution of compound 7 (125 mg, 0.24 mmol) in CH$_2$Cl$_2$ (3 mL) at 0° C., was added 2M HCl in Et$_2$O (3 mL, 6 mmol). The reaction mixture was gradually warmed to RT and stirred for 16 h. The volatiles were removed in vacuo and the crude was purified (preparative HPLC) to afford compound 1-230 (45 mg, 41%) as a colorless oil. $^1$H NMR (400 MHz, CD$_3$OD): δ 7.62 (s, 1H), 7.31 (s, 1H), 6.84 (m, 1H), 6.78 (m, 1H), 6.73 (m, 1H), 5.06 (m, 1H), 4.95 (m, 1H), 4.39 (m, 1H), 4.29 (s, 4H), 3.69-3.99 (m, 4H), 3.63 (m, 1H), 3.50 (m, 1H), as a mixture of rotamers; LCMS Mass: 416.0 (M$^+$+1).

Example 93: Racemic-trans-(3-((4-(aminomethyl)-6-(trifluoromethyl)pyridin-2-yl)oxy)-4-(benzyloxy) phenyl)(3-fluoro-4-hydroxypyrrolidin-1-yl)methanone (Compound 1-231)

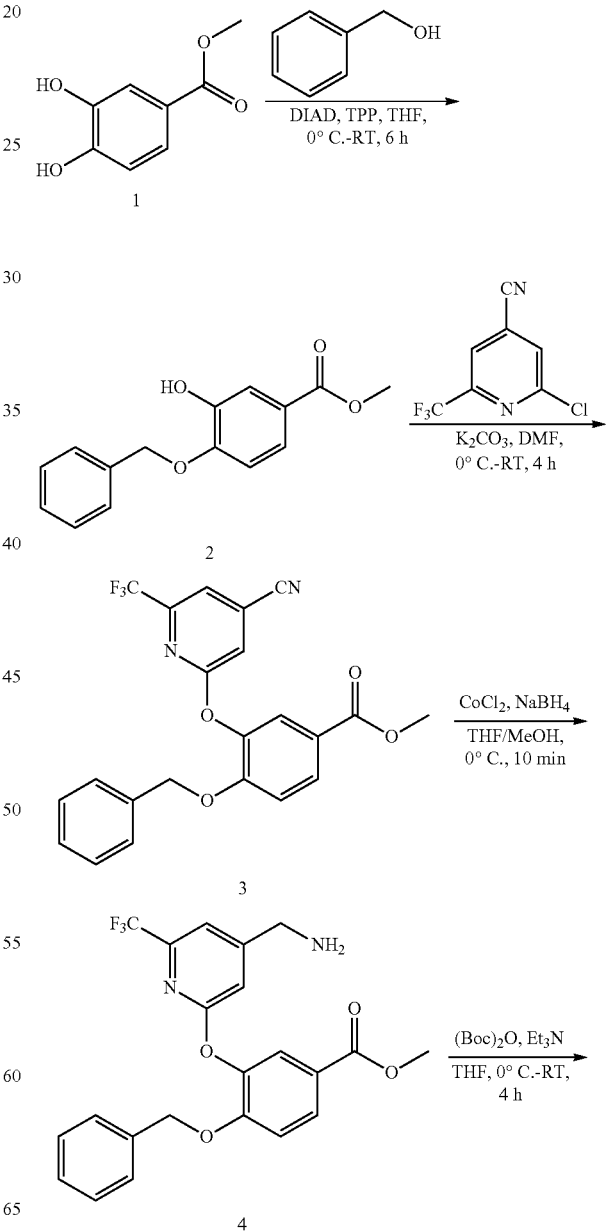

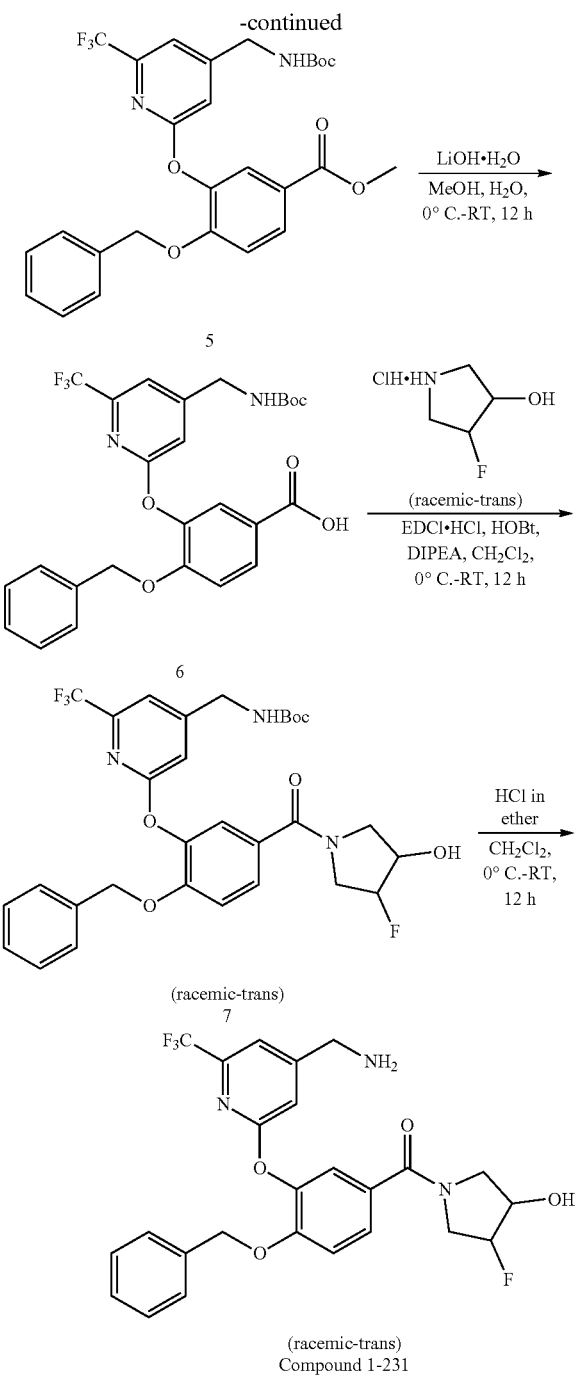

(m, 4H), 7.26 (s, 1H), 6.95 (m, 1H), 5.68 (s, 1H), 5.17 (s, 2H), 3.88 (s, 3H); LCMS Mass: 256.9 (M–H⁺).

Step 2: Methyl 4-(benzyloxy)-3-((4-cyano-6-(trifluoromethyl)pyridin-2-yl)oxy)benzoate (3)

To a stirred solution of compound 2 (350 mg, 1.36 mmol) in DMF (10 mL) at 0° C., were added 2-chloro-6-(trifluoromethyl)isonicotinonitrile (279 mg, 1.36 mmol) and K₂CO₃ (281 mg, 2.03 mmol). The mixture was gradually warmed to RT and stirred for 4 h. The mixture was diluted with water (20 mL) and extracted with EtOAc (2×30 mL). The combined organic extracts were washed with brine (20 mL), dried (Na₂SO₄), filtered and concentrated. The residue was purified (silica gel; eluting 2% EtOAc/hexanes) to afford compound 3 (540 mg, 93%) as an off white solid. ¹H NMR (500 MHz, CDCl₃): δ 7.96 (m, 1H), 7.88 (m, 1H), 7.46 (s, 1H), 7.33 (s, 1H), 7.26-7.28 (m, 3H), 7.03-7.07 (m, 3H), 5.04 (s, 2H), 3.90 (s, 3H); LCMS Mass: 427.1 (M–H⁺).

Step 3: Methyl 3-((4-(aminomethyl)-6-(trifluoromethyl)pyridin-2-yl)oxy)-4-(benzyloxy)benzoate (4)

To a stirred solution of compound 3 (540 mg, 1.26 mmol) in THF (10 mL) and MeOH (20 mL) at 0° C. under an inert atmosphere, was added CoCl₂ (488 mg, 3.78 mmol), followed by NaBH₄ (479 mg, 12.62 mmol) portion wise. The mixture was stirred at 0° C. for 10 min. The mixture was quenched with ice cold water (30 mL) and filtered through celite. The filtrate was extracted with EtOAc (2×30 mL), washed with brine (20 mL), dried (Na₂SO₄), filtered and concentrated to afford compound 4 (540 mg) as a green oil. This was used without further purification. LCMS Mass: 433.3 (M⁺+1).

Step 4: Methyl 4-(benzyloxy)-3-((4-(((tert-butoxycarbonyl)amino)methyl)-6-(trifluoromethyl)pyridin-2-yl)oxy)benzoate (5)

To a stirred solution of compound 4 (540 mg, crude) in THF (50 mL) at 0° C., were added (Boc)₂O (0.34 mL, 1.5 mmol) and Et₃N (0.26 mL, 1.87 mmol). The reaction mixture was gradually warmed to RT and stirred for 4 h. The mixture was diluted with water (20 mL) and extracted with EtOAc (2×30 mL). The combined organic extracts were washed with brine (20 mL), dried (Na₂SO₄), filtered and concentrated. The residue was purified (silica gel; eluting 15% EtOAc/hexanes) to afford compound 5 (350 mg, 53% over two steps) as a colorless oil. ¹H NMR (500 MHz, CDCl₃): δ 7.90 (m, 1H), 7.86 (m, 1H), 7.23-7.25 (m, 4H), 7.06-7.10 (m, 2H), 6.96-7.02 (m, 2H), 5.06 (s, 2H), 4.90 (br s, 1H), 4.34 (m, 2H), 3.89 (s, 3H), 1.53 (s, 9H).

Step 5: 4-(Benzyloxy)-3-((4-(((tert-butoxycarbonyl)amino)methyl)-6-(trifluoromethyl)pyridin-2-yl)oxy)benzoic acid (6)

To a stirred solution of compound 5 (350 mg, 0.66 mmol) in MeOH (15 mL) and water (5 mL) at 0° C., was added LiOH.H₂O (55 mg, 1.31 mmol). The reaction mixture was gradually warmed to RT and stirred for 12 h. The mixture was concentrated and the obtained residue was diluted with water (20 mL) and acidified with citric acid to pH ~4. The precipitated solid was filtered and dried under vacuum to afford compound 6 (208 mg, 61%) as an off white solid. ¹H NMR (500 MHz, DMSO-d₆): δ 12.86 (br s, 1H), 7.86 (m, 1H), 7.72 (m, 1H), 7.60 (m, 1H), 7.47 (s, 1H), 7.32 (m, 1H), 7.22-7.26 (m, 3H), 7.12 (s, 1H), 6.98-7.01 (m, 2H), 5.13 (s, 2H), 4.25 (m, 2H), 1.38 (s, 9H); LCMS Mass: 519.0 (M⁺+1).

Step 6: Racemic-trans-tert-butyl ((2-(2-(benzyloxy)-5-(3-fluoro-4-hydroxypyrrolidine-1-carbonyl)phenoxy)-6-(trifluoromethyl)pyridin-4-yl)methyl)carbamate (7)

To a stirred solution of compound 6 (208 mg, 0.4 mmol) in CH$_2$Cl$_2$ (15 mL) at 0° C., were added racemic-trans-4-fluoropyrrolidin-3-ol hydrochloride (73 mg, 0.52 mmol), EDCI hydrochloride (115 mg, 0.6 mmol), HOBt (54 mg, 0.4 mmol) and DIEA (0.21 mL, 1.2 mmol). The reaction mixture was gradually warmed to RT and stirred for 12 h. The mixture was diluted with water (15 mL) and extracted with CH$_2$Cl$_2$ (2×20 mL). The combined organic extracts were washed with brine (10 mL), dried (Na$_2$SO$_4$), filtered and concentrated. The residue was purified (silica gel; eluting 40% EtOAc/hexanes) to afford compound 7 (113 mg, 46%) as an off white solid. $^1$H NMR (400 MHz, DMSO-d$_6$): δ 7.59 (br m, 1H), 7.45-7.52 (m, 3H), 7.22-7.29 (m, 4H), 7.13 (s, 1H), 7.01-7.04 (m, 2H), 5.56 (m, 1H), 5.11 (s, 2H), 5.00 (m, 1H), 4.25 (m, 2H), 4.20 (m, 1H), 3.38-3.92 (m, 4H), 1.39 (s, 9H), as a mixture of rotamers.

Step 7: Racemic-trans-(3-((4-(aminomethyl)-6-(trifluoromethyl)pyridin-2-yl)oxy)-4-(benzyloxy)phenyl)(3-fluoro-4-hydroxypyrrolidin-1-yl)methanone (Compound 1-231)

To a stirred solution of compound 7 (110 mg, 0.2 mmol) in CH$_2$Cl$_2$ (5 mL) at 0° C., was added 2M HCl in Et$_2$O (12 mL, 24 mmol) and the mixture was warmed to RT and stirred for 12 h. The mixture was concentrated and the residue purified (preparative HPLC) to afford compound 1-231 (40 mg, 40%) as a colorless oil. $^1$H NMR (400 MHz, CD$_3$OD): δ 7.56 (s, 1H), 7.50 (m, 1H), 7.44 (m, 1H), 7.33 (s, 1H), 7.23-7.28 (m, 4H), 7.12-7.15 (m, 2H), 5.10 (s, 2H), 4.96 (m, 1H), 4.36 (m, 1H), 4.25 (s, 2H), 4.02 (m, 1H), 3.69-3.94 (m, 3H), 3.60 (n, 1H), as a mixture of rotamers; LCMS Mass: 506.3 (M⁺+1).

Example 94: Racemic-trans-(3-((4-(aminomethyl)-6-(trifluoromethyl)pyridin-2-yl)oxy)-5-methoxyphenyl)(3-fluoro-4-hydroxypyrrolidin-1-yl)methanone hydrochloride (Compound 1-232)

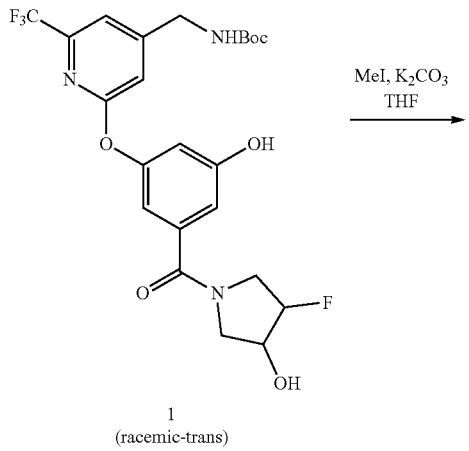

1
(racemic-trans)

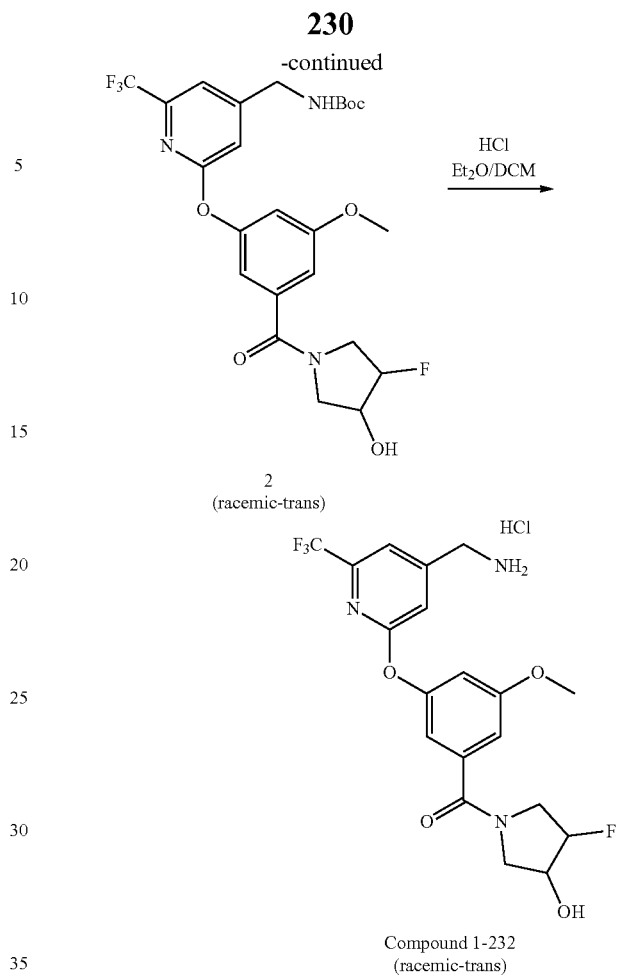

2
(racemic-trans)

Compound 1-232
(racemic-trans)

Step 1: Racemic-trans-tert-butyl ((2-(3-(3-fluoro-4-hydroxypyrrolidine-1-carbonyl)-5-methoxyphenoxy)-6-(trifluoromethyl)pyridin-4-yl)methyl)carbamate (2)

To a stirred solution of racemic-trans-tert-butyl ((2-(3-(3-fluoro-4-hydroxypyrrolidine-1-carbonyl)-5-hydroxyphenoxy)-6-(trifluoromethyl)pyridin-4-yl)methyl)carbamate 1 (24 mg, 0.046 mmol) (from Example 92, Step 5) in THF (3 mL) at 0° C., were added K$_2$CO$_3$ (13 mg, 0.091 mmol) and iodomethane (13 mg, 0.091 mmol). The mixture was warmed to RT and stirred for 16 h. The mixture was cooled to 0° C. and to this were added iodomethane (26 mg, 0.183 mmol) and DMF (1.5 mL). The mixture was stirred at RT for 3 h. The mixture was concentrated under reduced pressure and dried under vacuum to afford 2 (45 mg) as a white solid, which was not purified further. LCMS Mass: 530.0 (M⁺+1).

Step 2: Racemic-trans-(3-((4-(aminomethyl)-6-(trifluoromethyl)pyridin-2-yl)oxy)-5-methoxyphenyl)(3-fluoro-4-hydroxypyrrolidin-1-yl)methanone hydrochloride (Compound 1-232)

The title compound (1-232) was prepared from compound 2 (37 mg) using the procedure for Example 1, Step 2. $^1$H NMR (300 MHz, DMSO-d$_6$): δ 8.80 (br s, 3H), 7.87 (m, 1H), 7.52 (m, 1H), 6.91-6.95 (m, 3H), 5.67 (m, 1H), 4.79-5.08 (m, 2H), 4.10-4.30 (m, 3H), 3.79 (s, 3H), 3.40-3.70 (br m, 3H); LCMS Mass: 430.0 (M⁺+1).

Example 95: 1-(3-((4-(Aminomethyl)-6-(trifluoromethyl)pyridin-2-yl)oxy)phenyl)pyridin-2(1H)-one (Compound 1-169)

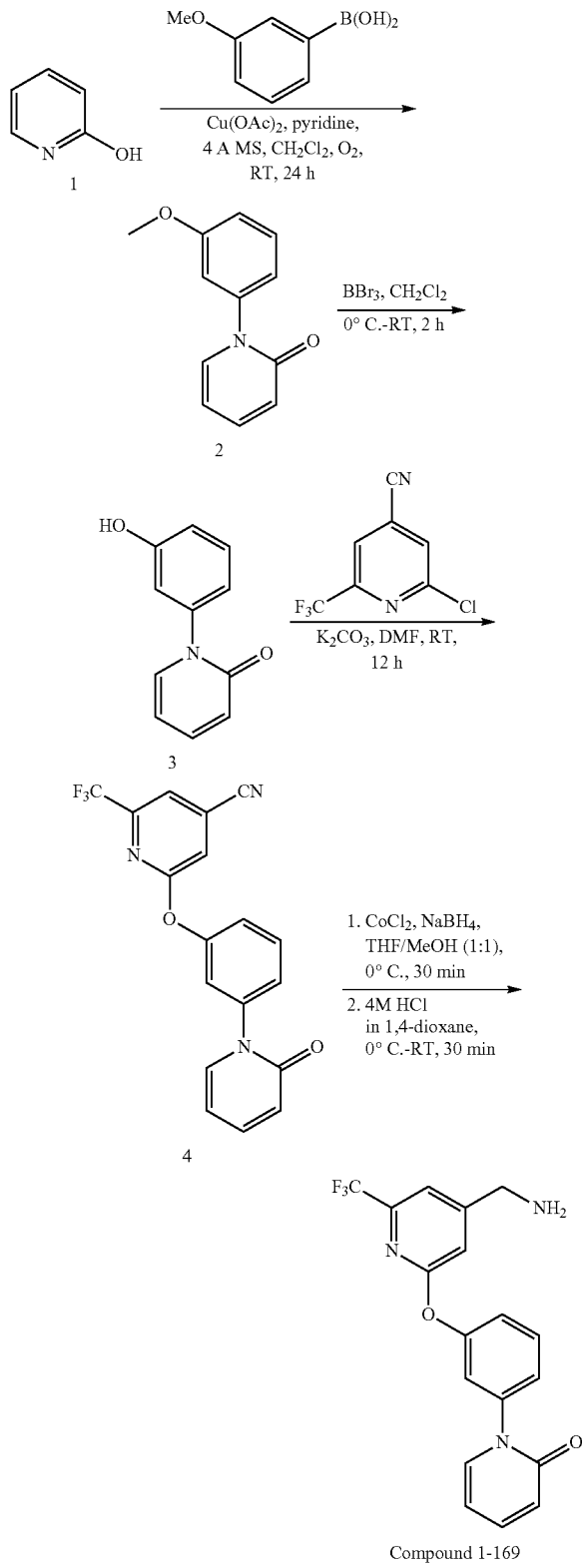

Step 1: 1-(3-Methoxyphenyl)pyridin-2(1H)-one (2)

To a stirred solution of pyridin-2-ol 1 (500 mg, 5.26 mmol) in $CH_2Cl_2$ (40 mL) at RT, were added (3-methoxyphenyl)boronic acid (1.59 g, 10.53 mmol), $Cu(OAc)_2$ (209 mg, 1.05 mmol), pyridine (0.8 mL, 10.53 mmol) and 4 Å MS (cat.). The mixture was stirred at RT under O2 atmosphere for 24 h. The mixture was filtered through celite, washed with EtOAc (50 mL) and the filtrate was concentrated. The residue was dissolved in water (20 mL), diluted with sat. aq. $CuSO_4$ (20 mL), then extracted with $CH_2Cl_2$ (2×30 mL). The combined organic extracts were washed with brine (20 mL), dried ($Na_2SO_4$), filtered, and concentrated. The obtained residue was purified (silica gel; eluting 35% EtOAc/hexanes) to afford compound 2 (760 mg, 76%) as an off-white solid. $^1$H NMR (500 MHz, DMSO-$d_6$): δ 7.61 (m, 1H), 7.49 (m, 1H), 7.40 (m, 1H), 7.01 (m, 1H), 6.91-6.97 (m, 2H), 6.45 (m, 1H), 6.29 (m, 1H), 3.77 (s, 3H); LCMS Mass: 201.9 ($M^+$+1).

Step 2: 1-(3-Hydroxyphenyl)pyridin-2(1H)-one (3)

To a stirred solution of compound 2 (170 mg, 0.84 mmol) in $CH_2Cl_2$ (10 mL) at 0° C. under an inert atmosphere, was added $BBr_3$ (0.16 mL, 1.69 mmol). The mixture was warmed to RT and stirred for 2 h. The mixture was quenched with sat. aq. $NaHCO_3$(20 mL) and extracted with $CH_2Cl_2$ (2×20 mL). The combined organic extracts were washed with brine (10 mL), dried over $Na_2SO_4$, filtered and concentrated. The crude was triturated with $Et_2O$ (2×5 mL) to afford compound 3 (65 mg, 41%) as an off white solid. $^1$H NMR (500 MHz, DMSO-$d_6$): δ 9.81 (s, 1H), 7.59 (dd, J=6.9, 1.7 Hz, 1H), 7.46-7.51 (m, 1H), 7.29 (t, J=8.0 Hz, 1H), 6.83 (dd, J=8.1, 1.4 Hz, 1H), 6.74-6.78 (m, 2H), 6.45 (d, J=9.3 Hz, 1H), 6.28 (td, J=6.7, 1.2 Hz, 1H); LCMS Mass: 187.9 ($M^+$+1).

Step 3: 2-(3-(2-Oxopyridin-1(2H)-yl)phenoxy)-6-(trifluoromethyl)isonicotinonitrile (4)

A mixture of 2-chloro-6-(trifluoromethyl)isonicotinonitrile (200 mg, 0.97 mmol), compound 3 (181 mg, 0.97 mmol), $K_2CO_3$ (268 mg, 1.94 mmol), and DMF (5 mL), was stirred at RT for 12 h. The mixture was diluted with water (20 mL) and extracted with EtOAc (2×20 mL). The combined organic extracts were washed with brine (15 mL), dried ($Na_2SO_4$), filtered and concentrated. The residue was purified (silica gel; eluting 50% EtOAc/hexanes) to afford compound 4 (220 mg, 77%) as an off-white solid. $^1$H NMR (400 MHz, DMSO-$d_6$): δ 8.23 (s, 1H), 8.05 (s, 1H), 7.58-7.67 (m, 2H), 7.50 (m, 1H), 7.33-7.41 (m, 3H), 6.49 (m, 1H), 6.33 (m, 1H); LCMS Mass: 357.9 ($M^+$+1).

Step 4: 1-(3-((4-(Aminomethyl)-6-(trifluoromethyl) pyridin-2-yl)oxy)phenyl) pyridin-2(1H)-one (Compound 1-169)

To a stirred solution of compound 5 (150 mg, 0.42 mmol) in THF/MeOH (1:1, 10 mL) at 0° C. under an inert atmosphere, were added $CoCl_2$ (136 mg, 1.05 mmol) and $NaBH_4$ (80 mg, 2.11 mmol) portion wise. The mixture was stirred at 0° C. for 30 min. The mixture was diluted with EtOAc (20 mL) and water (20 mL), filtered through a pad of celite and washed with EtOAc (15 mL). The filtrate was washed with water (15 mL), brine (10 mL), dried ($Na_2SO_4$), filtered and concentrated to obtain the desired amine. To this amine was added 4 M HCl in 1,4-dioxane (5 mL) at 0° C. and stirred at RT for 30 min. Then the mixture was concentrated in vacuo to obtain the crude which was purified (via preparative HPLC) to afford compound 1-169 (24 mg, 15%) as an off white solid. $^1$H NMR (400 MHz, DMSO-$d_6$): δ 7.64-7.68 (m, 2H), 7.57 (m, 1H), 7.50 (m, 1H), 7.25-7.34 (m, 4H), 6.48 (m, 1H), 6.32 (m, 1H), 3.84 (s, 2H), 2.21 (br s, 2H); LCMS Mass: 361.9 (M$^+$+1).

Example 96: 5-((4-(Aminomethyl)-6-(trifluoromethyl)pyridin-2-yl)oxy)-1-(2-hydroxyethyl)-3,4-dihydroquinolin-2(1H)-one hydrochloride (Compound 1-60)

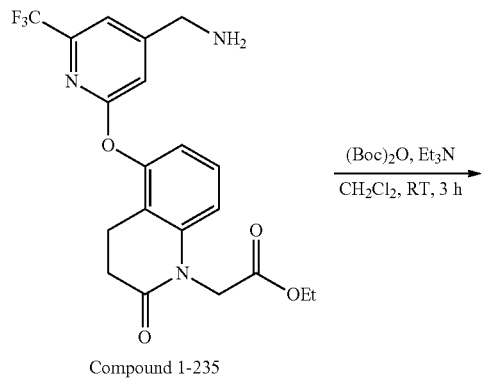

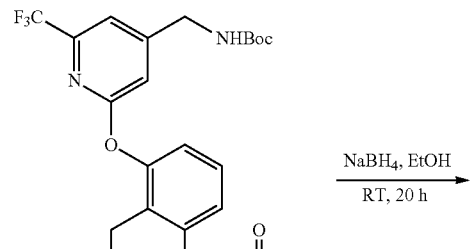

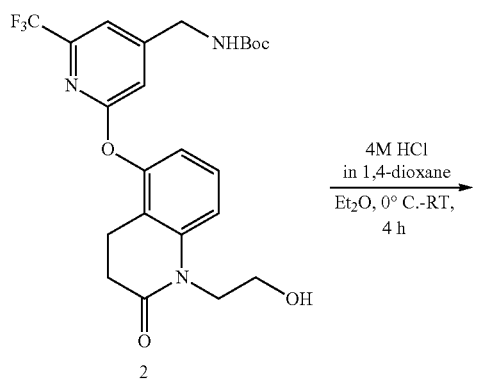

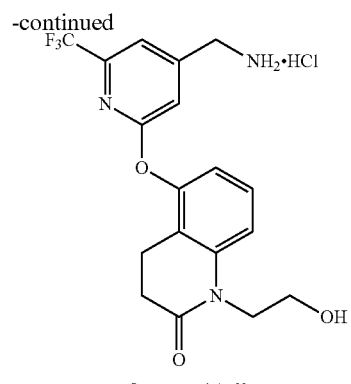

Step 1: Ethyl 2-(5-((4-(((tert-butoxycarbonyl)amino)methyl)-6-(trifluoromethyl) pyridin-2-yl)oxy)-2-oxo-3,4-dihydroquinolin-1(2H)-yl)acetate (1)

To a stirred solution of ethyl 2-(5-((4-(aminomethyl)-6-(trifluoromethyl)pyridin-2-yl)oxy)-2-oxo-3,4-dihydroquinolin-1(2H)-yl)acetate (120 mg, 0.28 mmol) (from Example 97) in CH$_2$Cl$_2$ (20 mL) at RT, were added (Boc)$_2$O (0.1 mL, 0.42 mmol) and TEA (0.08 mL, 0.57 mmol). The mixture was stirred at RT for 3 h. The mixture was diluted with water (15 mL) and extracted with CH$_2$Cl$_2$ (2×15 mL), washed with brine (10 mL), dried (Na$_2$SO$_4$), filtered and concentrated. The residue was purified (silica gel; eluting 20% EtOAc/hexanes) to afford compound 1 (100 mg, 67%) as an off white solid. $^1$H NMR (500 MHz, DMSO-$d_6$): δ 7.58 (m, 1H), 7.47 (s, 1H), 7.29 (m, 1H), 7.06 (s, 1H), 6.90 (m, 2H), 4.67 (s, 2H), 4.24 (m, 2H), 4.13 (m, 2H), 2.61-2.67 (m, 2H), 2.51-2.53 (m, 2H), 1.36 (s, 9H), 1.19 (m, 3H); LCMS Mass: 546.1 (M$^+$+Na).

Step 2: tert-Butyl ((2-((1-(2-hydroxyethyl)-2-oxo-1, 2,3,4-tetrahydroquinolin-5-yl)oxy)-6-(trifluoromethyl)pyridin-4-yl)methyl)carbamate (2)

To a stirred solution of compound 1 (50 mg, 0.009 mmol) in EtOH (2 mL) at RT under an inert atmosphere, was added NaBH$_4$ (54 mg, 1.43 mmol), and the mixture was stirred at RT for 20 h. The mixture was diluted with water (15 mL), acidified with citric acid to pH ~3 and extracted with EtOAc (2×15 mL), washed with brine (10 mL), dried over Na$_2$SO$_4$, filtered and concentrated. The residue was purified (silica gel; eluting 40% EtOAc/hexanes) to afford compound 2 (20 mg, 43%) as a pale brown sticky solid. $^1$H NMR (400 MHz, CDCl$_3$): δ 7.29 (s, 1H), 7.25 (m, 1H), 6.93-7.02 (m, 2H), 6.85 (m, 1H), 5.03 (br s, 1H), 4.38 (m, 2H), 4.18 (m, 2H), 3.98 (m, 2H), 2.74-2.80 (m, 2H), 2.59-2.64 (m, 2H), 1.46 (s, 9H); LCMS Mass: 482.1 (M$^+$+1).

Step 3: 5-((4-(Aminomethyl)-6-(trifluoromethyl) pyridin-2-yl)oxy)-1-(2-hydroxyethyl)-3,4-dihydroquinolin-2(1H)-one hydrochloride (Compound 1-60)

To a stirred solution of compound 2 (20 mg, 0.04 mmol) in Et$_2$O (5 mL) at 0° C., was added 4 M HCl in 1,4-dioxane (2 mL). The mixture was gradually warmed to RT and stirred for 4 h. The volatiles were removed under reduced pressure. The residue was triturated with Et$_2$O (2×1 mL), n-pentane (2×1 mL) and dried under vacuum. The crude was dissolved in water (2 mL) and concentrated under reduced pressure to afford compound 1-60 (10 mg, 58%) as an off white sticky solid. $^1$H NMR (400 MHz, CD$_3$OD): δ 7.62 (s, 1H), 7.31-7.38 (m, 2H), 7.26 (m, 1H), 6.87 (m, 1H), 4.30 (s, 2H), 4.13 (m, 2H), 3.80 (m, 2H), 2.73-2.78 (m, 2H), 2.54-2.59 (m, 2H); LCMS Mass: 381.9 (M$^+$+1).

Example 97: Ethyl 2-(5-((4-(aminomethyl)-6-(trifluoromethyl)pyridin-2-yl)oxy)-2-oxo-3,4-dihydroquinolin-1(2H)-yl)acetate (Compound 1-235)

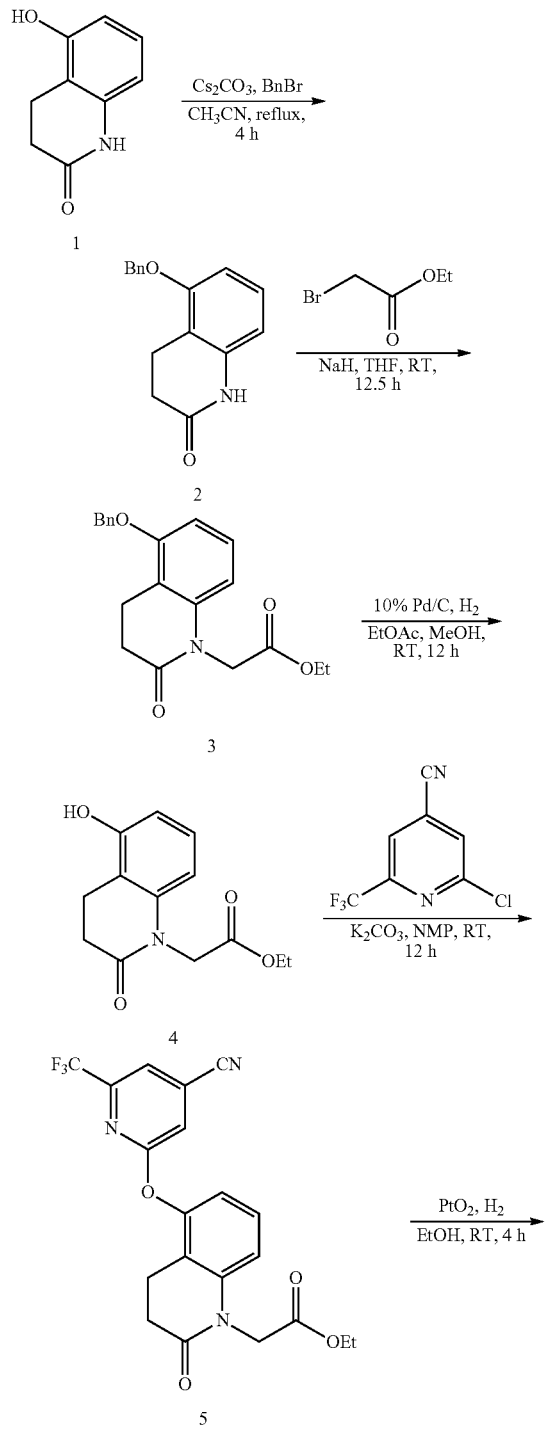

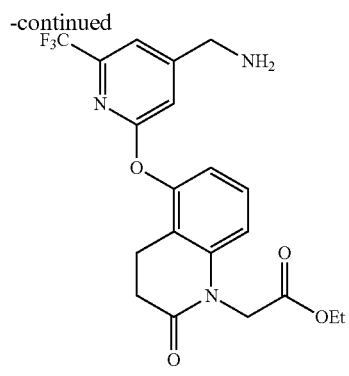

Compound 1-235

Step 1: 5-(Benzyloxy)-3,4-dihydroquinolin-2(1H)-one (2)

To a stirred solution of 5-hydroxy-3,4-dihydroquinolin-2(1H)-one 1 (2 g, 12.27 mmol) in acetonitrile (80 mL) at RT, were added Cs$_2$CO$_3$ (6 g, 18.4 mmol) and benzyl bromide (1.46 mL, 12.27 mmol). The mixture was heated to reflux for 4 h. After cooling to RT, the mixture was diluted with water (50 mL) and stirred for 20 min. The precipitated solid was collected via filtration, washed with water (15 mL) and dried under vacuum to afford compound 2 (2.5 g, 81%) as an off white solid. $^1$H NMR (500 MHz, DMSO-d$_6$): δ 10.05 (s, 1H), 7.44-7.47 (m, 2H), 7.40 (m, 2H), 7.33 (m, 1H), 7.08 (m, 1H), 6.70 (m, 1H), 6.49 (m, 1H), 5.10 (s, 2H), 2.84 (m, 2H), 2.41 (m, 2H); LCMS Mass: 254.0 (M$^+$+1).

Step 2: Ethyl 2-(5-(benzyloxy)-2-oxo-3,4-dihydroquinolin-1(2H)-yl)acetate (3)

To a stirred solution of compound 2 (2.5 g, 9.88 mmol) in THF (80 mL) at RT under an inert atmosphere, was added NaH (60% in mineral oil, 593 mg, 14.82 mmol) at RT, and the mixture stirred for 30 min. To this was added ethyl 2-bromoacetate (2.47 g, 14.82 mmol), and the mixture was stirred at RT for 12 h. The mixture was quenched with ice cold water (50 mL) and extracted with EtOAc (2×50 mL). The combined organic extracts were washed with brine (25 mL), dried (Na$_2$SO$_4$), filtered and concentrated. The residue was purified (silica gel; eluting 20% EtOAc/hexanes) to afford compound 3 (2 g, 61%) as an off white solid. $^1$H NMR (500 MHz, DMSO-d$_6$): δ 7.43-7.47 (m, 2H), 7.39 (m, 2H), 7.32 (m, 1H), 7.16 (m, 1H), 6.83 (m, 1H), 6.57 (m, 1H), 5.13 (s, 2H), 4.62 (s, 2H), 4.11 (m, 2H), 2.86 (m, 2H), 2.53 (m, 2H), 1.18 (t, J=7.2 Hz, 3H); LCMS Mass: 340.0 (M$^+$+1).

Step 3: Ethyl 2-(5-hydroxy-2-oxo-3,4-dihydroquinolin-1(2H)-yl)acetate (4)

To a stirred solution of compound 3 (2 g, 5.9 mmol) in EtOAc (50 mL) and MeOH (20 mL) at RT, was added 10% Pd/C (50% wet, ~800 mg). The mixture was stirred at RT under H2 (1 atmosphere) for 12 h. The mixture was filtered through celite washing with MeOH (30 mL). The filtrate was concentrated under reduced pressure and the crude was triturated with n-pentane (2×10 mL) to afford compound 4 (1.4 g, 95%) as an off white solid. $^1$H NMR (400 MHz, DMSO-d$_6$): δ 9.61 (s, 1H), 7.00 (m, 1H), 6.57 (m, 1H), 6.38

(m, 1H), 4.60 (s, 2H), 4.12 (m, 2H), 2.76-2.81 (m, 2H), 2.51-2.54 (m, 2H), 1.19 (m, 3H); LCMS Mass: 250.0 (M$^+$+1).

Step 4: Ethyl 2-(5-((4-cyano-6-(trifluoromethyl) pyridin-2-yl)oxy)-2-oxo-3,4-dihydroquinolin-1(2H)-yl)acetate (5)

To a stirred solution of compound 4 (200 mg, 0.8 mmol) in N-methyl-2-pyrrolidone (5 mL) at RT, were added K$_2$CO$_3$ (222 mg, 1.61 mmol) and 2-chloro-6-(trifluoromethyl)isonicotinonitrile (182 mg, 0.88 mmol) and the mixture was stirred for 12 h. The mixture was diluted with water (15 mL) and stirred for 20 min. The obtained solid was collected via filtration, which was dissolved in CH$_2$Cl$_2$ (50 mL), dried (Na$_2$SO$_4$), filtered and concentrated. The residue was triturated with n-pentane (2×2 mL) to afford compound 5 (210 mg, 62%) as an off white solid. $^1$H NMR (500 MHz, DMSO-d$_6$): δ 8.21 (s, 1H), 8.04 (s, 1H), 7.32 (m, 1H), 6.94 (m, 2H), 4.70 (s, 2H), 4.15 (m, 2H), 2.65-2.70 (m, 2H), 2.50-2.55 (m, 2H), 1.20 (m, 3H); LCMS Mass: 420.0 (M$^+$+1).

Step 5: Ethyl 2-(5-((4-(aminomethyl)-6-(trifluoromethyl)pyridin-2-yl)oxy)-2-oxo-3,4-dihydroquinolin-1(2H)-yl)acetate (Compound 1-235)

To a stirred solution of compound 5 (158 mg, 0.38 mmol) in ethanol (10 mL) at RT, was added PtO$_2$ (16 mg). The reaction mixture was stirred at RT under H2 (1 atmosphere) for 4 h. The mixture was filtered through a pad of celite washing with EtOH (10 mL). The filtrate was concentrated under reduced pressure and the crude was triturated with n-pentane (2×5 mL) to afford compound 1-235 (126 mg, 79%) as a pale brown solid. $^1$H NMR (400 MHz, DMSO-d$_6$): δ 7.62 (s, 1H), 7.26-7.33 (m, 2H), 6.89 (dd, J=8.2, 4.0 Hz, 2H), 4.69 (s, 2H), 4.15 (q, J=7.1 Hz, 2H), 3.83 (s, 2H), 2.65-2.70 (m, 2H), 2.51-2.55 (m, 2H), 2.03 (br s, 2H), 1.21 (t, J=7.2 Hz, 3H); LCMS Mass: 424.3 (M$^+$+1).

Example 98: 2-(5-((4-(Aminomethyl)-6-(trifluoromethyl)pyridin-2-yl)oxy)-2-oxo-3,4-dihydroquinolin-1(2H)-yl)acetic acid hydrochloride (Compound 1-236)

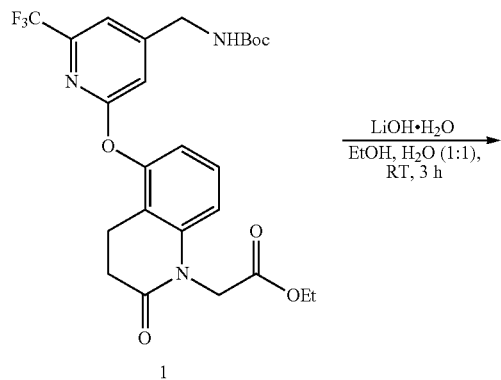

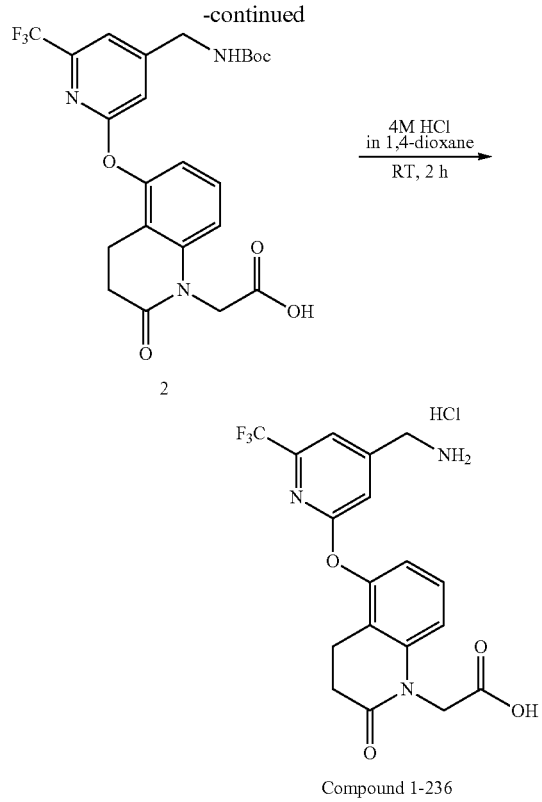

Compound 1-236

Step 1: 2-(5-((4-(((tert-Butoxycarbonyl)amino) methyl)-6-(trifluoromethyl)pyridin-2-yl)oxy)-2-oxo-3,4-dihydroquinolin-1(2H)-yl)acetic acid (2)

To a stirred solution of ethyl 2-(5-((4-(((tert-butoxycarbonyl)amino)methyl)-6-(trifluoromethyl)pyridin-2-yl)oxy)-2-oxo-3,4-dihydroquinolin-1 (2H)-yl)acetate 1 (35 mg, 0.07 mmol) (from Example 96, Step 1) in a mixture of ethanol/water (1:1, 10 mL) at RT, was added LiOH monohydrate (3 mg, 0.13 mmol), and the mixture was stirred for 3 h. The volatiles (ethanol) were removed under reduced pressure. The residue was diluted with water (10 mL), acidified with citric acid to pH ~4 and extracted with EtOAc (2×10 mL). The combined organic extracts were washed with brine (8 mL), dried (Na$_2$SO$_4$), filtered, and concentrated under reduced pressure. The residue was purified via trituration with Et$_2$O (2×3 mL), followed by n-pentane (2×3 mL) and dried under vacuum to afford compound 2 (28 mg, 85%) an off white solid. LCMS Mass: 496.1 (M$^+$+1).

Step 2: 2-(5-((4-(Aminomethyl)-6-(trifluoromethyl) pyridin-2-yl)oxy)-2-oxo-3,4-dihydroquinolin-1(2H)-yl)acetic acid hydrochloride (Compound 1-236)

To compound 2 (28 mg, 0.06 mmol) was added HCl (4M solution in 1,4-dioxane, 5 mL, 20 mmol). The mixture was stirred at RT for 2 h. The mixture was concentrated under reduced pressure. The residue was purified via trituration with Et$_2$O (2×2 mL), followed by n-pentane (2×2 mL) and dried under vacuum to afford compound 1-236 (19 mg, 76%) as an off white solid.

$^1$H NMR (400 MHz, DMSO-d$_6$): δ 12.63 (br s, 1H), 8.61 (br s, 3H), 7.83 (s, 1H), 7.47 (s, 1H), 7.33 (t, J=8.3 Hz, 1H), 6.90 (dd, J=8.3, 1.8 Hz, 2H), 4.60 (s, 2H), 4.21 (s, 2H), 2.64-2.69 (m, 2H), 2.52-2.55 (m, 2H); LCMS Mass: 395.9 (M⁺+1).

Example 99: 2-(4-((4-(Aminomethyl)-6-(trifluoromethyl)pyridin-2-yl)oxy)-1H-indol-1-yl)-1-(piperazin-1-yl)ethan-1-one dihydrochloride (Compound 1-233)

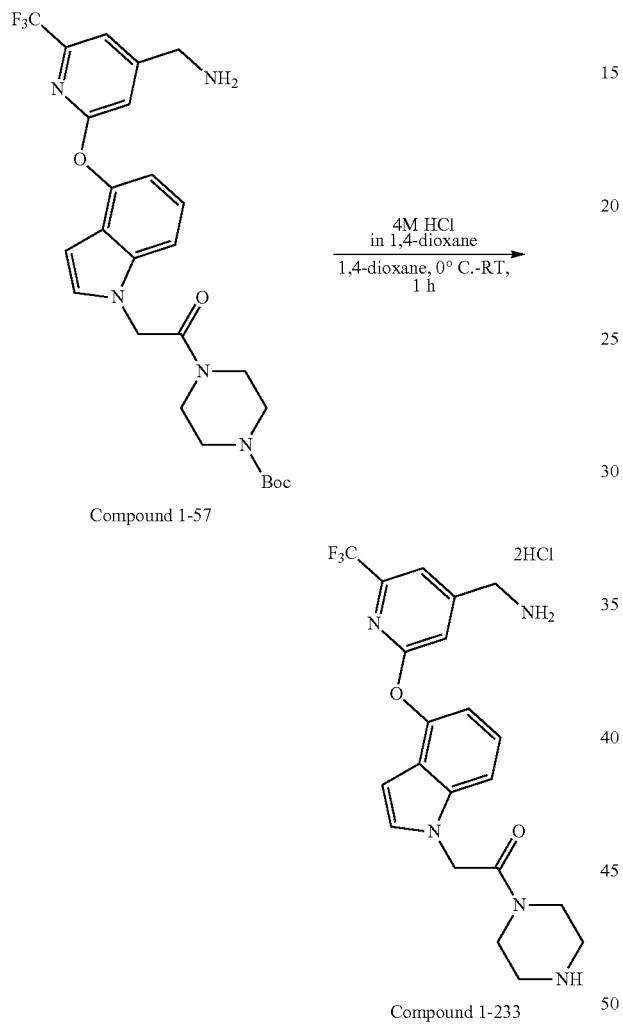

To a stirred solution of tert-butyl 4-(2-(4-((4-(aminomethyl)-6-(trifluoromethyl)pyridin-2-yl)oxy)-1H-indol-1-yl)acetyl)piperazine-1-carboxylate 1-57 (100 mg, 0.19) (from Example 52) in 1,4-dioxane (1 mL) at 0° C., was added 4 M HCl in 1,4-dioxane (5 mL). The mixture was warmed to RT and stirred for 1 h. The mixture was concentrated in vacuo and the crude triturated with EtOAc (2×3 mL) then purified (preparative HPLC) to afford the title compound (18 mg, 22%) as an off-white solid. ¹H NMR (400 MHz, DMSO-d₆): δ 8.97 (br s, 2H), 8.39 (br s, 3H), 7.77 (s, 1H), 7.42 (s, 1H), 7.33 (m, 1H), 7.23 (m, 1H), 7.15 (m, 1H), 6.85 (m, 1H), 6.16 (m, 1H), 5.27 (s, 2H), 4.21-4.23 (m, 2H), 3.78-3.80 (m, 2H), 3.65-3.67 (m, 2H), 3.25-3.27 (m, 2H), 3.05-3.16 (m, 2H); LCMS Mass: 433.9 (M⁺+1).

Example 100: 2-(4-((4-(Aminomethyl)-6-(trifluoromethyl)pyridin-2-yl)oxy)-1H-indol-1-yl)-N-carbamimidoylacetamide dihydrochloride (Compound 1-234)

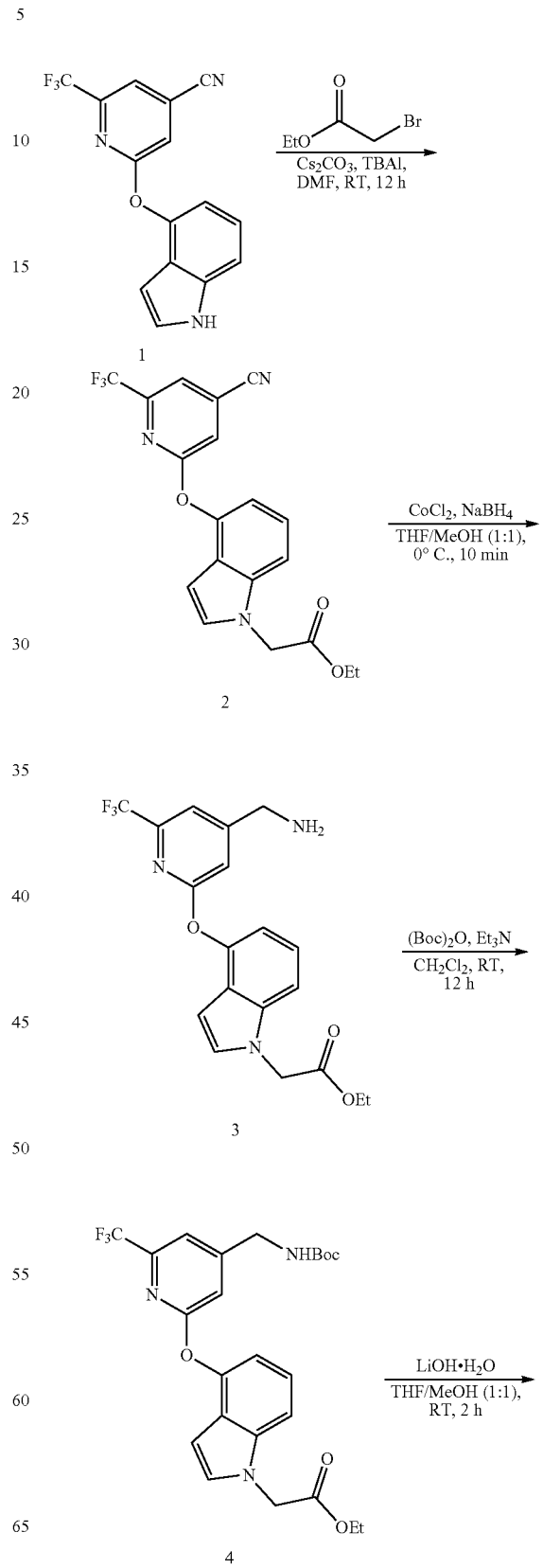

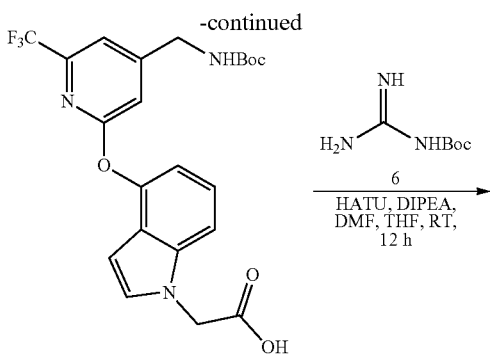

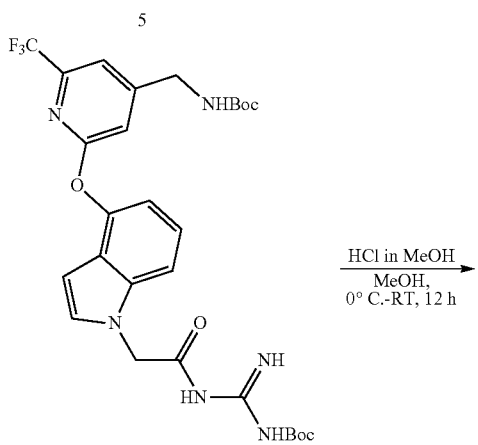

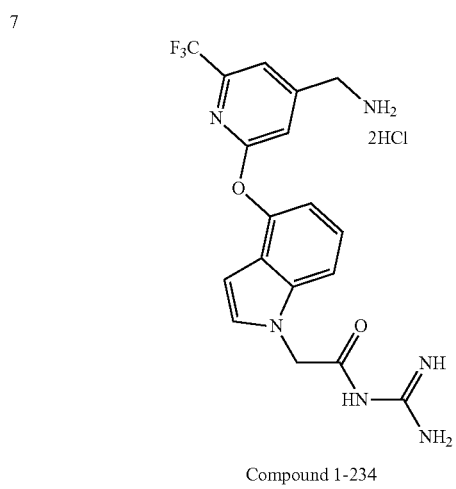

Compound 1-234

Step 1: Ethyl 2-(4-((4-cyano-6-(trifluoromethyl) pyridin-2-yl)oxy)-1H-indol-1-yl)acetate (2)

To a stirred solution of 2-((1H-indol-4-yl)oxy)-6-(trifluoromethyl)isonicotinonitrile 1 (440 mg, 1.46 mmol) (from Example 49, Step 1) in DMF (5 mL) at RT, were added ethyl 2-bromoacetate (487 mg, 2.91 mmol), $Cs_2CO_3$ (983 mg, 4.37 mmol) and $NBu_4I$ (234 mg, 0.73 mmol). The mixture was stirred at RT for 12 h. The mixture was diluted with water (25 mL) and extracted with EtOAc (2×30 mL). The combined organic extracts were washed with brine (15 mL), dried ($Na_2SO_4$), filtered and concentrated. The crude was purified (silica gel; eluting 10% EtOAc/hexanes) to afford compound 2 (370 mg, 65%) as an off white solid. $^1$H NMR (500 MHz, DMSO-$d_6$): δ 8.17 (s, 1H), 7.95 (s, 1H), 7.30- 7.37 (m, 2H), 7.16 (m, 1H), 6.90 (m, 1H), 6.18 (m, 1H), 5.15 (s, 2H), 4.13 (m, 2H), 1.19 (m, 3H); LCMS Mass: 390.0 ($M^+$+1).

Step 2: Ethyl 2-(4-((4-(aminomethyl)-6-(trifluoromethyl)pyridin-2-yl)oxy)-1H-indol-1-yl)acetate (3)

To a stirred solution of compound 2 (310 mg, 0.8 mmol) in THF/MeOH (1:1, 20 mL) at 0° C. under an inert atmosphere, were added $CoCl_2$ (76 mg, 2.0 mmol) followed by $NaBH_4$ (257 mg, 2.0 mmol) portion wise, and the mixture stirred for 10 min. The mixture was filtered through a pad of celite and the filtrate was concentrated to afford compound 3 (230 mg) as a pale brown semi solid which was used without further purification. LCMS Mass: 394.3 ($M^+$+1).

Step 3: Ethyl 2-(4-((4-(((tert-butoxycarbonyl)amino) methyl)-6-(trifluoromethyl) pyridin-2-yl)oxy)-1H-indol-1-yl)acetate (4)

To a stirred solution of compound 3 (230 mg, crude) in $CH_2Cl_2$ (40 mL) at RT, were added TEA (0.24 mL, 1.76 mmol) followed by $(Boc)_2O$ (0.15 mL, 0.64 mmol), and the mixture was stirred for 12 h. The mixture was quenched with water (20 mL) and extracted with EtOAc (2×20 mL). The combined organic extracts were washed with brine (15 mL), dried ($Na_2SO_4$), filtered and concentrated. The crude was purified (silica gel; eluting 10% EtOAc/hexanes) to afford compound 4 (191 mg, 49% over two steps) as a pale brown solid. $^1$H NMR (500 MHz DMSO-$d_6$): δ 7.56 (m, 1H), 7.47 (s, 1H), 7.31-7.35 (m, 2H), 7.16 (m, 1H), 7.02 (s, 1H), 6.85 (m, 1H), 6.17 (m, 1H), 5.16 (s, 2H), 4.22 (m, 2H), 4.16 (m, 2H), 1.34 (s, 9H), 1.22 (m, 3H); LCMS Mass: 494.1 ($M^+$+1).

Step 4: 2-(4-((4-(((tert-Butoxycarbonyl)amino) methyl)-6-(trifluoromethyl)pyridin-2-yl)oxy)-1H-indol-1-yl)acetic acid (5)

To a stirred solution of compound 4 (140 mg, 0.28 mmol) in THF/MeOH (1:1, 10 mL) at RT, was added $LiOH·H_2O$ (60 mg, 1.42 mmol), and the mixture stirred for 2 h. The volatiles were removed under reduced pressure. The residue was diluted with water (15 mL) and washed with EtOAc (2×5 mL). The organic layer was separated, and the aqueous layer was acidified with saturated citric acid solution to pH ~3 and extracted with $CH_2Cl_2$ (2×15 mL). The combined organic extracts were washed with brine (10 mL), dried ($Na_2SO_4$), filtered and concentrated in vacuo to afford compound 5 (110 mg, 83%) as an off white solid, which did not require further purification. $^1$H NMR (400 MHz, DMSO-$d_6$): δ 7.52 (m, 1H), 7.47 (s, 1H), 7.28-7.32 (m, 2H), 7.14 (m, 1H), 6.99 (s, 1H), 6.82 (m, 1H), 6.13 (m, 1H), 4.89 (s, 2H), 4.20 (m, 2H), 1.34 (s, 9H).

Step 5: 2-(4-((4-(Aminomethyl)-6-(trifluoromethyl) pyridin-2-yl)oxy)-1H-indol-1-yl)-N-Boc-carbamimidoylacetamide (7)

To a stirred solution of compound 5 (31 mg, 0.07 mmol) in DMF (5 mL) and THF (1 mL) at RT, were added HATU (38 mg, 0.1 mmol) and DIEA (0.03 mL, 0.2 mmol), and the mixture stirred for 15 min. To this was added N-Boc-guanidine 6 (16 mg, 0.1 mmol) and the mixture was stirred at RT stirred for 12 h. The mixture was concentrated, and the residue was diluted with water (10 mL) then extracted with EtOAc (2×10 mL). The combined organic extracts were washed with brine (8 mL), dried ($Na_2SO_4$), filtered and concentrated. The residue was purified (silica gel; eluting 10% EtOAc/hexanes) to afford compound 7 (35 mg, 62%) as an off white solid. ¹H NMR (500 MHz, DMSO-d₆): δ 11.11 (br s, 1H), 8.62 (br s, 1H), 7.54 (m, 1H), 7.47 (s, 1H), 7.26-7.34 (m, 2H), 7.15 (m, 1H), 7.01 (s, 1H), 6.83 (m, 1H), 6.16 (br s, 1H), 5.01 (br s, 2H), 4.21 (m, 2H), 1.43 (s, 9H), 1.34 (s, 9H); LCMS Mass: 629.2 (M⁺+Na).

Step 6: 2-(4-((4-(Aminomethyl)-6-(trifluoromethyl)pyridin-2-yl)oxy)-1H-indol-1-yl)-N-carbamimidoylacetamide dihydrochloride (Compound 1-234)

To a stirred solution of compound 7 (30 mg, 0.05 mmol) in MeOH (1 mL) at 0° C., was added HCl in MeOH (2 mL). The reaction mixture was gradually warmed to RT and stirred for 12 h. The volatiles were removed and the crude was purified (preparative HPLC) to afford compound 1-234 (10 mg, 43%) as an off white solid. ¹H NMR (400 MHz, CD₃OD): δ 7.61 (s, 1H), 7.33 (m, 1H), 7.21-7.28 (m, 3H), 6.93 (m, 1H), 6.31 (m, 1H), 5.21 (s, 2H), 4.25 (s, 2H); LCMS Mass: 407.0 (M⁺+1).

Example 101: 1-(2-((4-(Aminomethyl)-6-(trifluoromethyl)pyridin-2-yl)oxy)-6-azaspiro[3.4]octan-6-yl)ethanone hydrochloride (Compound 1-244)

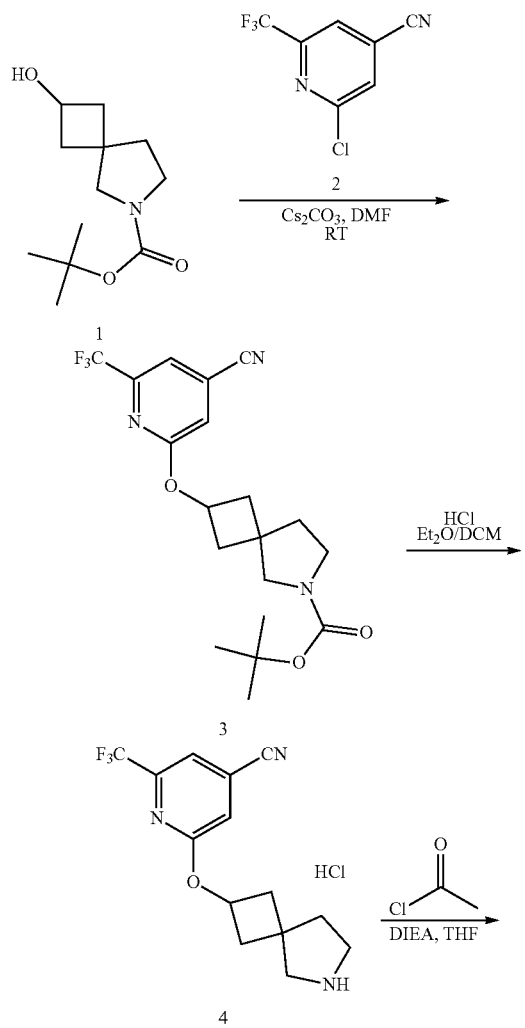

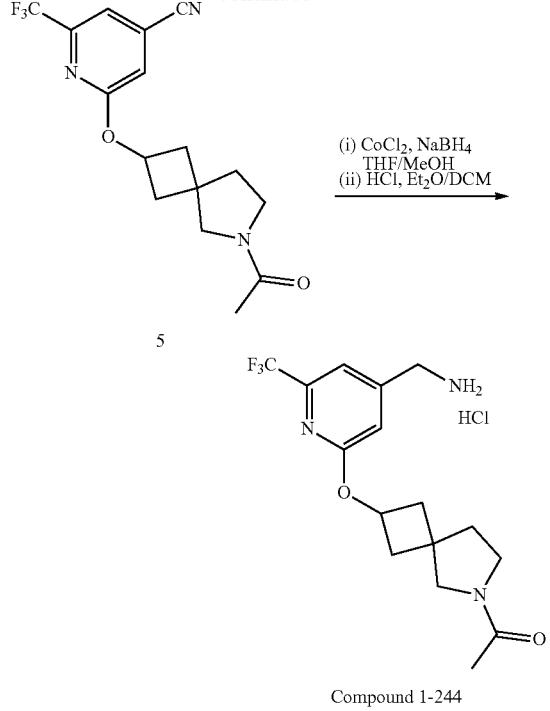

Compound 1-244

Step 1: tert-Butyl 2-((4-cyano-6-(trifluoromethyl)pyridin-2-yl)oxy)-6-azaspiro[3.4]octane-6-carboxylate (3)

A mixture of tert-butyl 2-hydroxy-6-azaspiro[3.4]octane-6-carboxylate 1 (950 mg, 4.18 mmol), 2-chloro-6-(trifluoromethyl)isonicotinonitrile 2 (1.03 g, 4.99 mmol), Cs₂CO₃ (2.73 g, 8.4 mmol), and DMF (22 mL), was stirred at RT for 16 h. The mixture was partitioned between water, brine, aq. 1M HCl, and EtOAc. The organic layer was separated and the aq. layer re-extracted with additional EtOAc. The combined organic layers were dried (MgSO₄), filtered, and concentrated under reduced pressure. The residue was purified (silica gel; eluting 0-40% EtOAc/hexanes) to afford compound 3 (1.04 g, 63%) as a yellow oil. ¹H NMR (300 MHz, DMSO-d₆): δ 8.00 (m, 1H), 7.77 (m, 1H), 5.14 (m, 1H), 3.10-3.30 (m, 6H), 2.00-2.20 (m, 2H), 1.80-2.00 (m, 2H), 1.36 (s, 9H); LCMS Mass: 342.0 (M⁺+1−C₄H9).

Step 2: 2-(6-Azaspiro[3.4]octan-2-yloxy)-6-(trifluoromethyl)isonicotinonitrile hydrochloride (4)

A mixture of compound 3 (935 mg, 2.35 mmol), HCl (2M in Et₂O, 5 mL, 10 mmol), and DCM (5 mL), was stirred at RT for 16 h. The mixture was concentrated under reduced pressure and dried, to afford compound 4 (775 mg, 99%) as a white solid, which did not require further purification.

¹H NMR (300 MHz, DMSO-d₆): δ 9.11 (br s, 2H), 8.02 (m, 1H), 7.78 (m, 1H), 5.15 (m, 1H), 3.00-3.40 (m, 5H), 2.62 (m, 1H), 2.10-2.40 (m, 2H), 2.00-2.20 (m, 2H); LCMS Mass: 298.0 (M⁺+1).

Step 3: 2-((6-Acetyl-6-azaspiro[3.4]octan-2-yl)oxy)-6-(trifluoromethyl)isonicotinonitrile (5)

To a stirred mixture of compound 4 (100 mg, 0.30 mmol), DIEA (0.116 mg, 0.899 mmol), and THF (1.5 mL) at RT, was added acetyl chloride (23 mg, 0.30 mmol). The mixture was stirred at RT for 3 h. The mixture was concentrated under reduced pressure. The residue was purified directly (silica gel; eluting 0-100% EtOAc/hexanes) to afford compound 5 (38 mg, 38%) as a colorless oil. $^1$H NMR (300 MHz, DMSO-d$_6$): δ 8.01 (m, 1H), 7.78 (m, 1H), 5.15 (m, 1H), 3.20-3.40 (m, 6H), 2.10-2.30 (m, 2H), 1.80-2.00 (m, 5H); LCMS Mass: 340.0 (M$^+$+1).

Step 4: 1-(2-((4-(Aminomethyl)-6-(trifluoromethyl) pyridin-2-yl)oxy)-6-azaspiro[3.4]octan-6-yl)etha-none hydrochloride (Compound 1-244)

To a stirred solution of compound 5 (38 mg, 0.112 mmol) in THF/MeOH (1:1, 2 mL) at 0° C. were added CoCl$_2$ (29 mg, 0.224 mmol) and NaBH$_4$ (42 mg, 1.12 mmol) portion-wise under inert atmosphere. The reaction was warmed to RT and stirred for 45 min. The reaction mixture was concentrated under reduced pressure and the residue obtained was dissolved in EtOAc. This was filtered through a pad of celite and the residue was washed with 10% MeOH/CH$_2$Cl$_2$. The filtrate was washed with brine (10 mL), dried (MgSO$_4$), filtered, and concentrated under reduced pressure to obtain the desired amine.

To this amine in CH$_2$Cl$_2$ (2 mL) was added HCl (2M in Et$_2$O, 2 mL, 4 mmol) and the mixture stirred at RT for 10 min. The obtained solid was filtered and dried under vacuum to afford compound 1-244 (25 mg, 59%) as a white solid. LCMS Mass: 344.0 (M$^+$+1).

Example 102: 3-((4-(Aminomethyl)-6-(trifluoromethyl)pyridin-2-yl)thio)-N-phenylbenzamide hydrochloride (Compound 1-68)

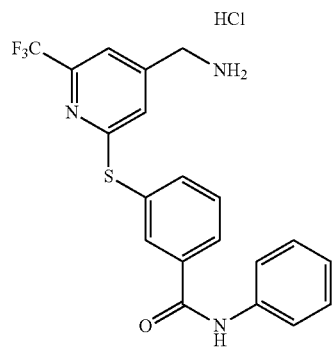 [SMILES: Cl ; NCc1cc(Sc2cccc(C(=O)Nc3ccccc3)c2)nc(C(F)(F)F)c1]

The title compound (1-68) was prepared using the procedure for Example 1, using Int-M in Step 1.

$^1$H NMR (500 MHz, DMSO-d$_6$): δ 10.40 (s, 1H), 8.45 (br s, 3H), 8.21 (m, 1H), 8.12 (m, 1H), 7.72-7.85 (m, 4H), 7.67 (m, 1H), 7.48 (m, 1H), 7.30-7.35 (m, 2H), 7.10 (m, 1H), 4.07-4.17 (m, 2H); LCMS Mass: 404.0 (M$^+$+1).

Example 103: 3-(((4-(Aminomethyl)-6-(trifluoromethyl)pyridin-2-yl)amino)methyl)-N-phenylbenzamide hydrochloride (Compound 1-105)

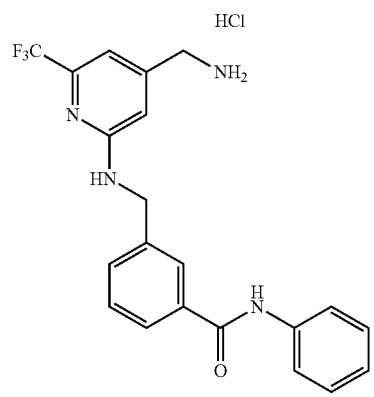 [SMILES: Cl ; NCc1cc(NCc2cccc(C(=O)Nc3ccccc3)c2)nc(C(F)(F)F)c1]

The title compound (1-105) was prepared using the procedure for Example 1, using Int-L in Step 1.

$^1$H NMR (500 MHz, DMSO-d$_6$): δ 10.21 (s, 1H), 8.24 (br s, 3H), 7.90-7.96 (m, 2H), 7.82 (m, 1H), 7.74 (m, 2H), 7.53 (m, 1H), 7.47 (m, 1H), 7.33 (m, 2H), 7.05-7.11 (m, 2H), 6.79 (s, 1H), 4.57 (m, 2H), 3.99 (m, 2H); LCMS Mass: 401.3 (M$^+$+1).

Example 104: 3-(((4-(Aminomethyl)-6-(trifluoromethyl)pyridin-2-yl)amino)methyl)-N-(2-(methyl-sulfonyl)ethyl)benzamide hydrochloride (Compound 1-106)

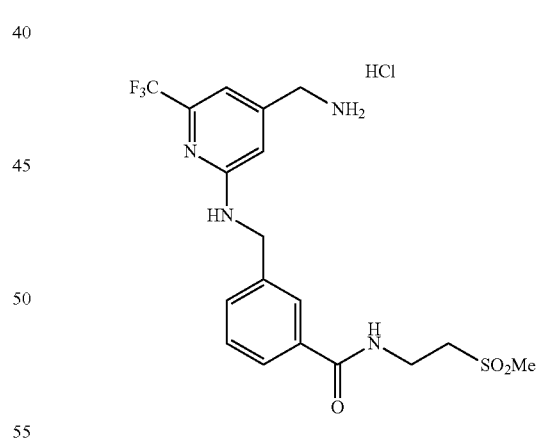

The title compound (1-106) was prepared using the procedure for Example 1, using Int-L and 2-(methylsulfonyl)ethan-1-amine hydrochloride in Step 1. $^1$H NMR (400 MHz, DMSO-d$_6$): δ 8.70 (m, 1H), 8.34 (br s, 3H), 7.91 (m, 1H), 7.84 (s, 1H), 7.69 (m, 1H), 7.49 (m, 1H), 7.40 (m, 1H), 7.08 (s, 1H), 6.80 (s, 1H), 4.53 (m, 2H), 3.98 (m, 2H), 3.61-3.69 (m, 2H), 3.32-3.37 (m, 2H), 3.01 (s, 3H); LCMS Mass: 431.3 (M$^+$+1).

Example 105: (S)-(3-(((4-(Aminomethyl)-6-(trifluoromethyl)pyridin-2-yl)amino)methyl)phenyl)(3-hydroxypyrrolidin-1-yl)methanone hydrochloride (Compound 1-237)

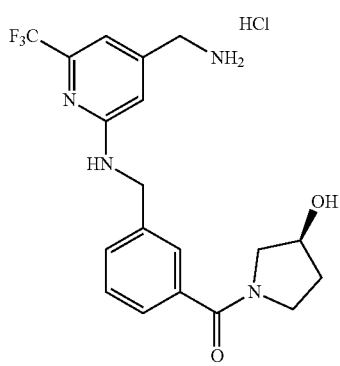 [SMILES: Cl ; NCc1cc(NCc2cccc(C(=O)N3CC[C@H](O)C3)c2)nc(C(F)(F)F)c1]

The title compound (1-237) was prepared using the procedure for Example 1, using Int-L and (S)-pyrrolidin-3-ol in Step 1. $^1$H NMR (500 MHz, DMSO-d$_6$): δ 8.48 (br s, 3H), 7.93 (br s, 1H), 7.41-7.48 (m, 2H), 7.33-7.39 (m, 2H), 7.11 (s, 1H), 6.83 (s, 1H), 4.53 (s, 2H), 4.31 (m, 1H), 4.20 (m, 1H), 3.96-3.99 (m, 2H), 3.45-3.59 (m, 2H), 3.34 (m, 1H), 3.14 (m, 1H), 1.70-1.97 (m, 2H); LCMS Mass: 395.1 (M$^+$+1).

Example 106: N'-(4-(Aminomethyl)-6-(trifluoromethyl)pyridin-2-yl)-N$^3$-phenylisophthalamide trifluoroacetate (Compound 1-240)

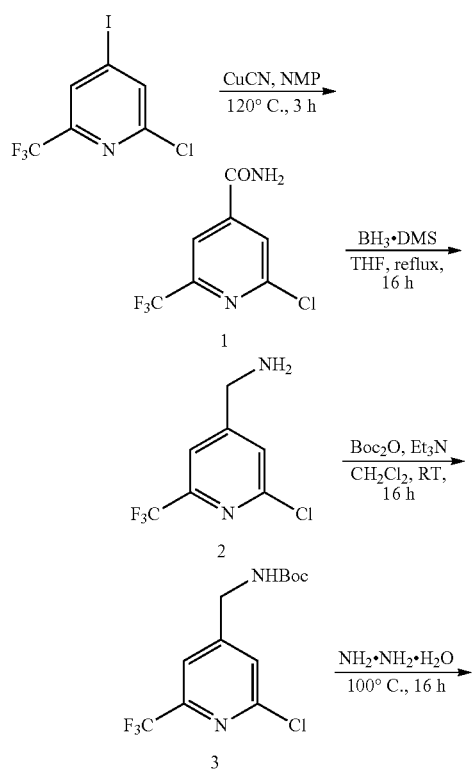

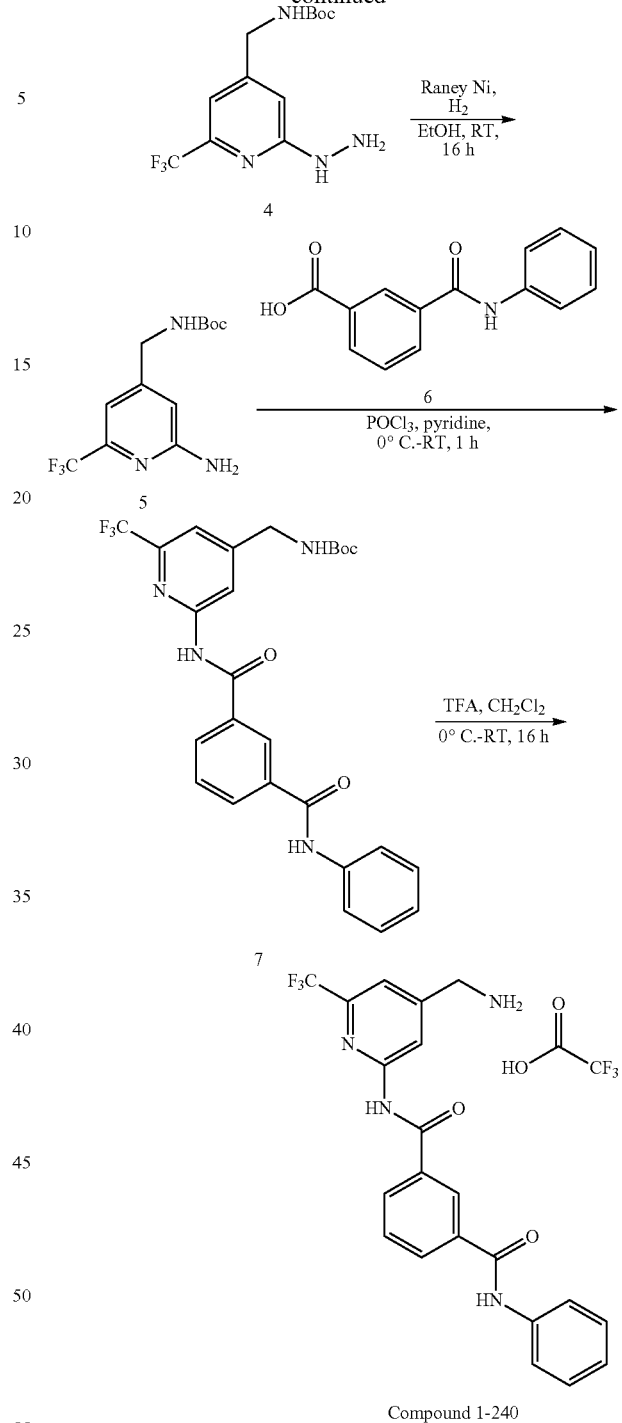

Compound 1-240

Step 1: 2-Chloro-6-(trifluoromethyl)isonicotinamide (1)

To a stirred solution of 2-chloro-4-iodo-6-(trifluoromethyl)pyridine (5 g, 16.29 mmol) in N-methyl-2-pyrrolidone (20 mL) at RT under an inert atmosphere, was added CuCN (5.84 g, 65.15 mmol). The reaction mixture was heated at 120° C. for 3 h. The mixture was cooled to RT, diluted with EtOAc (25 mL), and filtered through a pad of celite and washed with EtOAc (20 mL). The filtrate was diluted with water (60 mL), extracted with EtOAc (2×50 mL), washed with brine (40 mL), dried (Na$_2$SO$_4$), filtered and concentrated under reduced pressure. The residue was purified (silica gel; eluting 2-4% EtOAc/hexanes followed by 30% EtOAc/hexanes) to afford compound 1 (500 mg, 7%) as pale brown solid. $^1$H NMR (400 MHz, CDCl$_3$): δ 7.96 (m, 1H), 7.89 (s, 1H), 6.03-6.32 (m, 2H); LCMS Mass: 222.9 (M–H$^+$).

Step 2: (2-Chloro-6-(trifluoromethyl)pyridin-4-yl) methanamine (2)

To a stirred solution of compound 1 (5 g, 22.32 mmol) in THF (60 mL) at 0° C. under an inert atmosphere, was added BH$_3$. DMS (5 M sol. in Et$_2$O, 22.3 mL, 111.61 mmol) drop-wise. The reaction mixture was heated to reflux and stirred for 16 h. The mixture was poured into ice cold water (80 mL) and extracted with EtOAc (2×80 mL). The combined organic extracts were washed with brine (40 mL), dried (Na$_2$SO$_4$), filtered and concentrated to afford compound 2 (5.3 g) as a pale yellow oil, which was used without further purification.

Step 3: tert-Butyl ((2-chloro-6-(trifluoromethyl) pyridin-4-yl)methyl)carbamate (3)

To a stirred solution of compound 2 (5.3 g, crude) in CH$_2$Cl$_2$ (60 mL) at RT, were added (Boc)$_2$O (6.95 mL, 30.28 mmol) and TEA (7.03 mL, 50.48 mmol), and the mixture was stirred for 16 h. The mixture was quenched with water (80 mL) and extracted with CH$_2$Cl$_2$ (2×80 mL). The combined organic extracts were washed with brine (40 mL), dried (Na$_2$SO$_4$), filtered and concentrated. The residue was purified (silica gel; eluting 15% EtOAc/hexanes) to afford compound 3 (2 g, 29% over two steps) as pale yellow crystals. $^1$H NMR (500 MHz, CDCl$_3$): δ 7.51 (s, 1H), 7.43 (s, 1H), 5.03 (br s, 1H), 4.39 (m, 2H), 1.47 (br s, 9H); LCMS Mass: 310.9 (M$^+$+1).

Step 4: tert-Butyl (E)-((2-hydrazono-6-(trifluoromethyl)-1,2-dihydropyridin-4-yl)methyl)carbamate (4)

To compound 3 (2 g, 6.45 mmol) was added hydrazine hydrate (35 mL) at RT. The reaction mixture was heated to 100° C. and stirred for 16 h. After cooling to RT, the mixture was concentrated under reduced pressure. To the residue was added Et$_2$O (10 mL) and MeOH (5 mL) and was stirred for 30 min. The mixture was filtered, and the filtrate was concentrated under reduced pressure to afford compound 4 (2 g) as a pale brown viscous liquid, which did not require further purification.
$^1$H NMR (500 MHz, CD$_3$OD): δ 6.90 (s, 1H), 6.85 (s, 1H), 4.20 (s, 2H), 1.46 (s, 9H); LCMS Mass: 307.2 (M$^+$+1).

Step 5: tert-Butyl ((2-amino-6-(trifluoromethyl) pyridin-4-yl)methyl)carbamate (5)

To a stirred solution of compound 4 (50 mg, crude) in EtOH (5 mL) at RT under an inert atmosphere, was added Raney Ni (5 mg). The reaction mixture was stirred at RT under H2 (1 atmosphere) for 16 h. The mixture was filtered through a pad of celite and washed with MeOH (10 mL). The filtrate was concentrated under reduced pressure to afford compound 5 (35 mg) as an off white solid, which was used without further purification. $^1$H NMR (500 MHz, DMSO-d$_6$): δ 7.44 (m, 1H), 6.99-7.25 (m, 2H), 6.75 (s, 1H), 6.51 (m, 1H), 4.03 (m, 2H), 1.38 (s, 9H).

Step 6: tert-Butyl ((2-(3-(phenylcarbamoyl)benzamido)-6-(trifluoromethyl) pyridin-4-yl)methyl) carbamate (7)

To a stirred solution of 3-(phenylcarbamoyl)benzoic acid (124 mg, 0.51 mmol) in pyridine (4 mL) at 0° C., were added compound 5 (150 mg, 0.51 mmol) followed by POCl$_3$ (0.47 mL, 5.15 mmol). The mixture was stirred at 0° C. for 1 h. The mixture was poured into ice cold water (20 mL) and extracted with CH$_2$Cl$_2$ (2×20 mL). The organic layer was separated, washed with aq. CuSO$_4$ (20 mL), brine (15 mL), dried (Na$_2$SO$_4$), filtered and concentrated. The residue was purified (silica gel; eluting 30-35% EtOAc/hexanes) to afford compound 7 (90 mg, 34%) as a pale blue solid. $^1$H NMR (500 MHz, DMSO-d$_6$): δ 11.27 (s, 1H), 10.35 (s, 1H), 8.57 (s, 1H), 8.40 (s, 1H), 8.16 (m, 2H), 7.77 (m, 2H), 7.67 (m, 1H), 7.62 (m, 1H), 7.51 (s, 1H), 7.36 (m, 2H), 7.11 (m, 1H), 4.28 (m, 2H), 1.40 (s, 9H); LCMS Mass: 513.2 (M–H$^+$).

Step 7: N'-(4-(Aminomethyl)-6-(trifluoromethyl) pyridin-2-yl)-N$^3$-phenylisophthalamide trifluoroacetate (Compound 1-240)

To a stirred solution of compound 7 (20 mg, 0.04 mmol) in CH$_2$Cl$_2$ (2 mL) at 0° C., was added TFA (0.1 mL). The reaction mixture was gradually warmed to RT and stirred for 16 h. The mixture was concentrated and the residue was purified via trituration with Et$_2$O (2×1 mL), then n-pentane (2×2 mL), and dried under vacuum to afford compound 1-240 (12 mg, 75%) as an off white solid.

$^1$H NMR (500 MHz, DMSO-d$_6$): δ 11.44 (s, 1H), 10.36 (s, 1H), 8.60 (m, 2H), 8.34 (br s, 3H), 8.19 (m, 2H), 7.75-7.81 (m, 3H), 7.69 (m, 1H), 7.37 (m, 2H), 7.12 (m, 1H), 4.26 (s, 2H); LCMS Mass: 415.0 (M+H$^+$).

Example 107: (S)—N-(4-(Aminomethyl)-6-(trifluoromethyl)pyridin-2-yl)-3-(3-hydroxypyrrolidine-1-carbonyl)benzamide trifluoroacetate (Compound 1-241)

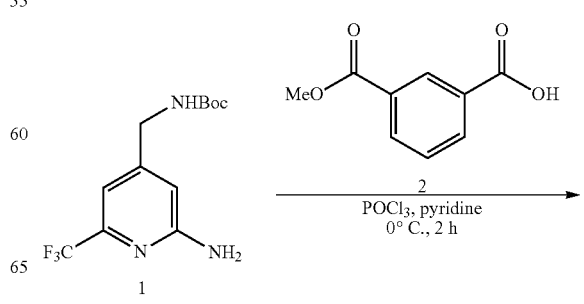

251

-continued

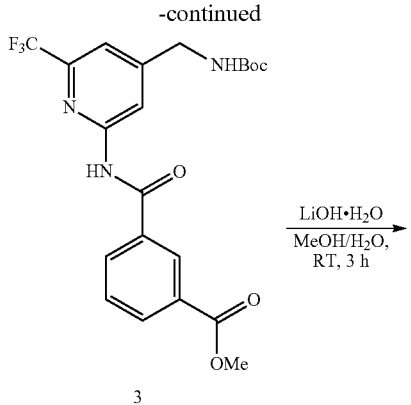

3

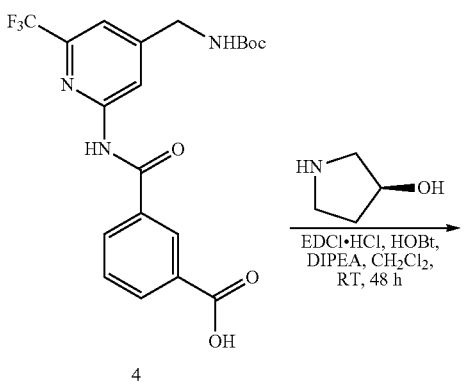

4

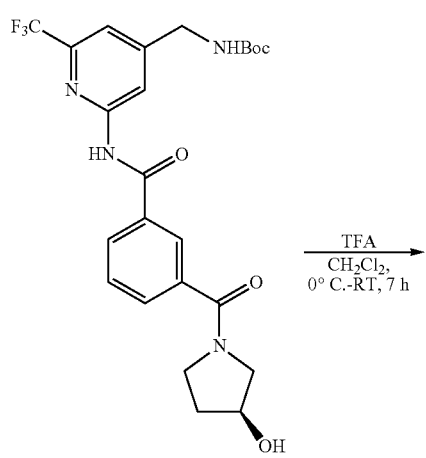

5

252

-continued

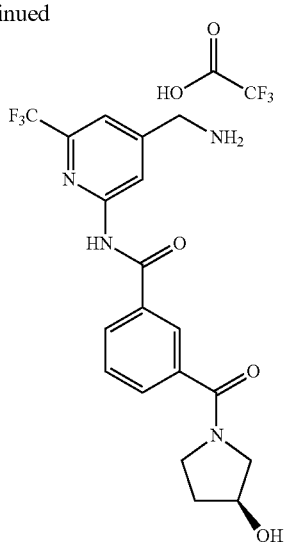

Compound 1-241

Step 1: Methyl 3-((4-(((tert-butoxycarbonyl)amino)methyl)-6-(trifluoromethyl)pyridin-2-yl)carbamoyl)benzoate (3)

To a stirred solution of 3-(methoxycarbonyl)benzoic acid 2 (100 mg, 0.55 mmol) in pyridine (3 mL) at 0° C., were added tert-butyl ((2-amino-6-(trifluoromethyl)pyridin-4-yl)methyl)carbamate 1 (162 mg, 0.55 mmol) (from Example 106, Step 5) followed by POCl₃ (0.51 mL, 5.55 mmol) drop-wise. The mixture was stirred at 0° C. for 2 h. The mixture was quenched with ice cold water (20 mL), washed with CuSO₄ solution (20 mL) and extracted with EtOAc (2×20 mL). The combined organic extracts were washed with brine (10 mL), dried (Na₂SO₄), filtered and concentrated. The residue was purified (silica gel; eluting 25-30% EtOAc/hexanes) to afford compound 3 (50 mg, 20%) as a pale yellow sticky solid. $^1$H NMR (500 MHz, CDCl₃): δ 8.71 (br s, 1H), 8.51-8.57 (m, 2H), 8.27 (m, 1H), 8.16 (m, 1H), 7.63 (m, 1H), 7.41 (s, 1H), 5.08 (br s, 1H), 4.38-4.49 (m, 2H), 3.99 (s, 3H), 1.49 (s, 9H); LCMS Mass: 476.1 (M$^+$+Na).

Step 2: 3-((4-(((tert-Butoxycarbonyl)amino)methyl)-6-(trifluoromethyl)pyridin-2-yl)carbamoyl)benzoic acid (4)

To a stirred solution of compound 3 (175 mg, 0.39 mmol) in MeOH:H₂O (1:1, 4 mL) was added LiOH.H₂O (18 mg, 0.77 mmol), and the mixture was stirred at RT for 3 h. The MeOH was removed under reduced pressure and the mixture then diluted with water (15 mL), acidified with citric acid to pH ~3, and extracted with EtOAc (2×20 mL). The combined organic extracts were washed with brine (10 mL), dried (Na₂SO₄), filtered and concentrated in vacuo afford compound 4 (200 mg) as an off white solid, which was used without further purification. LCMS Mass: 438.1 (M−H$^+$).

Step 3: tert-Butyl (S)-((2-(3-(3-hydroxypyrrolidine-1-carbonyl)benzamido)-6-(trifluoromethyl)pyridin-4-yl)methyl)carbamate (5)

To a stirred solution of compound 4 (220 mg, crude) in CH₂Cl₂ (6 mL) at RT, were added EDCI hydrochloride (191 mg, 1.0 mmol), HOBt (34 mg, 0.25 mmol), (S)-pyrrolidin-3-ol (65 mg, 0.75 mmol) and DIEA (0.17 mL, 1.0 mmol). The mixture was stirred at RT for 48 h. The mixture was quenched with water (20 mL) and extracted with CH$_2$Cl$_2$ (2×20 mL). The combined organic extracts were washed with brine (10 mL), dried (Na$_2$SO$_4$), filtered and concentrated. The residue was purified (silica gel; eluting 90-95% EtOAc/hexanes) to afford compound 5 (50 mg, 25% over two steps) as an off-white solid. $^1$H NMR (500 MHz, DMSO-d$_6$): δ 11.30 (m, 1H), 8.38 (s, 1H), 8.14 (m, 1H), 8.09 (m, 1H), 7.73 (m, 1H), 7.56-7.64 (m, 2H), 7.50 (s, 1H), 5.00 (m, 1H), 4.23-4.37 (m, 3H), 3.52-3.64 (m, 2H), 3.41 (m, 1H), 3.20 (m, 1H), 1.76-1.97 (m, 2H), 1.42 (s, 9H); LCMS Mass: 507.2 (M–H$^+$).

Step 4: (S)—N-(4-(Aminomethyl)-6-(trifluoromethyl)pyridin-2-yl)-3-(3-hydroxypyrrolidine-1-carbonyl)benzamide trifluoroacetate (Compound 1-241)

To a stirred solution of compound 5 (20 mg, 0.04 mmol) in CH$_2$Cl$_2$ (2 mL) at 0° C., was added TFA (0.03 mL, 0.39 mmol). The reaction mixture was gradually warmed to RT and stirred for 7 h. The mixture was concentrated under reduced pressure, and the residue was triturated with Et$_2$O (2×1 mL), n-pentane (2×1 mL), then dried under vacuum to afford compound 1-241 (10 mg, 62%) as an off white solid. $^1$H NMR (500 MHz, CD$_3$OD): δ 8.69 (s, 1H), 8.15 (m, 1H), 8.11 (m, 1H), 7.80 (m, 1H), 7.62-7.69 (m, 2H), 4.53 (br s, 1H), 4.41 (br s, 1H), 4.33 (s, 2H), 3.62-3.85 (m, 3H), 3.50 (m, 1H), 1.92-2.20 (m, 2H), 1.35 (m, 1H); LCMS Mass: 409.0 (M+H$^+$).

Example 108: N'-(4-(Aminomethyl)-6-(trifluoromethyl)pyridin-2-yl)-N$^3$-(2-(methylsulfonyl)ethyl) isophthalamide trifluoroacetate (Compound 1-242)

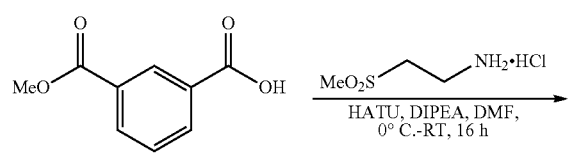

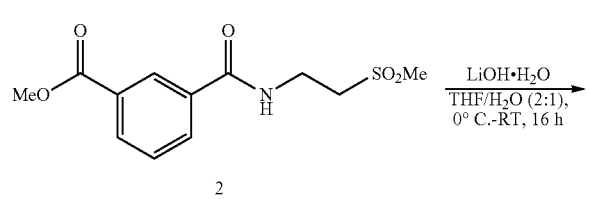

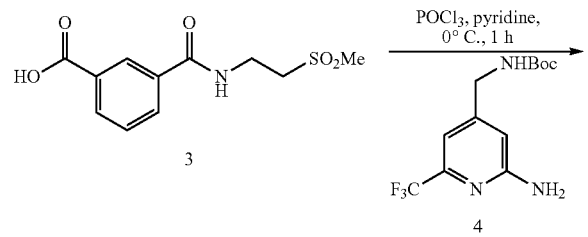

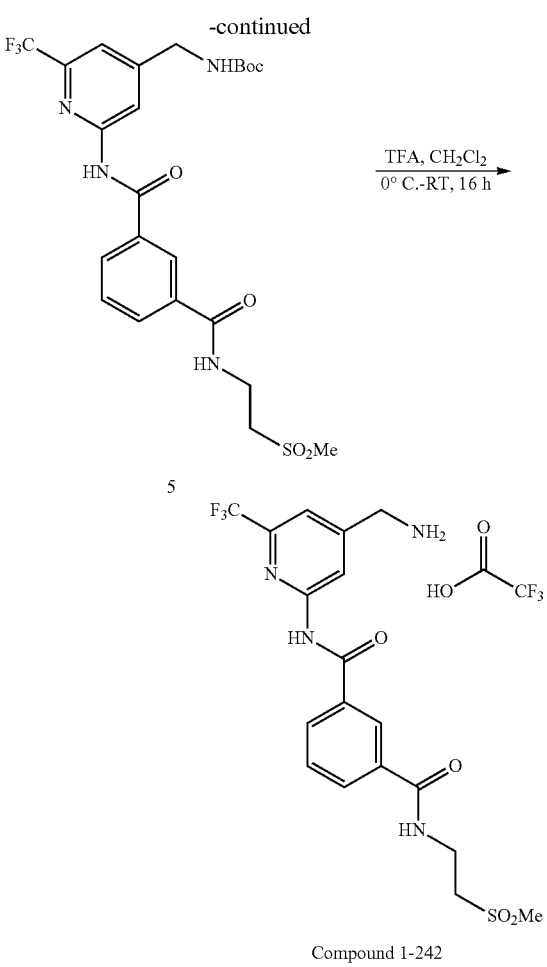

Compound 1-242

Step 1: Methyl 3-((2-(methylsulfonyl)ethyl)carbamoyl)benzoate (2)

To a stirred solution of 3-(methoxycarbonyl)benzoic acid 1 (500 mg, 2.78 mmol) in DMF (5 mL) at 0° C., were added 2-(methylsulfonyl)ethan-1-amine hydrochloride (443 mg, 2.78 mmol), HATU (1.58 g, 4.17 mmol), and DIEA (1.45 mL, 8.33 mmol). The reaction mixture was gradually warmed to RT and stirred for 16 h. The mixture was diluted with water (30 mL) and extracted with EtOAc (2×30 mL). The combined organic extracts were washed with brine (20 mL), dried (Na$_2$SO$_4$), filtered and concentrated. The residue was purified (silica gel; eluting 3% MeOH/CH$_2$Cl$_2$) to afford compound 2 (450 mg, 57%) as an off white solid. $^1$H NMR (500 MHz, DMSO-d$_6$): δ 8.93 (m, 1H), 8.42 (s, 1H), 8.06-8.11 (m, 2H), 7.63 (m, 1H), 3.88 (s, 3H), 3.68 (m, 2H), 3.38 (m, 2H), 3.02 (s, 3H); LCMS Mass: 285.9 (M+H$^+$).

Step 2: 3-((2-(Methylsulfonyl)ethyl)carbamoyl)benzoic acid (3)

To a stirred solution of compound 2 (450 mg, 1.58 mmol) in a mixture of THF:H$_2$O (2:1, 8 mL) at 0° C., was added LiOH.H$_2$O (133 mg, 3.16 mmol). The reaction mixture was gradually warmed to RT and stirred for 16 h. The volatiles were removed under reduced pressure, and the residue was diluted with water (30 mL) then acidified with citric acid to pH ~4. The precipitated solid was collected via filtration, and dried under vacuum to afford compound 3 (400 mg, 94%) as white solid. LCMS Mass: 271.8 (M+H⁺).

Step 3: tert-Butyl ((2-(3-((2-(methylsulfonyl)ethyl) carbamoyl)benzamido)-6-(trifluoromethyl)pyridin-4-yl)methyl)carbamate (5)

To a stirred solution of tert-butyl ((2-amino-6-(trifluoromethyl)pyridin-4-yl)methyl)carbamate 4 (50 mg, 0.17 mmol) (from Example 106, Step 5) and compound 3 (46 mg, 0.17 mmol) in pyridine (3 mL) at 0° C., was added POCl₃ (0.16 mL, 1.72 mmol) drop-wise. The mixture was stirred at 0° C. for 1 h, then poured into ice cold water (15 mL) and extracted with EtOAc (2×15 mL). The combined organic extracts were washed with brine (10 mL), dried (Na₂SO₄), filtered and concentrated. The residue was purified (silica gel; eluting 1-5% MeOH/CH₂Cl₂; followed by trituration with Et₂O (2×2 mL)) to afford compound 5 (15 mg, 16%) as a pale yellow solid. LCMS Mass: 543.1 (M−H⁺).

Step 4: N'-(4-(Aminomethyl)-6-(trifluoromethyl) pyridin-2-yl)-N³-(2-(methylsulfonyl)ethyl)isophthalamide trifluoroacetate (Compound 1-242)

To a stirred solution of compound 5 (15 mg, 0.03 mmol) in CH₂Cl₂ (3 mL) at 0° C., was added TFA (0.004 mL, 0.05 mmol). The reaction mixture was gradually warmed to RT and stirred for 16 h. The volatiles were removed and the crude was triturated with Et₂O (2×1 mL) to afford compound 1-242 (10 mg, 67%) as a pale yellow solid. ¹H NMR (400 MHz, CD₃OD): δ 8.69 (s, 1H), 8.46 (m, 1H), 8.16 (m, 1H), 8.07 (m, 1H), 7.63-7.68 (m, 2H), 4.33 (s, 2H), 3.88-3.93 (m, 2H), 3.45-3.50 (m, 2H), 3.06 (s, 3H); LCMS Mass: 444.9 (M+H⁺).

Example 109: Methyl 3-((4-(aminomethyl)-6-(trifluoromethyl)pyridin-2-yl)carbamoyl)benzoate trifluoroacetate (Compound 1-238)

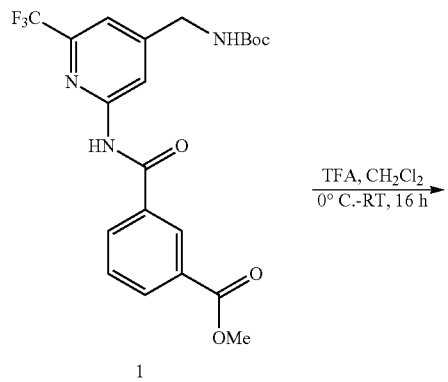

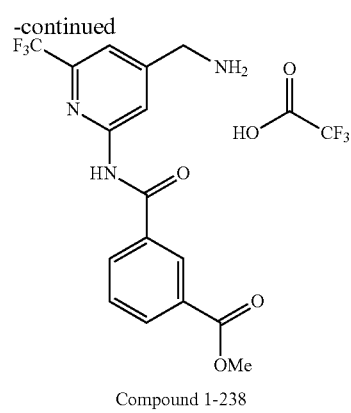

Compound 1-238

To a stirred solution of methyl 3-((4-(((tert-butoxycarbonyl)amino)methyl)-6-(trifluoromethyl)pyridin-2-yl)carbamoyl)benzoate 1 (50 mg, 0.11 mmol) (from Example 107, Step 1) in CH₂Cl₂ (3 mL) at 0° C., was added TFA (0.08 mL, 1.1 mmol). The reaction mixture was gradually warmed to RT and stirred for 16 h. The mixture was concentrated under reduced pressure and the crude was triturated with Et₂O (2×2 mL) and dried under vacuum to afford compound 1-238 (25 mg, 65%) as a white solid. ¹H NMR (500 MHz, CD₃OD): δ 8.67 (s, 1H), 8.62 (t, J=1.6 Hz, 1H), 8.19-8.27 (m, 2H), 7.63-7.68 (m, 2H), 4.32 (s, 2H), 3.96 (s, 3H); LCMS Mass: 353.8 (M⁺+1).

Example 110: 3-((4-(Aminomethyl)-6-(trifluoromethyl)pyridin-2-yl)carbamoyl)benzoic acid trifluoroacetate (Compound 1-239)

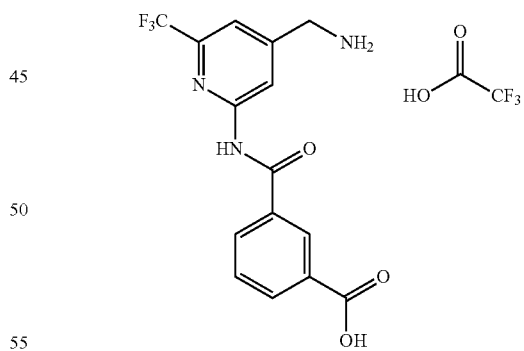

The title compound (1-239) was prepared from 3-((4-(((tert-butoxycarbonyl)amino)methyl)-6-(trifluoromethyl) pyridin-2-yl)carbamoyl)benzoic acid (from Example 107, Step 2) using the procedure for Example 109. ¹H NMR (500 MHz, CD₃OD): δ 8.70 (s, 1H), 8.65 (s, 1H), 8.28 (m, 1H), 8.22 (m, 1H), 7.65-7.70 (m, 2H), 4.34 (s, 2H); LCMS Mass: 339.9 (M⁺+1).

Example 111: 3-((4-(Aminomethyl)-6-(trifluoromethyl)pyridin-2-yl)methyl)-1-benzyl-6-methylpyrimidine-2,4(1H,3H)-dione hydrochloride (Compound 1-134)

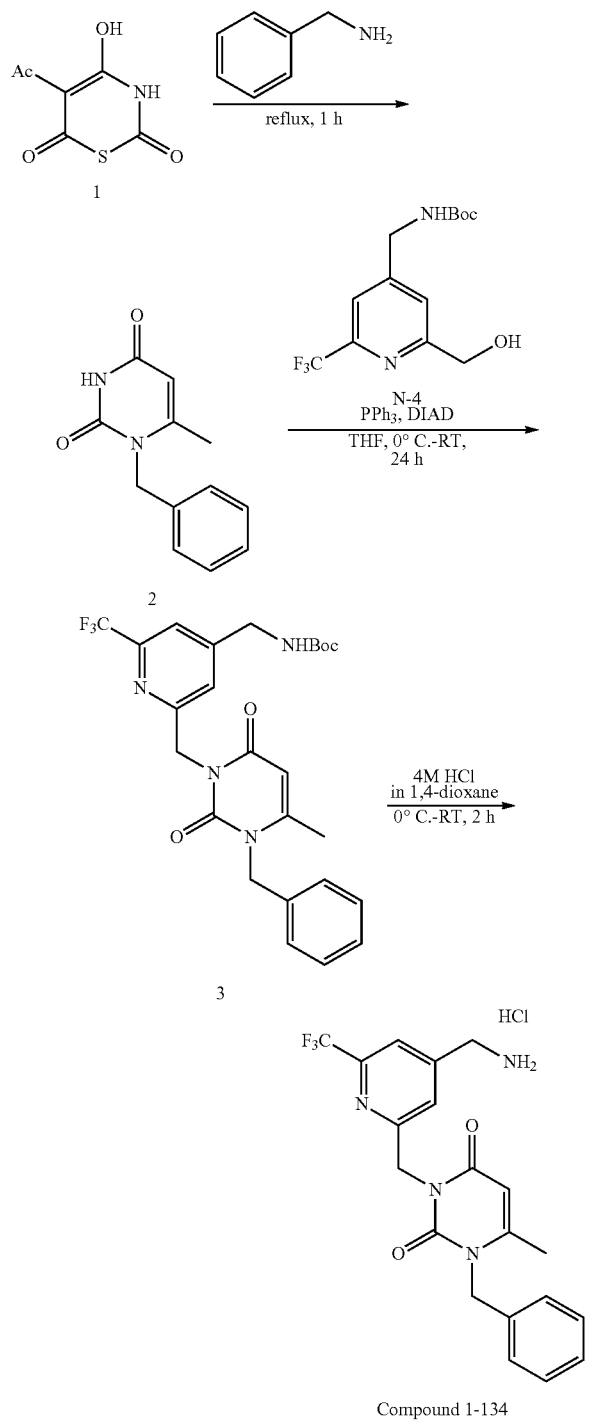

Step 1:
1-Benzyl-6-methylpyrimidine-2,4(1H,3H)-dione (2)

To 5-acetyl-4-hydroxy-2H-1,3-thiazine-2,6(3H)-dione 1 (1 g, 5.35 mmol) was added benzyl amine (15 mL) at RT under inert atmosphere. The reaction mixture was stirred and heated to reflux for 1 h. The excess of benzyl amine was distilled off under reduced pressure. The residue was diluted with 0.5 N aq. NaOH solution (30 mL) and stirred at RT for 30 min. The mixture was filtered (to remove solid), and the filtrate was acidified with 2 N aq. HCl solution (20 mL). The precipitated solid was collected via filtration and dried under vacuum to afford compound 2 (250 mg, 28%) as pale yellow solid. $^1$H NMR (500 MHz, DMSO-$d_6$): δ 11.32 (br s, 1H), 7.32-7.37 (m, 2H), 7.26 (m, 1H), 7.16 (d, J=7.5 Hz, 2H), 5.54 (s, 1H), 5.03 (s, 2H), 2.10 (s, 3H); LCMS Mass: 216.9 ($M^+$+1).

Step 2: tert-Butyl ((2-((3-benzyl-4-methyl-2,6-dioxo-3,6-dihydropyrimidin-1(2H)-yl)methyl)-6-(trifluoromethyl)pyridin-4-yl)methyl)carbamate (4)

To a stirred solution of compound 2 (40 mg, 0.18 mmol) in anhydrous THF (10 mL) at 0° C. under an inert atmosphere, were added tert-butyl ((2-(hydroxymethyl)-6-(trifluoromethyl)pyridin-4-yl)methyl)carbamate N-4 (62 mg, 0.2 mmol) (from Int-N, Step 3), $PPh_3$ (73 mg, 0.28 mmol), followed by diisopropyl azodicarboxylate (0.05 mL, 0.28 mmol). The reaction mixture was warmed to RT and stirred for 24 h. The reaction mixture was diluted with water (10 mL) and extracted with EtOAc (2×10 mL). The combined organic extracts were washed with brine (7 mL), dried ($Na_2SO_4$), filtered, and concentrated under reduced pressure. The residue was purified by preparative HPLC to afford compound 4 (8 mg, 9%) as colorless viscous syrup. $^1$H NMR (400 MHz, $CDCl_3$): δ 7.51 (m, 1H), 7.44 (s, 1H), 7.36 (m, 1H), 7.30 (m, 1H), 7.18 (d, J=7.0 Hz, 2H), 5.69 (d, J=0.7 Hz, 1H), 5.37 (s, 2H), 5.15 (s, 2H), 4.34-4.43 (m, 2H), 2.20 (s, 3H), 1.58 (br s, 9H), 1.47 (br s, 3H); LCMS Mass: 527.2 ($M^+$+Na).

Step 3: 3-((4-(Aminomethyl)-6-(trifluoromethyl)pyridin-2-yl)methyl)-1-benzyl-6-methylpyrimidine-2,4(1H,3H)-dione hydrochloride (Compound 1-134)

To compound 4 (8 mg, 0.01) at 0° C., was added HCl (4 M in 1,4-dioxane, 0.5 mL, 2 mmol). The reaction mixture was warmed to RT and stirred for 2 h. The mixture was concentrated under reduced pressure. The residue was purified via trituration with $Et_2O$ (2×1 mL) and dried under vacuum to afford compound 1-134 (6 mg, 86%) as colorless viscous syrup. $^1$H NMR (400 MHz, $CD_3OD$): δ 7.91 (m, 1H), 7.80 (s, 1H), 7.69 (s, 1H), 7.25-7.37 (m, 2H), 7.21 (br d, J=7.2 Hz, 2H), 5.79 (s, 1H), 5.39 (s, 2H), 5.23 (s, 2H), 4.27-4.35 (m, 2H), 2.25 (s, 3H); LCMS Mass: 405.3 ($M^+$+1).

Example 112: 3-((4-(Aminomethyl)-6-(trifluoromethyl)pyridin-2-yl)methyl)-1-(2-hydroxyethyl)-6-methylpyrimidine-2,4(1H,3H)-dione hydrochloride (Compound 1-135)

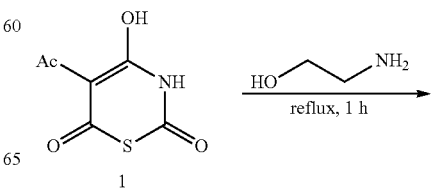

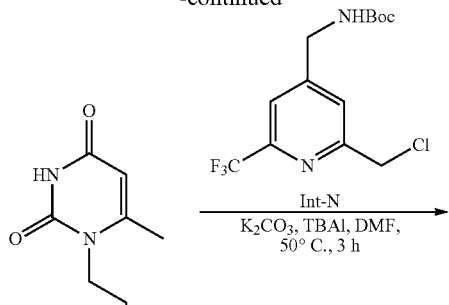

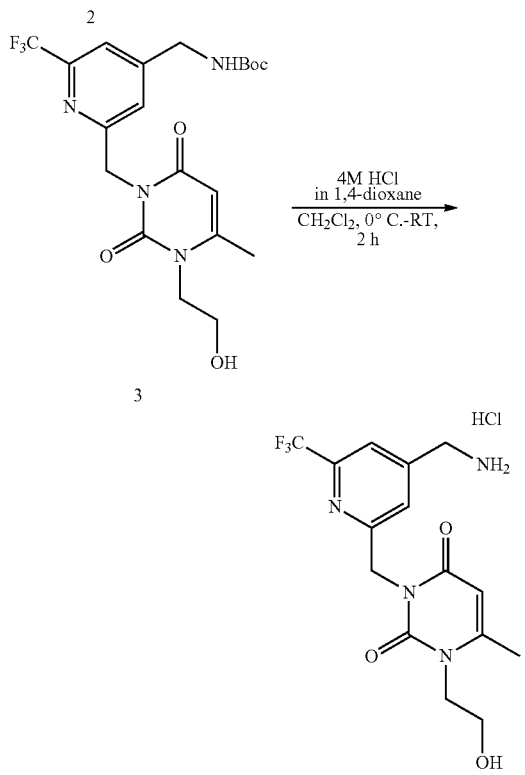

Compound 1-135 lammonium iodide (cat.). The reaction mixture was heated at 50° C. for 3 h. The reaction mixture was diluted with water (10 mL) and extracted with EtOAc (2×15 mL). The combined organic extracts were washed with brine (8 mL), dried ($Na_2SO_4$), filtered, and concentrated under reduced pressure. The residue was purified (silica gel; eluting 2% MeOH/$CH_2Cl_2$; followed by preparative HPLC) to afford compound 3 (13 mg, 12%) as colorless viscous syrup. $^1$H NMR (400 MHz, DMSO-$d_6$): δ 7.59 (s, 1H), 7.55 (br t, J=5.9 Hz, 1H), 7.28 (s, 1H), 5.71 (s, 1H), 5.13 (s, 2H), 4.96 (t, J=5.6 Hz, 1H), 4.22 (br d, J=6.1 Hz, 2H), 3.86 (t, J=5.6 Hz, 2H), 3.57 (q, J=5.6 Hz, 2H), 2.35 (s, 3H), 1.38 (s, 9H); LCMS Mass: 459.2 (M$^+$+1).

Step 3: 3-((4-(Aminomethyl)-6-(trifluoromethyl)pyridin-2-yl)methyl)-1-(2-hydroxyethyl)-6-methylpyrimidine-2,4(1H,3H)-dione hydrochloride (Compound 1-135)

To a stirred solution of compound 3 (16 mg, 0.03) in $CH_2Cl_2$ (1 mL) at 0° C., was added HCl (4 M solution in 1,4-dioxane, 1 mL, 4 mmol). The reaction mixture was warmed to RT and stirred for 2 h. Then the reaction mixture was concentrated under reduced pressure. The residue was triturated with $Et_2O$ (2×2 mL) and dried under vacuum to afford compound 1-135 (11 mg, 78%) as an off white solid. $^1$H NMR (400 MHz, DMSO-$d_6$): δ 8.43 (br s, 3H), 7.93 (s, 1H), 7.59 (s, 1H), 5.73 (s, 1H), 5.16 (s, 2H), 5.01 (br s, 1H), 4.19 (br s, 2H), 3.87 (br t, J=5.6 Hz, 2H), 3.57-3.61 (m, 2H), 2.37 (s, 3H); LCMS Mass: 359.3 (M$^+$+1).

Example 113: 3-((4-(Aminomethyl)-6-(trifluoromethyl)pyridin-2-yl)methyl)-6-methyl-1-(pyrimidin-4-ylmethyl)pyrimidine-2,4(1H,3H)-dione hydrochloride (Compound 1-243)

Step 1: 1-(2-Hydroxyethyl)-6-methylpyrimidine-2,4(1H,3H)-dione (2)

The title compound (2) (300 mg, 33%) was prepared using the procedure for Example 111, Step 1, using 2-aminoethan-1-ol in Step 1. $^1$H NMR (500 MHz, DMSO-$d_6$): δ 11.11 (br s, 1H), 5.45 (s, 1H), 4.93 (br s, 1H), 3.77 (t, J=5.6 Hz, 2H), 3.56 (br t, J=5.5 Hz, 2H), 2.26 (s, 3H); LCMS Mass: 171.3 (M$^+$+1).

Step 2: tert-Butyl ((2-((3-(2-hydroxyethyl)-4-methyl-2,6-dioxo-3,6-dihydropyrimidin-1(2H)-yl)methyl)-6-(trifluoromethyl)pyridin-4-yl)methyl)carbamate (3)

To a stirred solution of compound 2 (40 mg, 0.23 mmol) in DMF (6 mL) at 0° C., were added compound Int-N (84 mg, 0.26 mmol), $K_2CO_3$ (97 mg, 0.7 mmol) and tetrabuty- The title compound (1-243) was prepared using the procedure for Example 112, using pyrimidin-4-ylmethanamine in Step 1. $^1$H NMR (400 MHz, DMSO-$d_6$): δ 9.12 (d, J=1.3 Hz, 1H), 8.75 (d, J=5.2 Hz, 1H), 8.52 (br s, 3H), 7.94 (s, 1H), 7.63 (s, 1H), 7.47 (dd, J=5.2, 1.1 Hz, 1H), 5.86 (s, 1H), 5.20 (s, 2H), 5.16 (s, 2H), 4.18 (q, J=5.6 Hz, 2H), 2.26 (s, 3H); LCMS Mass: 407.3 (M$^+$+1).

Example 114: 4'-(Aminomethyl)-6'-(trifluoromethyl)-2H-[1,2'-bipyridin]-2-one

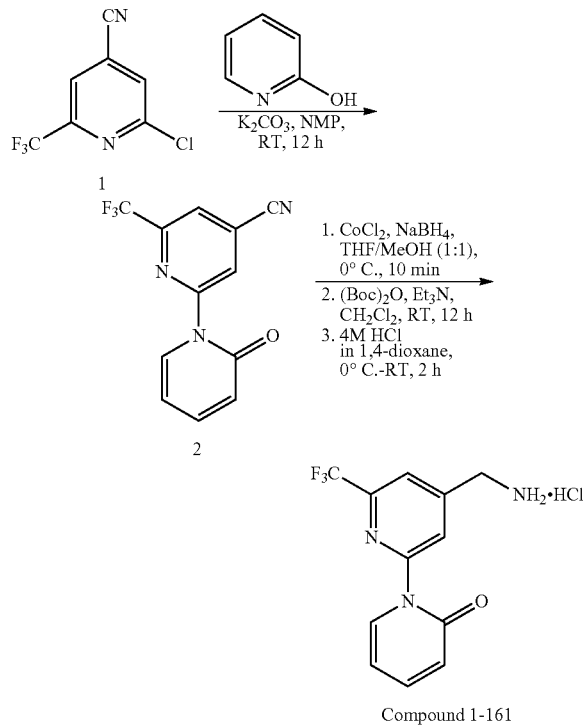

Step 1: 2-Oxo-6'-(trifluoromethyl)-2H-[1,2'-bipyridine]-4'-carbonitrile (2)

To a stirred solution of 2-chloro-6-(trifluoromethyl)isonicotinonitrile 1 (500 mg, 2.43 mmol) in N-methyl-2-pyrrolidone (10 mL) at RT, were added pyridin-2-ol (461 mg, 4.85 mmol) followed by $K_2CO_3$ (1 g, 7.28 mmol). The mixture was stirred at RT for 12 h. Water (30 mL) was added and extracted with $Et_2O$ (2×30 mL). The combined organic extracts were washed with brine (15 mL), dried ($Na_2SO_4$), filtered and concentrated. The residue was purified (silica gel; eluting 10% EtOAc/hexanes) to afford compound 2 (520 mg, 81%) as a pale yellow solid. $^1$H NMR (500 MHz, DMSO-$d_6$): δ 8.71 (s, 1H), 8.62 (s, 1H), 7.90 (m, 1H), 7.61 (m, 1H), 6.59 (m, 1H), 6.47 (m, 1H); LCMS Mass: 265.9 ($M^+$+1).

Step 2: 4'-(Aminomethyl)-6'-(trifluoromethyl)-2H-[1,2'-bipyridin]-2-one hydrochloride (Compound 1-161)

To a stirred solution of compound 2 (500 mg, 1.89 mmol) in THF/MeOH (1:1, 20 mL) at 0° C. under an inert atmosphere, were added $CoCl_2$ (487 mg, 3.77 mmol) and $NaBH_4$ (179 mg, 4.72 mmol) portion wise. The mixture was stirred at 0° C. for 10 min. The mixture was filtered through a pad of celite washed with EtOAc (10 mL) and the filtrate concentrated in vacuo to obtain the desired amine.

To a stirred solution of the amine in $CH_2Cl_2$ (20 mL) at RT, were added $Et_3N$ (0.79 mL, 5.66 mmol) and $(Boc)_2O$ (0.65 mL, 2.83 mmol). The mixture was stirred at RT for 12 h. The mixture was quenched with water (15 mL) and extracted with $CH_2Cl_2$ (2×15 mL), washed with brine (15 mL), dried over $Na_2SO_4$, filtered and concentrated. The residue was purified (via preparative HPLC) to afford the Boc-protected amine. To this Boc-protected amine was added 4 M HCl in 1,4-dioxane (4 mL) at 0° C. under inert atmosphere and stirred at RT for 2 h. The volatiles were removed in vacuo, the crude was triturated with $Et_2O$ (2×2 mL) and dried under vacuum to afford compound 1-161 (18 mg, 3%) as a white solid. $^1$H NMR (400 MHz, $CD_3OD$): δ 8.20 (s, 1H), 8.02 (s, 1H), 7.96 (m, 1H), 7.67 (m, 1H), 6.69 (m, 1H), 6.56 (m, 1H), 4.38 (s, 2H); LCMS Mass: 269.9 ($M^+$+1).

Example 115: 3-((4-(Aminomethyl)-6-(trifluoromethyl)pyridin-2-yl)oxy)-N-(3-ethylphenyl)benzamide hydrochloride (Compound 1-245)

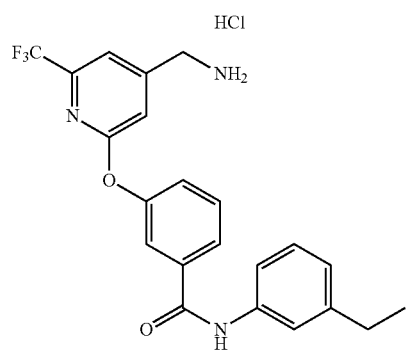 [SMILES: Cl ; CCc1cccc(NC(=O)c2cccc(Oc3cc(CN)cc(C(F)(F)F)n3)c2)c1]

The title compound (1-245) was prepared using the procedure for Example 1, using 3-ethylaniline in Step 1. LCMS Mass: 416.0 ($M^+$+1).

Example 116: 3-((4-(Aminomethyl)-6-(trifluoromethyl)pyridin-2-yl)oxy)-N-(4-ethylphenyl)benzamide hydrochloride (Compound 1-246)

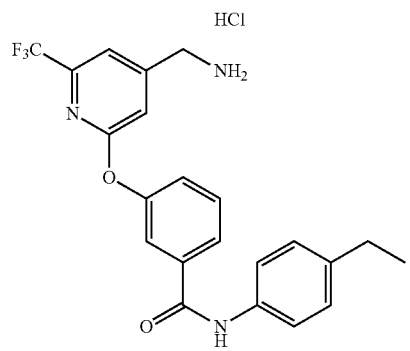 [SMILES: Cl ; CCc1ccc(NC(=O)c2cccc(Oc3cc(CN)cc(C(F)(F)F)n3)c2)cc1]

The title compound (1-246) was prepared using the procedure for Example 1, using 4-ethylaniline in Step 1. LCMS Mass: 416.0 ($M^+$+1).

Example 117: 3-((4-(Aminomethyl)-6-(trifluoromethyl)pyridin-2-yl)oxy)-N-(3-ethynylphenyl)benzamide hydrochloride (Compound 1-247)

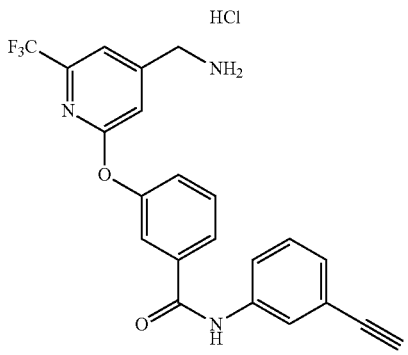 [SMILES: Cl ; C#Cc1cccc(NC(=O)c2cccc(Oc3cc(CN)cc(C(F)(F)F)n3)c2)c1]

The title compound (1-247) was prepared using the procedure for Example 1, using 3-ethynylaniline in Step 1. LCMS Mass: 412.0 (M$^+$+1).

Example 118: 3-((4-(Aminomethyl)-6-(trifluoromethyl)pyridin-2-yl)oxy)-N-(prop-2-yn-1-yl)benzamide hydrochloride (Compound 1-248)

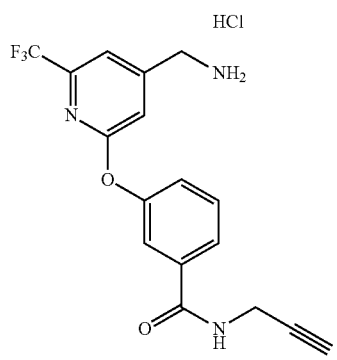 [SMILES: Cl ; C#CCNC(=O)c1cccc(Oc2cc(CN)cc(C(F)(F)F)n2)c1]

The title compound (1-248) was prepared using the procedure for Example 1, using propargylamine in Step 1. LCMS Mass: 350.0 (M$^+$+1).

Example 119: 3-((4-(Aminomethyl)-6-(trifluoromethyl)pyridin-2-yl)oxy)-N-(4-methyl-2-oxo-2H-chromen-7-yl)benzamide hydrochloride (Compound 1-249)

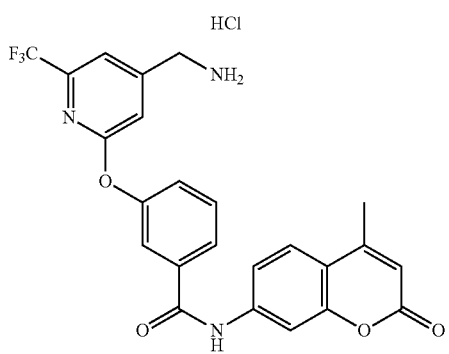 [SMILES: Cl ; Cc1cc(=O)oc2cc(NC(=O)c3cccc(Oc4cc(CN)cc(C(F)(F)F)n4)c3)ccc12]

The title compound (1-249) was prepared using the procedure for Example 1, using 7-amino-4-methylcoumarin in Step 1. LCMS Mass: 470.0 (M$^+$+1).

Example 120: (R,S) or (S,R)-cis-(3-((4-(Aminomethyl)-6-(trifluoromethyl)pyridin-2-yl)oxy)phenyl)(3-fluoro-4-hydroxypyrrolidin-1-yl)methanone hydrochloride (Enantiomer 1) (Compound 1-250)

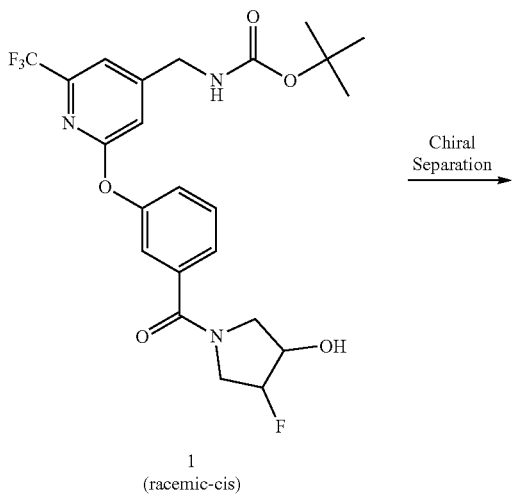

1
(racemic-cis)

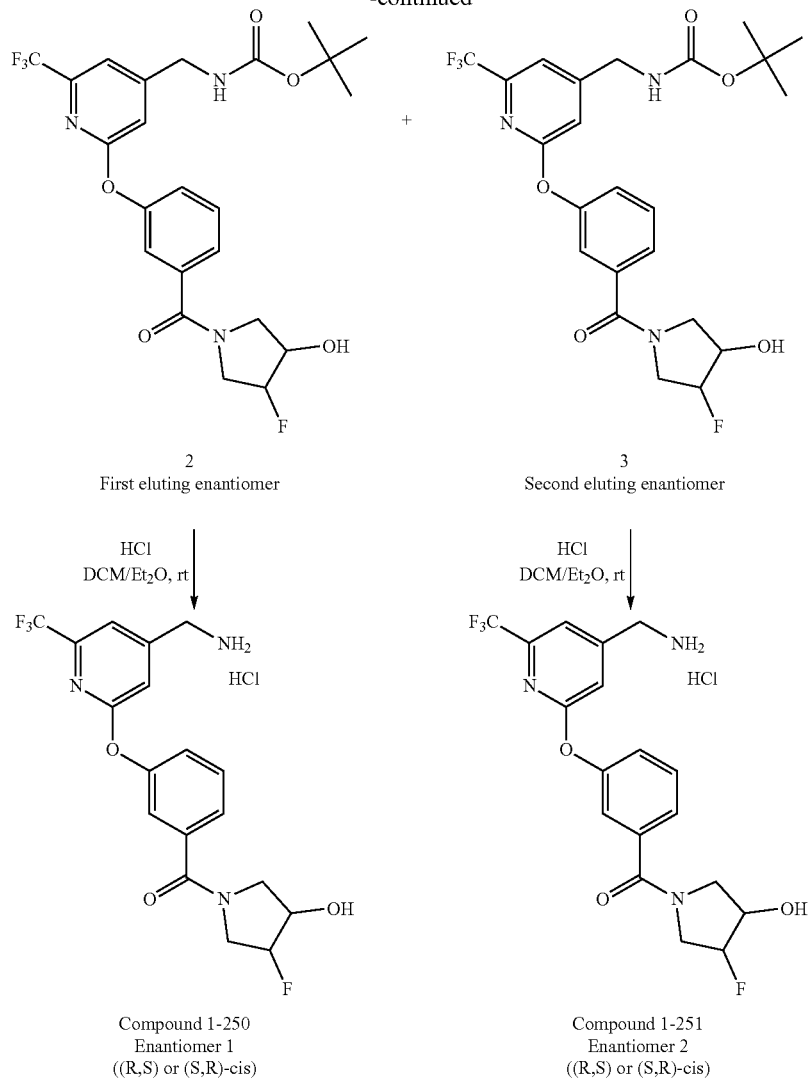

2
First eluting enantiomer

3
Second eluting enantiomer

Compound 1-250
Enantiomer 1
((R,S) or (S,R)-cis)

Compound 1-251
Enantiomer 2
((R,S) or (S,R)-cis)

Step 1: Single enantiomers of cis-tert-butyl ((2-(3-(3-fluoro-4-hydroxypyrrolidine-1-carbonyl)phenoxy)-6-(trifluoromethyl)pyridin-4-yl)methyl)carbamate (2) and (3)

Compound 2 (35 mg) and compound 3 (35 mg) were both obtained from compound 1 (160 mg, 0.32 mmol) (from Example 73, Step 2) via chiral HPLC separation (Chiral Pak ADH, 250×20 mm, 5 μm column, eluting isocratically with 10% MeOH:EtOH (1:1) and 90% hexanes (containing 0.1% DEA), flow rate 18 mL/min), wherein compound 2 was the first to elute and compound 3 was the second to elute.

Compound 2: $^1$H NMR (500 MHz, DMSO-$d_6$): δ 7.59 (m, 1H), 7.49-7.55 (m, 2H), 7.29-7.43 (m, 3H), 7.15 (s, 1H), 5.48 (m, 1H), 4.87 (m, 1H), 4.15-4.34 (m, 3H), 3.46-3.82 (m, 3H), 3.26 (m, 1H), 1.39 (s, 9H). Chiral HPLC analysis: R$_t$=14.21 min (Chiral Pak ADH, 250×4.6 mm, 5 μm column, eluting isocratically with 10% MeOH:EtOH (1:1) and 90% hexanes (containing 0.1% DEA) over 25 mins; flow rate 1.0 mL/min).

Compound 3: $^1$H NMR (500 MHz, DMSO-$d_6$): δ 7.59 (m, 1H), 7.49-7.55 (m, 2H), 7.29-7.43 (m, 3H), 7.15 (s, 1H), 5.48 (m, 1H), 4.87 (m, 1H), 4.15-4.34 (m, 3H), 3.46-3.82 (m, 3H), 3.26 (m, 1H), 1.39 (s, 9H). Chiral HPLC analysis: R$_t$=15.31 min (Chiral Pak ADH, 250×4.6 mm, 5 μm column, eluting isocratically with 10% MeOH:EtOH (1:1) and 90% hexanes (containing 0.1% DEA) over 25 mins; flow rate 1.0 mL/min).

Step 2: (R,S) or (S,R)-cis-(3-((4-(Aminomethyl)-6-(trifluoromethyl)pyridin-2-yl)oxy)phenyl)(3-fluoro-4-hydroxypyrrolidin-1-yl)methanone hydrochloride (Enantiomer 1) (Compound 1-250)

The title compound (1-250) (26 mg, 97%) was prepared from single enantiomer 2 (35 mg, 0.07 mmol) using the procedure for Example 1, Step 2. $^1$H NMR (400 MHz, CD$_3$OD): δ 7.64 (s, 1H), 7.58 (m, 1H), 7.45 (m, 1H), 7.30-7.38 (m, 3H), 5.09 (m, 1H), 4.26-4.48 (m, 3H), 3.63-3.95 (m, 3H), 3.46 (n, 1H); LCMS Mass: 400.0 (M$^+$+1); Chiral HPLC analysis: R$_t$=14.86 min (Chiralpak-IA, 250×4.6 mm, 5 μm column, eluting isocratically with 20% MeOH:DCM (1:1) and 80% hexanes (containing 0.1% DEA); flow rate 1.0 mL/min).

Example 121: (R,S) or (S,R)-cis-(3-((4-(Aminomethyl)-6-(trifluoromethyl)pyridin-2-yl)oxy)phenyl) (3-fluoro-4-hydroxypyrrolidin-1-yl)methanone hydrochloride (Enantiomer 2) (Compound 1-251)

The title compound (1-251) (23 mg, 85%) was prepared from single enantiomer 3 (35 mg, 0.07 mmol) (from Example 120, Step 1) using the procedure for Example 1, Step 2. $^1$H NMR (400 MHz, CD$_3$OD): δ 7.65 (s, 1H), 7.58 (m, 1H), 7.45 (m, 1H), 7.32-7.40 (m, 3H), 5.09 (m, 1H), 4.26-4.50 (m, 3H), 3.63-3.96 (m, 3H), 3.46 (m, 1H); LCMS Mass: 400.0 (M$^+$+1); Chiral HPLC analysis: R$_f$=17.53 min (Chiralpak-IA, 250×4.6 mm, 5 m column, eluting isocratically with 20% MeOH:DCM (1:1) and 80% hexanes (containing 0.1% DEA); flow rate 1.0 mL/min).

Example 122: 4-((4-(Aminomethyl)-6-(trifluoromethyl)pyridin-2-yl)oxy)-N-phenylpicolinamide hydrochloride (Compound 1-252)

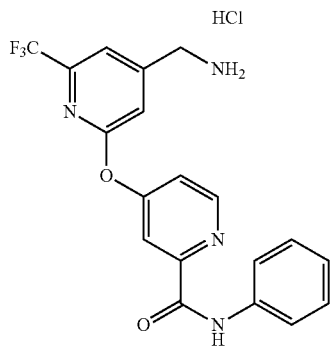 [SMILES: Cl ; NCc1cc(Oc2ccnc(C(=O)Nc3ccccc3)c2)nc(C(F)(F)F)c1]

The title compound (1-252) was prepared using the procedure for Example 1, using Int-O in Step 1. LCMS Mass: 389.0 (M$^+$+1).

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: Human LOXL2 Amine Oxidase Activity Assay

LOXL2 amine oxidase activity is evaluated by measuring Amplex Red fluorescence using 10-20× concentrated conditioned media from CHO cells stably expressing human LOXL2. To assay for amine oxidase activity, 10 μL of the concentrated conditioned media is incubated with 2 μL of test compound in DMSO and 73 μL Assay Buffer (50 mM Borate Buffer, pH8) for 2 h at 37° C. After the 2 h incubation, 5 ul of 10 mM 1,5-Diaminopentane (DAP) diluted in Assay Buffer and 10 μl of Amplex Red Mix (8.5 μl Assay Buffer+0.5 μl of 10 mM Amplex Red+1 μl of 500 U/ml Horseradish Peroxidase) are added and the plate mixed and immediately placed on the FlexStaion for fluorescence measurements. Fluorescence is read in kinetic mode every 2 min for 1 hour at excitation=544 and emission=590. The amine oxidase activity is calculated from the slope of the linear portion of the curve.

TABLE 2

| Example | Compound | IC$_{50}$ |
|---------|----------|-----------|
| 1 | 1-7 | A |
| 2 | 1-9 | A |
| 3 | 1-10 | A |
| 4 | 1-11 | A |
| 5 | 1-12 | A |
| 6 | 1-13 | A |
| 7 | 1-14 | A |
| 8 | 1-15 | A |
| 9 | 1-16 | A |
| 10 | 1-17 | A |
| 11 | 1-18 | A |
| 12 | 1-19 | A |
| 13 | 1-20 | A |
| 14 | 1-21 | A |
| 15 | 1-22 | A |
| 16 | 1-23 | A |
| 17 | 1-24 | C |
| 18 | 1-25 | B |

TABLE 2-continued

| Example | Compound | IC$_{50}$ |
|---|---|---|
| 19 | 1-26 | A |
| 20 | 1-27 | A |
| 21 | 1-28 | A |
| 22 | 1-29 | A |
| 23 | 1-30 | A |
| 24 | 1-31 | A |
| 25 | 1-32 | A |
| 26 | 1-33 | A |
| 27 | 1-34 | A |
| 28 | 1-35 | A |
| 29 | 1-36 | A |
| 30 | 1-8 | A |
| 31 | 1-39 | A |
| 32 | 1-40 | A |
| 33 | 1-43 | B |
| 34 | 1-44 | A |
| 35 | 1-46 | A |
| 36 | 1-47 | A |
| 37 | 1-48 | A |
| 38 | 1-49 | A |
| 39 | 1-50 | A |
| 40 | 1-51 | B |
| 41 | 1-52 | A |
| 42 | 1-45 | B |
| 43 | 1-41 | B |
| 44 | 1-42 | A |
| 45 | 1-53 | A |
| 46 | 1-54 | A |
| 47 | 1-55 | A |
| 48 | 1-58 | A |
| 49 | 1-37 | A |
| 50 | 1-38 | A |
| 51 | 1-56 | B |
| 52 | 1-57 | A |
| 53 | 1-59 | A |
| 54 | 1-1 | A |
| 55 | 1-2 | A |
| 56 | 1-3 | A |
| 57 | 1-4 | A |
| 58 | 1-5 | A |
| 59 | 1-6 | A |
| 60 | 1-198 | A |
| 61 | 1-199 | A |
| 62 | 1-200 | A |
| 63 | 1-201 | A |
| 64 | 1-202 | A |
| 65 | 1-203 | A |
| 66 | 1-204 | A |
| 67 | 1-205 | A |
| 68 | 1-206 | A |
| 69 | 1-207 | A |
| 70 | 1-208 | A |
| 71 | 1-209 | A |
| 72 | 1-210 | A |
| 73 | 1-211 | A |
| 74 | 1-212 | A |
| 75 | 1-213 | A |
| 76 | 1-214 | A |
| 77 | 1-215 | A |
| 78 | 1-216 | A |
| 79 | 1-217 | A |
| 80 | 1-218 | B |
| 81 | 1-219 | A |
| 82 | 1-220 | A |
| 83 | 1-221 | B |
| 84 | 1-222 | A |
| 85 | 1-223 | B |
| 86 | 1-224 | B |
| 87 | 1-225 | A |
| 88 | 1-226 | A |
| 89 | 1-227 | A |
| 90 | 1-228 | A |
| 91 | 1-229 | B |
| 92 | 1-230 | A |
| 93 | 1-231 | A |
| 94 | 1-232 | B |
| 95 | 1-169 | A |
| 96 | 1-60 | B |
| 97 | 1-235 | B |
| 98 | 1-236 | C |
| 99 | 1-233 | B |
| 100 | 1-234 | C |
| 101 | 1-244 | B |
| 102 | 1-68 | A |
| 103 | 1-105 | A |
| 104 | 1-106 | A |
| 105 | 1-237 | B |
| 106 | 1-240 | A |
| 107 | 1-241 | A |
| 108 | 1-242 | A |
| 109 | 1-238 | A |
| 110 | 1-239 | A |
| 111 | 1-134 | A |
| 112 | 1-135 | C |
| 113 | 1-243 | B |
| 114 | 1-161 | C |
| 115 | 1-245 | A |
| 116 | 1-246 | A |
| 117 | 1-247 | A |
| 118 | 1-248 | A |
| 119 | 1-249 | A |
| 120 | 1-250 | A |
| 121 | 1-251 | A |
| 122 | 1-252 | A |

A is <300 nM;
B is 300 nM to 1000 nM;
C is >1000 nM

Example B-2: LOXL2 Human Blood Amine Oxidase Activity Assay

The amine oxidase activity of human LOXL2 in the context of human whole blood is measured using an Amplex Red assay. Since Human, recombinant human LOXL2 (purchased from Sino Biologicals, Beijing, China) is added to human blood collected in heparin vacutainer tubes. Briefly, 0.5-2 µg recombinant, human LOXL2 (reconstituted in water) and 2 µl test compound in DMSO is added to 192 l blood, mixed and incubated at 37° C. for 2 h. After the 2 h incubation, the blood is centrifuged at 2000×g for 15 min at room temperature to isolate the plasma. 50 µl of plasma is removed and mixed with 25 µl of 40 mM DAP (diluted in water) and 25 µl Amplex Red Mix (23.5 µl 50 mM Borate Buffer, pH8+0.5 µl 10 mM Amplex Red+1 µl 500 U/ml Horseradish Peroxidase). Samples are mixed and immediately placed on the FlexStaion for fluorescence measurements. Fluorescence is read in kinetic mode every 2 min for 1 hour at excitation=544 and emission=590. The amine oxidase activity is calculated from the slope of the linear portion of the curve.

Example B-3: Mouse Oropharyngeal Bleomycin Model of Lung Fibrosis

Lung fibrosis is induced in C57Bl/6 male mice by administering bleomycin (0.1-4 U/kg) via oropharyngeal instillation. Mice are either pretreated with vehicle or test compound (1 day to 1 hour) orally, intraperitoneally, intravenously or subcutaneously before bleomycin installation (prophylactic dosing) or 7-14 days post bleomycin instillation (therapeutic dosing). The route and frequency of dosing are based on previously determined pharmacokinetic properties for the LOXL2 inhibitor in mouse. After bleomycin instillation animals are monitored daily for weight loss and clinical signs for 14-28 days prior to sacrifice. Animals are euthanized at study termination and weighed and blood (for isolation of plasma) and bronchoalveolar lavage are collected and frozen for subsequent analyses. Lungs are removed, weighed, then either inflated and fixed by instillation of 10% formalin and prepared for histological examination or homogenized in 1 ml PBS for collagen determination using a hydroxyproline assay. For histological examination, lung slices are stained with Masson's trichrome or Picro-Sirius red to measure cross-linked collagen as an indicator of fibrosis and an Ashcroft score of lung fibrotic and inflammatory damage determined. In addition, immunohistochemistry of fibrotic proteins such as a-smooth muscle actin can be recorded. For lung hydroxyproline content, 0.5 ml of the lung homogenate is removed and added to 0.5 ml 12 N HCl and the samples heated at 120° C. overnight. After the acid hydrolysis, 25-100 µl of the supernatant is dried down, resuspended in 25 µl water and the hydroxyproline content determined by the addition of 0.5 ml Chloramine T solution (140 mg Chloramine T in 6.5 ml ddH$_2$O+1 ml n-propanol+2.5 ml 1M sodium acetate) and incubation at room temperature for 20 min. After the incubation, 0.5 ml Erlich's solution (1.48 g of 4-(dimethylamino (benzaldehyde) in 7 ml n-propanol+2.88 ml 60% perchloric acid and 0.12 ml ddH$_2$O) is added and incubated at 65° C. for 15 min before reading the absorbance at 550 nm. The concentration of hydroxyproline in each skin biopsy is determined from a hydroxyproline (purchased from Sigma) standard curve.

Compounds 1-7, 1-15, 1-19, 1-20, 1-21 1-30 and 1-59 (dosed prophylactically at 60 mg/kg p.o.) were efficacious in this model. Compounds 1-19, 1-20 and 1-21 (dosed therapeutically at 60 mg/kg p.o.) were efficacious in this model.

Example B-4: Mouse Subcutaneous Bleomycin Model of Skin and Lung Fibrosis

Skin and lung fibrosis is induced in female C57Bl/6 mice by administering bleomycin via subutaneous injection to two sites (50 µg bleo/site) on the backs of mice. Animals are anesthetized with isoflurane and bleomycin (100 µl, or PBS control) is injected at the same site daily for 28 days to induce skin and lung fibrosis. Mice are either pretreated with vehicle or test compound (1 day to 1 hour) orally, intraperitoneally, intravenously or subcutaneously before bleomycin injection (prophylactic dosing) or 7-14 days post bleomycin injection (therapeutic dosing). Animals are euthanized at study termination and weighed and blood (for isolation of plasma) and bronchoalveolar lavage are collected and frozen for subsequent analyses. Lungs are either removed, weighed, then homogenized in PBS for determination of collagen content using a hydroxyproline assay or inflated and fixed by instillation of 10% formalin and prepared for histological examination by trichrome staining or Picrosirius red staining. Skin biopsies are taken from each injection site using a 6 mm dermal punch biopsy (Acuderm). One punch biopsy is sandwiched in a cassette with a sponge, placed in formalin and prepared for histological examination by H&E staining, trichrome staining and/or Picrosirius red staining. The other punch biopsy is placed in 0.5 ml PBS and minced using fine scissors. 500 µl 12 N HCl is then added and the samples heated at 120° C. overnight. After the acid hydrolysis, 25-100 µl of the supernatant is dried down, resuspended in 25 µl water and the hydroxyproline content determined by the addition of 0.5 ml Chloramine T solution (140 mg Chloramine T in 6.5 ml ddH$_2$O+1 ml n-propanol+ 2.5 ml 1M sodium acetate) and incubation at room temperature for 20 min. After the incubation, 0.5 ml Erlich's solution (1.48 g of 4-(dimethylamino(benzaldehyde) in 7 ml n-propanol+2.88 ml 60% perchloric acid and 0.12 ml ddH$_2$O) is added and incubated at 65° C. for 15 min before reading the absorbance at 550 nm. The concentration of hydroxyproline in each skin biopsy is determined from a hydroxyproline (purchased from Sigma) standard curve.

Example B-5: Rat/Mouse CCl$_4$ Model of Liver Fibrosis

Liver fibrosis is induced in mice (Balb/c or C57Bl/6) by intraperitoneal administration of CCl$_4$ (0.5-2 ml/kg body weight) diluted in corn oil twice weekly for 4-8 weeks or by oral administration two-three times weekly using an escalating dose protocol (Popov et al. 2011 Gastroenetrology; 140(5): 1642-1652.). Liver fibrosis is induced in rats by either intraperitoneal administration (1-2.5 ml/kg) or by oral administration in oil (mineral, olive or corn) twice weekly for 6-12 weeks. LOXL2 inhibitors are delivered orally, intraperitoneally, intravenously or subcutaneously 1 day to 1 hour prior to the initial CCl$_4$ dosing (prophylactic dosing) or 1-4 weeks after the initial CCl$_4$ dosing (therapeutic dosing). At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E staining and Picrosirius red staining. The remaining tissue is snap frozen at −80° C. for subsequent hydroxyproline analysis of total collagen content.

Example B-6: Mouse Mdr2 Knockout Model of Biliary Fibrosis

Liver disease develops in the BALB/cMdr2−/− mouse model with bridging fibrosis/early cirrhosis between 8 and 12 weeks of age (Ikenaga et al. 2015 Am J Pathology, 185: 325-334). LOXL2 inhibitors are delivered orally, intraperitoneally, intravenously or subcutaneously into BALB/ c.Mdr2−/− mice once daily for 6 weeks beginning at week 6 after birth. At the end of the study, mice are anesthetized with isoflurane (1.5% v/v) via precise vaporizer. After laparotomy, portal pressure is measured directly by inserting a high-fidelity pressure catheter into the portal vein and measuring pressure signals for 5 minutes. Serum is collected for analysis of liver (ALT, AST, ALP, and bilirubin) and kidney (creatinine) biochemistries. Part of the liver is fixed in 10% neutral buffered formalin for histopathological analysis of inflammation, necrosis and fibrosis by H&E staining and Picrosirius red staining.

Collagen content is determined from a portion of the liver tissue using hydroxyproline analysis.

Example B-7: Mouse Alport Model of Kidney Fibrosis

Mice with mutations in one of the genes of glomerular basement membrane collagen, Collagen IV-a3/a4/a5, have defects in glomerular function with development of kidney fibrosis These mice develop renal dysfunction and die prematurely of renal failure with specific timing dependent on the strain background upon which the mutation is present. LOXL2 inhibitors are administered orally to Col4A3 deficient mice on a SV129 background either prophylactically (ca. weeks 2-3 of age) or therapeutically (ca. weeks 4-6 wks of age). Mice are either sacrificed at a predefined time (7-9 wks of age) or continually dosed until they lose >15% of their body weight which preceeds death by 1-3 days. If specifically terminated, mice are perfused transcardially with PBS, and one kidney clamped at the renal artery and the other perfused with Dynabeads for magnetic isolation of glomeruli. The other kidney is halved and a small sample of renal cortex fixed for transmission electron microscopic (TEM) analysis and a second sample of renal cortex used for RNA isolation. The other half of the bisected kidney is embedded in OCT for immunohistochemical analysis. RNA from glomeruli and renal cortex is analyzed by real time RT-PCR for genes of interest including MMP-10, MMP-12, IL6, MCP-1, TGF-b1, CTGF, MMP-2, and MMP-9. Immunohistochemical analysis will include staining for collagen 1, CD45, fibronectin, smooth muscle actin, WT-1, and integrin alpha 8/laminin a5. Collagen 1 staining is blindly analyzed for fibrosis scoring, and fibronectin staining is blindly analyzed for glomerulosclerosis scoring. For all studies albuminuria is assessed weekly and BUN at the time of tissue harvest.

Compound 1-21 (dosed prophylactically at 30 mg/kg p.o.) was efficacious in this model.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt or solvate thereof:

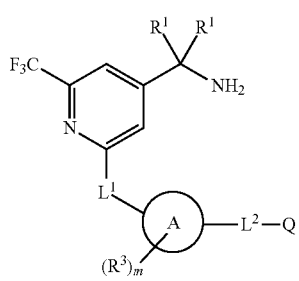

Formula (I)

wherein,
each $R^1$ is independently H, D, or F;
$L^1$ is absent, $X^1$, $X^1$—$C_1$-$C_6$alkylene, or $C_1$-$C_6$alkylene;
  $X^1$ is —O—, —S—, —S(=O)—, —S(=O)$_2$—, —C(=O)—, —C(=O)O—, —C(=O)NR$^2$—, —NR$^2$C(=O)—, or —NR$^2$—;
  $R^2$ is H, substituted or unsubstituted $C_1$-$C_6$alkyl, $C_1$-$C_6$fluoroalkyl, or $C_1$-$C_6$deuteroalkyl;
each $R^3$ is independently H, D, halogen, —CN, —OR$^5$, —SR$^5$, —S(=O)R$^4$, —S(=O)$_2$R$^4$, —S(=O)$_2$N(R$^5$)$_2$, —NR$^2$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^2$C(=O)R$^4$, —NR$^2$C(=O)OR$^4$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
m is 0, 1, or 2;
each $R^4$ is independently selected from $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl;
each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, and substituted or unsubstituted heteroaryl; or two $R^5$ on the same N atom are taken together with the N atom to which they are attached to a substituted or unsubstituted N-containing heterocycle;
Ring A is monocyclic carbocycle, bicyclic carbocycle, monocyclic heterocycle, or bicyclic heterocycle;
$L^2$ is absent, —$X^2$—, or —$C_1$-$C_6$alkylene-$X^2$—;
  $X^2$ is —O—, —S—, —S(=O)—, —S(=O)$_2$—, —S(=O)$_2$NR$^6$—, —C(=O)—, —C(=O)O—, —C(=O)NR$^6$—, —C(=O)NR$^6$O—, —NR$^6$C(=O)—, —NR$^6$S(=O)$_2$—, or —NR$^6$—;
  $R^6$ is H, $C_1$-$C_6$alkyl, $C_1$-$C_6$fluoroalkyl, or $C_1$-$C_6$deuteroalkyl;
Q is H, substituted or unsubstituted $C_1$-$C_6$alkyl, substituted or unsubstituted $C_1$-$C_6$fluoroalkyl, substituted or unsubstituted $C_1$-$C_6$heteroalkyl, substituted or unsubstituted $C_3$-$C_8$cycloalkyl, —$C_1$-$C_4$alkylene-(substituted or unsubstituted $C_3$-$C_8$cycloalkyl), substituted or unsubstituted $C_2$-$C_8$heterocycloalkyl, —$C_1$-$C_4$alkylene-(substituted or unsubstituted $C_2$-$C_8$heterocycloalkyl), substituted or unsubstituted aryl, —$C_1$-$C_4$alkylene-(substituted or unsubstituted aryl), substituted or unsubstituted heteroaryl, or —$C_1$-$C_4$alkylene-(substituted or unsubstituted heteroaryl); wherein if Q is substituted then Q is substituted with one or more $R^8$;
or Q and $R^6$ are taken together with the N atom to which they are attached to form ring B, wherein ring B is a substituted or unsubstituted N-containing heterocycle, wherein if ring B is substituted then ring B is substituted with 1-3 $R^8$;
each $R^8$ is independently D, halogen, CN, —OR$^5$, —SR$^5$, —S(=O)R$^4$, —S(=O)$_2$R$^4$, —OS(=O)$_2$R$^4$, —S(=O)$_2$N(R$^5$)$_2$, —NR$^5$S(=O)$_2$R$^4$, C(=O)R$^4$, OC(=O)R$^4$, —CO$_2$R$^5$, —OCO$_2$R$^4$, —N(R$^4$)$_2$, —OC(=O)N(R$^5$)$_2$, —NHC(=O)R$^4$, —NHC(=O)OR$^4$, $C_1$-$C_6$alkyl, $C_2$-$C_6$alkenyl, $C_1$-$C_6$alkynyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl;
or two $R^8$ groups attached to the same carbon atom are taken together with carbon atom to which they are attached to form either a substituted or unsubstituted carbocycle or substituted or unsubstituted heterocycle.

2. The compound of claim 1, or a pharmaceutically acceptable salt, or solvate thereof, wherein:
each $R^1$ is H; and
$L^1$ is absent, $X^1$, $X^1$—CH$_2$—, or —CH$_2$—.

3. The compound of claim 2, or a pharmaceutically acceptable salt, or solvate thereof, wherein the compound has the structure of Formula (II):

Formula (II)

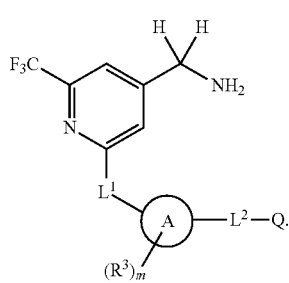

4. The compound of claim 3, or a pharmaceutically acceptable salt, or solvate thereof, wherein:

X$^1$ is —O—, —S—, —S(=O)$_2$—, —C(=O)NR$^2$—, —NR$^2$C(=O)—, or —NR$^2$—.

5. The compound of claim 4, or a pharmaceutically acceptable salt, or solvate thereof, wherein:

Ring A is phenyl, a monocyclic heterocycle containing 1-4 N atoms and 0 or 1 O or S atom, monocyclic heterocycle containing 0-4 N atoms and 1 O or S atoms, bicyclic heterocycle containing 1-4 N atoms and 0 or 1 O or S atoms, or bicyclic heterocycle containing 0-4 N atoms and 1 O or S atoms.

6. The compound of claim 4, or a pharmaceutically acceptable salt, or solvate thereof, wherein:

Ring A is

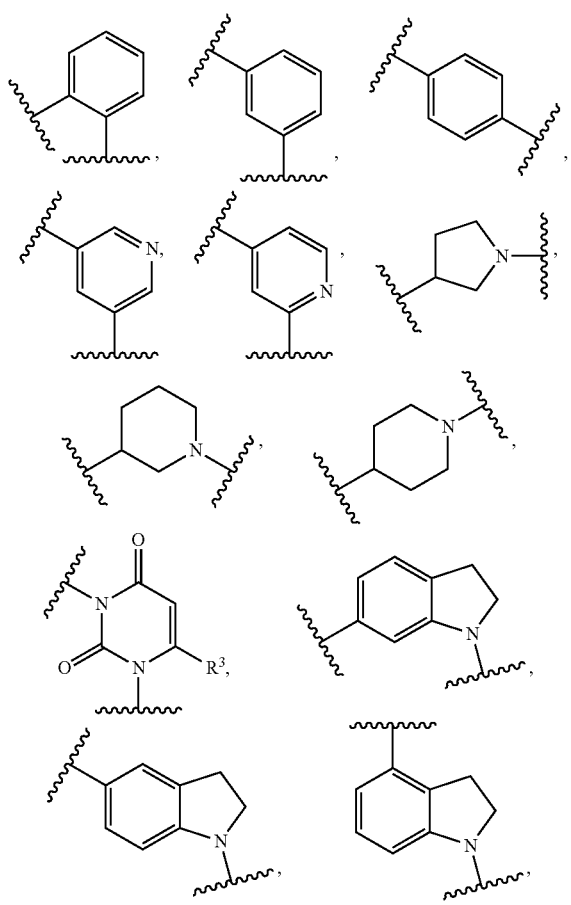

-continued

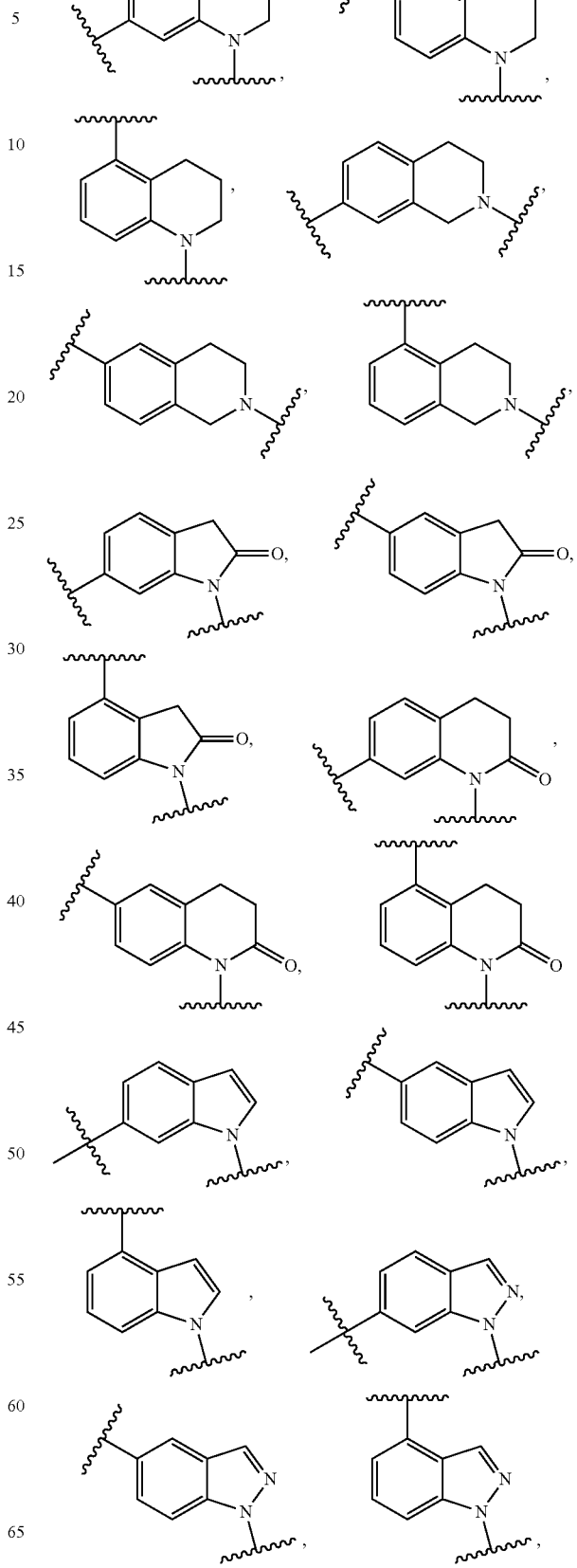

-continued

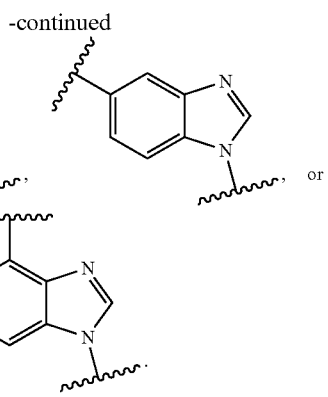

7. The compound of claim 4, or a pharmaceutically acceptable salt, or solvate thereof, wherein:
Ring A is

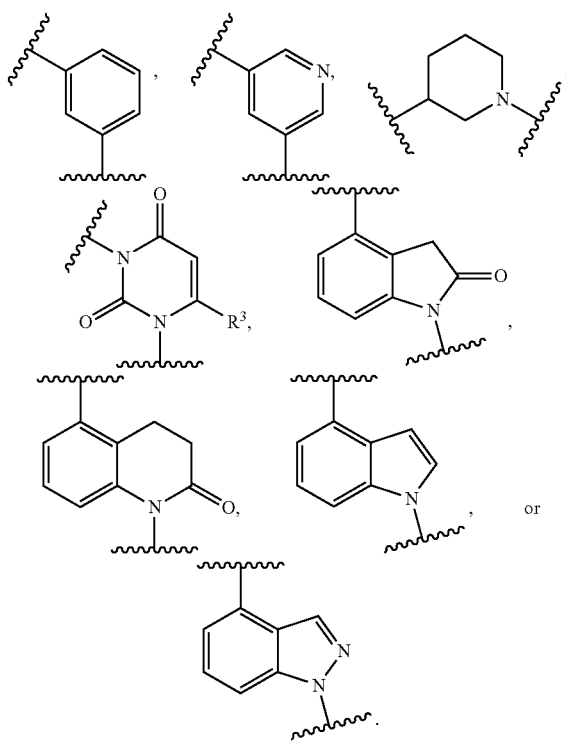

8. The compound of claim 5, or a pharmaceutically acceptable salt, or solvate thereof, wherein:
$L^2$ is absent, —O—, —O—CH$_2$—, —C(=O)—, —C(=O)NR$^6$—, —NR$^6$C(=O)—, —NR$^6$—, or —CH$_2$—C(=O)NR$^6$—.

9. The compound of claim 8, or a pharmaceutically acceptable salt, or solvate thereof, wherein:
Q is substituted or unsubstituted C$_3$-C$_6$cycloalkyl, —C$_1$-C$_2$alkylene-(substituted or unsubstituted C$_3$-C$_6$cycloalkyl), substituted or unsubstituted C$_2$-C$_8$heterocycloalkyl, —C$_1$-C$_2$alkylene-(substituted or unsubstituted C$_2$-C$_8$heterocycloalkyl), substituted or unsubstituted phenyl, —C$_1$-C$_2$alkylene-(substituted or unsubstituted phenyl), substituted or unsubstituted heteroaryl, or —C$_1$-C$_2$alkylene-(substituted or unsubstituted heteroaryl); wherein if Q is substituted then Q is substituted with one or more R$^8$;

or Q and R$^6$ are taken together with the N atom to which they are attached to form ring B, wherein ring B is a substituted or unsubstituted monocyclic N-containing heterocycle, or a substituted or unsubstituted bicyclic N-containing heterocycle, wherein if ring B is substituted then ring B is substituted with 1-3 R$^8$.

10. The compound of claim 8, or a pharmaceutically acceptable salt, or solvate thereof, wherein:
-L$^2$-Q is —C(=O)NR$^6$-Q; and
Q and R$^6$ are taken together with the N atom to which they are attached to form a ring B, wherein ring B is a substituted or unsubstituted monocyclic N-containing heterocycle, or a substituted or unsubstituted bicyclic N-containing heterocycle, wherein if ring B is substituted then ring b is substituted with 1-3 R$^8$.

11. The compound of claim 10, or a pharmaceutically acceptable salt, or solvate thereof, wherein the compound has the structure of Formula (V):

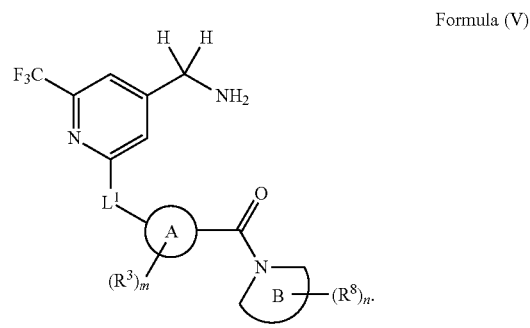

Formula (V)

12. The compound of claim 11, or a pharmaceutically acceptable salt, or solvate thereof, wherein:
Ring B is

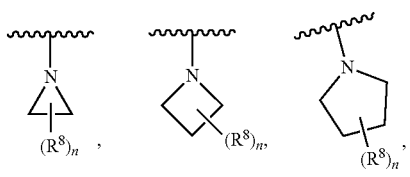

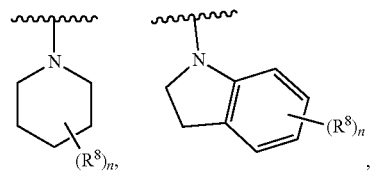

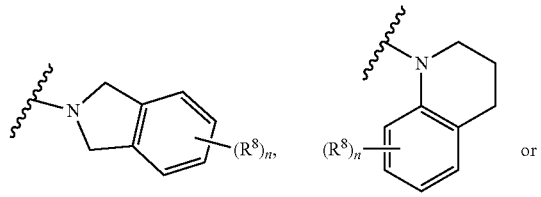

or

-continued

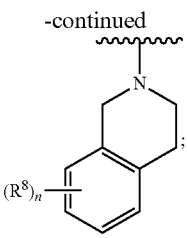

and n is 0, 1, or 2.

13. The compound of claim 11, or a pharmaceutically acceptable salt, or solvate thereof, wherein:

Ring B is

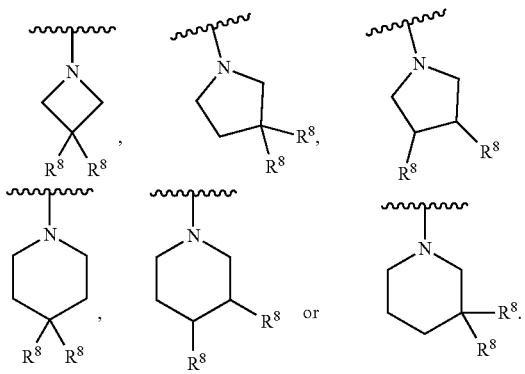

14. The compound of claim 11, or a pharmaceutically acceptable salt, or solvate thereof, wherein:

Ring B is

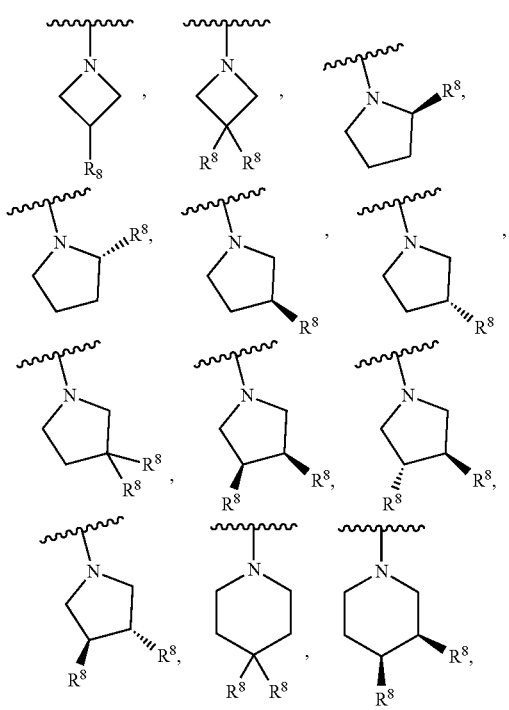

-continued

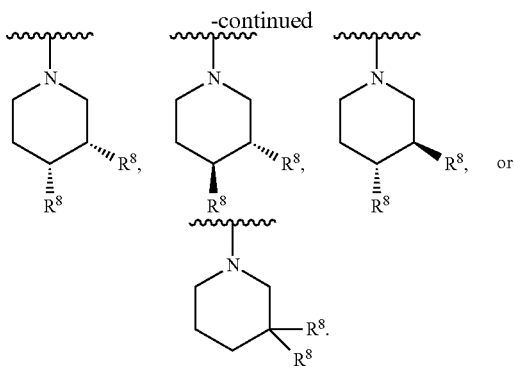

15. The compound of claim 1, wherein the compound is:
(6-(Trifluoromethyl)-[2,3'-bipyridin]-4-yl)methanamine;
(2-((1-(1-Methyl-1H-pyrazol-4-yl)-1H-indol-4-yl)oxy)-6-(trifluoromethyl)pyridin-4-yl) methanamine;
2-(4-((4-(Aminomethyl)-6-(trifluoromethyl)pyridin-2-yl)oxy)-1H-indol-1-yl)-N-methyl-N-phenylacetamide;
(R)-3-((4-(Aminomethyl)-6-(trifluoromethyl)pyridin-2-yl)oxy)-N-phenylpyrrolidine-1-carboxamide;
(S)-3-((4-(Aminomethyl)-6-(trifluoromethyl)pyridin-2-yl)oxy)-N-phenylpyrrolidine-1-carboxamide;
4-((4-(Aminomethyl)-6-(trifluoromethyl)pyridin-2-yl)oxy)-N-phenylpiperidine-1-carboxamide;
4-(((4-(Aminomethyl)-6-(trifluoromethyl)pyridin-2-yl)oxy)methyl)-N-phenylpiperidine-1-carboxamide;
(R)-3-((4-(Aminomethyl)-6-(trifluoromethyl)pyridin-2-yl)oxy)-N-phenylpiperidine-1-carboxamide;
(S)-3-((4-(Aminomethyl)-6-(trifluoromethyl)pyridin-2-yl)oxy)-N-phenylpiperidine-1-carboxamide;
(S)-3-(((4-(Aminomethyl)-6-(trifluoromethyl)pyridin-2-yl)oxy)methyl)-N-phenylpiperidine-1-carboxamide;
(S)-1-(3-((4-(Aminomethyl)-6-(trifluoromethyl)pyridin-2-yl)oxy)piperidin-1-yl)-2-phenylethanone;
(S)-1-(3-((4-(Aminomethyl)-6-(trifluoromethyl)pyridin-2-yl)oxy)piperidin-1-yl)-2-(3,4-dichlorophenyl)ethanone;
(S)-2-(3-((4-(Aminomethyl)-6-(trifluoromethyl)pyridin-2-yl)oxy)piperidine-1-carbonyl)-4H-chromen-4-one;
(S)-(3-((4-(Aminomethyl)-6-(trifluoromethyl)pyridin-2-yl)oxy)piperidin-1-yl)(pyridin-3-yl)methanone;
(S)-(3-((4-(Aminomethyl)-6-(trifluoromethyl)pyridin-2-yl)oxy)piperidin-1-yl)(pyrimidin-5-yl)methanone;
(S)-(3-((4-(Aminomethyl)-6-(trifluoromethyl)pyridin-2-yl)oxy)piperidin-1-yl)(5-methyl-1,3,4-oxadiazol-2-yl)methanone;
(S)-1-(3-((4-(Aminomethyl)-6-(trifluoromethyl)pyridin-2-yl)oxy)piperidin-1-yl)-2-methylpropan-1-one;
5-((4-(Aminomethyl)-6-(trifluoromethyl)pyridin-2-yl)oxy)-N-(2-(methylsulfonyl)ethyl)nicotinamide;
(R)-(5-((4-(Aminomethyl)-6-(trifluoromethyl)pyridin-2-yl)oxy)pyridin-3-yl)(3-aminopyrrolidin-1-yl)methanone;
Racemic-trans-(5-((4-(aminomethyl)-6-(trifluoromethyl)pyridin-2-yl)oxy)pyridin-3-yl)(-3-fluoro-4-hydroxypyrrolidin-1-yl)methanone;
2-(4-((4-(Aminomethyl)-6-(trifluoromethyl)pyridin-2-yl)oxy)-1H-indol-1-yl)-1-(piperidin-1-yl)ethanone;
tert-Butyl 4-(2-(4-((4-(aminomethyl)-6-(trifluoromethyl)pyridin-2-yl)oxy)-1H-indol-1-yl)acetyl)piperazine-1-carboxylate;
(2-((1H-Indol-4-yl)oxy)-6-(trifluoromethyl)pyridin-4-yl) methanamine;

5-((4-(Aminomethyl)-6-(trifluoromethyl)pyridin-2-yl)oxy)-3,4-dihydroquinolin-2(1H)-one;
5-((4-(Aminomethyl)-6-(trifluoromethyl)pyridin-2-yl)oxy)-1-(2-hydroxyethyl)-3,4-dihydroquinolin-2(1H)-one;
3-((4-(Aminomethyl)-6-(trifluoromethyl)pyridin-2-yl)methyl)-1-benzyl-6-methylpyrimidine-2,4(1H,3H)-dione;
3-((4-(Aminomethyl)-6-(trifluoromethyl)pyridin-2-yl)methyl)-1-(2-hydroxyethyl)-6-methylpyrimidine-2,4(1H,3H)-dione;
4'-(Aminomethyl)-6'-(trifluoromethyl)-2H-[1,2'-bipyridin]-2-one;
2-(4-((4-(Aminomethyl)-6-(trifluoromethyl)pyridin-2-yl)oxy)-1H-indol-1-yl)-1-(piperazin-1-yl)ethan-1-one;
2-(4-((4-(Aminomethyl)-6-(trifluoromethyl)pyridin-2-yl)oxy)-1H-indol-1-yl)-N-carbamimidoylacetamide;
Ethyl 2-(5-((4-(aminomethyl)-6-(trifluoromethyl)pyridin-2-yl)oxy)-2-oxo-3,4-dihydroquinolin-1(2H)-yl)acetate;
2-(5-((4-(Aminomethyl)-6-(trifluoromethyl)pyridin-2-yl)oxy)-2-oxo-3,4-dihydroquinolin-1(2H)-yl)acetic acid;
3-((4-(Aminomethyl)-6-(trifluoromethyl)pyridin-2-yl)methyl)-6-methyl-1-(pyrimidin-4-ylmethyl)pyrimidine-2,4(1H,3H)-dione;
1-(2-((4-(Aminomethyl)-6-(trifluoromethyl)pyridin-2-yl)oxy)-6-azaspiro[3.4]octan-6-yl)ethanone;
4-((4-(Aminomethyl)-6-(trifluoromethyl)pyridin-2-yl)oxy)-N-phenylpicolinamide;
or a pharmaceutically acceptable salt, or solvate thereof.

16. A pharmaceutical composition comprising a compound of claim 1, or a pharmaceutically acceptable salt, or solvate thereof, and at least one pharmaceutically acceptable excipient.

17. A pharmaceutical composition comprising a compound of claim 15, or a pharmaceutically acceptable salt, or solvate thereof, and at least one pharmaceutically acceptable excipient.

* * * * *